US007183099B2

(12) United States Patent
Taga et al.

(10) Patent No.: US 7,183,099 B2
(45) Date of Patent: Feb. 27, 2007

(54) INHIBITORS OF AUTOINDUCER TRANSPORTERS

(75) Inventors: Michiko E. Taga, Princeton, NJ (US); Bonnie L. Bassler, Princeton, NJ (US); Douglas T. McKenzie, San Diego, CA (US)

(73) Assignee: Princeton University, Princeton, NJ (US)

( * ) Notice: Subject to any disclaimer, the term of this patent is extended or adjusted under 35 U.S.C. 154(b) by 0 days.

(21) Appl. No.: 10/284,084

(22) Filed: Oct. 28, 2002

(65) Prior Publication Data

US 2003/0165932 A1    Sep. 4, 2003

Related U.S. Application Data

(60) Provisional application No. 60/336,324, filed on Oct. 29, 2001.

(51) Int. Cl.
C12N 1/21 (2006.01)
(52) U.S. Cl. ............................... 435/252.33; 435/252.3
(58) Field of Classification Search ............. 435/252.1, 435/252.8
See application file for complete search history.

(56) References Cited

OTHER PUBLICATIONS

Taga, M.E., Semmelhack, J.L. and Bassler, B.L., "The LuxS-dependent autoinducer AI-2 controls the expression of an ABC transporter that functions in AI-2 uptake in *Salmonella typhimurium*", 2001, Molecular Microbiology, 42(3), 777-793.
Bassler, B.L., "How bacteria talk to each other: regulation of gene expression by quorum sensing", 1999, Current Opinion in Microbiology, 2, 582-587.
Bassler, B.L., et al., "Cross-Species Induction of Luminescence in the Quorum-Sensing Bacterium *Vibrio harveyi*", 1997, Journal of Bacteriology, 179(12), 4043-4045.
Bassler, B.L., et al., "Intercellular signalling in *Vibrio harveyi*: sequence and function of genes regulating expression of luminescence", 1993, Molecular Microbiology, 9(4), 773-786.
Bassler, B.L., et al., "Multiple signalling systems controlling expression of luminescence in *Vibrio harveyi*: sequence and function of genes encoding a second sensory pathway", 1994, Molecular Microbiology, 13(2), 273-286.
Bassler, B.L., et al., "Sequence and function of LuxO, a negative regulator of luminescence in *Vibrio harveyi*", 1994, Molecular Microbiology, 12(3), 403-412.
Blattner, F.R., et al., "The Complete Genome Sequence of *Escherichia coli* K-12", 1997, Science, vol. 277, 1453-1474.
Boos, W., et al., "Periplasmic Binding Protein-Dependent ABC Transporters", 1996, In *Escherichia coli* and *Salmonella typhimurium* Cellular and Molecular Biology, vol. 1 Neidhardt, F.(ed) Washington D.C.:ASM Press, 1175-1209.
Cao, J.G., et al., "Purification and Structural Identification of an Autoinducer for the Luminescence System of *Vibrio harveyi*", 1989, Journal of Biological Chemistry, 264(36), 21670-21676.

Day, Jr., W.A., et al., "*Shigella flexneri* LuxS Quorum-Sensing System Modulates virB Expression but is Not Essential for Virulence", 2001, 69(1), 15-23.
Freeman, J.A. and Bassler, B.L., "A genetic analysis of the function of LuxO, a two-component response regulator involved in quorum sensing in *Vibrio harveyi*", 1999, Molecular Microbiology, 31(2), 665-677.
Freeman, J.A. and Bassler, B.L., "Sequence and Function of LuxU: a Two-Component Phosphorelay Protein That Regulates Quorum Sensing in *Vibrio harveyi*", 1999, Journal of Bacteriology, 181(3), 899-906.
Freeman, J.A., Lilley, B.N. and Bassler, B.L., "A genetic analysis of the functions of LuxN: a two-component hybrid sensor kinase that regulates quorum sensing in *Vibrio harveyi*", 2000, Molecular Microbiology, 35(1), 139-149.
Greenberg, E.P., et al., "Induction of Luciferase Synthesis In *Beneckea harveyi* by Other Marine Bacteria", 1979, Arch Microbiol., 120, 87-91.
Lilley, B.N., and Bassler, B.L., "Regulation of quorum sensing in *Vibrio harveyi* by LuxO and Sigma-54", 2000, Molecular Microbiology, 36(4), 940-954.
Lyon, W.R., et al., "Mutation of luxS affects growth and virulence factor expression in *Streptococcus pyogenes*", 2001, Molecular Microbiology, 42(1), 145-157.
Miller, M.B., and Bassler, B.L., "Quorum Sensing in Bacteria", 2001, Annu. Rev. Microbiol. 55: 165-199.
Schauder, S., and Bassler, B.L., "The languages of Bacteria", 2001, Genes and Dev., 15: 1468-1480.
Schauder, S., Shokat, K., Surette, M.G., and Bassler, B.L., "The LuxS family of bacterial autoinducers: biosynthesis of a novel quorum-sensing signal molecule", 2001, Molecular Microbiology, 41(2), 463-476.
Sperandio, V., et al., "Quorum sensing controls expression of the type III secretion gene transcription and protein secretion in enterohemorrhagic and enteropathogenic *Escherichia coli*", 1999, Proc. Natl. Acad. Sci. USA, 96(26), 15196-15201.
Surette, M.G., and Bassler, B.L., "Quorum sensing in *Escherichia coli* and *Salmonella typhimurium*", 1998, Proc. Natl. Acad. Sci. USA, 95: 7046-7050.
Surette, M.G., and Bassler, B.L., "Regulation of autoinducer production in *Salmonella typhimurium*", 1999, Molecular Microbiology, 31(2), 585-595.
Surette, M.G., Miller, M.B., and Bassler, B.L., "Quorum sensing in *Escherichia coli, Salmonella typhimurium*, and *Vibrio harveyi*: A new family of genes responsible for autoinducer production", Proc. Natl. Acad. Sci. USA, 96: 1639-1644.

*Primary Examiner*—Nancy Vogel
(74) *Attorney, Agent, or Firm*—Mathews, Sherpherd, McKay & Bruneau, P.A.

(57) ABSTRACT

The present invention relates to the discovery of the lsr operon, the genes therein, and the polypeptides encoded by these genes. The present invention also includes strains with altered expression levels of the polypeptides encoded by the genes and the lsr operon relative to wild type cells. In some embodiments, the strains express a transporter that transports an autoinducer into the cell at a level higher than that of wild type cells. The present invention also includes methods for identifying compounds that modulate the transport of the autoinducer into cells.

6 Claims, 25 Drawing Sheets

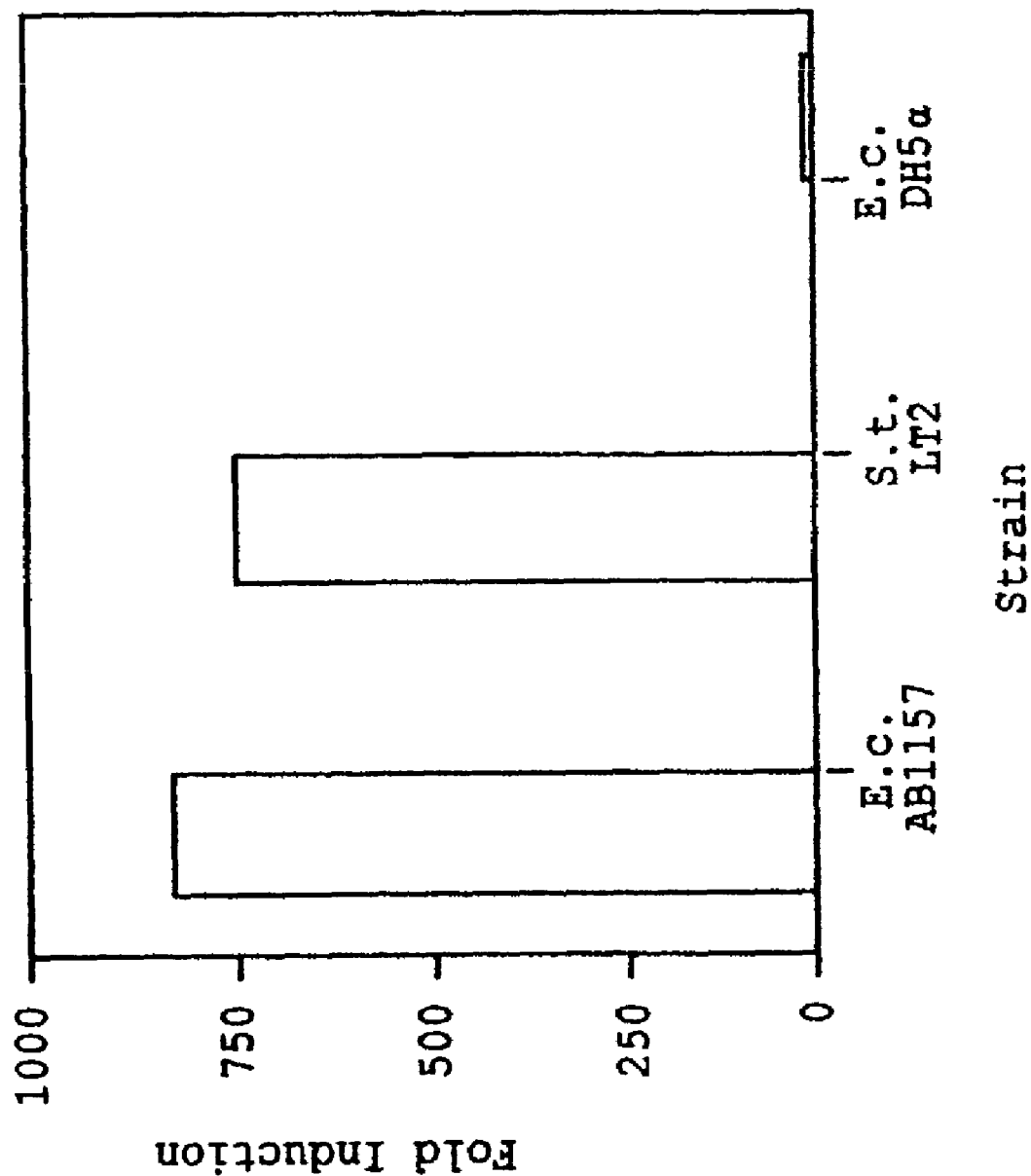

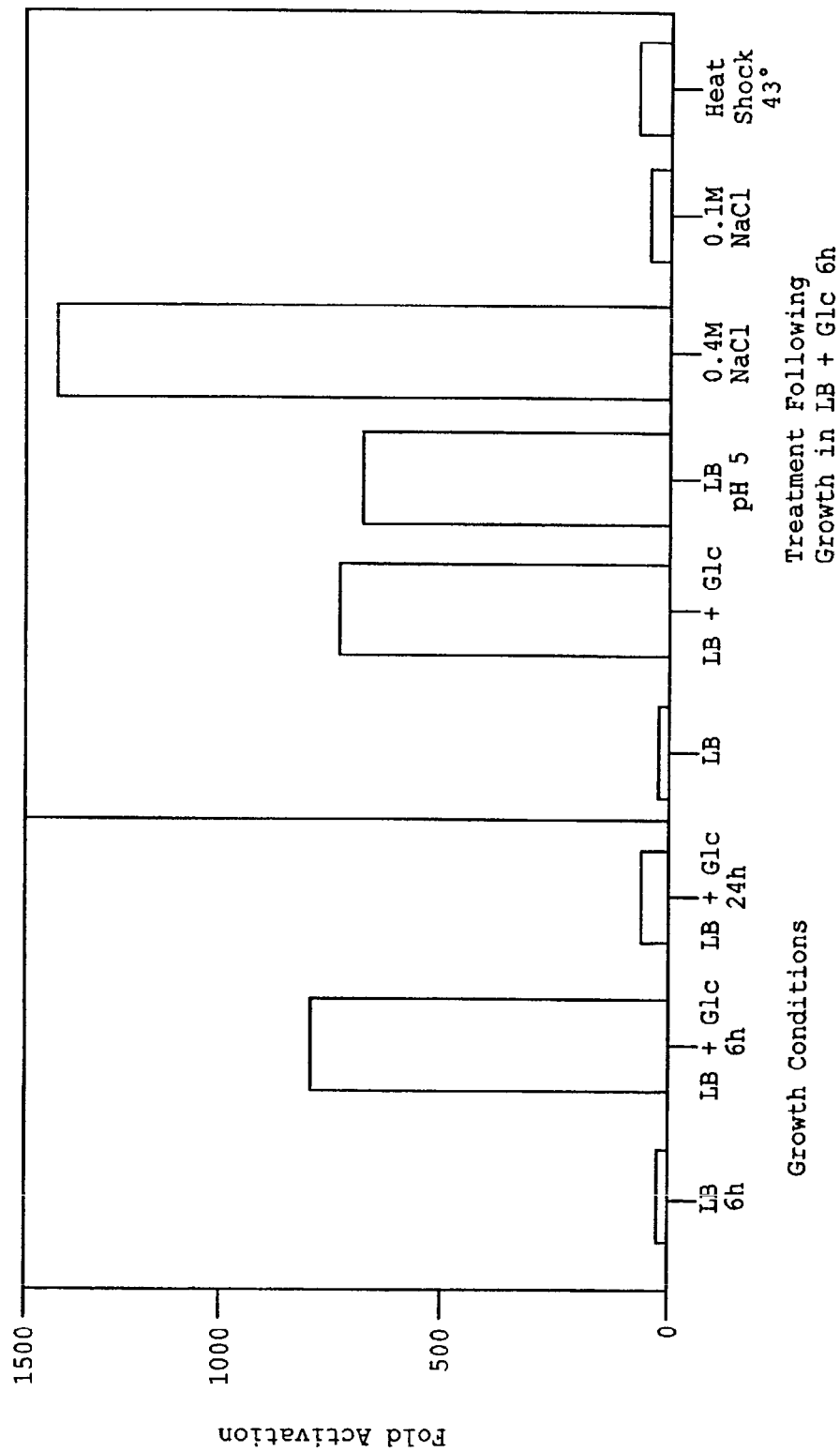

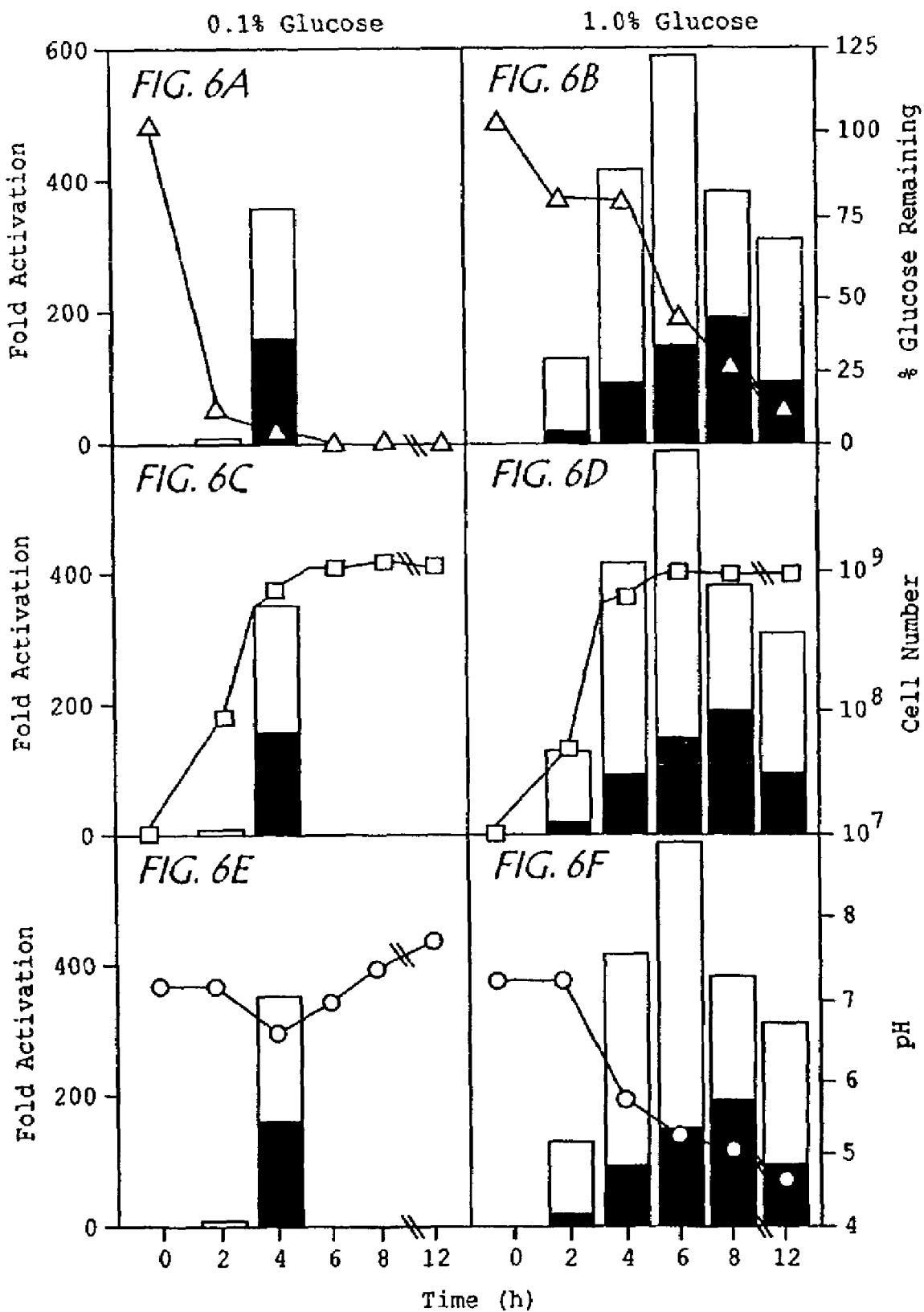

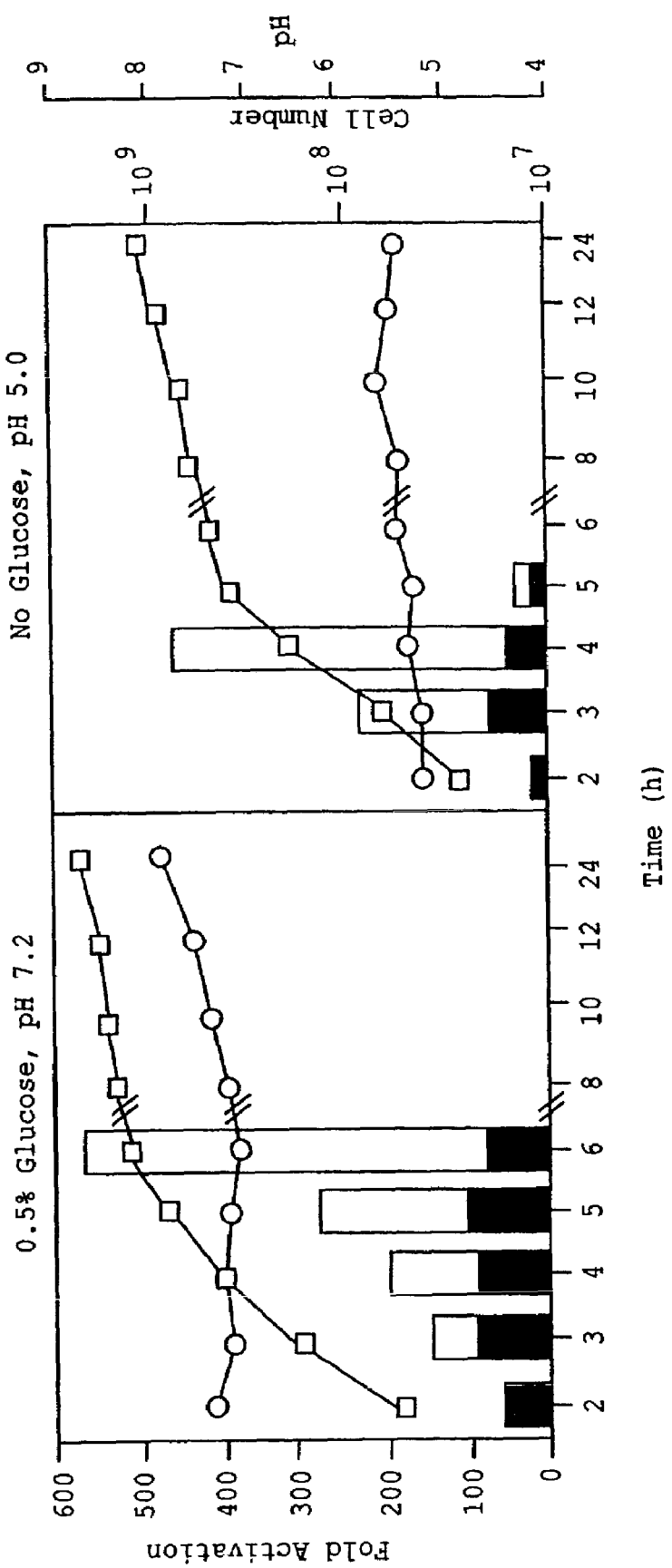
FIG. 7A  0.5% Glucose, pH 7.2
FIG. 7B  No Glucose, pH 5.0

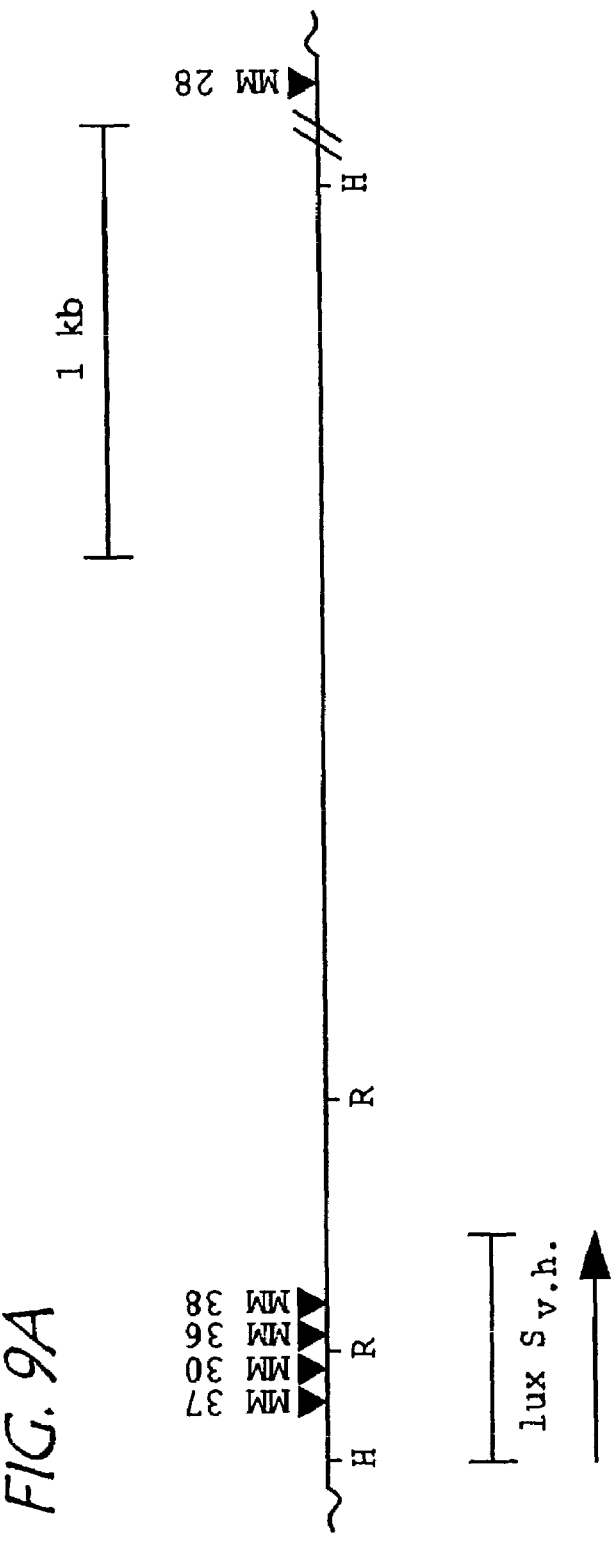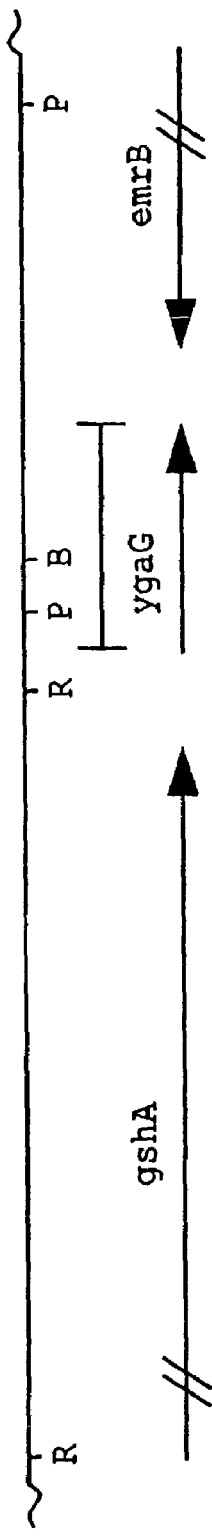

Figure 13

```
V.h.  BB120   1   MPLLDSFTVDHTRMMAPAVRVAKTMQTPRGDTITVFDLRFTAPNKDILSEKGIHTLEHLYAGFMRNHLNGDSVIIDISPMGCRTG
E.c.  MG1655  1   MPLLDSFTVDHTRMEAPAVRVAKTMQTPMGDAITVFDLRFCVPNLEVMPERGIHTLEHLFAGFMRNHLNGNGVEIIDISPMGCRTG
E.c.  0157:H7 1   MPLLDSFTVDHTRMEAPAVRVAKTMQTPMGDAITVFDLRFCVPNLEVMPERGIHTLEHLFAGFMRNHLNGNGVEIIDISPMGCRTG
S.t.  LT2     1       NSDHTRMQAPAVRVAKTMQTPMGDAITVFDLRFCIPNKEVMPEKGIHTLEHLFAGFMRDHLNGNGVEIIDISPMGCRTG
E.c.  DH5α    1   MPLLDSFTVDHTRMEAPAVRVAKTMQTPMGDAITVFDLRFCVPNLEVMPERGIHTLEHLFAGFMRNHLNGNGVEIIDISPMGCRTG

V.h.  BB120   87  FYMSLIGTPSKQQVADAWIAAMEDVLKVENQNKIPELNEYQCGTAAMHSLDEAKQIAKNILEVGVAVNKNDELALPESMLRELRID
E.c.  MG1655  87  FYMSLIGTPDKQRVADAWKAAMEDVLKVQDQNQIPELNVYQCGTYQMHSLQEAQDIARSILERDVRINSNEELALPKEKLQELHI
E.c.  0157:H7 87  FYMSLIGTPDKQRVADAWKAAMEDVLKVQDQNQIPELNVYQCGTYQMHSLQEAQDIARSILERDVRINSNEELALPKEKLQELHI
S.t.  LT2     87  FYMSLIGTPDKQRVADAMAMADVLKVQDQNQIPELNVYQCGTYQMHSLSEAQDIARHILERDVRVNSNKELALPKEKLQELHI

E.c.  DH5α    87  FYMSLLVRQMSSVLLMPKGKRQWKTC
```

Hybrid quorum sensing circuit of Vibrio harveyi

Figure 21

```
                          T    H  P
                          ↓    ↓  ↓
     Δ5'
 1   MSDNTLVSDYGMCEEEQVARIAWFYYHDGLTQSEISERLGLTRLKVSRLLEKGHQSGIIRVQ
                                                          T
                                                          ↓
63   INSRFEGCLEYENALRNHFALQNIRVLPALPDADIGLRLGIGAAHMLMESLRPQQLLAVGFGE
                 P          Q
                 ↓          ↓
126  ATMTTLKRLSGFISAQQIRLVTLSGGVGPYMTGIGQLDAACSVSIMPAPLRASSQEIACTLR
                                 R
                                 ↓
188  NENSVRDVMLTAQAADAAIVGIGAINQKDQASILKSGYITQGEQLMIGRKGAVGDILGYFFDA

251  HGEIIPDIKIHNELIGLKLNSLSTIPTVIGVAGGEQKAEAIIAAMRGNYINALVTDQKTAGKI
```

INHIBITORS OF AUTOINDUCER TRANSPORTERS

RELATED APPLICATION INFORMATION

This application claims priority to U.S. Provisional Application No. 60/336,324, filed on Oct. 29, 2001 and entitled Inhibitors of Autoinducer Transporters, the disclosure of which is hereby incorporated by reference in its entirety.

STATEMENT OF GOVERNMENT INTEREST

The National Science Foundation Grants MCB-0083160, MCB-0094447, and. MCB-9506033 and The Office of Naval Research Grant Number N00014-99-0767 supported this work. Accordingly, the U.S. Government has certain rights in this invention.

BACKGROUND OF THE INVENTION

Several publications are referenced in this application to more fully describe the state of the art to which this invention pertains. The entire disclosure of each such publication is incorporated by reference herein.

Bacteria regulate gene expression in response to changes in cell population density by a process called quorum sensing. Specifically, quorum sensing bacteria release and detect chemical signals called autoinducers. Bacteria respond to the accumulation of a minimal threshold stimulatory concentration of autoinducer. Detection of autoinducers enables bacteria to distinguish between low and high cell population density, and to control target gene expression in response to fluctuations in cell number. Quorum sensing bacteria regulate processes that require the cooperation of a number of bacterial cells in order to be effective, and the individuals in the group profit from the activity of the entire assembly (Bassler, 1999; Fuqua et al., 1996; Kleerebezem et al., 1997; Lazazzera and Grossman, 1998; Miller and Bassler, 2001; Schauder and Bassler, 2001; de Kievit and Iglewski, 2000). These processes include bioluminescence, virulence, antibiotic production, sporulation and biofilm formation. Quorum sensing therefore allows a population of bacteria to coordinate behavior, and thus take on the characteristics of multi-cellular organisms.

In general, quorum sensing is controlled by acyl-homoserine lactone autoinducers in Gram-negative bacteria and by modified oligopeptide autoinducers in Gram-positive bacteria (Miller and Bassler, 2001; Schauder et al., 2001; Lazazzera and Grossman, 1998; de Kievit and Iglewski, 2000). Gram-negative quorum sensing circuits typically resemble the canonical circuit of *Vibrio fischeri*. Specifically, the acyl-HSL autoinducer synthase is similar to the *V. fischeri* LuxI enzyme, and a transcriptional activator similar to the *V. fischeri* LuxR protein is responsible for autoinducer recognition and target gene activation (Engebrecht et al., 1983; Engebrecht and Silverman, 1984; 1987; Miller and Bassler, 2001; de Kievit and Iglewski, 2000). In Gram-positive bacteria, the oligopeptide autoinducers are synthesized as precursor peptides that are processed, modified and subsequently secreted by ATP Binding Cassette (ABC) type exporters. Gram-positive bacteria detect and respond to oligopeptide autoinducers via two-component phosphorylation cascades (Kleerebezem et al., 1997; Lazazzera and Grossman, 1998; Miller and Bassler, 2001). Both acyl-HSL and oligopeptide autoinducers are highly specific to the species that produce them, as autoinducers produced by one species usually do not influence expression of genes in other species. It is remarkable that such signaling specificity exists in both types of quorum sensing circuits, given the similarity in the members of each class of signal.

Unlike all other quorum sensing bacteria, *Vibrio harveyi*, a bioluminescent Gram-negative bacterium, uses a novel regulatory circuit to control quorum sensing. Specifically, *V. harveyi* controls density dependent expression of the luciferase genes using a hybrid quorum sensing circuit, with components common to both Gram-negative and Gram-positive quorum sensing systems (Bassler, 1999). Like other Gram-negative quorum sensing bacteria, *V. harveyi* uses an acyl-homoserine lactone autoinducer (called AI-1) as a signal (Bassler et al., 1993; Cao and Meighen, 1989). However, similar to Gram-positive quorum sensing bacteria, *V. harveyi* employs a two-component signaling circuit for autoinducer detection and signal transduction (Bassler et al., 1993; Bassler et al., 1994a; b; Freeman and Bassler, 1999a; b; Freeman et al., 2000; Lilley and Bassler, 2000). In addition, a second, novel autoinducer, termed AI-2, also regulates quorum sensing in *V. harveyi* (Bassler et al., 1994a; Surette and Bassler, 1998; Surette et al., 1999). It is hypothesized that *V. harveyi* uses AI-1 for intra-species cell-cell communication and AI-2 for inter-species cell-cell signaling (Bassler et al., 1997; Bassler, 1999; Surette et al., 1999). These distinct signals presumably allow *V. harveyi*, which inhabits multi-species consortia, to vary its gene expression not only in response to changes in total cell number, but also in response to fluctuations in the species composition of the community.

Thus, *V. harveyi* has two independent density sensing systems (called Signaling Systems 1 and 2), and each is composed of a sensor-autoinducer pair. *V. harveyi* Signaling System 1 is composed of Sensor 1 and autoinducer 1 (AI-1), and this autoinducer is N-(3-hydroxybutanoyl)-L-homoserine lactone (see Bassler et al., Mol. Microbiol. 9: 773–786, 1993). *V. harveyi* Signaling System 2 is composed of Sensor 2 and autoinducer 2 (AI-2) (Bassler et al., Mol. Microbiol. 13: 273–286; 1994). Signaling System 1 is a highly specific system proposed to be used for intra-species communication and Signaling System 2 appears to be less species-selective, and is hypothesized to be for inter-species communication (Bassler et al., J. Bacteriol. 179: 4043–4045, 1997). Reporter strains of *V. harveyi* have been constructed that can produce light exclusively in response to Al-1 or to AI-2 (Bassler et al., 1993, supra; Bassler et al., 1994, supra).

Quorum sensing in *V. harveyi*, mediated by Signaling Systems 1 and 2, triggers the organisms to bioluminesce at a certain cell density. These same signaling systems, particularly Signaling System 2, are believed to trigger other physiological changes in *V. harveyi* and other bacteria possessing the same signaling system.

Consistent with a role for AI-2 as a universal signal used for bacterial inter-species communication, over 30 species of Gram-negative and Gram-positive bacteria have now been shown to produce AI-2 (Bassler et al., 1997; Miller and Bassler, 2001; Surette and Bassler, 1998, the disclosures of which are incorporated herein by reference in their entireties). In every case, an AI-2 synthase that is highly homologous to the *V. harveyi* AI-2 synthase called LuxS is required for AI-2 production (Surette et al., 1999). Recently, the biosynthetic pathway for AI-2 synthesis was described (Schauder and Bassler, 2001; Schauder et al., 2001). AI-2 is produced from S-ribosylhomocysteine (SRH), a product in the S-adenosylmethionine (SAM) utilization pathway. Specifically, LuxS cleaves SRH to form homocysteine and AI-2. Although not confirmed, AI-2 appears to be a furanone with structural similarity to ribose (Schauder et al., 2001). The current evidence suggests that, in contrast to the variable structures of acyl-homoserine lactone and peptide autoinducers, the structures of AI-2 from different species of bacteria are identical. If AI-2 is used for inter-species signalling in natural habitats, a common signal structure could be required for it to be recognized by multiple members of a mixed-species community (Schauder et al., 2001; Schauder and Bassler, 2001).

Although the role of AI-2 is understood in the regulation of bioluminescence in *V. harveyi*, what function AI-2 plays, if any, in other luxS-containing bacteria is not clear. There are reports showing that AI-2 is involved in regulating type III secretion in *E. coli* 0157:H7 (Sperandio et al., 1999), protease production in *Streptococcus pyogenes* (Lyon et al., 2001), hemolysin production in *V. vulnificus* (Kim et al., 2000), and regulation of the virulence factor VirB in *Shigella flexneri* (Day and Maurelli, 2001). Genetic experiments established how AI-2 regulates gene expression in *Salmonella typhimurium*, and show that AI-2 controls the expression of a previously uncharacterized operon encoding an ABC transporter apparatus that appears to function in the uptake of AI-2.

Definitions:

Various terms relating to the biological compounds of the present invention are used throughout the specifications and claims. The terms "substantially the same," "percent similarity" and "percent identity" are defined in detail below.

The novel signaling factor of the present invention is alternatively referred to herein as "signaling factor", "signaling compound", "autoinducer", and more specifically, "autoinducer-2" or AI-2". The terms "autoinducer-2" and "AI-2" refer specifically to the signaling factor as produced by *Vibrio harveyi*. The terms "signaling factor" or "signaling compound", "autoinducer" or "AI-2-like compound" refer generally to the signaling factors of the present invention, of which AI-2 is an example.

The term "isolated nucleic acid", when applied to DNA, refers to a DNA that is separated from sequences with which it is immediately contiguous (in the 5' and 3' directions) in the naturally occurring genome of the organism from which it was derived. For example, the "isolated nucleic acid" may comprise a DNA inserted into a vector, such as a plasmid or virus vector, or integrated into the genomic DNA of a procaryote or eucaryote. An "isolated nucleic acid" may also comprise a cDNA.

The term "isolated nucleic acid", when applied to RNA, refers to an RNA encoded by an isolated DNA as defined above. Alternatively, the term may refer to an RNA that has been sufficiently separated from RNAs with which it would be associated in its natural state (i.e., in cells or tissues), such that it exists in a "substantially pure" form (the term "substantially pure" is defined below).

The term "isolated protein" or "isolated and purified protein" refers primarily to a protein produced by expression of an isolated nucleic acid of the invention. Alternatively, this term may refer to a protein that has been sufficiently separated from other proteins with which it would naturally be associated, so as to exist in "substantially pure" form.

The term "substantially pure" refers to a preparation comprising at least 50–60% by weight the factor of interest (e.g., pathogenesis signaling factor, nucleic acid, oligonucleotide, protein, etc.). More preferably, the preparation comprises at least 75% by weight, and most preferably 90–99% by weight, the factor of interest. Purity is measured by methods appropriate for the factor of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but that do not substantially recognize and bind other compounds in a sample containing a mixed population of antigenic biological constituents.

With respect to oligonucleotides, the term "specifically hybridizing" refers to the association between two single-stranded nucleotides of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA of the invention, to the substantial exclusion of hybridization of the oligonucleotide with single-stranded nucleic acids of noncomplementary sequence.

The term "promoter region" refers to the transcriptional regulatory regions of a gene, which may be found at the 5' or 3' side of the coding region, or within the coding region, or within introns.

The term "selectable marker gene" refers to a gene encoding a product that, when expressed, confers a selectable phenotype such as antibiotic resistance on a transformed cell.

The term "reporter gene" refers to a gene that encodes a product that is easily detectable by standard methods, either directly or indirectly.

The term "operably linked" means that the regulatory sequences necessary for expression of the coding sequence are placed in the DNA in the appropriate positions relative to the coding sequence so as to enable expression of the coding sequence. This same definition is sometimes applied to the arrangement of transcription units and other regulatory elements (e.g., enhancers or translation regulatory sequences) in an expression vector.

The term "wild type cell" or "wild type strain" is used herein to describe cells or strains that serve as a reference point for cells or strains in which the expression level of a particular protein has been altered (i.e increased or decreased). Generally, the "wild type cell" or "wild type strain" and the cell or strain to which it is being compared will have the same genotype except for one or more difference that change the expression level of the protein. Thus, as used herein "wild type cells" or "wild type strains" may contain certain mutations that are shared with the cells or strains to which they are being compared but they do not share the genotype that confers altered expression levels of the protein of interest. For example, if a strain or cell expresses a higher level of a transporter than a wild type strain or cell, it may be genetically identical to the wild type strain or cell except for one or more mutations that are responsible for the increased expression level of the transporter.

BRIEF DESCRIPTION OF THE DRAWINGS

FIG. 2. Active secretion of the signaling compound by viable *E. coli* and *S. typhimurium*. The response of the *V. harveyi* reporter strain BB170 (Sensor 1−, Sensor 2+) to a signaling substance produced and secreted by *E. coli* AB1157 and *S. typhimurium* LT2 but not *E. coli* DH5 is shown. *V. harveyi* reporter strain BB170 was diluted 1:5000 in AB medium and light output per cell was monitored during growth. At the start of the experiment, either $1 \times 10^6$ *E. coli* AB1157, *S. typhimurium* LT2 or *E. coli* DH5 washed and resuspended viable cells (left-hand, white bars) or UV-killed cells (right-hand, black bars) was added. The data are presented as the fold-activation above the endogenous level of luminescence expressed by *V. harveyi* BB170 at the 5 hour time point. Abbreviations used for the different strains are: S.t; *Salmonella typhimurium*, and E.c; *Escherichia coli*.

FIG. 5. Conditions affecting autoinducer production in *S. typhimurium*. *S. typhimurium* LT2 was subjected to a variety of treatments after which cell-free culture fluids or osmotic shock fluids were prepared. These preparations were added to a diluted culture of the *V. harveyi* AI-2 reporter strain BB170 at 10% (v/v) and light output was measured thereafter. Fold activation is the level of light produced by the reporter following addition of the specified *S. typhimurium* preparation divided by the light output of the reporter when growth medium alone was added The bars in FIG. 5A represent cell-free fluids prepared from *S. typhimurium* after the following treatments: LB 6h; 6 h growth in LB at 30° C., LB+Glc 6 h; 6 h growth in LB+0.5% glucose at 30° C., LB+Glc 24 h; 24 h growth in LB+0.5% glucose at 30° C. In all the experiments presented in FIG. 5B, the *S. typhimurium* were pregrown at 30° C. for 6 h in LB containing 0.5% glucose, then pelleted and resuspended for 2 h under the following conditions: LB; in LB at 30° C., LB+Glc; in LB+0.5% glucose at 30° C., LB pH 5; in LB at pH 5.0 at 30° C., 0.4 M NaCl; in 0.4 M NaCl at 30° C., 0.1 M NaCl; in 0.1 M NaCl at 30° C., and Heat Shock 430; in LB+0.5% glucose at 43° C. After these two hour treatments, cell-free fluids were prepared from each sample and assayed.

FIG. 6. *S. typhimurium* signaling activity in limiting and non-limiting concentrations of glucose. *S. typhimurium* LT2 was grown in LB in the presence of limiting (0.1%) and non-limiting (1.0%) concentrations of glucose. The activity present in the cell-free culture fluids (black bars) was assayed at the times indicated and normalized to that produced by $1 \times 10^9$ cells. The increase in signaling activity measured in the 0.4 M NaCl osmotic shock fluids prepared from the same cells is shown as the white bars on top of the black bars. These data are also normalized for $1 \times 10^9$ cells. The signaling activity for limiting glucose is shown in FIGS. 6A, 6C, and 6E, and that for non-limiting glucose is shown in FIGS. 6B, 6D, and 6F. FIGS. 6A and 6B also show the percent glucose remaining (triangles), FIGS. 6C and 6D show the cell number (squares), and Panels E and F show the pH (circles) at each time point.

FIG. 7. Effects of glucose and pH on signal production by *S. typhimurium*. The quorum sensing signal released by *S. typhimurium* LT2 was measured when the cells were grown in LB medium containing 0.5% glucose at pH 7.2 (FIG. 7A, bars), and when the cells were grown in LB at pH 5.0 without an added carbon source (FIG. 7B, bars). The level of signal present in cell free culture fluids (black bars) and in 0.4 M NaCl osmotic shock fluids was measured (white bars on top of black bars) at the time points indicated. In each panel, the circles represent the pH of the medium, and the squares show the cell number at the different time points.

FIG. 9. The luxS and ygaG genes from *V. harveyi* and *E. coli* MG1655. FIG. 9A shows a restriction map of the *V. harveyi* luxS$_{V.h.}$ chromosomal region that was defined by Tn5 insertion. The sites of Tn5 insertions that disrupted the AI-2 production function and one control Tn5 insertion outside of the luxS$_{V.h.}$ locus are shown (triangles). FIG. 9B depicts the ygaG region in the *E. coli* MG1655 chromosome. This ORF is flanked by the emrB and gshA genes. The direction of transcription of each gene is indicated by the horizontal arrows. The corresponding position of the MudJ insertion that eliminated AI-2 production in *S. typhimurium* LT2 is shown by a vertical arrow. H, R, P, and B denote HindIII, EcoRI, PstI and BamHI restriction sites respectively.

FIG. 10. Autoinducer production phenotypes of *V. harveyi* and *S. typhimurium* strains. Cell-free culture fluids from *V. harveyi* and *S. typhimurium* strains were prepared and tested for AI-2 activity in the *V. harveyi* BB170 bioassay.

FIG. 13. Alignment of LuxS and YgaG protein sequences. The translated protein sequences for the AI-2 production family of proteins are shown. We determined the sequences for the luxS$_{V.h.}$ gene from *V. harveyi* BB120 (SEQ ID NO:10), and the ygaG genes (renamed herein as luxS$_{E.C}$ from *E. coli* MG1655 (SEQ ID NO: 11), *E. coli* 0157:H7 (SEQ ID NO: 11), and *E. coli* DH5 (SEQ ID NO: 18). The *S. typhimurium* LT2 ygaG (renamed herein luxS$_{S.t.}$ partial sequence (SEQ ID NO: 12) came from the *S. typhimurium* database. Amino acid residues that are not identical to the LuxS$_{V.h.}$ protein are underlined and not in bold font. The site of the frame shift mutation in the *E. coli* DH5 DNA sequence is denoted by an "*". The 20 altered amino acid residues that are translated following the frame shift are enclosed by the box.

FIG. 21 shows the activity of LsrR suppressor mutants. Eight spontaneous mutations in lsrR were identified that conferred a Lac$^+$ phenotype to an *S. typhimurium* lsrC::MudJ, luxS null strain. The LsrR protein sequence and the amino acid alterations causing a suppressor phenotype are shown. The spontaneous deletion that resulted in a suppressor phenotype is shown by a single underline (denoted Δ5'). The predicted helix-turn-helix DNA binding motif is shown by the double underline.

SUMMARY OF THE INVENTION

Figure 1B:
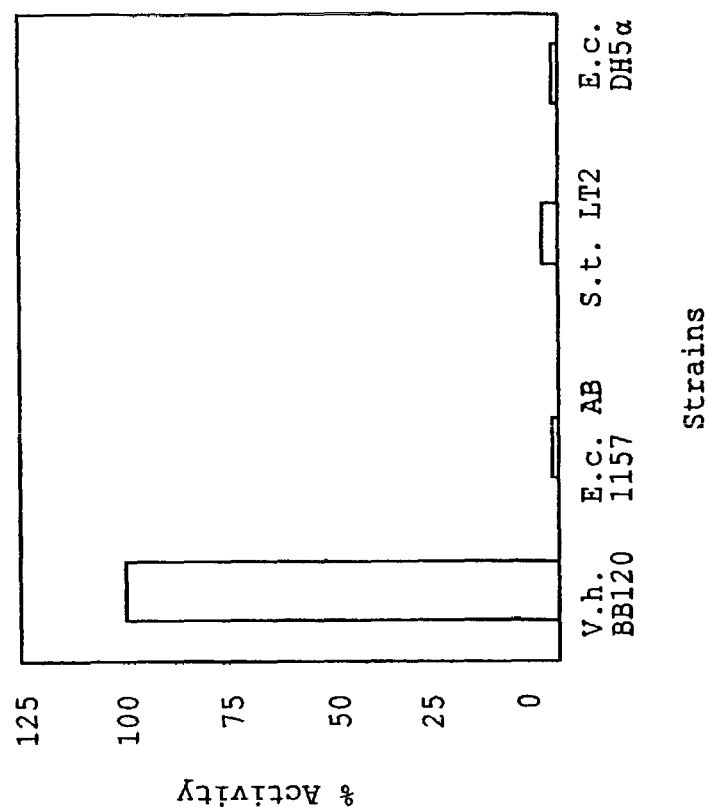
FIG. 1. Signaling substance from *E. coli* AB1157 and *S. typhimurium* LT2 cell-free culture fluids that induces luminescence in *V. harveyi*. The responses of *V. harveyi* reporter strains BB170 (Sensor 1$^-$, Sensor 2$^+$) (FIG. 1A), and BB886 (Sensor 1$^+$, Sensor 2$^-$) (FIG. 1B) to signaling substances present in cell-free culture fluids from *E. coli, S. typhimurium* and *V. harveyi* strains are shown. A bright culture of each reporter strain was diluted 1:5000 into fresh medium, and the light production per cell was then measured during the growth of the diluted culture. Cell-free culture fluids or sterile growth medium were added at a final concentration of 10% (v/v) at the start of the experiment. The data for the 5 hour time point are shown and are presented as the percent of the activity obtained when *V. harveyi* cell-free spent culture fluids are added. Abbreviations used for the different strains are: V.h; *Vibrio harveyi*, S.t; *Salmonella typhimurium*, and E.c; *Escherichia coli*.

Some aspects of the invention are described in the following numbered paragraphs:

1. An isolated bacterial strain having an increased expression level of a transporter that transports an autoinducer into the strain relative to a wildtype strain, wherein the autoinducer is not an acyl-homoserine lactone and can interact with the *Vibrio harveyi* LuxQ protein, thereby inducing expression of a *Vibrio harveyi* operon comprising the luxCDABE genes.

2. The strain of Paragraph 1, wherein the strain has been genetically engineered to increase expression of the transporter.

3. The strain of Paragraph 1, wherein the transporter comprises at least one polypeptide comprising a sequence selected from the group consisting of SEQ ID NOs.: 37–40 and a sequence having at least 25% amino acid identity as determined through use of FASTA version 3.0t78 with the default parameters to one of SEQ ID NOs.: 37–40.

4. The strain of Paragraph 1, wherein the transporter comprises a complex comprising each of the sequences of SEQ ID NOs. 37–40 or sequences having at least 25% identity as determined through use of FASTA version 3.0t78 with the default parameters to each of the sequences of SEQ ID NOs.: 37–40.

5. The strain of Paragraph 2, wherein the strain comprises at least one vector from which one or more polypeptides included in the transporter are expressed.

6. The strain of Paragraph 1, wherein the strain comprises a mutation that increases expression of the transporter.

7. The strain of Paragraph 6, wherein the mutation is in a gene encoding a repressor that reduces expression of the transporter.

8. The strain of Paragraph 7, wherein the mutation is in a gene comprising the sequence of SEQ ID NO: 28.

9. The strain of Paragraph 8, wherein the mutation is in a gene comprising a sequence having at least 30% identity to SEQ ID NO: 28 as determined through use of BLASTN version 2.0 with the default parameters.

10. The strain of Paragraph 7, wherein the mutation is in a gene encoding a polypeptide comprising the sequence of SEQ ID NO: 36.

11. The strain of Paragraph 7, wherein the mutation is in a nucleic acid comprising a sequence that hybridizes to a probe comprising at least 30 consecutive nucleotides of SEQ ID NO: 28 in 6×SSC at about 45° C. followed by one or more washes in 0.1×SSC/0.2% SDS at about 68° C.

12. The strain of Paragraph 7, wherein the mutation is in a polypeptide comprising a sequence having at least 25% identity to SEQ ID NO: 36 as determined through use of FASTA version 3.0t78 with the default parameters.

13. The strain of Paragraph 7 further comprising a mutation in a gene that inhibits the production of the autoinducer.

14. The strain of Paragraph 13, wherein the mutation is in a luxS gene.

15. The strain of Paragraph 14, wherein the mutation is in a nucleic acid comprising a sequence selected from the group consisting of SEQ ID NOs: 1–9.

16. The strain of Paragraph 13, wherein the mutation is in a nucleic acid comprising a sequence having at least 30% identity as determined through use of BLASTN version 2.0 with the default parameters to a sequence selected from the group consisting of SEQ ID NOs: 1–9.

17. The strain of Paragraph 13, further comprising a mutation that inhibits the detection of a second autoinducer that is an acylho-moserine lactone.

18. The method of Paragraph 17, wherein the second autoinducer is an acyl-homoserine lactone.

19. The method of Paragraph 17, wherein the second autoinducer is N-(3-hydroxyacyl)-L-homoserine lactone and the acyl group comprises 4–12 carbon atoms.

20. The method of Paragraph 19, wherein the acyl group comprises four carbon atoms.

21. The strain of Paragraph 17, wherein the mutation is in the luxN gene.

22. The strain of Paragraph 1, wherein the autoinducer is the autoinducer-2 produced by *Vibrio harveyi*.

23. The strain of Paragraph 1, wherein the autoinducer is a pentanedione.

24. The strain of Paragraph 20, wherein the pentanedione is 4,5-dihydroxy-2,3-pentanedione.

25. The strain of Paragraph 1, wherein the strain belongs to a species selected from the group consisting of *S. typhimurium* and *E. coli*.

26. The strain of Paragraph 1, wherein the strain belongs to a species selected from the group consisting of *Haemophilus influenzae, Helicobacter pylori, Bacillus subtilis, Borrelia burgdorferi* and *Vibrio cholerae*.

27. The strain of Paragraph 1, wherein the strain is a strain of *Vibrio harveyi*.

28. A method for identifying a compound that modulates the response to a first autoinducer that is not an acyl-homoserine lactone and that can interact with the *Vibrio harveyi* LuxQ protein, thereby inducing expression of a *Vibrio harveyi* operon comprising the luxCDABE genes, comprising:

obtaining a cell having increased expression of a transporter that transports the autoinducer into the cell, wherein the cell produces a detectable signal in response to the first autoinducer;

measuring the response of the cell to the first autoinducer in the presence and absence of a test compound; and comparing the responses to determine whether the test compound modulates the response to the first autoinducer.

29. The method of Paragraph 28, wherein the cell has been genetically engineered to increase expression of the transporter.

30. The method of Paragraph 28, wherein the transporter comprises at least one polypeptide comprising a sequence selected from the group consisting of SEQ ID NOs.: 37–40 and a sequence having at least 25% identity as determined through use of FASTA version 3.0t78 with the default parameters to one of SEQ ID NOs.: 37–40.

31. The method of Paragraph 28, wherein the transporter comprises a complex comprising each of the amino acid sequences of SEQ ID NOs. 37–40 or amino acid sequences having at least 25% identity as determined through use of FASTA version 3.0t78 with the default parameters to each of the sequences of SEQ ID NOs.: 37–40.

32. The method of Paragraph 29, wherein the cell comprises at least one vector from which one or more polypeptides included in the transporter are expressed.

33. The method of Paragraph 29, wherein the cell comprises a mutation that increases expression of the transporter.

34. The method of Paragraph 33, wherein the mutation is in a gene encoding a repressor that reduces expression of the transporter.

35. The method of Paragraph 34 wherein the mutation is in a gene comprising the sequence of SEQ ID NO: 28.

36. The method of Paragraph 34, wherein the mutation is in a gene comprising a sequence having at least 30% identity to SEQ ID NO: 28 as determined through use of BLASTN version 2.0 with the default parameters.

37. The method of Paragraph 34, wherein the mutation is in a gene encoding a polypeptide comprising the sequence of SEQ ID NO: 36

38. The method of Paragraph 34, wherein the mutation is in a nucleic acid comprising a sequence that hybridizes to a probe comprising at least 20 consecutive nucleotides of SEQ ID NO: 28 in 6×SSC at about 45° C. followed by one or more washes in 0.1×SSC/0.2% SDS at about 68° C.

39. The method of Paragraph 34, wherein the mutation is in a polypeptide comprising a sequence having at least 25% identity to SEQ ID NO: 36 as determined through use of FASTA version 3.0t78 with the default parameters.

40. The method of Paragraph 34 wherein the cell further comprises a mutation in a gene that inhibits the production of the autoinducer.

41. The method of Paragraph 40, wherein the mutation that inhibits the production of the autoinducer is in a luxS gene.

42. The method of Paragraph 41, wherein the mutation that inhibits the production of the autoinducer is in a nucleic acid comprising a sequence selected from the group consisting of SEQ ID NOs: 1–9.

43. The method of Paragraph 40, wherein the mutation is in a nucleic acid comprising a sequence having at least 30% nucleotide identity as determined through use of BLASTN version 2.0 with the default parameters to a sequence selected from the group consisting of SEQ ID NOs: 1–9.

44. The method of Paragraph 40, wherein the cell further comprises a mutation that inhibits the detection of a second autoinducer that is an acylhomoserine lactone.

45. The method of Paragraph 44, wherein the second autoinducer is N-(3-hydroxyacyl)-L-homoserine lactone and the acyl group comprises 4–12 carbon atoms.

46. The method of Paragraph 45, wherein the acyl group comprises four carbon atoms.

47. The method of Paragraph 44, wherein the mutation that inhibits the detection of the second autoinducer is in the luxN gene.

48. The method of Paragraph 28, wherein the autoinducer is the autoinducer-2 produced by *Vibrio harveyi*.

49. The method of Paragraph 28, wherein the autoinducer is a pentanedione.

50. The method of Paragraph 49, wherein the pentanedione is 4,5-dihydroxy-2,3-pentanedione.

51. The method of Paragraph 28, wherein the cell belongs to a species selected from the group consisting of *S. typhimurium* and *E. coli*.

52. The method of Paragraph 28, wherein the cell belongs to a species selected from the group consisting of *Haemophilus influenzae, Helicobacter pylori, Bacillus subtilis, Borrelia burgdorferi* and *Vibrio cholerae*.

53. The method of Paragraph 1, wherein the cell is a *Vibrio harveyi* cell.

54. A method for screening a candidate compound for the ability to bind to a transporter that transports an autoinducer into a cell, wherein the autoinducer is not an acyl-homoserine lactone and can interact with the *Vibrio harveyi* LuxQ protein thereby inducing expression of a *Vibrio harveyi* operon comprising the luxCDABE genes, comprising:

contacting the transporter with the candidate compound; and determining whether the compound specifically binds to the transporter.

55. The method of Paragraph 54, wherein the compound comprises a detectable label.

56. The method of Paragraph 54, wherein the transporter comprises at least one polypeptide comprising an amino acid sequence selected from the group consisting of SEQ ID NOs.: 37–40 and a sequence having at least 25% amino acid identity as determined through use of FASTA version 3.0t78 with the default parameters to one of SEQ ID NOs.: 37–40.

57. The method of Paragraph 54, wherein the transporter comprises a complex comprising each of the amino acid sequences of SEQ ID NOs. 37–40 or amino acid sequences having at least 25% amino acid identity as determined through use of FASTA version 3.0t78 with the default parameters to each of the amino acid sequences of SEQ ID NOs.: 37–40.

58. A method of screening a candidate compound for the ability to modulate the binding of an autoinducer to a transporter, wherein the autoinducer is not an acyl-homoserine lactone and can interact with the *Vibrio harveyi* LuxQ protein thereby inducing expression of a *Vibrio harveyi* operon comprising the luxCDABE genes, comprising:

comparing the binding of the autoinducer to the transporter in the presence and absence of the candidate compound; and determining whether the the extent of binding of the autoinducer to the transporter in the presence of the compound increases or decreases relative to the extent of binding in the absence of the compound.

59. A method of screening a candidate compound for the ability to bind a polypeptide comprising:

contacting a polypeptide comprising a sequence selected from the group consisting of SEQ ID NO. 37–40 and a sequence having at least 25% identity as determined through use of FASTA version 3.0t78 with the default parameters to one of the sequences of SEQ ID NOs.: 37–40 with the compound; and determining whether the compound specifically binds to the polypeptide.

60. An isolated bacterial strain comprising a mutation that inhibits the transport of an autoinducer that is not an acyl-homoserine lactone and that can interact with the *Vibrio harveyi* LuxQ protein thereby inducing expression of a *Vibrio harveyi* operon comprising the luxCDABE genes.

61. The bacterial strain of Paragraph 60, wherein the mutation is in a gene selected from the group consisting of the lsrA, lsrB, lsrC, and lsrD genes.

62. The bacterial strain of Paragraph 61, wherein the strain is a *Salmonella typhimurium* strain.

63. The bacterial strain of Paragraph 62, wherein the mutation is in a sequence selected from the group consisting of SEQ ID NOs.: 29–32.

64. The bacterial strain of Paragraph 63, wherein the mutation is in a gene encoding a polypeptide comprising a sequence selected from the group consisting of SEQ ID NOs.: 37–40.

65. The bacterial strain of Paragraph 63, wherein the mutation is in a nucleic acid comprising a sequence selected from the group consisting of a sequence having at least 30% nucleotide identity to one of SEQ ID NOs.: 29–32 as determined through use of BLASTN version 2.0 with the default parameters.

66. A bacterial strain that overexpresses or underexpresses a polypeptide comprising a sequence selected from the group consisting of SEQ ID NOs. 36–43 and a sequence having at least 25% identity to one of SEQ ID NOs: 36–43 relative to a wildtype strain.

67. A bacterial strain that overexpresses or underexpresses a polypeptide comprising a sequence selected from the group consisting of SEQ ID NOs. 36–43 and a sequence having at least 25% identity to one of SEQ ID NOs: 36–43 relative to a wildtype strain.

68. An isolated or purified nucleic acid comprising a sequence selected from the group consisting of SEQ ID NOs.: 28–35 and a fragment comprising at least 20 consecutive nucleotides of one of of SEQ ID NOs.: 28–35.

69. An isolated or purified nucleic acid comprising a fragment of one of SEQ ID NOs.: 28–35 that encodes a polypeptide that can facilitate the transport of an autoinducer into a cell, wherein the autoinducer is not an acyl-homoserine lactone and can interact with the *Vibrio harveyi* LuxQ protein thereby inducing expression of a *Vibrio harveyi* operon comprising the luxCDABE genes.

70. A recombinant vector comprising a sequence selected from the group consisting of SEQ ID NOs: 28–35 operably linked to a heterologous promoter.

71. An isolated or purified protein comprising a sequence selected from the group consisting of SEQ ID NOs.: 36–43 and a fragment comprising at least 10 consecutive amino acids of one of of SEQ ID NOs. 36–43.

72. An isolated or purified polypeptide comprising a fragment of one of SEQ ID NOs.: 36–43 that encodes a polypeptide that can facilitate the transport of an autoinducer into a cell, wherein the autoinducer is not an acyl-homoserine lactone and can interact with the *Vibrio harveyi* LuxQ protein thereby inducing expression of a *Vibrio harveyi* operon comprising the luxCDABE genes.

73. An antibody that binds to a polypeptide selected from the group consisting of SEQ ID NOs.: 36–43.

DETAILED DESCRIPTION OF THE PREFERRED EMBODIMENT

The present invention relates to the identification of genes and polypeptides whose expression level is regulated by the autoinducer AI-2. AI-2 has been described in U.S. patent application Ser. Nos. 09/853,832, entitled Compounds and Methods for Regulating Bacterial Growth and Pathogenesis, filed May 10, 2001, U.S. Provisional Patent Application Ser. No. 60/203,000 entitled Compounds and Methods for Regulating Bacterial Growth and Pathogenesis filed May 10, 2000, U.S. Provisional Patent Application Ser. No. 60/254, 398, entitled Composition and Methods for Regulating Bacterial Growth and Pathogenesis, filed Dec. 7, 2000 and U.S. patent application Ser. No. 09/453,976, entitled Compositions and Methods for Regulating Bacterial Pathogenesis, filed Dec. 2, 1999, the disclosures of which are incorporated herein by reference in their entireties. As discussed briefly above a variety of bacterial species, some of them mammalian pathogens, secrete an organic signaling compound that stimulates the expression of luminescence in *V. harveyi*. The compound secreted by these organisms mimics *V. harveyi* AI-2 in its physical and functional features. The production in bacteria of this novel signaling compound is regulated by changes in environmental, conditions associated with a shift from a free-living existence to a colonizing or pathogenic existence in a host organism. Thus, in addition to stimulating luminescence genes (specifically luxCDABE) through its interaction with the luxQ protein in *V. harveyi*, the signaling compound is expected to stimulate a variety of pathogenesis related genes in the bacterial species that produce it.

The signaling factor is produced by a variety of bacteria, including but not limited to: *Vibrio harveyi, Vibrio cholerae, Vibrio parahaemolyticus, Vibrio alginolyticus, Pseudomonas phosphoreum, Yersinia enterocolitica, Escherichia coli, Salmonella typhimurium, Haemophilus influenzae, Helicobacter pylori, Bacillus subtilis, Borrelia burgfdorferi, Neisseria meningitidis, Neisseria gonorrhoeae, Yersinia pestis, Campylobacter jejuni, Deinococcus radiodurans, Mycobacterium tuberculosis, Enterococcus faecalis, Streptococcus pneumoniae, Streptococcus pyogenes* and *Staphylococcus aureus*.

Figure 17:
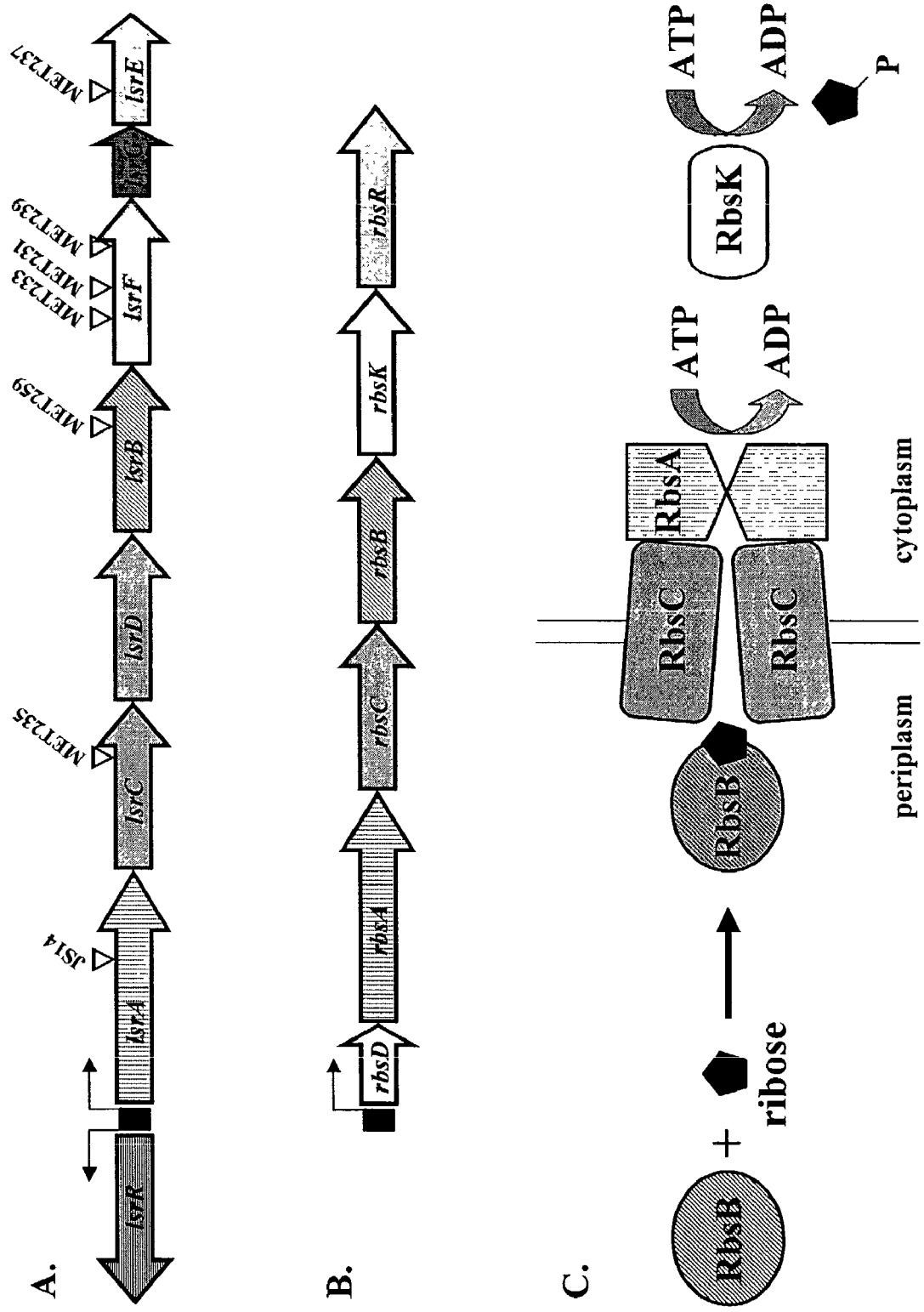
FIG. 17 shows the lsr and rbs Operons of *S. typhimurium*. Panel A: The lsr operon of *S. typhimurium* contains genes homologous to the transport component of the rbs operon (Panel B). In Panel A, triangles denote the sites of the MudJ insertions, with strain names above. A gene called lsrR is transcribed divergently from the lsr operon and encodes a protein (LsrR) required for AI-2 regulation of the lsr operon (see text). Panel B: The rbsDACBKR operon of *E. coli* and *S. typhimurium* encodes proteins required for the high affinity transport and phosphorylation of ribose. rbsD encodes a protein of unknown function. The ABC transport apparatus is encoded by rbsACB. rbsK encodes the cytoplasmic ribokinase, which phosphorylates ribose. rbsR encodes a repressor protein that regulates transcription of the rbs operon. In both panels, black boxes represent promoters, and thin arrows indicate the direction of transcription. Panel C: A schematic of the ribose transport system is shown. Similar shading patterns indicate homologous genes in panels A and B, and protein functions in panel C.
Figure 19:
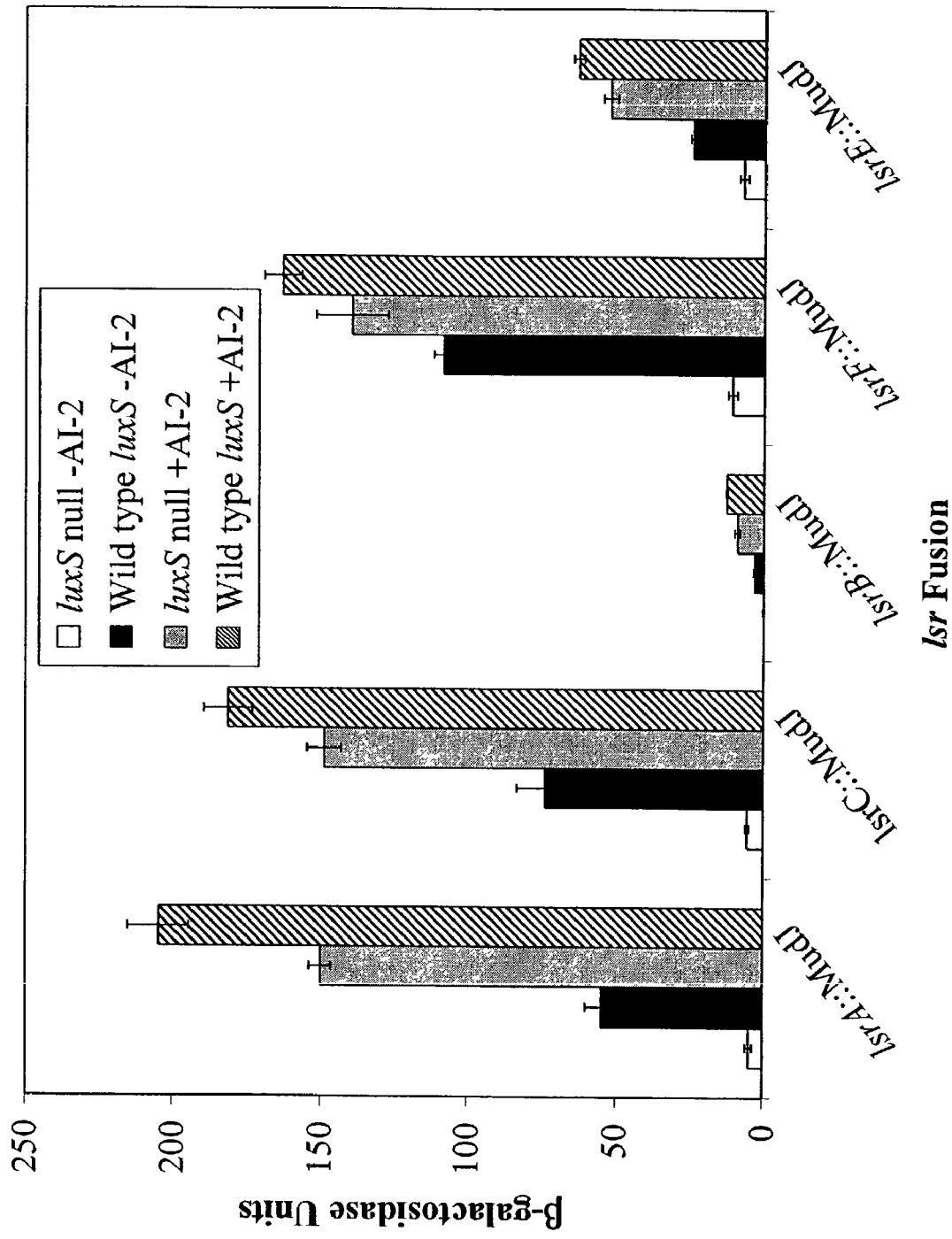
FIG. 19 shows how AI-2 regulates lsr operon expression. The β-galactosidase activity of strains carrying MudJ fusions in five lsr genes was assayed in luxS::T-POP (denoted luxS null) and wild type luxS backgrounds. Cultures were grown in LB containing either a control reaction mixture (denoted -AI-2) or in vitro synthesized AI-2 (denoted +AI-2). In vitro AI-2 was prepared by incubating S-adenosylhomocysteine and the purified Pfs and LuxS proteins as described by Schauder et al. (in press). The control mixture (−AI-2) was prepared by an identical procedure except that the reaction was carried out the absence of LuxS protein. (D,L)-homocysteine was added to this control preparation following the reaction to compensate for the homocysteine produced in the reaction containing LuxS. AI-2 was used at an estimated concentration of 70 μM in this experiment.
Figure 20:
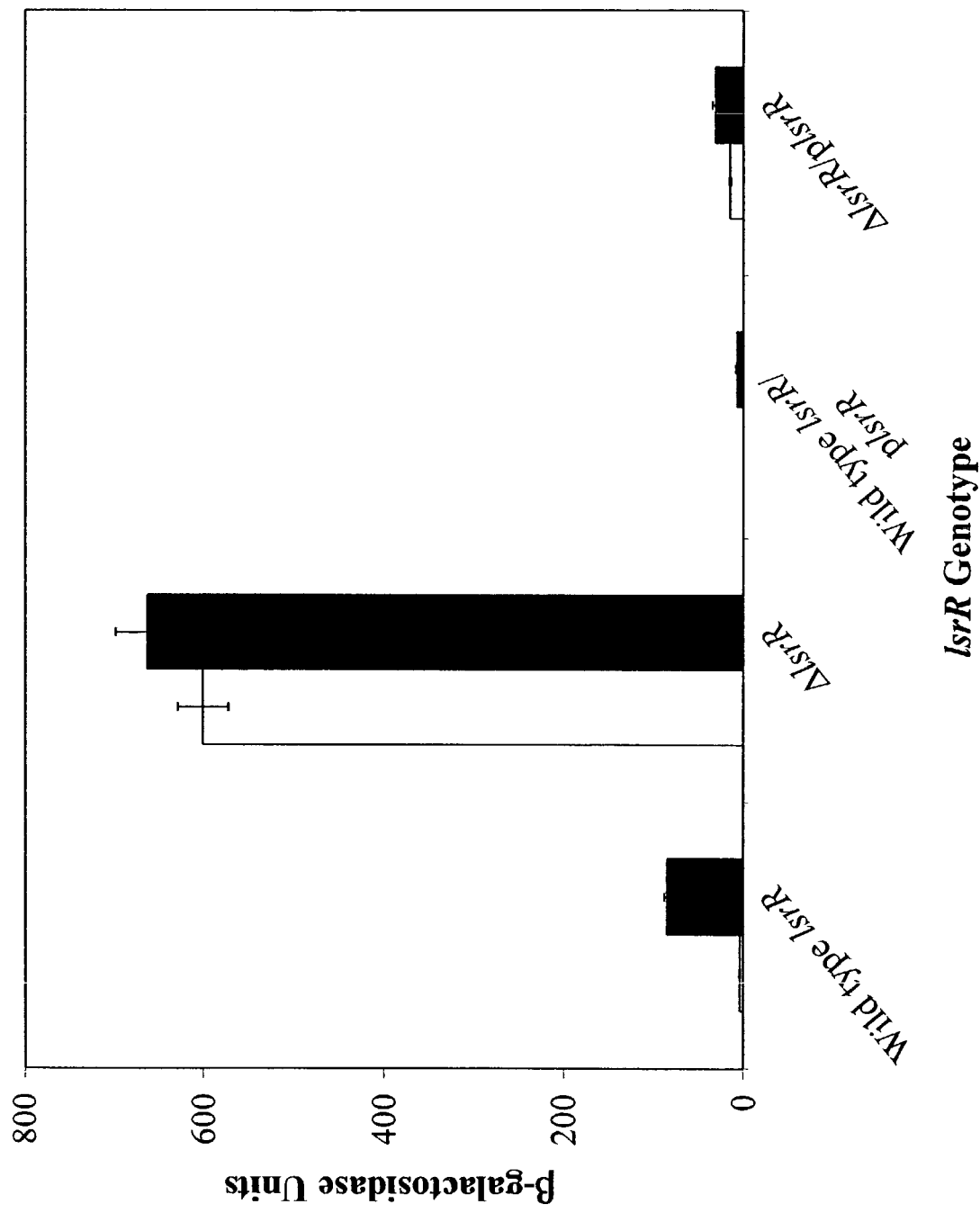
FIG. 20 shows that AI-2 control of lsr operon expression requires the LsrR protein. β-galactosidase activity was measured from the lsrC::MudJ reporter in wild type lsrR and ΔlsrR *S. typhimurium* strains. Additionally, the β-galactosidase activity was measured in these same strains following the introduction of the vector pMET1035 that carries the wild type lsrR gene (denoted plsrR). The white bars show the activities in a luxS null *S. typhimurium* strain background and the black bars show the activities in a wild type luxS *S. typhimurium* strain background.
Figure 22:
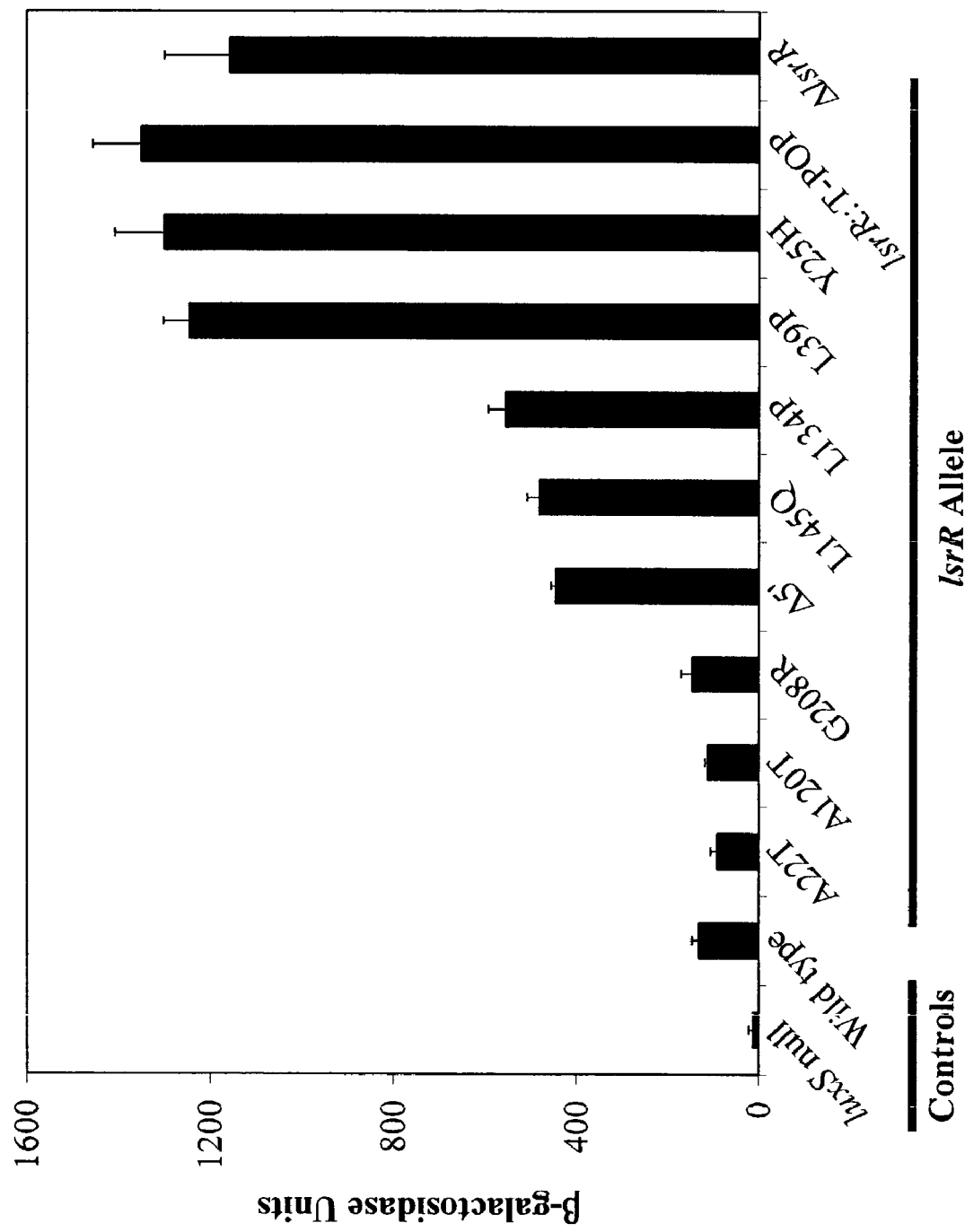
FIG. 22 shows the corresponding β-galactosidase activity for the lsrC::MudJ reporter in each of the eight suppressor strains and the activity for one of the lsrR::T-POP suppressors we obtained. In every case, the chromosomal copy of the luxS gene has been inactivated by insertion. As a reference, the β-galactosidase activity from the lsrC::MudJ reporter is also shown for *S. typhimurium* strains containing the wild type lsrR gene (controls) and an in-frame deletion of lsrR (denoted ΔlsrR).
Figure 23:
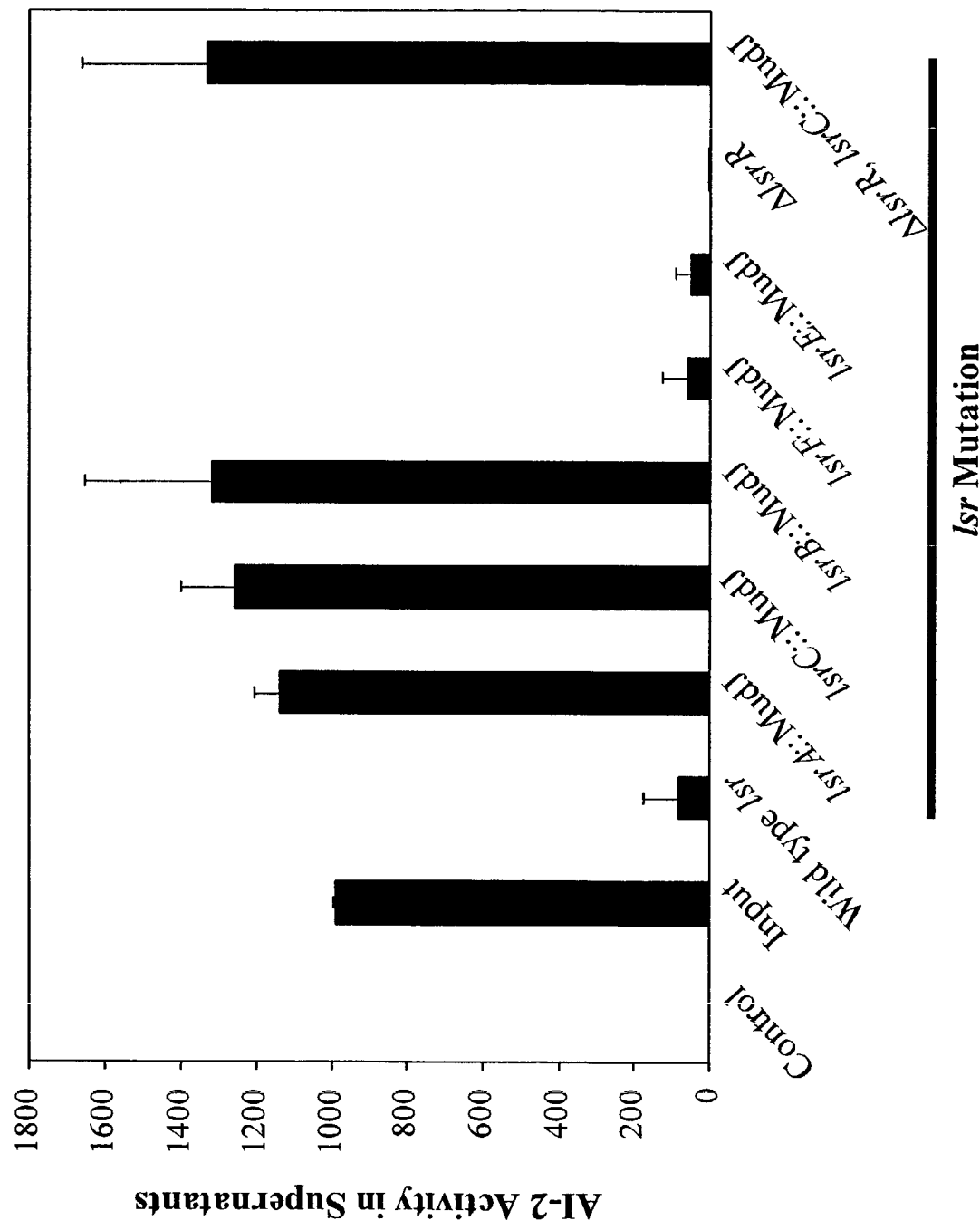
FIG. 23 shows that removal of AI-2 from *S. typhimurium* culture fluids requires the Lsr ABC transporter. The figure shows the quantity of AI-2 remaining in cell-free culture fluids of *S. typhimurium* strains containing various mutations in lsr genes. AI-2 activity in the culture fluids was measured through use of the *V. harveyi* BB170 AI-2 bioassay. All strains tested contained a null mutation in luxS, so the only AI-2 present was that that was added exogenously. Various *S. typhimurium* strains were grown for 4 h. In vitro prepared AI-2 was included in the cultures during the final hour of growth. The control bar represents the AI-2 activity for the culture fluid of the *S. typhimurum* luxS null parent strain SS007 (luxS::T-POP) when no AI-2 was added. The input bar represents the amount of AI-2 activity added to each culture. The rest of the bars show the AI-2 activity remaining in the culture fluids of the wild type lsr strain and the various lsr mutants following the 1 h incubation period.
Figure 24:
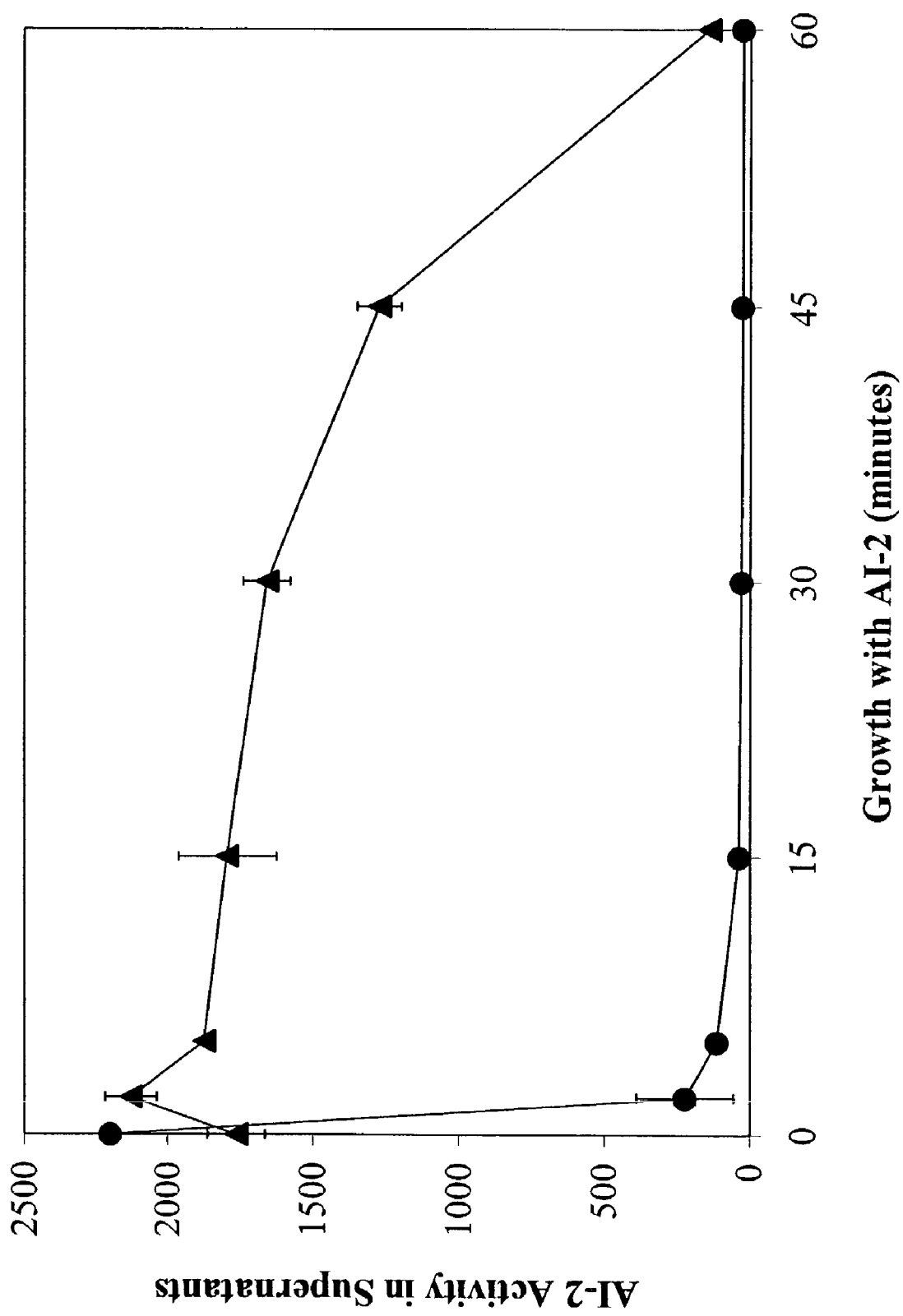
FIG. 24 Time courses of elimination of AI-2 from the culture fluids are shown for the wild type lsrR strain SS007 (luxS::T-POP, Triangles) and the ΔlsrR strain MET342 (ΔlsrR, luxS::T-POP, Circles). These cultures were grown for a total of 4 h. During the final hour of growth, AI-2 was included in the cultures for the times specified on the X-axis.

In a genetic screen for functions regulated by AI-2 in *S. typhimurium*, we identified an operon predicted to encode an ABC transporter with similarity to the ribose transporter of *E. coli* and *S. typhimurium* (FIG. 17). This operon (the lsr operon, SEQ ID NO: 44) is induced in the presence of luxS and AI-2 (FIG. 19), and AI-2 regulation of lsr operon expression requires the LsrR DNA binding regulatory protein (FIG. 20 and FIGS. 22 and 23). The function of the Lsr transporter is to import AI-2 from the external environment because strains possessing mutations in the Lsr transporter do not remove AI-2 from the culture medium, whereas AI-2 disappears from culture fluids of *S. typhimurium* strains possessing a wild type Lsr transporter. Additionally, strains derepressed for lsr expression by inactivation of lsrR remove AI-2 more rapidly than wild type (FIG. 24). In earlier work we showed that accumulation of AI-2 by *S. typhimurium* is maximal in late exponential phase, and all the AI-2 activity disappears from the medium by the time stationary phase is reached (Surette and Bassler, 1998). Thus, the Lsr transporter is involved in AI-2 removal.

Figure 25:
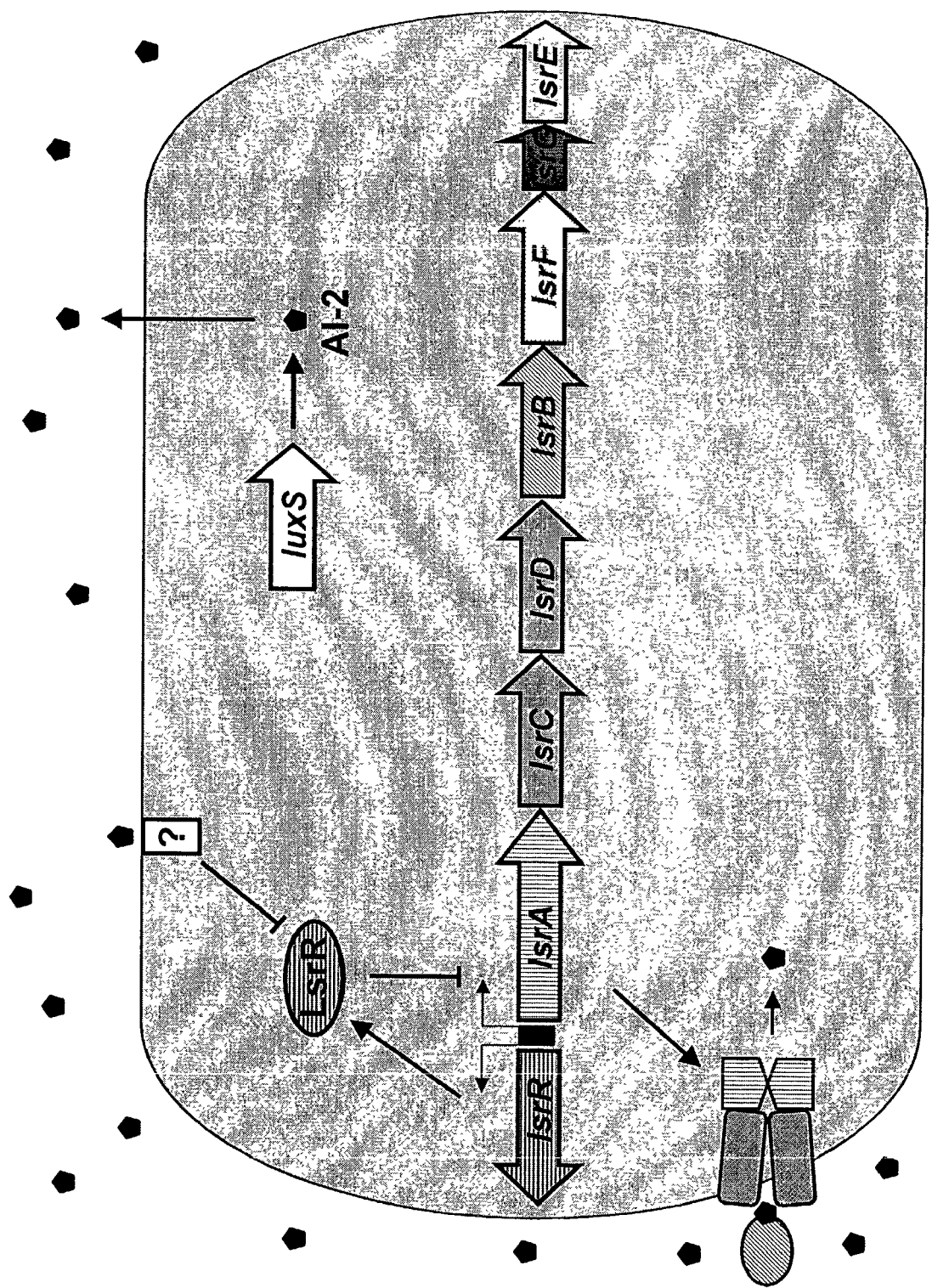
FIG. 25 shows a model for regulation and function of the Lsr ABC transporter in *S. typhimurium*. In the absence of AI-2, the LsrR DNA binding protein represses transcription of the lsr operon. LuxS synthesizes AI-2 (black pentagons), and AI-2 is released from the cell by an unknown mechanism. External AI-2 signals to the LsrR protein. This step inactivates the LsrR repressor function, which promotes transcription of the lsr operon. The mechanism of AI-2 signalling to LsrR is not known, but we propose that a sensor exists that couples AI-2 detection to LsrR activity. The white box containing the question mark represents the putative sensor. Transcription of the lsr operon results in the production of the Lsr ABC transporter complex that functions to import AI-2 into *S. typhimurium*. In the figure, the LsrACBD components are shown as the complex in the bacterial membrane. We hypothesize that AI-2 interacts with the periplasmic LsrB protein (represented by the stippled oval), and that LsrB-AI-2 binding facilitates interaction with the channel and ATPase components of the Lsr complex for transport. Note that the ABC transporter is predicted to reside in the inner-membrane with LsrB in the periplasm (gray and striped boxes). In the figure we have not drawn the outer-membrane of the bacterial cell.

FIG. 25 shows a model for the function of the Lsr transporter and its regulation by AI-2 and LsrR. LuxS synthesizes AI-2 in the cytoplasm. AI-2 is released to the external environment by an unknown mechanism. Extracellular AI-2 signals to the LsrR protein, again, by an unknown mechanism. In FIG. 25 we suggest that a sensor exists that is responsible for detection of extracellular AI-2 and signal transduction to LsrR. Other possibilities exist, and are discussed herein. In the absence of AI-2, LsrR acts to repress transcription of the lsr operon, most likely by binding at the lsr operon promoter analogous to RbsR binding at the rbs promoter (Mauzy and Hermodson, 1992). AI-2 signalling to LsrR alleviates LsrR repression of the lsr operon, resulting in transcription of the genes encoding the Lsr ABC transport apparatus. The Lsr transporter, in turn, imports AI-2 from the extracellular environment into the cells. We do not know what becomes of the AI-2 following import.

Two main types of ABC transporters exist in bacteria. One type of ABC transporters consists of binding protein-dependent transporters that function to import small molecules into the cell (Boos and Lucht, 1996; Holland and Blight, 1999; Nikaido and Hall, 1998). The Lsr transporter has the highest homology to this class of ABC transporters, whose members include the RbsACB ribose transporter, the MglBAC galactose transporter, and the HisJQMP histidine transporter (Boos and Lucht, 1996). The second class of ABC transporters functions to export compounds out of the cell. These transporters do not require a periplasmic binding protein, and their ligands vary greatly in size and composition (Boos and Lucht, 1996). The LmrA multidrug resistance transporter, the HlyB hemolysin transporter of *E. coli*, and the ComAB and SapTE oligopeptide autoinducer transporters of *Streptococcus pneumoniae* and *Lactobacillus sake* are examples of this second type of ABC exporter (Holland and Blight, 1999; Kleerebezem et al., 1997). Additionally, ABC transporters are employed for the transport of compounds in higher organisms, including humans. Deficiency in the function of ABC transporters has been implicated in many human diseases, the most well studied example being the CFTR chloride ion transporter that is nonfunctional in cystic fibrosis patients (Holland and Blight, 1999).

The homology between the Lsr complex and the family of ABC transporters suggests a role for the Lsr complex in the transport of a ligand. Furthermore, because AI-2 is a ribose derivative, because the Lsr transporter most closely resembles the ribose transporter, and because our evidence shows that the lsr genes are required for removal of AI-2 from the external environment, we demonstrate that AI-2 is the ligand for the Lsr transporter. These findings, coupled with the facts that the Lsr transporter most closely resembles the importer type of ABC transporter and that the Lsr complex is not required for export of AI-2, lead us to the conclusion that the Lsr complex transports AI-2 into the cell. However, it remains possible that the Lsr complex is required for the modification or degradation of AI-2 on the cell surface.

We have shown previously that a secreted enzyme is not responsible for elimination of AI-2 from the medium because AI-2 is stable for long periods of time in *S. typhimurium* cell-free spent culture fluids (Surette and Bassler, 1999). We have also observed that AI-2 does not disappear from the supernatants of dead cells (not shown). These results together indicate that elimination of AI-2 occurs either at the surface of living cells, or more likely, based on the findings in this report, disappearance of AI-2 is mediated by its transport into the cell via the Lsr complex. However, at least one other Lsr independent mechanism for AI-2 elimination must exist in *S. typhimurium* because in both wild type and lsrA, lsrB and lsrC mutant strains, although AI-2 activity does not decrease during the first hour of incubation, the AI-2 activity decreases in culture fluids after longer periods of incubation (20 h) (data not shown).

The mechanism of AI-2 signalling to LsrR to derepress transcription of the lsr operon can be from the inside or the outside of the cell. If AI-2 acts from the inside, then AI-2 must enter the cells by some mechanism that is not dependent on the Lsr transporter. We conclude this because *S. typhimurium* strains harboring mutations in the lsr operon, while deficient in the process of internalization of AI-2, remain capable of AI-2-dependent derepression of transcription of the lsr operon. Therefore, if AI-2 is required to enter the cell to signal to LsrR, it does not require the Lsr apparatus, and furthermore, only a minor amount of AI-2 internalization can be required for the signalling process. We say this because we cannot detect any disappearance of AI-2 from culture fluids prepared from strains containing mutations in the lsr transport genes. The alternative possibility is that AI-2 signals to LsrR from outside of the cell. Conceivably, an AI-2 sensor exists that detects external AI-2 and initiates a signalling cascade that culminates in LsrR-mediated derepression of the transcription of the lsr operon. We favor an external mechanism for AI-2 signal relay to LsrR because it is more consistent with our results. Specifically, regulation of transcription of the lsr operon can occur in the absence of a detectable level of internalization of AI-2. FIG. 25 includes a putative AI-2 sensor. Because LsrR contains a predicted helix-turn-helix DNA binding domain, and because in bacteria, genes specifying regulatory proteins are frequently located adjacent to the promoter at which they bind, LsrR may repress transcription of the lsr operon by binding at the lsr promoter.

Evidence that the ligand for the Lsr complex is AI-2 includes findings that the Lsr transporter resembles the ribose transporter, because AI-2 is derived from, and has structural similarity to ribose, and because of the transport data shown in FIG. 24. Consistent with this idea, the LuxP protein in *V. harveyi* is the primary receptor for AI-2. The LuxP-AI-2 complex initiates the quorum sensing signalling cascade (Bassler et al., 1994a). LuxP is a periplasmic protein homologous to the ribose binding protein RbsB, and to LsrB, the ribose binding protein homologue we identified in the present work. We suggest that LsrB is the AI-2 binding protein in *S. typhimurium*. In this case, instead of initiating a signalling cascade, the function of LsrB is to bring AI-2 in contact with the membrane bound components of the Lsr apparatus for transport into the cell.

We do not yet fully understand the benefit that *S. typhimurium* derives from synthesizing and releasing AI-2 only to internalize it at later times. One possibility is that AI-2 is initially used as a signal, then, at subsequent times, when AI-2 is no longer required for signal transduction, *S. typhimurium* internalizes it for use as a carbon source. To test this idea, we attempted to grow wild type *S. typhimurium* on in vitro prepared AI-2 as a sole carbon source. We found that *S. typhimurium* could not grow on AI-2, suggesting that *S. typhimurium* does not use AI-2 as a carbon source (not shown). Therefore, growth on AI-2 cannot account for its disappearance from the medium. A second possibility is that the removal of AI-2 activity is required for its modification to another signal. For example, the LsrE epimerase, or another enzyme, could convert AI-2 into an internal signal. Finally, AI-2 could be internalized for degradation. In this case, elimination of AI-2 could serve to terminate the signalling process. Signal production coupled to subsequent elimination could allow *S. typhimurium* the flexibility to transition between several modes of existence. For example, as AI-2 is associated with the presence of many species of bacteria, high levels of AI-2 could be indicative of the transition from outside a host to the intestinal environment, whereas low levels of AI-2 could signal *S. typhimurium* that it has exited the intestinal tract for the next location in the infection (i.e., the macrophage) where *S. typhimurium* is not in association with high numbers of commensal bacteria. Many possibilities exist, the point being that accumulation and disappearance of AI-2 could each initiate a different series of behavioral changes in *S. typhimurium*.

The genetic screen that led to the identification of the lsr operon was designed to reveal the entire collection of genes regulated by AI-2. However, this experiment only yielded the lsr operon and metE. For reasons discussed above, we do not believe that metE is a genuine target of AI-2 regulation. It is possible that the sole target of AI-2 regulation in *S. typhimurium* is the lsr operon. Alternatively, we favor the idea that some bias in our screen exists that only allowed us to identify the lsr operon. It is possible that lsr is the only exclusive target of AI-2. Other AI-2 targets could exist, but their regulation may require AI-2 to act in conjunction with another signal(s). Under the conditions we perform our experiments, it is possible that we are not supplying this additional hypothetical signal. Alternatively, two *S. typhimurium* quorum sensing signals could exist, either of which is sufficient to regulate other target genes. Precedent for redundant signalling factors involving AI-2 exists. In the *V. harveyi* quorum sensing circuit in which AI-2 was originally discovered, two autoinducers (AI-1 and AI-2) operate in parallel to regulate the expression of bioluminescence. Inactivation of genes involved in either signalling system alone does not abolish density-dependent expression of luminescence in *V. harveyi* (Bassler et al., 1993; Bassler et al., 1994a; b). Moreover, nearly all LuxI/LuxR quorum sensing systems have now been shown to be controlled by multiple autoinducers, and in many cases, intricate hierarchies of regulation exist in these systems (de Kievit and Iglewski, 2000; Miller and Bassler, 2001). The architecture of the *S. typhimurium* quorum sensing circuit could resemble that of *V. harveyi* or other quorum sensing bacteria in that a complex and/or a redundant signalling circuit could govern the process. Finally, it is possible that additional targets of AI-2 are only regulated when *S. typhimurium* is grown in mixed-species consortium. We believe that AI-2 is a signal used by many species of bacteria for inter-species cell-cell communication. We assume that inter-species communication is a complex phenomenon that involves multiple sensory inputs. Therefore, AI-2 plus additional signals, cell-cell contact and/or some other stimulus provided by other species of bacteria could be required for *S. typhimurium* to react.

Discovery of LsrB, LsrR, LsrE epimerase, LsrC, lsrD channel components, and lsrA transporter ATPase suggests their use as drug targets for development of antibacterial agents. Each of these species can be used in screening for inhibitors of autoinducer-2 binding or response, and specifically to find compounds that inhibit binding of autoinducer-2 to the species and/or block autoinducer-2 mediated responses, such as gene expression. Using methods well-known to those of ordinary skill in the art, one can screen one or more compound libraries against each or any of the above-mentioned targets to find which members of the library interact with the target in the desired fashion. Typically such interaction inhibits the physiological function of the target; for example, for an enzyme, such as lsrE epimerase, inhibits its catalysis of the reaction with which it is usually associated.

Methods of screening such libraries generally entail construction of an assay that measures binding to or inhibition of the target. For example, members of the library can be tagged with a fluorescent, radioactive, or other label, and their affinity for binding to the target can be assessed. Alternatively, the ability of library members to alter the catalytic activity of an enzymatic target can be measured. Such screening methods are widely used, and hence are familiar to those skilled in drug discovery. Examples of such screens are described in U.S. Pat. No. 5,684,711, U.S. Pat. No. 6,046,002, U.S. Pat. No. 5,998,159 and U.S. Pat. No. 5,824,485, U.S. Pat. No. 6,455,263, U.S. Pat. No. 6,434,490, U.S. Pat. No. 6,245,937, U.S. Pat. No. 6,207,861, and U.S. Pat. No. 6,054,047, U.S. Pat. No. 6,001,579, U.S. Pat. No. 5,721,099 the disclosures of which are incorporated herein by reference in their entireties. Other methods are disclosed in PCT publications No. WO9935494, WO9819162, WO9954728, the disclosures of which are incorporated herein by reference in their entireties, each of which is hereby incorporated by reference in its entirety.

Thus, in the present invention, strains carrying transposon insertions in genes whose expression was reduced in luxS null strains relative to wildtype strains (i.e. strains having insertions in genes that exhibited elevated expression levels in the presence of the signaling factor) were identified in a screen. Among the identified strains were strains carrying insertions in some of the genes encoding a transporter involved in transporting the signaling factor into the cell. The proteins that make up the transporter are encoded by the lsrA, lsrB, lsrC and lsrD genes that comprise SEQ ID NO. 29, SEQ ID NO: 32, SEQ ID NO: 30, and SEQ ID NO: 31 respectively and that encode the LsrA, LsrB, LsrC and LsrD proteins comprising SEQ ID NO 37, SEQ ID NO: 40, SEQ ID NO: 38, and SEQ ID NO: 39 respectively. In particular, strains carrying insertions in the lsrA, lsrB and lsrC genes were identified in the screen. Other strains identified in the screen were found to carry insertions in the lsrE and lsrF genes (SEQ ID NO: 35 and SEQ ID NO: 33 respectively, encoded the LsrE and LsrF proteins of SEQ ID NO: 43 and SEQ ID NO: 41 respectively). . The lsrA, lsrB, lsrC, lsrD, lsrE, lsrF, and lsrG genes lie in an operon that the LsrR repressor regulates (the lsrR gene comprises SEQ ID NO: 28 and the LsrR protein has SEQ ID NO: 36). The lsrE, lsrF, lsrG and lsrR genes comprise SEQ ID NO: 35, SEQ ID NO: 33, SEQ ID NO: 34 and SEQ ID NO: 28 respectively that encode proteins comprising SEQ ID NO: 43, SEQ ID NO:41, SEQ ID NO:42 and 36 respectively.

One aspect of the present invention is an isolated or purified nucleic acid comprising one of SEQ ID NOs: 28–35, a nucleic acid homologous to one of SEQ ID NOs: 28–35, fragments comprising at least 20, at least 30, at least 40, at least 50, at least 60, at least 70, at least 80, at least 100, at least 150, at least 200 or more than 200 consecutive nucleotides of one of SEQ ID NOs.: 28–35, fragments comprising at least 20, at least 30, at least 40, at least 50, at least 60, at least 70, at least 80, at least 100, at least 150, at least 200 or more than 200 consecutive nucleotides of a nucleic acid homologous to one of SEQ ID NOs.: 28–35, or a nucleic acid complementary to any of the foregoing. In a preferred embodiment, the isolated or purified nucleic acid comprising one of SEQ ID NOs.: 28–35, a nucleic acid homologous thereto, or a fragment thereof is inserted into a vector. In some embodiments, the vector is not included in a genomic library that contains a large number of vectors most of which contain a nucleic acid other than one of SEQ ID NOs.: 28–35, a nucleic acid homologous thereto, or a fragment thereof inserted therein. Thus, in a preferred embodiment, the nucleic acid of one of SEQ ID NOs.: 28–35, a nucleic acid homologous thereto, or a fragment thereof represents at least 90%, at least 80%, at least 70%, at least 60%, at least 50%, at least 40%, or at least 30%, of the nucleic acid inserts in the vector.

In a further preferred embodiment, the insert in the vector does not contain a substantial amount of genomic DNA that is naturally adjacent to the nucleic acid of one of SEQ ID NOs.: 28–35, a nucleic acid homologous thereto, or a fragment thereof or that is naturally adjacent to the operon in which the one of SEQ ID NOs.: 28–35, a nucleic acid homologous thereto, or fragment thereof lies. Preferably, in this embodiment, the insert in the vector encodes one or more of the polypeptides of SEQ ID NOs.: 36–43 but does not encode a polypeptide other than the foregoing.

The nucleic acid that is homologous to one of one of SEQ ID NOs.: 28–35 may have at least 97%, at least 95%, at least 90%, at least 85%, at least 80%, at least 70%, at least 60%, at least 50%, at least 40%, at least 30%, or at least 20% sequence identity to a sequence selected from the group consisting of SEQ ID NOS.: 28–35 or the sequence complementary thereto. Identity may be measured using BLASTN version 2.0 with the default parameters or tBLASTX with the default parameters. (Altschul, S. F. et al. Gapped BLAST and PSI-BLAST: A New Generation of Protein Database Search Programs, Nucleic Acid Res. 25: 3389–3402 (1997), the disclosure of which is incorporated herein by reference in its entirety) Alternatively a homologuous nucleic acid could be identified by membership of the gene of interest to a functional orthologue cluster. All other members of that orthologue cluster would be considered homologues. Such a library of functional orthologue clusters can be found at http://www.ncbi.nlm.nih.gov/COG. A gene can be classified into a cluster of orthologous groups or COG by using the COGNITOR program available at the above web site, or by direct BLASTP comparison of the gene of interest to the members of the COGs and analysis of these results as described by Tatusov, R. L., Galperin, M. Y., Natale, D. A. and Koonin, E. V. (2000) The COG database: a tool for genome-scale analysis of protein functions and evolution. Nucleic Acids Research v. 28 n. 1, pp33–36.

The homologous nucleic acid may also comprise sequences that encode polypeptides having at least 99%, 95%, at least 90%, at least 85%, at least 80%, at least 70%, at least 60%, at least 50%, at least 40% or at least 25% amino acid identity or similarity to a polypeptide comprising the sequence of one of SEQ ID NOs:36–43 or fragments comprising at least 5, 10, 15, 20, 25, 30, 35, 40, 50, 75, 100, or 150 consecutive amino acids thereof as determined using the FASTA version 3.0t78 algorithm with the default parameters. Alternatively, protein identity or similarity may be identified using BLASTP with the default parameters, BLASTX with the default parameters, TBLASTN with the default parameters, or tBLASTX with the default parameters. (Altschul, S. F. et al. Gapped BLAST and PSI-BLAST: A New Generation of Protein Database Search Programs, Nucleic Acid Res. 25: 3389–3402 (1997), the disclosure of which is incorporated herein by reference in its entirety).

The homologous nucleic acid may also be a nucleic acid that hybridizes under stringent conditions to a nucleic acid selected from the group consisting of the sequences complementary to one of SEQ ID NOS.: 28–35 and nucleic acids comprising sequences that hybridize under stringent conditions to a fragment comprising at least 10, 15, 20, 25, 30, 35, 40, 50, 75, 100, 150, 200, 300, 400, or 500 consecutive nucleotides of the sequences complementary to one of SEQ ID NOS.: 28–35. As used herein, "stringent conditions" means hybridization to filter-bound nucleic acid in 6×SSC at about 45° C. followed by one or more washes in 0.1×SSC/0.2% SDS at about 68° C. Other exemplary stringent conditions may refer, e.g., to washing in 6×SSC/0.05% sodium pyrophosphate at 37° C., 48° C., 55° C., and 60° C. as appropriate for the particular probe being used.

The homologous nucleic acid may also be a nucleic acid comprising a sequence that hybridizes under moderate conditions to a sequence selected from the group consisting of the sequences complementary to one of SEQ ID NOS 28–35 and nucleic acids comprising sequences that hybridize under moderate conditions to a fragment comprising at least 10, 15, 20, 25, 30, 35, 40, 50, 75, 100, 150, 200, 300, 400, or 500 consecutive nucleotides of the sequences complementary to one of SEQ ID NOS.: 28–35. As used herein, "moderate conditions" means hybridization to filter-bound DNA in 6× sodium chloride/sodium citrate (SSC) at about 45° C. followed by one or more washes in 0.2×SSC/0.1% SDS at about 42–65° C.

The homologous nucleic acids may also be a nucleic acid comprising a sequence that encodes a gene product whose activity may be complemented by one of the polypeptides of SEQ ID NOs. 36–43. In some embodiments, the homologous nucleic acid may encode a gene product whose activity is complemented by the gene product encoded by a nucleic acid comprising a sequence selected from the group consisting of SEQ ID NOS.: 28–35.

Nucleic acids homologous to the luxS nucleic acids of SEQ ID NOs.: 1–9 or the luxN nucleic acid of SEQ ID NO: 57 have the same relationships to the reference sequences of SEQ ID NOs.:1–9 and SEQ ID NO: 57 as the above-described nucleic acids homologous to SEQ ID NOs. 28–35 have to the reference sequences of SEQ ID NOs. 28–35.

Another embodiment of the present invention is an isolated or purified polypeptide comprising one of SE IT) NOs. 36–43, a polypeptide homologous thereto, or a fragment comprising at least 10, at least 20, at least 30, at least 40, at least 50, at least 60, at least 70, at least 80, at least 90, at least 100, or more than one consecutive amino acids thereof. The homologous polypeptide may have at least 99%, 95%, at least 90%, at least 85%, at least 80%, at least 70%, at least 60%, at least 50%, at least 40% or at least 25% amino acid identity or similarity to a polypeptide comprising one of SEQ ID NOs.: 36–43, or polypeptides having at least 99%, 95%, at least 90%, at least 85%, at least 80%, at least 70%, at least 60%, at least 50%, at least 40% or at least 25% amino acid identity or similarity to a to a fragment comprising at least 5, 10, 15, 20, 25, 30, 35, 40, 50, 75, 100, or 150 consecutive amino acids of a polypeptide comprising one of SEQ ID NOs.: 36–43. Identity or similarity may be determined using the FASTA version 3.0t78 algorithm with the default parameters. Alternatively, protein identity or similarity may be identified using BLASTP with the default parameters, BLASTX with the default parameters, or TBLASTN with the default parameters. (Altschul, S. F. et al. Gapped BLAST and PSI-BLAST: A New Generation of Protein Database Search Programs, Nucleic Acid Res. 25: 3389–3402 (1997), the disclosure of which is incorporated herein by reference in its entirety).

Polypeptides homologous to the luxS polypeptides of SEQ ID NOs.: 10–17 or the luxN polypeptide of SEQ ID NO: 58 have the same relationships to the reference sequences of SEQ ID NOs.:10–17 and SEQ ID NO: 58 as the above-described nucleic acids homologous to SEQ ID NOs. 36–43 have to the reference sequences of SEQ ID NOs. 36–43.

Another embodiment of the present invention is an isolated bacterial strain having an increased or decreased transcription level of a nucleic acid comprising one of SEQ ID NOs: 28–35 or an increased or decreased expression level of a polypeptide comprising one of SEQ ID NOs: 36–43 relative to a wild type strain. In a preferred aspect of this embodiment, the strain overexpresses or underexpresses a transporter that transports an autoinducer into the cell. Preferably, the autoinducer is not an acyl-homoserine lactone and is able to interact with the *Vibrio harveyi* luxQ protein, thereby inducing expression of a *Vibrio harveyi* operon comprising the luxCDABE genes. In a preferred embodiment the autoinducer is AI-2 from *Vibrio harveyi* or the corresponding autoinducer from another organism.

The strain may be obtained using genetic engineering techniques familiar to those skilled in the art. For example, strains that have an increased expression level of the transporter may be obtained by introducing a vector in which one or more genes encoding one or more polypeptides making up the transporter are under the control of a promoter that provides a level of transcription resulting in elevated expression of the transporter relative to a wild type cell into a cell. In some embodiments, an operon comprising the lsrA, lsrB, lsrC and lsrD genes or genes encoding proteins homologous thereto may be placed under the control of the promoter.

Strains that have a decreased expression level of the transporter relative to a wild type cell may also be obtained using genetic engineering. For example, the strains may be obtained by introducing a vector that directs the transcription of a ribozyme that cleaves a RNA encoding one or more genes encoding one or more polypeptides making up the transporter into a cell. Alternatively, strains that have a decreased expression level of the transporter relative to a wild type cell may be obtained by overexpressing the lsrR repressor protein or a protein homologous thereto in the cell. Such strains may be useful, for example, for evaluating whether AI-2 has any cellular effects in the absence of its transport into the cell.

In some embodiments, the strains that overexpress or underexpress the transporter relative to a wild type cell may possess a mutation that is responsible for the overexpression or underexpression of the transporter. For example, strains that overexpress the transporter may have a mutation in the lsrR gene that reduces the level of repression of the lsr operon by the lsrR protein or a mutation in the promoter from which the lsr operon is transcribed that increases the strength of the promoter. Such strains will have an increased transcription level of the mRNA encoding the LsrA, LsrB, lsrC and lsrD proteins that make up the transporter relative to a wild type cell. Strains that underexpress the transporter may have a mutation in the lsrR gene that increases the level of repression of the lsr operon by the lsrR protein or may have a mutation in the promoter from which the lsr operon is transcribes that reduces the level of transcription therefrom.

The mutation that causes overexpression or underexpression of the transporter may be generated via chemical mutagenesis techniques, transpon mediated mutagenesis techniques, including methods such as those described herein, site directed mutagenesis techniques, or other methods familiar to those skilled in the art. Alternatively, strains containing the mutation may be isolated from naturally occurring populations.

Another aspect of the present invention is a method for screening a test compound for the ability to modulate the response to an autoinducer. Preferably, the autoinducer is not an acyl-homoserine lactone and is able to interact with the *Vibrio harveyi* luxQ protein, thereby inducing expression of a *Vibrio harveyi* operon comprising the luxCDABE genes. In a preferred embodiment the autoinducer is AI-2. In some embodiments, the autoinducer may be AI-2 from *Vibrio harveyi* or the corresponding autoinducer from another organism.

Cells that produce a detectable response to the autoinducer and that have an increased expression level of an autoinducer that transports the autoinducer into the cell are contacted with the autoinducer. The responses of the cells to the autoinducer in the presence and absence of the test compound are measured and compared to identify compounds that modulate the response to the autoinducer.

The cell may be from any desired species that produces a detectable signal in response to the autoinducer or a cell that has been engineered to produce a detectable signal in response to the autoinducer. In some embodiments, the cell is a *Salmonella typhimurium* cell. For example, in some embodiments, the cell may be a *Salmonella typhimurium* cell carrying a mutation in the lsrR gene that causes the transporter to be expressed at a higher level than it is expressed in wild type cells. Alternatively, in some embodiments, the cell is from a species other than *Salmonella typhimurium* and carries a mutation in a gene encoding a polypeptide homologous to the lsrR polypeptide that causes the transporter to be expressed at a level higher than it is expressed in wild type cell.

In other embodiments, the cell may be a *Vibrio harveyi, E. coli, Haemophilus influenza, Helicobacter pylori, Bacillus subtilis, Borrelia burdorferi* or *Vibrio cholerae* cell. In some embodiments, the cell may carry a mutation in a gene encoding a protein homologous to the lsrR protein of *Salmonella typhimurium* that causes the expression level of the transporter to be higher than that of a wild type cell.

The cell may produce any detectable signal in response to the autoinducer. For example, in some embodiments, the cell produces bioluminescence in response to the autoinducer. Thus, in some embodiments, the cell is a *Vibrio harveyi* cell that produces bioluminescence in response to the autoinducer via induction of the luxCDABE operon.

Alternatively, in some embodiments, the detectable signal may be induction of mRNA transcription or protein expression in response to the autoinducer Induction of mRNA transcription may be measured with any of a variety of techniques familiar to those skilled in the art, including Northern analysis or detection of the transcript through use of nucleic acid amplification techniques such as PCR. Induction of protein expression may also be measured with any of a variety of techniques familiar to those skilled in the art including gel electrophoresis, Western blotting, or enzymatic activity assays. For example, in some embodiments, the cell may be genetically engineered to express a marker protein such as β-galactosidase, chloramphenicol acetyltransferase, β-glucuronidase, luciferase or green fluorescent protein in response to the autoinducer. Thus, in some embodiments, a nucleic acid encoding the marker protein may be operably linked to the promoter from the lsr operon or to the luxCDABE promoter and introduced into the cell such that expression of the marker protein is induced by the autoinducer. Alternatively, in other embodiments, an autoinducer responsive promoter other than the lsr or luxCDABE promoter may be operably linked to a nucleic acid encoding the marker protein. The the autoinducer responsive promoter may be from the same species as the cell to be used in the method or, alternatively, the the autoinducer responsive promoter may be from a heterologous organism.

In some embodiments, the cell may be a *Salmonella typhimurium* cell in which the expression of lacZ is regulated by AI-2, such as the cells carrying mudJ insertions described herein.

In some embodiments, in addition to expressing the transporter at a higher level than wild type cells, the cell that produces a detectable signal in response to the autoinducer has a genetic alteration that inhibits production of the autoinducer. In some embodiments, the genetic alteration is introduced into the cell through use of such genetic engineering techniques as site directed mutagenesis, insertional mutagenesis, or chemical mutagenesis followed by appropriate selection. Alternatively, cells containing the genetic alteration may be isolated or selected from a natural population.

In some embodiments, the genetic alteration that inhibits production of the autoinducer is in the *Vibrio harveyi* luxS gene, a gene having homology to the *Vibrio harveyi* luxS gene, or a gene encoding a polypeptide having homology to the *Vibrio harveyi* luxS polypeptide. For example, the genetic alteration may be in a gene having a sequence with at least 50%, at least 60%, or at least 80% sequence homology to the *Vibrio harveyi* luxs gene. In other embodiments the genetic alteration is in a gene encoding a polypeptide having at least 57% or at least 85% homology to the *Vibrio harveyi* luxS polypeptide. In still further embodiments, the genetic alteration is in a gene encoding a polypeptide having at least 32%, at least 45%, at least 74% or at least 80% sequence identity to the *Vibrio harveyi* luxS polypeptide.

In some embodiments, in addition to expressing the transporter at a level higher than wild type cells, the cells have a first genetic alteration that inhibits production of an autoinducer that is not an acyl-homoserine lactone and a second genetic alteration that inhibits detection or response to another autoinducer that is an acyl-homoserine lactone. For example, in some embodiments, the cell may be a *Salmonella typhimurium* cell having a mutation in the lsrR gene of SEQ ID NO: 28, the luxS gene comprising SEQ ID NO: 4 and a gene homologous to the *Vibrio harveyi* luxN gene. In other embodiments, the cells is a *Vibrio harveyi* cell with a mutation in a gene encoding a polypeptide homologous to the lsrR polypeptide of SEQ ID NO. 36, the first genetic alteration is in the luxS gene and the second genetic alteration is in the luxN gene. Thus, in some embodiments, the cell may be a *Vibrio harveyi* MM32 cell as described herein. However, the first and second genetic alterations may be in any gene that provides the phenotypes discussed above, including the genes discussed above, and the cell may be from any suitable species, including the species specifically enumerated herein.

The response of the cell to the autoinducer is measured in the presence and absence of a test compound. The test compound may be naturally-occuring, such as a compound from a natural products library, or may be of synthetic origin, such as a compound generated through use of combinatorial chemistry.

The response of the cell to the autoinducer in the presence and absence of the test compound is compared. In some embodiments, the test compound alters the response to the autoinducer at least two fold, at least 10 fold, at least 20 fold, at least 50 fold, at least 100 fold, at least 1000 fold, or even more than 1000 fold.

Another embodiment of the present invention is a method for screening a candidate compound for the ability to bind to a polypeptide comprising the sequence of one of SEQ ID NOs.: 36–43 or a fragment thereof, a polypeptide comprising a sequence homologous to the sequence of one of SEQ ID NOs.: 36–43 or a fragment thereof, a transporter that transports an autoinducer into a cell or to one of the polypeptides that make up the transporter. Preferably, the autoinducer is not an acyl-homoserine lactone and is able to interact with the *Vibrio harveyi* luxQ protein, thereby inducing expression of a *Vibrio harveyi* operon comprising the luxCDABE genes. In a preferred embodiment the autoinducer is AI-2 from *Vibrio harveyi* or the corresponding autoinducer from another organism.

The candidate compound may be from any source, including chemical libraries generated using combinatorial chemistry or natural product libraries. U.S. Pat. Nos. 5,463,564 and 5,574, 656, to Agrafiotis, et al., entitled "System and Method of Automatically Generating Chemical Compounds with Desired Properties," the disclosures of which are incorporated herein by reference in their entireties, disclose methods for generating libraries of compounds. Preferably, the candidate compound is labeled with a detectable label such as a radioactive or fluorescent moeity. Alternatively, the compound may be detectable using a labeled antibody.

The candidate compound is placed in contact with the polypeptide comprising the sequence of one of SEQ ID NOs.: 36–43 or a fragment thereof, a polypeptide comprising a sequence homologous to the sequence of one of SEQ ID NOs.: 36–43 or a fragment thereof, a transporter or a polypeptide that makes up the transporter under conditions that facilitate the binding of the compound to the transporter or polypeptide. A washing step is then performed under conditions that would remove nonspecifically bound compound. The amount of compound bound to the transporter or polypeptide is then measured to determine whether the compound specifically binds to the transporter or polypeptide.

The transporter or polypeptide may be fixed to a solid support such as a microtiter plate or bead or, alternatively, may be present in a membrane or vesicle. Methods for attaching the transporter or polypeptide to such solid supports and methods for preparing membranes or vesicles containing the transporter or polypeptide are familiar to those skilled in the art.

Methods for screening compounds for desired structural, binding, and functional properties are disclosed in U.S. Pat. No. 5,684,711, U.S. Pat. No. 6,046,002, U.S. Pat. No. 5,998,159 and U.S. Pat. No. 5,824,485, U.S. Pat. No. 6,455,263, U.S. Pat. No. 6,434,490, U.S. Pat. No. 6,245,937, U.S. Pat. No. 6,207,861, and U.S. Pat. No. 6,054,047, U.S. Pat. No. 6,001,579, U.S. Pat. No. 5,721,099 the disclosures of which are incorporated herein by reference in their entireties. Other methods are disclosed in PCT publications No. WO9935494, WO9819162, WO9954728, the disclosures of which are incorporated herein by reference in their entireties.

A further aspect of the present invention is a method for screening a candidate compound for the ability to modulate the binding of an autoinducer to a transporter. Preferably, the autoinducer is not an acyl-homoserine lactone and is able to interact with the *Vibrio harveyi* luxQ protein, thereby inducing expression of a *Vibrio harveyi* operon comprising the luxCDABE genes. In a preferred embodiment the autoinducer is AI-2. In some embodiments, the autoinducer may be AI-2 from *Vibrio harveyi* or the corresponding autoinducer from another organism.

In the foregoing method, the extent of binding of the autoinducer to the transporter is compared in the presence and absence of the candidate compound to determine whether the extent of binding of the autoinducer to the transporter in the presence of the candidate compound is significantly increased or decreased relative to the extent of binding in the absence of the candidate compound.

In one embodiment, the extent of binding of the autoinducer to the transporter is measured by contacting a cell expressing the transporter (such as a cell that expresses the transporter at a level higher than a wild type cell) with a solution containing the autoinducer in the presence or absence of the compond. After a sufficient amount of time has elapsed, the solution is removed from the cells and placed in contact with cells that produce a detectable response to the autoinducer, such as those described herein. If the compound inhibits the transport of the autoinducer into the cell, then the solution from cells contacted with the compound will contain a significantly higher amount of the autoinducer than the solution from cells that were not contacted with the compound. Thus, the level of the detectable response to the autoinducer will be greater in cells contacted with the solution from cells contacted with the compound than the level of detectable response in cells contacted with the solution from cells that were not contacted with the compound. If the compound increases the transport of the autoinducer into the cell, the level of the detectable response to the autoinducer will be lower in cells contacted with the solution from cells contacted with the compound than the level of detectable response in cells contacted with the solution from cells that were not contacted with the compound.

In some embodiments of the foregoing method, the transporter may be fixed to a solid support or may be present on a cell. The transporter is contacted with detectably labeled autoinducer in the presence or absence of the compound and the extents of binding in the presence and absence of the compound are compared. Alternatively, in some embodiments, the autoinducer may not be detectably labeled and the extent of autoinducer binding is measured using an antibody that recognizes the autoinducer.

The compounds identified using any of the methods above may be further optimized if desired. For example, the identified compounds may be used as the basis for a second generation of compound libraries more closely focused around the original hit to determine what structural features of the original hit need be modified to improve, e.g., the activity, physicochemical properties, or toxicity profile of the hit. Such applications of this approach in an iterative fashion lead to an optimized drug candidate.

Compounds identified using any of the methods above may be useful either as antimicrobial agents or as therapeutic agents. The compounds may be provided in a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, antioxidants, chelating agents and inert gases. Other pharmaceutically acceptable carriers include aqueous solutions, nontoxic excipients, including salts, preservatives, buffers and the like, as described, for instance, in Remington's Pharmaceutical Sciences, 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference.

As used herein, "administering a therapeutically effective amount" is intended to include methods of giving or applying a pharmaceutical composition of the invention to a subject that allow the composition to perform its intended therapeutic function. The therapeutically effective amounts will vary according to factors such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids and other natural conditions that may inactivate the pharmaceutical composition. The pharmaceutical composition can also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5 to about 80% of the weight of the unit. The amount of pharmaceutical composition in such therapeutically useful compositions is such that a suitable dosage will be obtained.

The tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the agent, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed. In addition, the pharmaceutical composition can be incorporated into sustained-release preparations and formulations.

As used herein, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional medium or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the individual to be treated; each unit containing a predetermined quantity of pharmaceutical composition is calculated to produce the desired therapeutic effect in association with the required pharmaceutical carrier. The specification for the novel dosage unit forms of the invention are dictated by and directly dependent on (a) the unique characteristics of the pharmaceutical composition and the particular therapeutic effect to be achieve, and (b) the limitations inherent in the art of compounding such an pharmaceutical composition for the treatment of a pathogenic infection in a subject.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the ingredients.

As discussed briefly above, an extracellular signaling factor produced by several strains of pathogenic bacteria, including *Salmonella typhimurium* and *Escherichia coli*, that has a role in regulating the pathogenesis or virulence of these bacteria has been identified. We have also identified and cloned genes involved in the biosynthesis of this signaling factor, genes that this signaling factor regulates, and genes that encode a transporter that transports the signaling factor into the cell. The purification and/or cloning of this signaling compound and the genes that encode proteins that catalyze its biosynthesis open a new avenue for drug design aimed at either inhibition of production of or response to this compound by bacteria. Drugs that interfere with signaling by this compound will constitute a new class of antibiotics. The invention further provides methods for detecting an autoinducer and methods for the in vitro production of autoinducer-2.

Description of the Signaling Factor

The present application provides a heterologous bioassay that has enabled the identification of an extracellular signaling factor produced by *S. typhimurium* and *E. coli*, among other pathogenic bacteria. The factor is sometimes referred to herein as a "pathogenesis signaling" factor or compound, though it acts as a signal for a variety of physiological changes in bacteria other than pathogenesis. The factor mimics the action of AI-2 (autoinducer-2) of the quorum sensing bacterium *Vibrio harveyi*, and it acts specifically through the *V. harveyi* Signaling System 2 detector, LuxQ.

The signaling factor is a small, soluble, heat labile organic compound that is involved in intercellular communication in all three bacteria. In *E. coli* and Salmonella, maximal secretion of the compound occurs in mid-exponential phase and the extracellular activity is degraded as glucose becomes depleted from the medium or by the onset of stationary phase. Destruction of the signaling compound in stationary phase indicates that in contrast to other quorum sensing systems, quorum sensing in bacteria that utilize the signaling compound is critical for regulating behavior in the pre-stationary phase of growth. Protein synthesis is required for degradation of the activity, indicating that a complex regulatory circuitry controls quorum sensing in these enteric bacteria.

Increased signaling activity is observed if, after growing in the presence of glucose, the bacteria are transferred to a high osmolarity (e.g., 0.4 M NaCl) or to a low pH (e.g., pH 5.0) environment. Moreover, degradation of the signal is induced by conditions of low osmolarity (e.g., 0.1 M NaCl. High osmolarity and low pH are two conditions encountered by pathogenic enteric bacteria, such as S. typhimurium and E. coli, when they undergo the transition to a pathogenic existence inside a host organism. Thus, quorum sensing in these bacteria appears to play a role in regulating their virulence, by way of directing the bacteria to undergo the transition between a host-associated (i.e., pathogenic) and a free-living existence.

Other factors that regulate the activity of the signaling compound are described in greater detail in Example 2. Particularly exemplified is the regulation of the compound in S. typhimurium.

The timing of lux induction in the bioassay and the shape of the response curve of V. harveyi to the S. typhimurium and E. coli signals are indistinguishable from those of V. harveyi responding to its own Signaling System 2 inducer, AI-2. Furthermore, each of the signaling compounds from S. typhimurium, E. coli and V. harveyi can be partially purified according to the same protocol. These results indicate that the signaling compounds from each of the aforementioned organisms are either identical or very closely related. Accordingly, AI-2 from V. harveyi is a signaling compound of the invention, but appears to play a different role in that organism than it does in pathogenic enteric bacteria such as Salmonella and Escherichia.

A. Structure of the AI-2 Signaling Factor

Autoinducer-2 (AI-2) signaling factor and derivatives thereof can be used to regulate bacterial growth in a variety of applications. Autoinducer-2 compounds may have the structure:

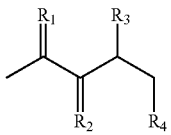

wherein $R_1$, $R_2$, $R_3$ and $R_4$ are independently selected from hydrido, halo, alkyl, haloalkyl, cycloalkyl, cycloalkenyl, heterocyclyl, methyl, cyano, alkoxycarbonyl, amino, carboxyl, hydroxyl, formyl, nitro, fluoro, chloro, bromo, methyl, aryl, heteroaryl, aralkyl, heteroarylalkyl, alkylsulfonyl, haloalkylsulfonyl, arylsulfonyl, heteroarylsulfonyl, hydroxyalkyl, mercaptoalkyl, alkoxyalkyl, ary-loxyalkyl, heteroaryloxyalkyl, aralkyloxyalkyl, heteroarylalkyloxyalkyl, alkylthioalkyl, arylthioalkyl, heteroarylthioalkyl, aralkylthioalkyl, heteroarylalkylthioalkyl, haloalkylcarbonyl, haloalkyl(hydroxy)alkyl, alkylcarbonyl, arylcarbonyl, aralkylcarbonyl, heteroarylcarbonyl, heteroarylalkylcarbonyl, carboxyalkyl, alkoxycarbonylalkyl, alkylcarbonyloxyalkyl, aminoalkyl, alkylaminoalkyl, arylaminoalkyl, aralkylaminoalkyl, heteroarylaminoalkyl, heteroarylalkylaminoalkyl, alkoxy, and aryloxy; phenyl, cyclohexyl, cyclohexenyl, benzofuryl, benzodioxolyl, furyl, imidazolyl, thienyl, thiazolyl, pyrrolyl, oxazolyl, isoxazolyl, triazolyl, pyrimidinyl, isoquinolyl, quinolinyl, benzimidazolyl, indolyl, pyrazolyl and pyridyl, aminosulfonyl, fluoro, chloro, bromo, methylthio, methyl, ethyl, isopropyl, tertbutyl, isobutyl, pentyl, hexyl, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, methylcarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, methylenedioxy, ethoxy, propoxy, n-butoxy, hydroxymethyl, hydroxyethyl, methoxymethyl, ethoxymethyl, trifluoromethoxy, methylamino, N,N-dimethylamino, phenylamino, ethoxycarbonylethyl, and methoxycarbonylmethyl, methyl, ethyl, fluoromethyl, difluoromethyl, trifluoromethyl, cyano, methoxycarbonyl, ethoxycarbonyl, tertbutoxycarbonyl, benzyl, phenylethyl, phenylpropyl, methylsulfonyl, phenylsulfonyl, trifluoromethylsulfonyl, hydroxymethyl, hydroxyethyl, methoxymethyl, ethoxymethyl, methylcarbonyl, ethylcarbonyl, trifluoromethylcarbonyl, trifluoro(hydroxy)ethyl, phenylcarbonyl, benzylcarbonyl, methoxycarbonylmethyl, ethoxycarbonylethyl, carboxymethyl, carboxypropyl, methylcarbonyloxymethyl, phenyloxy, phenyloxymethyl, thienyl, furyl, and pyridyl, wherein the thienyl, furyl, pyridyl, methylthio, methylsulfinyl, methyl, ethyl, isopropyl, tertbutyl, isobutyl, pentyl, hexyl, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, methylenedioxy, ethoxy, propoxy, n-butoxy, hydroxymethyl, hydroxyethyl and trifluoromethoxy.

The chemical groups disclosed herein are known to those of skill in the art. In addition, alkyl groups refer to "lower alkyl" groups having one to about ten carbon atoms. Most preferred are lower alkyl groups having one to about six carbon atoms. Examples of such groups include methyl, ethyl, n-propyl, isopropyl, n-butyl, isobutyl, sec-butyl, tertbutyl, pentyl, isoamyl, hexyl and the like. The term "halo" means halogens such as fluorine, chlorine, bromine or iodine. The terms "carboxy" or "carboxyl" denotes —CO2H. The term "carbonyl", whether used alone or with other terms, denotes —(S=O)—.

Preferably, the autoinducer-2 is 4,5-dihydroxy-2,3-pentanedione:

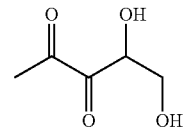

As used herein, an "autoinducer-2 (AI-2)" includes a compound that acts as a diffusable sensor for quorum sensing Signaling System 2. For example, AI-2 can regulate gene expression by increasing or decreasing expression of genes associated with pathogenesis of a microorganism. Typically, autoinducers are produced by microorganisms, such as bacteria, during metabolism. For example, the autoinducer-2 (AI-2) of the invention can interact with LuxP, which is the protein encoded by the homologue of the luxP gene of pathogenic bacteria such as V. cholerae, S. typhimurium and E. coli. In turn, the AI-2-LuxP complex can interact with LuxQ, which is the protein product encoded by the luxQ gene. The AI-2-LuxP-LuxQ interaction promotes luminescence in bacteria such as Vibrio spp. The AI-2-LuxP-LuxQ interaction has been linked to the activation of biochemical pathways required for bacterial pathogenicity. Thus, bacterial gene expression can be controlled and bacterial pathogenicity can be regulated by modulating AI-2-LuxP-LuxQ interactions.

AI-2 enters the cell through the action of a transporter such as that comprising the LsrA, LsrB, LsrC and LsrD proteins provided herein. Accordingly, bacterial gene expression can be controlled and bacterial pathogenicity can be regulated by modulating the expression or activity of the LsrA, LsrB, LsrC and LsrD proteins or proteins homologous thereto.

Homocysteine may also be used as an autoinducer. The structure of homocysteine is as follows:

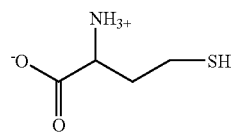

Figure 16:
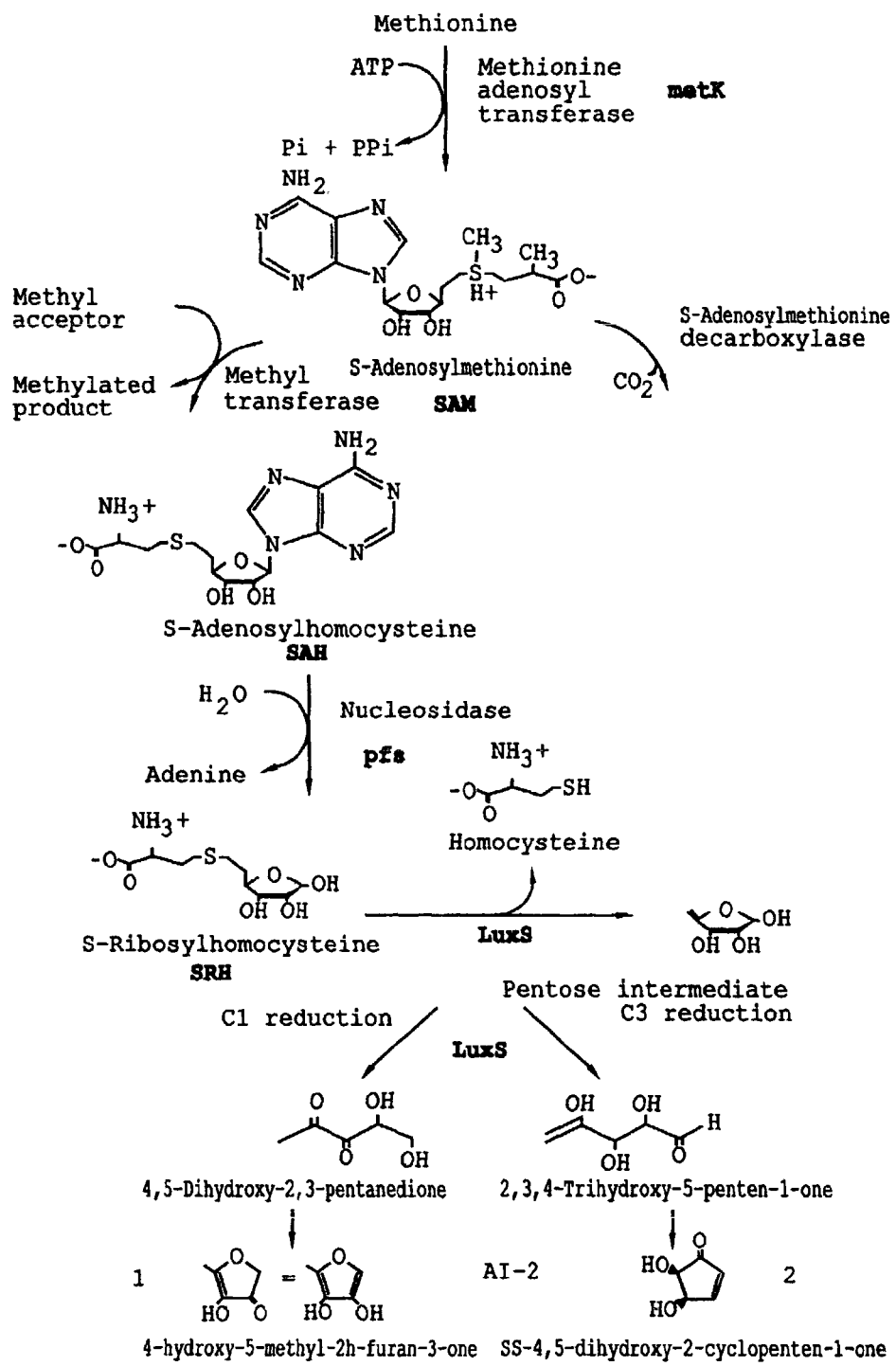
FIG. 16. A diagram of the biosynthetic pathway of autoinducer-2 (AI-2), including the structure of AI-2, is shown.

Homocysteine is produced by the activity of the LuxS protein on S-ribosylhomocysteine (FIG. 16). Thus, homoserine may be used as an autoinducer.

Isomers of an autoinducer-2, including both optical isomers and structural isomers may also be used in the methods of the present invention.

In addition to isomers, analogs of an autoinducer-2 may be used in the methods of the present invention. As used herein, an AI-2 "analog" includes compounds that are structurally similar but not identical to the claimed autoinducer 4,5-dihydroxy-2,3-pentanedione. Analogs of AI-2 can include compounds that inhibit rather than stimulate the activity of the LuxP protein or compounds that block the transport of AI-2 into the cell. For example, an analog of AI-2 that can interact nonproductively with LuxP or that block the transport of AI-2 into the cell can be produced. Such a compound can retain the ability to bind to LuxP or to the AI-2 transporter (such as an AI-2 transporter comprising the LsrA, LsrB, LsrC and LsrD proteins or proteins homologous thereto), but the analog AI-2-LuxP complex will not be able to productively interact with LuxQ or the analog AI-2-transporter complex will block the entry of AI-2 into the cell, resulting in an inhibition of bacterial pathogenicity. Thus, an AI-2 analog of the invention can inhibit bacterial pathogenesis by competing with endogenous AI-2 for binding to LuxP or to the AI-2 transporter. In addition, an analog of AI-2 can be constructed such that the analog AI-2-LuxP complex can interact nonproductively with LuxQ. In this case, the analog AI-2-LuxP-LuxQ complex is rendered nonfunctional for subsequent biochemical processes such as, for example, transcriptional activation of genes required for pathogenicity. The invention also includes AI-2 analogs that act synergistically to enhance the ability of AI-2 to increase the activity of the LuxP protein.

B. Preparation of the Signaling Factor

Initial strategies for purifying the signaling compound resulted in a partially purified preparation comprising the compound with a specific signaling activity estimated at about 0.1–1.0 mg of the partially purified material stimulating a 1,000-fold increase in luminescence, as measured in the *V. harveyi* bioassay. The signaling activity does not extract quantitatively into organic solvents and it does not bind to either a cation or an anion exchange column. The compound is a small (less than 1,000 kDa), polar but uncharged organic factor. The activity is acid stable and base labile, and it is heat resistant to 80° C. but not 100° C. These features of the signaling compound make clear that the compound differs from any previously described autoinducer.

The signaling factor of the present invention may be purified from its natural sources, i.e. the bacteria that produce it. With regard to purifying AI-2 from natural sources, altering the culture medium, e.g., by adding glucose or another sugar, by increasing the osmolarity, and/or decreasing pH, can increase production of the signaling compound in Salmonella and other enteric bacteria, has also enabled purification of the signaling compound to near-homogeneity. Thus, the compound has now been highly purified from culture fluids of enteric bacteria (e.g., *E. coli, S. typhimurium*) using the following protocol:

1. Grow a culture of the signal producing enteric bacterium overnight in LB containing 0.5% glucose or another sugar (37° C., with aeration). Inoculate fresh LB containing glucose or another sugar at 0.5% with the overnight culture, at a 1:100 dilution. Grow the diluted culture to mid-exponential phase (3.5 h, 37° C., with aeration).

2. Pellet the cells (10,000 rpm, 10 min, 4° C.). Discard the culture medium. Resuspend the cells and wash in 1/10 th the original volume of low osmolarity NaCl solution (0.1 M NaCl in water).

3. Pellet the cells again (10,000 rpm, 10 min, 4° C.). Discard the low osmolarity culture fluid. Resuspend the cells in 1/10 th the original volume of high osmolarity NaCl solution (0.4 M NaCl in water). Incubate the suspension at 37° C. for 2 h with aeration. During this time, increased production and secretion of the signaling compound occurs.

4. Pellet the cells (10,000 rpm, 10 min, 4° C.). Collect the supernatant containing the secreted signaling compound, filter the supernatant through a 0.2 M bacterial filter to remove any remaining cells.

5. Evaporate the aqueous filtrate using a rotary evaporator at 30° C. Extract the dried filtrate in 1/10 th the original volume of chloroform:methanol (70:30).

6. Evaporate the organic extract using a rotary evaporator at room temperature. Redissolve the dried extract in methanol at 1/100 th of the original volume.

7. Subject the partially purified signal to High Performance Liquid Chromatography (HPLC), using a preparative reverse phase C18 column. Elute the compound with a linear gradient of 0–100% acetonitrile in water at 5 ml per minute. Collect 30 fractions, 5 ml each.

8. Assay the HPLC fractions in the *V. harveyi* BB170 AI-2 assay, and pool the active fractions.

The product from the C18 column contains the signaling compound and a small number of other organic compounds. This highly purified preparation of the signaling compound has activity 50–100 times greater than that of the partially purified material described above (the preparation of which did not include the high osmoticum step or the final HPLC step), i.e., 1–10 μg material stimulates a 1,000-fold increase in luminescence in the *V. harveyi* bioassay.

Subsequent strategies for purifying the AI-2 signaling compound have led to the identification of a novel in vitro system for producing AI-2. Thus, in addition to providing a cloned, overexpressed and purified *S. typhimurium* LuxS protein, the application also provides a method for producing AI-2 in vitro. The application provides a mechanism for generating large quantities of pure AI-2 useful for mass spectral and NMR analysis, and for screening compounds that regulate the activity of AI-2. Moreover, the present application provides a method for determining the in vivo biosynthetic pathway for AI-2 synthesis. The in vitro method for AI-2 production is described below in Example 5 and FIG. 16. The method provides a novel means for efficiently producing autoinducers for further study. The method also provides a means for producing substantial quantities of AI-2 for use in commercial applications Such applications include, but are not limited to, adding AI-2 of the invention to a growth medium to increase bacterial growth. Such a method is particularly useful in the in the production of antibiotics from cultured bacteria. The addition of AI-2 can increase the antibiotic production of such organisms by promoting cell growth. Preferably, the signaling factor AI-2 is produced by the in vitro method set forth in Example 5 of the disclosure.

C. Uses of the Signaling Factor

The isolated and purified signaling compounds of the present invention are used as targets for the design of compounds that regulate the activity of AI-2, such as compounds that modulate the transport of AI-2 into the cell. As used herein, "regulate" includes increasing or decreasing the activity of AI-2. As used herein, the "activity" of AI-2 encompasses any aspect of the compound's ability to act as a signaling factor in bacterial quorum sensing. A "compound" can be any agent or composition that effects the activity of AI-2 For example, a compound of the invention can be a nucleic acid, a protein or small molecule. Thus, the invention provides a means for identifying a new class of antibiotics that inhibit the activity of the AI-2 or otherwise block the signaling pathway in which the compound participates. Such inhibitors may be identified by large-scale screening of a variety of test compounds, using the *V. harveyi* or *Salmonella typhimurium* bioassay in the presence of the purified signaling compound. A reduction in signaling activity in the presence of a test compound would be indicative of the ability of that compound to inhibit the activity of the signaling compound or to block some other part of the pathogenesis signaling pathway such as the transport of AI-2 into the cell.

Further, the invention provides a basis for the rational design of specific inhibitors or nonfunctional analogs of AI-2. Such structure-specific inhibitors or analogs may be tested in the *V. harveyi* or *Salmonella typhimurium* bioassay for their ability to inhibit the signaling compound, the ability to inhibit the transport of the signaling compound into the cell, or the ability to block the pathogenesis signaling pathway.

The invention also encompasses methods for identifying naturally produced compounds that inhibit the activity of a signaling compound such as autoinducer-2 or the transport of the signaling compound into the cell. For example, a defensive strategy employed by eucaryotic organisms to avoid bacterial colonization is to specifically target and inhibit quorum sensing controlled functions. Such a mechanism has been identified in *D. pulchra*. Recent studies indicate that halogenated furanones produced by *D. pulchra* inhibit quorum sensing by competing for the homoserine-lactone (HSL) autoinducer-binding site in LuxR. Thus, by providing a novel auto-inducer and the cellular components that interact with the autoinducer, the present application also provides a method to screen naturally produced compounds for their effect on quorum sensing system-2. For example, naturally produced compounds can be screened for their effect on the autoinducer-2-LuxP interaction or their effect on the transport of AI-2 into the cell. Alternatively, such compounds can be screened for their effect on autoinducer-2-LuxP-LuxQ interactions.

It will be appreciated by persons skilled in the art that, now that targets for the signaling compound have been identified in *E. coli*, inhibition of the *E. coli* target can also be used to screen potential signaling compound inhibitors or analogs. The inventors have prepared a ler-lacZ reporter fusion construct to be used in testing for reduction of expression of the Type III secretion gene in *E. coli* O157:H7 (pathogenic strain) directly. Alternatively, *E. coli* strains having an altered expression level of a transporter that transports AI-2 into the cell may be generated using methods such as those described herein and used to screen signaling compound inhibitors or analogs. Furthermore, a similar locus exists in *S. typhimurium*.

Thus, the application provides a method for selecting inhibitors or synergists of the autoinducer-2, 4,5-dihydroxy-2,3-pentanedione. As used herein, an "inhibitor" of AI-2 is intended to include compounds that interfere with the ability of the autoinducer to act as a signal for luminescence or pathogenesis. Inhibitors include compounds that degrade or bind to AI-2. The method comprises contacting the autoinducer with a suspected inhibitor or synergist, measuring the ability of the treated autoinducer to stimulate the activity of a selected gene then determining whether the suspected inhibitor or synergist represses or enhances the activity of the autoinducer. Actual inhibitors and synergists of the autoinducer are then selected. For example, a suspected inhibitor can be mixed with 4,5-dihydroxy-2,3-pentanedione and the mixture then combined with a reporter strain of *V. harveyi* disclosed herein. The amount of luminescence in the presence of the suspected inhibitor can be compared with a control mixture that does not include the inhibitor. A decrease in luminescence indicates AI-2 inhibition In this manner, compounds that regulate bacterial pathogenesis can be rapidly screened.

One aspect of the invention is a method for identifying a compound that modulates (i.e. increases or decreases) the response to an autoinducer that is not an acyl-homoserine lactone. Such compounds may be useful either as antimicrobial agents or as therapeutic agents. In some embodiments, the autoinducer may be AI-2 from *Vibrio harveyi*, a pentadione, or 4,5-dihydroxy-2,3-pentadione, or an autoinducer that is not an acylhomoserine lactone and that is able to interact with the *Vibrio harveyi* luxQ protein, thereby inducing expression of a *Vibrio harveyi* operon comprising the luxCDABE genes. A cell that produces a detectable signal in response to the autoinducer is obtained and the response of the cell to the autoinducer is measured in the presence and absence of a test compound. The responses of the cells to the autoinducer in the presence and absence of the test compound are compared to determine whether the compound modulates the response to the autoinducer.

The cell may be from any desired species that produces a detectable signal in response to the autoinducer or a cell that has been engineered to produce a detectable signal in response to the autoinducer. In some embodiments, the cell is a *Vibrio harveyi* cell. In other embodiments, the cell may be a *Salmonella typhimurium*, *E. coli*, *Haemophilus influenza*, *Helicobacter pylori*, *Bacillus subtilis*, *Borrelia burdorferi* or *Vibrio cholerae* cell.

The cell may produce any detectable signal in response to the autoinducer. For example, in some embodiments, the cell produces bioluminescence in response to the autoinducer. Thus, in some embodiments, the cell is a *Vibrio harveyi* cell that produces bioluminescence in response to the autoinducer via induction of the luxCDABE operon.

Alternatively, in some embodiments, the detectable signal may be induction of mRNA transcription or protein expression in response to the autoinducer. Induction of mRNA transcription may be measured with any of a variety of techniques familiar to those skilled in the art, including Northern analysis or detection of the transcript through use of nucleic acid amplification techniques such as PCR. Induction of protein expression may also be measured with any of a variety of techniques familiar to those skilled in the art including gel electrophoresis, Western blotting, or enzymatic activity assays. For example, in some embodiments, the cell may be genetically engineered to express a marker protein such as -galactosidase, chloramphenicol acetyltransferase, β-glucuronidase, luciferase, or green fluorescent protein in response to the autoinducer. Thus, in some embodiments, a nucleic acid encoding the marker protein may be operably linked to the luxCDABE promoter and introduced into the cell such that expression of the marker protein is induced by the autoinducer. Alternatively, in other embodiments, an autoinducer responsive promoter other than the luxCDABE promoter may be operably linked to a nucleic acid encoding the marker protein. The the autoinducer responsive promoter may be from the same species as the cell to be used in the method or, alternatively, the the autoinducer responsive promoter may be from a heterologous organism.

The response of the cell to the autoinducer is measured in the presence and absence of a test compound. The test compound may be naturally-occuring, such as a compound from a natural products library, or may be of synthetic origin, such as a compound generated through use of combinatorial chemistry.

The response of the cell to the autoinducer in the presence and absence of the test compound is compared. In some embodiments, the test compound alters the response to the autoinducer at least two fold, at least 10 fold, at least 20 fold, at least 50 fold, at least 100 fold, at least 1000 fold, or even more than 1000 fold.

In some embodiments, the cell that produces a detectable signal in response to the autoinducer has a genetic alteration that inhibits production of the autoinducer. In some embodiments, the genetic alteration is introduced into the cell through use of such genetic engineering techniques as site directed mutagenesis, insertional mutagenesis, or chemical mutagenesis followed by appropriate selection. Alternatively, cells containing the genetic alteration may be isolated or selected from a natural population.

In some embodiments, the genetic alteration that inhibits production of the autoinducer is in the *Vibrio harveyi* luxS gene, a gene having homology to the *Vibrio harveyi* luxS gene, or a gene encoding a polypeptide having homology to the *Vibrio harveyi* luxS polypeptide. For example, the genetic alteration may be in a gene having a sequence with at least 50%, at least 60%, or at least 80% sequence homology to the *Vibrio harveyi* luxS gene. In other embodiments the genetic alteration is in a gene encoding a polypeptide having at least 57% or at least 85% homology to the *Vibrio harveyi* luxS polypeptide. In still further embodiments, the genetic alteration is in a gene encoding a polypeptide having at least 32%, at least 45%, at least 74% or at least 80% sequence identity to the *Vibrio harveyi* luxS polypeptide.

In some embodiments, the cells have a first genetic alteration that inhibits production of an autoinducer that is not an acyl-homoserine lactone and a second genetic alteration that inhibits detection or response to another autoinducer that is an acyl-homoserine lactone. For example, in some embodiments, the cell is a *Vibrio harveyi* cell, the first genetic alteration is in the luxS gene and the second genetic alteration is in the luxN gene. Thus, in some embodiments, the cell may be a *Vibrio harveyi* MM32 cell as described herein. However, the first and second genetic alterations may be in any gene that provides the phenotypes discussed above, including the genes discussed above, and the cell may be from any suitable species, including the species specifically enumerated herein.

In another aspect, the invention also provides methods of selecting inhibitory and synergistic analogs of AI-2. The method comprises mixing a known amount of the autoinducer with a known amount of the suspected inhibitory or synergistic analog, measuring the ability of the treated autoinducer to stimulate the activity of a selected gene then determining whether the suspected inhibitory or synergistic analog represses or enhances the activity of the autoinducer. Actual inhibitory or synergistic analogs of the autoinducer are then selected.

Autoinducer-2 can be purified from the native source through use of conventional purification techniques, derived synthetically by chemical means, or preferably, produced by the in vitro method of the invention described below. As used herein, "purified from a native source" includes an autoinducer-2 of the above formula that has been manufactured by an organism. "Purified from the native source" includes isolating the autoinducer from the culture medium or cytoplasm of bacteria such as *S. typhimurium* through use of conventional purification techniques. As used herein, "synthesized by chemical means" includes autoinducers of the claimed formula that have been artificially produced outside of an organism. The invention includes an autoinducer of the invention manufactured by a person skilled in the art from chemical precursors through use of standard chemical synthesis techniques.

The application further provides methods of inhibiting the infectivity of a pathogenic organism as well as therapeutic compositions containing an AI-2 analog or AI-2 inhibitor of the invention. The methods comprise administering to a subject a therapeutically effective amount of an pharmaceutical composition that inhibits the activity of AI-2, the transport of AI-2 into the cell, or the repression of genes that encode polypeptides involved in the transport of AI-2 into the cell. As used herein, "inhibiting infectivity" includes methods of affecting the ability of a pathogenic organism to initially infect or further infect a subject that would benefit from such treatment. A pharmaceutical composition of the invention can include, but is not restricted to, an agent that prevents the transcriptional activation of extracellular virulence factors such as exotoxin A and elastolytic proteases or an agent that inhibits tht transport of AI-2 into the cell. As used herein, an "agent" includes compounds that inhibit the ability of the LuxP protein and LuxQ protein to activate transcription of extracellular virulence factors and compounds that inhibit the transport of AI-2 into the cell. Agents include inhibitors that interact directly with AI-2 such that AI-2 is prevented from acting as a sensor for quorum sensing Signaling System-2. Preferably, the agent interacts with 4,5-dihydroxy-2,3-pentanedione. Agents further include analogs of AI-2 that can compete with 4,5-dihydroxy-2,3-pentanedione for binding to LuxP, LuxQ, or the transporter that transports AI-2 into the cell.

The application further provides pharmaceutical compositions for preventing or treating pathogen-associated diseases by targeting factors involved in the Signaling System type-2 pathway. For example, LsrA, LsrB, LsrC, LsrD, LsrE, LsrF, LsrG, LsrR, LuxP or LuxQ, or homologues thereof, provide a common target for the development of a vaccine. Antibodies raised to LsrA, LsrB, LsrC, LsrD, LsrE, LsrF, LsrG, LsrR, LuxP or LuxQ or homologues thereof, can inhibit the activation of bacterial pathways associated with virulence. Thus, LsrA, LsrB, LsrC, LsrD, LsrE, LsrF, LsrG, LsrR, LuxP or LuxQ provide common antigenic determinants that can be used to immunize a subject against multiple pathogen-associated disease states. For example, the autoinducer Signaling System type-2 is believed to exist in a broad range of bacterial species including bacterial pathogens. As discussed above, the autoinducer-2 signaling factor is believed to be involved in interspecies as well as intraspecies communication. In order for the quorum sensing Signaling System type-2 to be effective for interspecies communication, it is likely to be highly conserved among various bacterial species. Thus, challenging a subject with the LsrA, LsrB, LsrC, LsrD, LsrE, LsrF, LsrG, LsrR, LuxP or LuxQ polypeptide, or an antigenic fragment thereof, isolated from a particular organism may confer protective immunity to other disease states associated with a different organism. For example, a vaccine developed to the LuxP protein isolated from *V. cholerae* may be capable of cross-reacting with a LuxP homologue expressed by a different organism. Thus, it is envisioned that methods of the present invention can be used to treat pathogen-associated disease states.

Generally, the terms "treating", "treatment", and the like are used herein to mean obtaining a desired pharmacologic and/or physiologic effect. The effect may be prophylactic in terms of completely or partially preventing a spirochete infection or disease or sign or symptom thereof, and/or may be therapeutic in terms of a partial or complete cure for an infection or disease and/or adverse effect attributable to the infection or disease. "Treating" as used herein covers any treatment of (e.g., complete or partial), or prevention of, an infection or disease in a mammal, particularly a human, and includes:

a) preventing the disease from occurring in a subject that may be predisposed to the disease, but has not yet been diagnosed as having it;

b) inhibiting the infection or disease, i.e., arresting its development; or c) relieving or ameliorating the infection or disease, i.e., cause regression of the infection or disease.

Thus, the invention includes various pharmaceutical compositions useful for ameliorating symptoms attributable to a bacterial infection or, alternatively, for inducing a protective immune response to prevent such an infection. For example, a pharmaceutical composition according to the invention can be prepared to include an antibody against, for example, LsrA, LsrB, LsrC, LsrD, LsrE, LsrF, LsrG, LsrR, LuxP or LuxQ, a peptide or peptide derivative of LsrA, LsrB, LsrC, LsrD, LsrE, LsrF, LsrG, LsrR, LuxP or LuxQ mimetic, or a LsrA, LsrB, LsrC, LsrD, LsrE, LsrF, LsrG, LsrR, LuxP or LuxQ-binding agent. The pharmaceutical agent may be formulated as described above.

In addition to generating antibodies that bind to antigenic epitopes of proteins of the invention, it is further envisioned that the method of the invention can be used to induce cellular responses, particularly cytotoxic T-lymphocytes (CTLs), to antigenic epitopes of, for example LsrA, LsrB, LsrC, LsrD, LsrE, LsrF, LsrG, LsrR, LuxP or LuxQ. Typically, unmodified soluble proteins fail to prime major histocompatibility complex (MHC) class I-restricted CTL responses whereas particulate proteins are extremely immunogenic and have been shown to prime CTL responses in vivo. CTL epitopes and helper epitopes have been identified in proteins from many infectious pathogens. Further, these epitopes can be produced concurrently such that multiple epitopes can be delivered in a form that can prime MHC class I restricted CTL responses. An example of a system that can produce recombinant protein particles carrying one or more epitopes entails the use of the p1 protein of the retrotransposon Tyl of *Saccharomyces cerevisiae* (Adams, et al., Nature, 329:68, 1987). Sequences encoding CTL epitopes can, for example, be fused to the C-terminus of p1 and the resulting Ty virus-like particles (Ty-VLPs) may be able to generate a CTL response. Thus, conserved regions of pathogenic antigens, such as those that are involved in, or result from, the activation of Signaling System type-2, can be identified and incorporated together in a particle that enables the host immune system to mount an effective immune response against multiple spirochetal organisms. Further, the method of the invention can be used to generate particles with multiple epitopes to a single protein, such as LuxP, or multiple epitopes from various proteins.

The method of the invention also includes slow release antigen delivery systems such as microencapsulation of antigens into liposomes. Such systems have been used as an approach to enhance the immunogenicity of proteins without the use of traditional adjuvants. Liposomes in the blood stream are generally taken up by the liver and spleen, and are easily phagocytosed by macrophages. Liposomes also allow coentrapment of immunomodulatory compounds along with the antigens, so that such compounds may be delivered to the site of antigen encounter, allowing modulation of the immune system towards protective responses.

In another embodiment, the invention provides a method for identifying a compound that binds to a protein of the invention, such as LsrA, LsrB, LsrC, LsrD, LsrE, LsrF, LsrG, LsrR, LuxP or LuxQ or to a complex comprising one or more of the foregoing proteins. The method includes incubating components comprising the compound and LsrA, LsrB, LsrC, LsrD, LsrE, LsrF, LsrG, LsrR, LuxP or LuxQ or a complex comprising one or more of the foregoing proteins under conditions sufficient to allow the components to interact and measuring the binding of the compound to LsrA, LsrB, LsrC, LsrD, LsrE, LsrF, LsrG, LsrR, LuxP or LuxQ or the complex comprising one or more of the foregoing proteins. Compounds that bind to LsrA, LsrB, LsrC, LsrD, LsrE, LsrF, LsrG, LsrR, LuxP or LuxO include peptides, peptidomimetics, polypeptides, chemical compounds and biologic agents as described above.

Incubating includes conditions that allow contact between the test compound and LsrA, LsrB, LsrC, LsrD, LsrE, LsrF, LsrG, LsrR, LuxP or LuxQ or a complex comprising one or more of the foregoing proteins. Contacting includes in solution and in solid phase. The test ligand(s)/compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., B—io/-Technology, 3:1008–1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229–237, 1988). Also included in the screening method of the invention are combinatorial chemistry methods for identifying chemical compounds that bind to LsrA, LsrB, LsrC, LsrD, LsrE, LsrF, LsrG, LsrR, LuxP or LuxQ. See, for example, Plunkett and Ellman, "Combinatorial Chemistry and New Drugs", Scientific American, April, p. 69, (1997).

The application further provides a method for promoting the production of a bacterial product, such as, for example, an antibiotic, by contacting a culture of bacteria with an AI-2 of the invention at a concentration effective to stimulate or promote cellular metabolism, growth or recovery. For example, it is known that antibiotic-producing bacteria only produce an antibiotic at or near the peak of log phase growth. By contacting a culture medium containing such antibiotic-producing bacteria with AI-2 of the invention, production of an antibiotic can be induced at an earlier phase of growth. Thus, AI-2 of the invention provides a method for increasing the amount of antibiotic produced by a culture. "Culture medium", as used herein, is intended to include a substance on which or in which cells grow. The autoinducer can be included in commercially available cell culture media including broths, agar, and gelatin.

The invention further provides a method for identifying factors that degrade or inhibit the synthesis of autoinducer-2. For example, it is known that autoinducer-1 concentration peaks in mid- to late log phase of a bacterial cell culture. In contrast, autoinducer-2 concentration increases earlier in log phase of bacterial cell culture growth and is present in lower amounts in late log phase and stationary phase. This data indicates that a mechanism exists for the degradation of autoinducer-2 at a specific point in bacterial growth. By providing isolated and purified autoinducer-2, the application allows for the identification of the mechanism whereby autoinducer-2 levels are controlled. For example, partially purified bacterial extracts can be assayed against isolated autoinducer-2 to identify those fractions that degrade autoinducer-2. Fractions that degrade autoinducer-2 can be further fractionated by techniques known to those skilled in the art until those cellular components involved in autoinducer degradation are isolated.

The present invention also provides a method of regulating the expression of a gene. The method comprises inserting a gene into bacteria chosen for enhancement of gene expression by an agent capable of stimulating the activity of the LuxQ protein and incubating the bacteria with an agent capable of stimulating the activity of the LuxP protein. Thus, the signaling compound of the invention can also be used in screens for other targets that it regulates. Cloned promoter-fusion libraries can be prepared from any species of bacteria and these libraries can be used to identify genes that are induced or repressed by the signaling factor, simply by screening for differences in reporter activity in Petri or microtiter plates containing the signaling compound compared to plates that do not contain the compound.

In addition, quorum sensing is a major regulator of biofilm control and quorum sensing blockers can therefore be used to prevent and/or inhibit biofilm formation. Also, quorum sensing blockers are effective in removing, or substantially decreasing the amount of, biofilms that have already formed on a surface. Thus, by providing the structure of autoinducer-2 (AI-2), the present invention provides a new approach to identifying compounds that inhibit bacterial infections by regulating biofilm formation.

It is known that quorum sensing blockers can reduce protease production by 50% in some strains of bacteria but the discovery that certain compounds can substantially eliminate protease production imparts clear clinical advantages. Furthermore, the unexpected finding that biofilm formation can be inhibited or prevented by quorum sensing blockers leads to the reasonable conclusion that other quorum sensing blockers that are known to exhibit quorum sensing blocking in other systems, such as protease production, will also be effective against biofilm formation.

The compounds of the invention are advantageously used to treat and/or prevent infections, such as those caused by $V.$ *angufflarum* or *Aeromonas* spp. Examples of this type of infection are vibriosis and furunculosis disease in fish. Inhibition of biofilm formation by the bacteria, optionally together with a reduction or elimination of extracellular protease production, renders the bacteria substantially nonpathogenic. The compounds of the invention may be formulated by conventional methods for use in the treatment and/or prevention of bacterial infection. For example, the compounds may be used as solid or liquid preparations (such as tablets, suspensions or solutions for oral administration or sterile injectable compositions), optionally together with pharmaceutically acceptable diluents, carriers or other additives.

For the treatment of vibriosis or furunculosis disease in fish, the compounds or compositions containing them may be applied directly to the fish or they may be added to the fish's food or water.

In another embodiment, the invention provides a method of removing a biofilm from a surface that comprises treating the surface with a compound of the invention. The surface is preferably the inside of an aqueous liquid distribution system, such as a drinking water distribution system or a supply line connected to a dental air-water system. The removal of biofilms from this type of surface can be particularly difficult to achieve. The compound is preferably applied to the surface as a solution of the compound either alone or together with other materials such as conventional detergents or surfactants.

A further embodiment of the invention is an antibacterial composition comprising a compound of the invention together with a bacteriocidal agent. In the antibacterial compositions, the compound of the invention helps to remove the biofilm whilst the bacteriocidal agent kills the bacteria. The antibacterial composition is preferably in the form of a solution or suspension for spraying and/or wiping on a surface.

In yet another aspect, the invention provides an article coated and/or impregnated with a compound of the invention in order to inhibit and/or prevent biofilm formation thereon. The article is preferably of plastics material with the compound of the invention distributed throughout the material Description of Nucleic Acids Encoding Proteins Involved in Signaling Factor Biosynthesis The genes responsible for production of the signaling compound of the invention in $V.$ *harveyi*, $S.$ *typhimurium* and $E.$ *coli* have been cloned and characterized. These genes encode a novel family of proteins responsible for autoinducer production. We have designated the members of this family of autoinducer production genes as luxS, specifically $luxS_{E.c.}$, $luxS_{S.t.}$, and $luxS_{V.h.}$ for $E.$ *coli*, $S.$ *typhimurium* and $V.$ *harveyi* respectively.

Mutagenesis of luxS in $V.$ *harveyi*, $S.$ *typhimurium* and $E.$ *coli* eliminates production of the signaling compound in all three species of bacteria. $S.$ *typhimurium* could be complemented to full production of the compound by the introduction of either the $E.$ *coli* O157:H7 $luxS_{E.c.}$ gene or the $V.$ *harveyi* BB120 $luxS_{V.h.}$ gene. These results indicate that both the $E.$ *coli* and $V.$ *harveyi* LuxS proteins can function with $S.$ *typhimurium* cellular components to produce the signaling compound. $E.$ *coli* DH5 was only partially complemented to production of the signaling compound by the introduction of either the $E.$ *coli* O157:H7 $luxS_{E.c.}$ or the $V.$ *harveyi* BB120 $luxS_{V.h.}$ gene. Because in trans expression of luxS genes in $E.$ *coli* DH5 did not completely restore signaling compound production, other biochemical or physiological factors may contribute to signal production.

The regulation of signaling compound production differs between pathogenic and nonpathogenic strains. For example $E.$ *coli* O157:H7 strains produce AI-2 at 30° and 37° C. with or without glucose while $E.$ *coli* K-12 strains do not produce the compound in the absence of a preferred carbon source. And, all of the *E. coli* O157 strains tested produce greater signaling activity than do non-pathogenic *E. coli* strains. Likewise, pathogenic *S. typhimurium* 14028 produces significantly more signaling activity than does *S. typhimurium* LT2.

Sequence analysis shows that the LuxS proteins are highly homologous, and complementation data suggest that the proteins can function across species. These results indicate that the enzymatic activity carried out by the LuxS proteins and any other cellular machinery that contributes to synthesis of the signaling compound are conserved. We did not identify any sequence motif in the LuxS proteins that indicates a particular function. Therefore, the LuxS proteins most likely catalyze one specific enzymatic step in biosynthesis of the signaling compound. The remainder of the steps involved in signaling compound biosynthesis could result from normal intermediary metabolic processes. The luxS genes identified here bear no homology to other genes known to be involved in production of acyl-homoserine lactone autoinducers (luxI-like (Fuqua et al., J. Bacteriol. 176, 269–275, 1994), luxLM-ainS-like (Bassler et al, 1993, supra; Gilson et al, J. Bacteriol. 177, 6946–6951, 1995), further indicating that the signaling compounds described herein are novel.

Database analysis of finished and unfinished bacterial genomes reveals that many other species of bacteria possess a gene homologous to luxS from *V. harveyi*, *S. typhimurium* and *E. coli*. The species of bacteria identified and the percent homology/identity (H/I) to the LuxS protein of *V. harveyi* are as follows: *Haemophilus influenzae* (88/72), *Helicobacter pylori* (62/40), *Bacillus subtilis* (58/38), *Borrelia burgfdorferi* (52/32), *Neisseria meningitidis* (89/80), *Neisseria gonorrhoeae* (89/80), *Yersinia pestis* (85/77), *Campylobacter jejuni* (85/74), *Vibrio cholerae* (95/90), *Deinococcus radiodurans* (65/45), *Mycobacterium tuberculosis* (59/41), *Enterococcus faecalis* (60/44), *Streptococcus pneumoniae* (57/36) and *Streptococcus pyogenes* (57/36). As reported earlier (Bassler et al., 1997, supra), a few of these species were tested for production of the signaling compound. We showed that *V. cholerae* and *Y. enterocolitica* but not *B. subtilis* produced signaling activity. We believe that *B. subtilis* does produce the compound but the environmental conditions that induce its synthesis have not yet been determined. Furthermore, we believe that all of the species identified in the database analysis produce an AI-2-like compound.

The sequences of the luxS genes from *V. harveyi*, *E. coli* and *S. typhimurium* are set forth at the end of the specification as SEQ ID NO:1, SEQ ID NO:2 and SEQ ID NOS:3 and 4, respectively (the sequences read in the 5' to 3' direction). These genes are sometimes referred to herein as "LuxS$_{V\ h.}$", "LuxS$_{E.c.}$" and "LuxS$_{S\ t.}$", respectively. The sequences deduced from SEQ ID NOS: 1–4 are set forth at the end of the specification (and in FIG. 13) as SEQ ID NO:10, SEQ ID NO:11 and SEQ ID NO:12, respectively. It is believed that SEQ ID NOS: 1 and 2 constitute full-length clones, whereas SEQ ID NO:3 and SEQ ID NO:4 do not.

The LuxS genes from *V. harveyi; E. coli* and *S. typhimurium* are described in greater detail in Example 3. Although those particular luxS genes and their encoded proteins are exemplified herein, this invention encompasses luxS genes and their encoded enzymes from any bacterial species, having the sequence, structural and functional properties of the luxS-encoded proteins described herein. As mentioned in Example 3, homologous nucleic acid sequences have been identified in a variety of bacterial species, but identity of those sequences as luxS genes heretofore had not been appreciated. LuxS nucleotide and deduced amino acid sequences from other bacterial species are set forth at the end of the specification as SEQ ID NOS: 5–9 and 13–17, respectively, and include sequences from the following species: *Haemophilus influenzae*, *Helicobacter pylori*, *Bacillus subtilis*, *Borrelia burgdorferi* and *Vibrio cholerae*.

In addition to LuxS homologs from species other than *V. harveyi*, *E. coli* or *S. typhimurium*, variants and natural mutants of SEQ ID NOS:1–9 are likely to exist within different species or strains of Vibrio, Escherichia and Salmonella (indeed, *E. coli* strain DH5 possesses a non-functional mutant form of the gene). Because such variants are expected to possess certain differences in nucleotide and amino acid sequence, this invention provides an isolated LuxS nucleic acid and encoded protein having at least about 50–60% (preferably 60–80%, most preferably over 80%) sequence homology in the coding region with the sequences set forth as SEQ ID NOS:1–9, respectively (and, preferably, specifically comprising the coding regions of SEQ ID NOS: 1–9), and the sequence of SEQ ID NOS:10–17. Because of the natural sequence variation likely to exist among these proteins and nucleic acids encoding them, one skilled in the art would expect to find up to about 40–50% sequence variation, while still maintaining the unique properties of the luxS-encoded proteins of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. the structural characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function. The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the University of Wisconsin, and the default parameters used by that program are the parameters intended to be used herein to compare sequence identity and similarity.

A. Preparation of Nucleic Acids, Encoded Proteins, and Immunologically Specific Antibodies 1. Nucleic Acids LuxS nucleic acids of the invention may be prepared by two general methods: (1) They may be synthesized from appropriate nucleotide triphosphates, or (2) they may be isolated from biological sources. Both methods utilize protocols well known in the art.

The availability of sequence information, such as the DNAs having SEQ ID NOS: 1–9, enables preparation of an isolated nucleic acid of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA of the present invention, must be synthesized in stages, due to the size limitations inherent in current oligonucleotide synthetic methods. Such long double-stranded nucleic acids may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.8 kb double-stranded nucleic acid. A synthetic DNA so constructed may then be cloned and amplified in an appropriate vector.

LuxS nucleic acids also may be isolated from appropriate biological sources using methods known in the art. In a preferred embodiment, a genomic clone is isolated from a cosmid expression library of an S. typhimurium or E. coli genome. In another embodiment, a genomic clone is isolated from a cosmid library of another bacterial genome.

In accordance with the present invention, nucleic acids having the appropriate level sequence homology with the protein coding region of any of SEQ ID NOS:1–9 may be identified by using hybridization and washing conditions of appropriate stringency. For example, hybridizations may be performed, according to the method of Sambrook et al., using a hybridization solution comprising: 5×SSC, 5× Denhardt's reagent, 1.0% SDS, 100 g/ml denatured, fragmented salmon sperm DNA, 0.05% sodium pyrophosphate and up to 50% formamide. Hybridization is carried out at 37–42NC for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65 N in 1×SSC and 1% SDS, changing the solution every 30 minutes.

One common formula for calculating the stringency conditions required to achieve hybridization between nucleic acids of a specified sequence homology (Sambrook et al., 1989):

$$T_m = 81.5C + 16.6 \log [Na^+] + 0.41(\% \ G+C) - 0.63 (\% \ \text{formamide}) - 600/\#bp \text{ in duplex}$$

As an illustration of the above formula, using $[Na^+]=[0.368]$ and 50% formamide, with GC content of 42% and an average probe size of 200 bases, the $T_m$ is 57C. The $T_m$ of a DNA duplex decreases by 1–1.5° C. with every 1% decrease in homology. Thus, targets with greater than about 75% sequence identity would be observed using a hybridization temperature of 42° C.

Another way to isolate the luxS nucleic acids is to search the publicly available databases for the luxS sequence in the bacterial genome of interest, design PCR primers from the sequence and amplify the gene directly from the chromosome. The PCR product can then be cloned. Alternatively, if the complete sequence of a specific bacterial genome is not available, the sequences set forth in the present invention, or any other luxS sequence, may be used to design degenerate oligonucleotides for PCR amplification and cloning of luxS from the chromosome.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable E. coli host cell.

LuxS nucleic acids of the invention include DNA, RNA, and fragments thereof that may be single- or double-stranded. Thus, this invention provides oligonucleotides (sense or antisense strands of DNA or RNA) having sequences capable of hybridizing with at least one sequence of a nucleic acid of the present invention, such as selected segments of the DNA having SEQ ID NOS:1, 2 or 3. Such oligonucleotides are useful as probes for detecting LuxS genes or transcripts.

LsrA, LsrB, LsrC, LsrD, LsrE, LsrF, LsrG, or LsrR nucleic acids and nucleic acids homologous thereto may also be prepared and used as described above.

2. Proteins and Antibodies

A full-length LuxS gene product of the present invention may be prepared in a variety of ways, according to known methods. The protein may be purified from appropriate sources, e.g., cultured bacteria such as S. typhimurium, E. coli or V. harveyi.

The availability of full-length LuxS nucleic acids enables production of the encoded protein using in vitro expression methods known in the art. According to a preferred embodiment, the enzyme may be produced by expression in a suitable expression system. For example, part or all of a DNA, such as the DNA having SEQ ID NO:1 or 2, may be inserted into a plasmid vector adapted for expression in a bacterial cell, such as E. coli, or a eucaryotic cell, such as Saccharomyces cerevisiae or other yeast. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The protein produced by LuxS gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The protein encoded by the LuxS gene of the invention, prepared by one of the aforementioned methods, may be analyzed according to standard procedures. For example, the protein may be subjected to amino acid sequence analysis, according to known methods. The stability and biological activity of the enzyme may be determined according to standard methods, such as by the ability of the protein to catalyze production of the signaling compound under different conditions.

The present invention also provides antibodies capable of immunospecifically binding to the LuxS-encoded protein of the invention. Polyclonal antibodies may be prepared according to standard methods. In a preferred embodiment, monoclonal antibodies are prepared, which react immunospecifically with various epitopes of the protein. Monoclonal antibodies may be prepared according to general methods of Kohler and Milstein, following standard protocols. Polyclonal or monoclonal antibodies that immunospecifically interact with the LuxS-encoded proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

LsrA, LsrB, LsrC, LsrD, LsrE, LsrF, LsrG, or LsrR proteins, proteins homologous thereto or antibodies that recognize the foregoing proteins may also be prepared as described above.

B. Uses of Nucleic acids, Encoded Protein and Immunologically Specific Antibodies LuxS nucleic acids may be used for a variety of purposes in accordance with the present invention. DNA, RNA, or fragments thereof may be used as probes to detect the presence of and/or expression of LuxS genes. Methods in which LuxS nucleic acids may be utilized as probes for such assays include, but are not limited to: (1) in situ hybridization; (2) Southern hybridization (3) northern hybridization; and (4) assorted amplification reactions such as polymerase chain reactions (PCR).

The LuxS nucleic acids of the invention may also be utilized as probes to identify related genes from other bacteria. As is well known in the art, hybridization stringencies may be adjusted to allow hybridization of nucleic acid probes with complementary sequences of varying degrees of homology.

As described above, LuxS nucleic acids are also used to advantage to produce large quantities of substantially pure encoded protein, or selected portions thereof. It should be noted in this regard that the cloned genes inserted into expression vectors can be used to make large quantities of the signaling compound itself, from any selected bacterial species, in a recombinant host such as $E.\ coli$ DH5. Specific luxS genes are cloned, a large quantity of the encoded protein produced, thereby producing a large quantity of the specific signaling compound. This will be particularly useful determining differences in the structures of signaling compounds from different species, if such differences are found to exist. Alternatively, a large quantity of signaling compound from the species of interest could be made using the cloned gene in an expression vector, and thereafter used in library screens for potential targets in petri plate assays, as described above.

Purified LuxS gene products, or fragments thereof, may be used to produce polyclonal or monoclonal antibodies that also may serve as sensitive detection reagents for the presence and accumulation of those proteins in cultured cells. Recombinant techniques enable expression of fusion proteins containing part or all of a selected LuxS-encoded protein. The full length protein or fragments of the protein may be used to advantage to generate an array of monoclonal or polyclonal antibodies specific for various epitopes of the protein, thereby providing even greater sensitivity for detection of the protein in cells or tissue. Other uses of the LuxS proteins include overproduction to make a quantity of the LuxS proteins sufficient for crystallization. Solving the crystal structure of the LuxS proteins would enable the exact determination of the LuxS active site for catalysis of production of the signaling compound. The LuxS crystal structure can therefore be used for computer modeling that would greatly facilitate design of signaling compound analogs, LuxS inhibitors, and rational drug design in general.

Polyclonal or monoclonal antibodies immunologically specific for a LuxS-encoded protein may be used in a variety of assays designed to detect and quantitate the protein. Such assays include, but are not limited to: (1) flow cytometric analysis; (2) immunochemical localization of a LuxS protein in cells or tissues; and (3) immunoblot analysis (e.g., dot blot, Western blot) of extracts from various cells and tissues. Additionally, as described above, antibodies can be used for purification of the proteins (e.g., affinity column purification, immunoprecipitation).

LsrA, LsrB, LsrC, LsrD, LsrE, LsrF, LsrG, or LsrR nucleic acids, nucleic acids homologous thereto, encoded proteins, proteins homologous thereto or antibodies that recognize the foregoing proteins may also be used as described above.

*Vibrio Harveyi* Screening Strain

Figure 15:
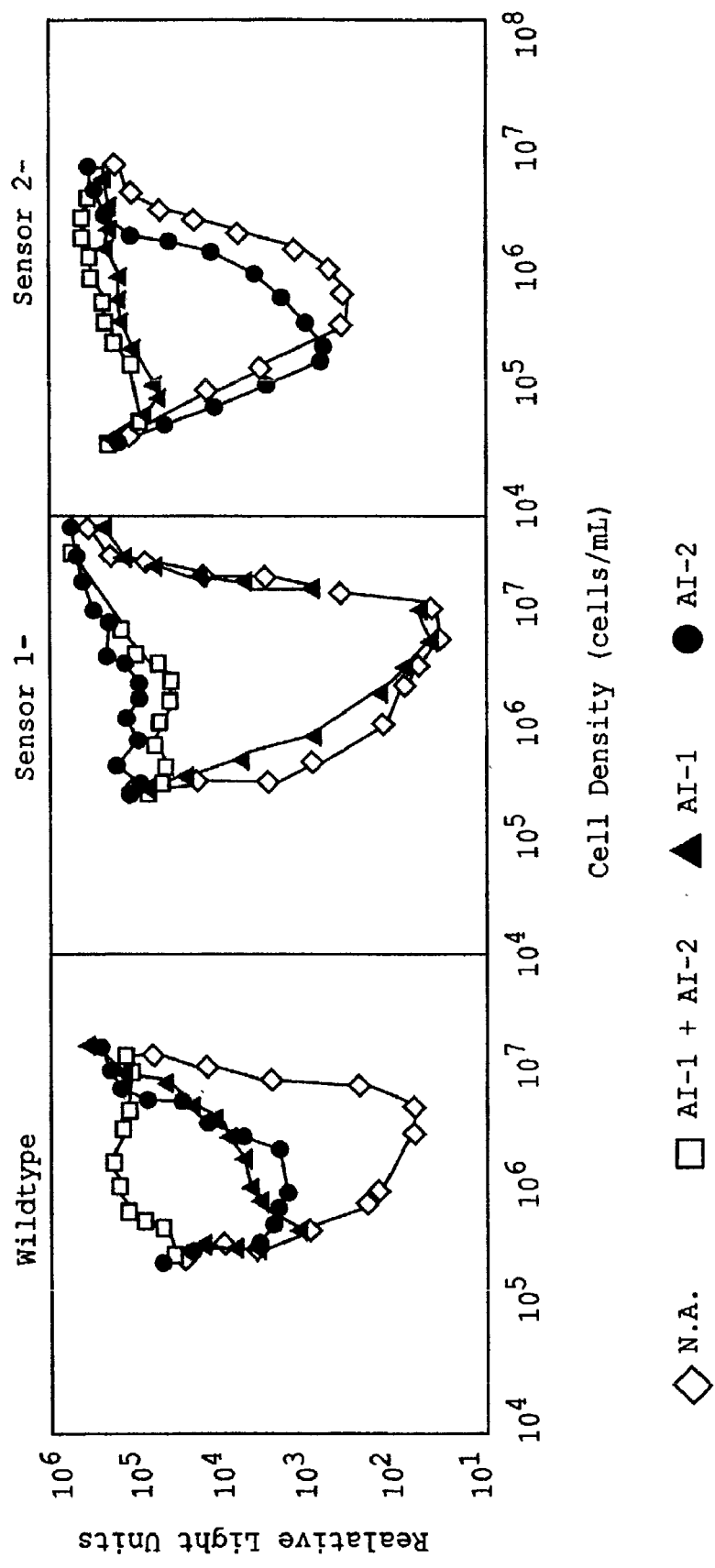
FIG. 15. Response phenotypes of *V. harveyi* wild-type and lux regulatory mutants. At the first time point, cell-free culture fluids (10%), or nothing (N.A) was added. Wild-type, cell-free culture fluid (AI-1+AI2); LuxS$^-$ cell-free culture fluid (AI-1); LuxM$^-$ cell-free culture fluid (AI-2). Relative light units are defined as cpm×10$^3$/CFU/ml.

In another aspect, the application provides a novel strain of *Vibrio Harveyi* having a genotype that is luxN$^-$, luxS$^-$. In some embodiments of the present invention, such a strain may be used to generate a strain that overexpresses or underexpresses a transporter that transports AI-2 into the cell relative to a wild type strain. The Gram-negative bacterium *Vibrio harveyi* contains two parallel quorum sensing circuits that synthesize and detect two different autoinducers (FIG. 13). Circuit 1 synthesizes AI-1 a HSL autoinducer similar in structure to autoinducers synthesized by the LuxI/R pathway found in other Gram-negative bacteria. Circuit 2 synthesizes AI-2, the structure of which has not been determined. Synthesis of AI-1 and AI-2 is dependent on LuxLM and LuxS respectively. Following the buildup of a critical external concentration of the autoinducers, signaling occurs via a series of a phosphorylation/dephosphorylation reactions. The AI-1 and AI-2 detectors, LuxN and LuxQ respectively, contain both a sensor kinase domain with a conserved histidine (H1) and an attached response regulator domain with a conserved aspartate (D1). Signals from both sensors are channeled to the shared integrator protein LuxU, which is phosphorylated on a histidine residue (H2). Subsequently, the signal is transduced to a conserved aspartate residue (D2) on the response regulator protein LuxO. LuxO-phosphate controls the expression of the luciferase structural operon luxCDABE that results in the emission of light. The presence of either AI-1 or AI-2 is sufficient to turn on light production in wild-type *V. harvyi* (strain BB120). For this reason, we have *V. harvyi* strains containing separate mutations in Lux genes L, M, S or Q that are defective in their ability to synthesize or detect AI-1 or AI-2, respectively. AI-2 is detectable using strain BB170 that is sensor 1$^-$, sensor 2$^+$ (LuxN$^-$, LuxQ$^+$). This strain was used to detect AI-2 in diverse bacteria. The light emission response of wild type, LuxN– and LuxQ– phenotypes to increasing cell density is shown in FIG. 15.

BB170 is a sensitive reporter for AI-2, however, the BB170 strain is not optimal for use as a reporter for inhibitors of the quorum pathway in a microtiter based assay. The desired strain is defective in its ability to detect AI-1 (sensor 1$^-$) and defective in its ability to synthesize AI-2. Thus, the invention provides a strain of *V. harveyi* that is genotypically luxN$^-$ and luxS$^-$. The new strain, designated MM32, is useful for identifying inhibitors of the quorum sensing pathway. For example, since the new strain is sensor 1$^-$, its growth or ability to luminesce will not be affected by those organisms producing AI-1. Further, since MM32 is defective for production of AI-2, the addition of exogenous AI-2, or analogs thereof, allows for the rapid identification of modulators (activators or inhibitors) of AI-2.

In addition, the materials described above are ideally suited for the preparation of a kit. Such a kit may comprise a carrier means being compartmentalized to receive in close confinement one or more container means such as vials, tubes, and the like, each of the container means comprising one of the separate elements to be used in the method.

The container means may comprise a strain of bacteria capable of detecting the presence of an autoinducer. Preferably, the bacterial strain will be capable of providing an easily detectable signal in the presence of autoinducer-2. More preferably, the desired strain is defective in its ability to detect AI-1 (sensor 1⁻) and defective in its ability to synthesize AI-2. Thus, the kit may provide a strain of *V. harveyi* that is genotypically luxN⁻ and luxS⁻ designated MM32. The bacterial strain is useful for identifying autoinducer-2 as well as modulators (activators and inhibitors) of autoinducer-2 and the quorum sensing pathway.

Methods for Detecting a Bacterial Biomarker

Many bacteria presently known to utilize the autoinducer-1 signaling factor associate with higher organisms, i.e., plants and animals, at some point during their lifecycles. For example, *Pseudomonas aeruginosa* is an opportunistic pathogen in humans with cystic fibrosis. *P.aeruginosa* regulates various virulence determinants with AI. Other examples of AI producing bacteria include *Erwinia carotovora, Pseudomonas aureofaciens, Yersinia enterocolitica, Vibrio harveyi*, and *Agrobacterium tumefaciens*. *E. carotovora* infects certain plants and creates enzymes that degrade the plant's cell walls, resulting in what is called "soft rot disease." *Yersinia enterocolitica* is a bacterium that causes gastrointestinal disease in humans and has been reported to produce an autoinducer. *P. aureofaciens* associates with the roots of plants and produces antibiotics that block fungus growth in the roots. The antibiotic synthesis is under autoinducer control. The present invention provides novel autoinducer-2 and methods of using autoinducer-2. In contrast to autoinducer-1, autoinducer-2 is believed to be an intra-species as well as inter-species signaling factor. Autoinducer-2 is further believed to regulate the expression of pathogenic and virulence factors not regulated by autoinducer-1. Thus, the present invention provides a method to identify and regulate the expression of bacterial biomarkers in, for example, pathogenic bacteria. Methods of the invention can be used to regulate the activity of bacterial pathogens that are present in both plants and animals.

The application further provides a method for detecting an autoinducer-associated bacterial biomarker by contacting at least one bacterial cell with an autoinducer under conditions and for such time as to promote induction of a bacterial biomarker. In some embodiments, the cell may have an increased expression level of a transporter that transports the autoinducer into the cell relative to a wild type cell. As used herein, an "autoinducer-associated bacterial biomarker" is any bacterial cell component that is regulated, modified, enhanced, inhibited or induced in response to an autoinducer. A biomarker can be any bacterial cell component that is identifiable by known microscopial, histological or molecular biological techniques. Such biomarkers can be used, for example, to distinguish pathogenic from nonpathogenic bacteria. Such a biomarker can be, for example, present on a cell surface, and it can be a protein, a nucleic acid, a phosphorylation event or any molecular or morphological characteristic of a bacterial cell that is modified as a result of the bacterium being contacted with an autoinducer. Preferably, the autoinducer is autoinducer-2. The method of the invention is particularly useful for identifying a biomarker that indicates bacterial pathogenicity. As previously noted, autoinducers are extracellular signalling factors used by a variety of bacteria to regulate cellular functions in response to various environmental stimuli, including high population density. It is believed that pathogenic bacteria express a biomarker, such as an antigenic determinant, as a result of increased autoinducer concentration in the surrounding environment. Thus, the present invention provides a method for identifying a biomarker by contacting a bacterium with autoinducer-2 and assaying for the presence of the biomarker.

The method of the invention contemplates the use of a probe to identify a biomarker present in a bacterial cell. As used herein, a "probe" can be a nucleic acid, protein, small molecule or antibody useful for detecting a bacterial biomarker present in a sample. The probe can be used in a screening assay to identify a biomarker present in a sample after the sample has been contacted with, for example, an autoinducer. For example, a bacterial biomarker produced by a bacterium following contact with an autoinducer can can be identified by contacting a sample containing the bacterium with a probe that binds to the biomarker. Such assays can be used to detect, prognose, diagnose, or monitor various conditions, diseases, and disorders, or monitor the treatment thereof. A probe can be detectably labeled such that the probe is detectable when bound to its target marker. Such means for detectably labeling a probe include a biotin-binding protein, such as avidin or streptavidin, bound to a reporter, such as an enzymatic, fluorescent, or radionuclide label. Other reporter means and labels are well known in the art.

In addition, the method of the invention can be used to analyze differential gene expression in a bacterial cell following contact with an autoinducer. In some embodiments, the cell may have an increased level of expression of a transporter that transports the autoinducer into the cell. For example, where the expression of genes in different cells, normally a cell of interest and a control, is compared and any discrepancies in expression are identified. In such assays, the presence of discrepancies indicates a difference in the classes of genes expressed in the cells being compared. Methods that can be used to carry out the foregoing are commonly known in the art.

The present invention provides a method for identifying a biomarker that can be a protein. For example, a bacterial protein expressed in response to an autoinducer can be detected using the appropriate antibody. In some embodiments, the bacterial protein may be expressed in a cell having an increased expression level of a transporter that transports an autoinducer into the cell relative to a wild type cell. The expressed protein can be, for example, an antigenic determinant indicative of a pathogenic bacterium. Antibodies used in the method of the invention are suited for use, for example, in immunoassays for the detection of such a determinant. The term "antibody" as used herein is meant to include intact polyclonal or monoclonal antibodies, as well as fragments thereof, such as Fab and F(ab')$_2$. For example, monoclonal antibodies are made from antigen containing fragments of a protein by methods well known to those skilled in the art (Kohler, et al., Nature, 256:495, 1975).

In addition, the monoclonal antibodies in these immunoassays can be detectably labeled in various ways. For example, radioisotopes may be bound to an immunoglobulin either directly or indirectly by using an intermediate functional group. Intermediate functional groups that often are used to bind radioisotopes that exist as metallic ions to immunoglobulins are the bifunctional chelating agents such as diethylenetriaminepentacetic acid (DTPA) and ethylenediaminetetraacetic acid (EDTA) and similar compounds.

Typical examples of metallic ions that can be bound to monoclonal antibodies are $^{111}$In, $^{97}$Ru, $^{67}$Ga, $^{68}$Ga, $^{72}$As, $^{89}$Zr, and $^{201}$Tl.

A probe useful in the method of the invention can also be a nucleic acid probe. For example, nucleic acid hybridization techniques are well known in the art and can be used to identify an RNA or DNA biomarker present in a sample containing a bacterium contacted with an autoinducer. Screening procedures that rely on nucleic acid hybridization make it possible to identify a biomarker from any sample, provided the appropriate probe is available. For example, oligonucleotide probes, which can correspond to a part of the sequence encoding a target protein, can be synthesized chemically. The DNA sequence encoding the protein can be deduced from the genetic code, however, the degeneracy of the code must be taken into account. For such screening, hybridization is preferably performed under in vitro or in in vivo conditions known to those skilled in the art.

In addition, the materials described above are ideally suited for the preparation of a kit. Such a kit may comprise a carrier means being compartmentalized to receive in close confinement one or more container means such as vials, tubes, and the like, each of the container means comprising one of the separate elements to be used in the method. A kit of the invention may contain a first container means comprising isolated autoinducer-2. The isolated autoinducer-2 can be used to regulate the expression of a biomarker in a target bacterium. For example, autoinducer-2 can be used to induce expression of a particular biomarker that can then be identified by a probe. Thus, the kit may contain a second container means comprising a probe that can be detectably labeled. The kit may also have a third container comprising a reporter-means, such as a biotin-binding protein, such as avidin or streptavidin, bound to a reporter, such as an enzymatic, fluorescent, or radionuclide label. Other reporter means and labels are well known in the art. For example, the kit of the invention may provide reagents necessary to perform nucleic acid hybridization analysis as described herein or reagents necessary to detect antibody binding to a target.

AI-2 regulated genes were identified using the following strategy based on the identification of luxS regulated target genes in S. typhimurium. MudJ transposon mutagenesis was employed to generate isogenic lacZ transcriptional fusions in wild type and luxS null strains of S. typhimurium (Hughes and Roth, 1988). Eleven thousand insertion mutants were made and subsequently screened for differential expression of the lacZ reporter gene. The MudJ insertions from candidate luxS regulated fusion strains were backcrossed by P22 transduction into S. typhimurium 14028 (wild type) and S. typhimurium SS007 (luxS::T-POP) to verify that the differences observed in lacZ expression were a consequence of the presence or absence of a functional luxS gene on the S. typhimurium chromosome. Eight lacZ fusions that appeared to produce higher levels of β-galactosidase in the strain carrying the wild type luxS gene than in the luxS null strain were identified.

The insertion sites of the eight luxS regulated MudJ fusions were determined by arbitrary PCR amplification of the MudJ-chromosome fusion junctions, followed by BLAST database analysis (Caetano-Anolles, 1993; Altschul et al., 1990). One MudJ insertion was located in the metE gene. MetE is involved in the biosynthesis of methionine, that is a precursor of SAM (Weissbach and Brot, 1991). Specifically, MetE catalyzes the final step in methionine biosynthesis in the absence of vitamin B12. Transcription of metE is induced when the substrate homocysteine is available and when the intracellular concentration of methionine is low (Urbanowski and Stauffer, 1989). We reason that metE is not a true target of AI-2 regulation, but instead metE transcription is induced in the wild type luxS strain relative to the luxS null strain because homocysteine is produced during the generation of AI-2 in the LuxS$^+$ strain. Consistent with this hypothesis, we found that addition of exogenous AI-2 to the metE-lacZ insertion mutant did not affect the transcription of the metE-lacZ fusion (not shown). We did not study the metE-lacZ fusion strain further.

The seven remaining MudJ insertions all resided in a single operon in S. typhimurium (FIG. 17, SEQ ID NO: 44). This operon is of unknown function but is predicted to encode an ABC transporter complex with striking similarity to the ribose transport operon (Rbs) of E. coli and S. typhimurium. We have named this operon the lsr operon for luxS-regulated. FIG. 17 shows the lsr operon of S. typhimurium and the sites of the luxS regulated MudJ insertions identified in our genetic screen.

The rbs operon of E. coli and S. typhimurium is shown in FIG. 17B. The functions encoded by the rbs operon are responsible for the high-affinity transport and phosphorylation of ribose (FIG. 17C) (Iida et al., 1984). The rbs operon has been most extensively studied in E. coli, although the rbs operon of S. typhimurium has the same arrangement and is predicted to encode proteins with identical functions. In the rbs operon of E. coli, the first gene, rbsD, encodes a protein with no known function. RbsA, RbsB and RbsC comprise the transport apparatus (Bell et al., 1986). RbsB is the periplasmic binding protein that recognizes ribose and interacts with RbsC. RbsC is the homodimeric channel-forming protein (Park et al., 1999). RbsA is the membrane-associated ATPase that supplies energy to drive the transport of the sugar into the cell (Buckel et al., 1986). RbsK is a cytoplasmic kinase that phosphorylates ribose upon entry into the cell (Hope et al., 1986). Finally, RbsR is the regulatory protein that functions at the rbs promoter to repress transcription of the operon in the absence of ribose (Mauzy and Hermodson, 1992).

In the lsr operon, the first gene, lsrA, encodes a protein homologous to the RbsA ATPase. The lsrC and lsrD genes are homologous to one another and to rbsC and are predicted to encode the components of a heterodimeric membrane channel. lsrB encodes a predicted sugar binding protein homologous to RbsB. In the lsr operon, three additional genes are located downstream of the putative ABC transporter. We have named these genes lsrF, lsrG and lsrE, respectively. The lsrF and lsrG genes encode proteins of unknown function, and lsrE, encodes a protein with homology to the E. coli ribulose phosphate epimerase (rpe) (Sprenger, 1995). The completed genome sequence of E. coli shows that it also possesses this operon (Blattner et al., 1997). In the E. coli genome, the operon has been designated the b1513 operon. The b1513 operon has an arrangement identical to the S. typhimurium lsr operon except that the E. coli b1513 operon does not contain a gene homologous to lsrE. We have not tested whether the b1513 operon is controlled by luxS in E. coli.

Figure 18:
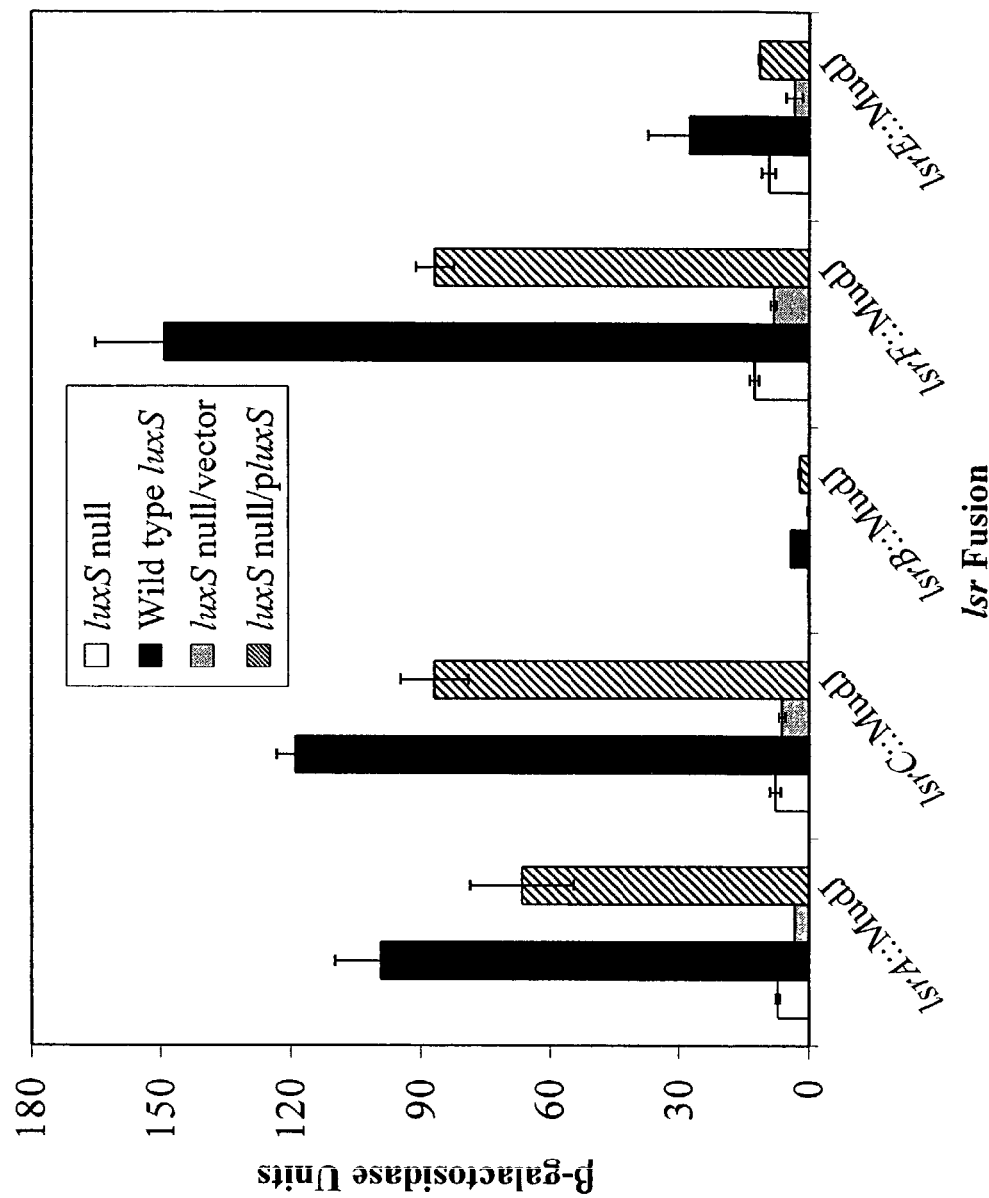
FIG. 18 shows luxS regulates the transcription of the lsr operon. The β-galactosidase activity is shown for five MudJ-lacZ reporter fusions in genes in the lsr operon. The white and black bars show the activity for the lsr::MudJ fusions in luxS::T-POP (denoted luxS null) and wild type luxS backgrounds, respectively. The gray and striped bars show the activity when the plasmids pUC18 (parental vector) and pAB15 (pUC18 expressing wild type luxS) were introduced into the luxS::T-POP strains, respectively.

Analysis of the luxS regulated fusions in the lsr operon. We obtained luxS regulated MudJ insertions in lsrA, lsrC, lsrB, lsrF and lsrE (FIG. 17). The β-galactosidase activity produced by each of these lacZ fusions was measured in wild type luxS and luxS null S. typhimurium strains (FIG. 18). Note that although we obtained three insertions in the lsrF gene, results for only one of these fusions appear in FIG. 18 because all three fusions have the same activity. The white bars show the β-galactosidase activity in the luxS null strain, and the black bars show the corresponding level of β-galactosidase activity for each fusion when wild type luxS is present. The figure shows that the lsrA, lsrC and lsrF fusions are induced 12- to 16-fold when wild type luxS is present.

The lsrB-lacZ and lsrE-lacZ fusions show lower activity than the fusions we obtained in the other three genes in this operon. In the case of lsrE, as this is the gene most distal to the promoter, the low activity may be explained by weak transcription. However, weak transcription cannot be the cause of the low activity observed for the lsrB-lacZ fusion because we observe high activity from the downstream lsrF-lacZ fusion. One explanation for the low activity in the lsrB-lacZ fusion is that a functional LsrB protein is required for the transcription of the lsr operon. To test this hypothesis, we constructed an inframe deletion of lsrB and demonstrated that it did not affect transcription of any of the other lsr-lacZ fusions (not shown). Furthermore, although the absolute P-galactosidase units are low for the lsrB-lacZ fusion, the fold induction of this fusion in the wild type luxS strain over the luxS null strain is about the same as that of all the other fusions we obtained in lsr genes. Based on these results, we conclude that this particular fusion joint is uncommonly polar, and results in lower than expected transcription of lacZ, which would account for its reduced β-galactosidase activity.

To verify that the induction of transcription of the lsr operon is due to luxS, we complemented the fusion strains with the luxS gene in trans. FIG. 18 shows these data. In a luxS null *S. typhimurium* background, introduction of the parent vector without luxS had no effect on the β-galactosidase expression of the lsr fusions (gray bars). However, introduction of the cloned luxS gene into each of the lsr-lacZ fusion strains restored β-galactosidase activity to nearly the level observed for the fusions in the wild type luxS background (striped bars).

AI-2 regulates the transcription of the lsr operon. The above results show that the lsr operon is induced in the presence of a functional luxS gene. In earlier work, we have shown that the LuxS enzyme catalyzes the final step in the biosynthesis of AI-2 (Schauder et al., 2001). We interpret our above results to mean that regulation of the lsr operon by luxS is mediated by the presence of AI-2. We further predict that AI-2 should exert its regulatory effect on the lsr operon by signalling from the outside of the cell. However, the strategy we used to identify the lsr operon relies on internal production of AI-2 in *S. typhimurium*. To prove that AI-2 is sufficient for lsr regulation, and also to prove that external AI-2 is capable of mediating this effect, we tested whether exogenously supplied AI-2 could induce the lsr-lacZ fusions in *S. typhimurium* strains containing a null mutation in luxS.

We have previously reported that AI-2 is synthesized from S-adenosylhomocysteine (SAH) in two steps by the action of the Pfs and LuxS enzymes (Schauder et al., 2001). Specifically, SAM is used as a ubiquitous intracellular methyl donor. SAH is formed when the methyl group of SAM is transferred to its various substrates. Pfs cleaves adenine from SAH to form SRH, and LuxS cleaves SRH to form homocysteine and AI-2. In that report we developed a procedure for the in vitro production of *S. typhimurium* AI-2 from SAH using purified Pfs and LuxS proteins (Schauder et al., 2001). We can estimate the AI-2 concentration in our in vitro preparations indirectly by measuring the concentration of homocysteine that is produced along with AI-2 by LuxS. Using AI-2 prepared by this method, we tested the effect of the exogenous addition of AI-2 on the regulation of the *S. typhimurium* lsr operon.

Various *S. typhimurium* lsr::MudJ fusion strains were grown to late exponential phase in LB medium supplemented with AI-2 prepared by our in vitro method at an approximate concentration of 70 µM. This is roughly twice the concentration of AT-2 that we estimate to be present in *S. typhimurium* cell-free supernatants (not shown). As a control, we performed the same experiment with material from in vitro reactions carried out with SAH and Pfs enzyme in the absence of the LuxS enzyme. This reaction produces adenine and SRH. Homocysteine was added to this control mixture following the reaction to compensate for the homocysteine that would be produced by LuxS. Therefore, the only component absent from the control reaction was AI-2. The β-galactosidase measurements in FIG. 19 show that, in the presence of the –AI-2 control reaction, low expression of the lsr-lacZ fusions occurs in the absence of luxS (white bars), and similar to those shown in FIG. 18, the fusions are induced to varying degrees in the presence of wild type luxS (black bars). In strains lacking luxS, addition of 70 µM exogenous AI-2 induces the expression of the lsr-lacZ fusions to levels above that when wild type luxS is present on the chromosome (gray bars). This experiment shows that exogenous AI-2 is sufficient for induction of the lsr operon in *S. typhimurium*.

We also supplied exogenous AI-2 to the *S. typhimurium* lsr-lacZ fusion strains that were wild type for luxS on the chromosome (striped bars). FIG. 19 shows that increasing the level of AI-2 above the endogenous level produced by chromosomal luxS results in an additional stimulation of the expression of the lsr-lacZ fusions. This result indicates that, under the conditions that we are performing our experiments, the lsr operon is not fully induced by the endogenously produced AI-2.

Identification of LsrR: a protein responsible for mediating AI-2 regulation of transcription of the lsr operon. The above results show that AI-2 induces the expression of the lsr operon. However, because no DNA binding protein is encoded in the lsr operon, we did not understand how the presence of AI-2 could modulate the transcription of the lsr operon. We hypothesized that a DNA binding protein must exist in *S. typhimurium* that functions to couple the presence of the AI-2 signal to expression of the lsr operon. To identify this regulatory factor, we performed a genetic selection for mutants in which the Lac⁻ phenotype of a luxS null, lsr-lacZ fusion strain was suppressed. Our reasoning was as follows: all of the luxS null strains containing lacZ fusions in the lsr operon do not grow on lactose minimal plates. However, the presence of a functional luxS gene on the chromosome induces the expression of the lacZ gene in these fusions to a sufficient level to restore growth on lactose minimal plates. Therefore, selection for growth of a luxS null, lsr-lacZ *S. typhimurium* strain on lactose minimal plates enabled us to isolate *S. typhimurium* colonies that had acquired spontaneous suppressor mutations that allowed increased expression of the lsr-lacZ fusion in the absence of luxS (i.e., in the absence of AI-2). We performed this experiment with the representative lsrC-lacZ strain. Eight spontaneous Lac⁺ colonies were isolated by this technique and studied further. We also used a transposon mutagenesis strategy to identify the putative regulatory factor. Mutagenesis with the transposon T-POP was performed on the luxS null, lsrC-lacZ fusion strain. 12,000 insertions were made, and two transposon insertion mutants were identified that restored growth to the luxS null, lsrC-lacZ strain on lactose minimal medium.

Linkage analysis showed that the T-POP insertions and the spontaneous suppressor mutations could be co-transduced with high frequency (76% co-transduction) with the lsrC::MudJ insertion. Database analysis of the *S. typhimurium* genome revealed that a gene encoding a predicted DNA binding protein of unknown function is located immediately upstream of the lsr operon but is transcribed divergently (FIG. 17). This protein is homologous to SorC, a DNA binding protein that functions as both an activator and a repressor of transcription of genes involved in sorbose metabolism in Klebsiella pneumoniae (Wehmeier and Lengeler, 1994). We predicted that the transposon and spontaneous suppressor mutations could be located in this gene. Indeed, we were able to PCR amplify the chromosome-T-POP fusion junction from both T-POP suppressor strains using primers specific to T-POP and the regions flanking this putative regulatory gene. In addition, we PCR amplified and sequenced this regulatory gene from the chromosome of the eight spontaneous suppressor strains. In every case, this gene was found to contain either a point mutation or a deletion. We have named this gene lsrR, for regulator of the lsr operon. Because inactivation of the lsrR gene results in high-level expression of the lsr operon in a luxS null background, these results strongly suggest that the wild type function of LsrR is to repress the expression of the lsr operon in the absence of AI-2.

Deletion of lsrR results in unregulated transcription of the lsr operon. To verify the role of LsrR in AI-2 regulation of lsr operon transcription, we constructed an inframe deletion of lsrR in *S. typhimurium* and assayed the expression of the lsr-lacZ fusions in the presence and absence of lsrR. The results are shown in FIG. 20 for the representative lsrC-lacZ reporter fusion. The first pair of bars shows that, as in FIG. 18, when wild type lsrR is present, lsrC-lacZ expression is repressed in a luxS null strain and derepressed 23-fold when luxS is present and the AI-2 signal is synthesized (white and black bar, respectively). In contrast, the second pair of bars shows that deletion of lsrR results in high-level expression (over 100-fold derepression) of the lsrC-lacZ reporter whether or not luxS is present. This result demonstrates that the lsr operon cannot be regulated by AI-2 in the absence of LsrR. We cloned the wild type lsrR gene and expressed it in trans under an exogenous promoter to show that LsrR could complement the ΔlsrR defect. The third and fourth pairs of bars in FIG. 20 show that in trans expression of lsrR in both wild type lsrR and ΔlsrR *S. typhimurium* strains causes repression of the lsrC-lacZ reporter fusion. Specifically, complete repression of lsrC-lacZ transcription occurs in the luxS null strains (white bars), and nearly complete repression of lsrC-lacZ transcription occurs in the wild type luxS strains (black bars). These results show that introduction of lsrR complements the ΔlsrR defect. However, when lsrR is overexpressed in a wild type luxS background, the AI-2 produced is apparently insufficient to compensate for the increased LsrR protein produced by the vector. This imbalance results in incomplete inactivation of LsrR by AI-2, so lsr operon repression occurs. We performed control experiments to show that expression of the parent vector without the cloned lsrR gene had no effect on lsrC-lacZ activity in any of these strains (not shown).

Analysis of the LsrR suppressor mutations. The sequence of the LsrR protein is shown in FIG. 21 as well as the spontaneous mutations we identified in the suppressor selection. The β-galactosidase activities of the spontaneous lsrR mutations were measured and compared to that of wild type lsrR and the lsrR deletion. Again, the lsrC-lacZ fusion is used as the representative reporter for the lsr operon. Results are shown in FIG. 22. The two left-most bars show the control experiments in which lsrC-lacZ expression is measured in the luxS null and wild type luxS strains. Both of these strains contain wild type lsrR. As shown above, expression of lsrC-lacZ is derepressed in the wild type luxS strain compared to the luxS null strain (in this case, 9-fold). The remaining bars in FIG. 22 represent the activities of various lsrR mutants in a luxS null background. Specifically, mutations A22T, A120T and G208R result in an increase in expression of the lsrC-lacZ fusion to about the same level as that when wild type luxS is present (6- to 10-fold). Compared to the ΔlsrR strain, we observe an intermediate level of lsrC-lacZ expression in an lsrR mutant with a deletion encompassing the N-terminus of the protein and part of the lsr promoter (Δ5') and from mutations resulting in the alterations L145Q and L134P (approximately 80-fold derepression). Maximal derepression of lsrC-lacZ occurs in the L39P and Y25H mutants. We know this is maximal derepression of the operon because the activities of these two missense mutants equal that caused by the null lsrR::T-POP and ΔlsrR mutations (approximately 250-fold derepression). The L39P point mutation is located in the predicted helix turn helix DNA binding domain, apparently eliminating the repressor function of the protein. Apparently, the Y25 residue is critical for function, or this particular alteration simply cannot be tolerated. Note that although we obtained two T-POP insertions in lsrR, the activity for only one of the insertions is shown. Both insertions gave identical results in this experiment.

The Lsr ABC transporter has a role in elimination of extracellular AI-2. The lsr operon apparently encodes an ABC transporter resembling the ribose transporter. As AI-2 is a ribose derivative, we hypothesize that AI-2 could be the ligand for the Lsr transporter complex. Therefore, one possible function of the Lsr operon is to transport the AI-2 synthesized by LuxS in the cytoplasm out of the *S. typhimurium* cell. This possibility seems unlikely because the lsr operon encodes a transporter with homology to binding protein-dependent ABC transporters that function to import compounds into the cytoplasm (Nikaido and Hall, 1998). Moreover, mutants with insertions in the lsr operon are not deficient in AI-2 production, indicating that the Lsr transporter is not required for export of the AI-2 signal into the medium (not shown).

We have previously reported that, in *S. typhimurium*, extracellular AI-2 activity accumulates to maximal levels in late exponential phase, and subsequently the AI-2 activity disappears from the medium (Surette and Bassler, 1998; 1999). Additionally, we have shown that AI-2 in cell-free culture fluids remains active for long periods of time, indicating that the disappearance of the activity from the extracellular environment is not due to instability of AI-2 (Surette and Bassler, 1999). Furthermore, we have shown that elimination of AI-2 from the medium requires protein synthesis (Surette and Bassler, 1999). Therefore, an alternative possibility for the function of the Lsr complex is to import extracellular AI-2 into the cytoplasm of *S. typhimurium*. We performed an experiment to investigate this possibility.

Cultures of *S. typhimurium* luxS null strains containing a wild type lsr operon or containing mutations inactivating lsr genes were grown to mid-exponential phase in LB at 37° C. AI-2 prepared by our in vitro method was added to the cultures, and the cultures were incubated with the AI-2 for an hour. Subsequently, the cells were removed from the culture fluid by centrifugation, and the resulting cell-free culture fluids were assayed for AI-2 activity using the *V. harveyi* AI-2 bioassay. This assay involves measuring the increase in light production of a *V. harveyi* quorum sensing reporter strain that induces bioluminescence exclusively in response to the presence of AI-2. In the present experiment, the bioassay allowed us to determine the level of AI-2 activity remaining in the culture fluids of the different *S. typhimurium* mutants. Since all the *S. typhimurium* strains we used in this experiment contained null mutations in luxS, the only AI-2 that could be present in the cell-free culture fluids came from that that we added exogenously.

FIG. 23 shows the results of this experiment. The control experiment shows that, as expected, no AI-2 activity is present in culture fluids prepared from the *S. typhimurium* luxS null strain used as the parent for these studies. The bar labeled "Input" shows that AI-2 sufficient to induce the *V. harveyi* bioluminescence reporter 1000-fold was added to the remainder of the cultures. The input activity was measured by adding AI-2 to the parent *S. typhimurium* culture and immediately chilling the culture on ice, followed by centrifugation of the cells and isolation of the cell-free culture fluid. The figure shows that 1 h incubation of the wild type lsr strain with the input AI-2 results in disappearance of 92% of the AI-2 activity from the culture fluid, as activity sufficient to induce the bioassay strain only 80-fold remained (see the bar labeled wild type lsr). In contrast, *S. typhimurium* strains containing MudJ insertion mutations in lsrA, lsrC and lsrB were unable to eliminate AI-2 from the culture fluids, as AI-2 activity equivalent to the input activity remained in the culture fluids after the incubation period. In addition, a strain containing an inframe deletion in lsrB is also unable to eliminate AI-2 from the supernatant in this assay (not shown). These results indicate that a functional Lsr ABC transporter is required for the process of removal of AI-2 from the medium. Presumably, inactivation of lsrD would result in a phenotype identical to that caused by mutation of lsrA, lsrC and lsrB, since we predict that LsrD is required to form the channel along with LsrC. Unfortunately, we did not obtain a MudJ insertion in lsrD, so this was not tested.

However, lsrD mutants may be obtained using the MudJ insertion procedure described herein, other transposon based mutagenesis procedures, genetic engineering techniques such as those described above (including site directed mutagenesis), chemical mutagenesis techniques or screens for isolating spontaneous mutants that are not responsive to AI-2. MudJ insertions in lsrF and lsrE did not impair the ability of *S. typhimurium* to remove AI-2 from the medium. The figure shows that, similar to when the wild type lsr operon is present, 95% of the input activity disappears after 1 h incubation in the lsrF and lsrE mutants. The lsrF and lsrE genes are located downstream of the genes encoding the structural components of the transport apparatus (FIG. 17). Therefore, although the MudJ insertions generating lacZ transcriptional fusions to lsrE and lsrF are induced by AI-2 by virtue of their presence in the lsr operon, LsrE and LsrF are not expected to be required for building a functional transport apparatus. Taken together, our results indicate that only the genes that encode the structural components of the Lsr transporter are required for removal of AI-2 from *S. typhimurium* cell-free culture fluids.

FIG. 23 also shows that inactivation of lsrR results in the highest level of removal of AI-2 from the extracellular culture fluids of *S. typhimurium*, as over 99% of the activity is gone after the 1 h incubation. To verify that elimination of AI-2 from the medium that we observed in this experiment depends on the Lsr transporter, we combined the ΔlsrR mutation with the lsrC::MudJ insertion and performed an identical experiment. The final bar in FIG. 23 shows that regardless of the presence or absence of lsrR, inactivation of the Lsr transporter renders *S. typhimurium* unable to eliminate AI-2 from the medium because in the ΔlsrR, lsrC::MudJ double mutant, the level of AI-2 did not decrease compared to the input activity.

Deletion of lsrR results in maximal removal of the AI-2 from the culture fluids. This result is expected because the ΔlsrR strain displays completely derepressed expression of the lsr operon, and this strain would therefore be predicted to have increased levels of the Lsr transporter compared to the wild type strain. If this is the case, the ΔlsrR strain should have an enhanced capability to remove AI-2 from the medium. To test this idea, we assayed the rate of disappearance of AI-2 from the medium over time for the ΔlsrR mutant and compared that to the rate of disappearance for the wild type strain (FIG. 24). This experiment shows that removal of AI-2 from the medium by the wild type lsrR strain occurs rather steadily over first 45 min of the incubation period, then more rapidly between 45 min and 1 h (triangles). Specifically 97, 85, 82, 75 and 6% of the input AI-2 activity remains at 2, 15, 30, 45 and 60 min, respectively. In contrast, in the ΔlsrR mutant, only 10% of the AI-2 activity remains after 2 minutes, and all but 2% of the activity is gone by 15 min (circles). This result demonstrates that the derepression of the expression of the Lsr transport complex increases the efficiency of elimination of AI-2 from the external environment of *S. typhimurium*.

In our previous investigations of the model luminous bacterium *V. harveyi*, we identified a quorum sensing signal called AI-2, and showed that it is involved in induction of the expression of luciferase (Bassler et al., 1993; Bassler et al., 1994a). Subsequently, we showed that AI-2 and the synthase required for its production, LuxS, are present in a wide variety of bacterial species (Bassler et al., 1997; Bassler, 1999; Miller and Bassler, 2001; Surette et al., 1999). We have suggested that AI-2 is used for inter-species communication among bacteria (Bassler et al., 1997; Miller and Bassler, 2001; Surette et al., 1999). However, prior to the present invention, it was not clear how AI-2 is detected nor what functions are regulated by this signal in most species of bacteria. In the present application, we provide the results of experiments aimed at identifying the AI-2 regulated genes and the mechanism of AI-2 signal transduction in the enteric pathogen *S. typhimurium*.

The following description sets forth the general procedures involved in practicing this aspect of the present invention. To the extent that specific materials are mentioned, it is merely for purposes of illustration and is not intended to limit the invention. Unless otherwise specified, general cloning procedures, such as those set forth in Sambrook et al., Molecular Cloning, Cold Spring Harbor Laboratory (1989) (hereinafter "Sambrook et al.") or Ausubel et al. (eds) Current Protocols in Molecular Biology, John Wiley & Sons (1998) (hereinafter "Ausubel et al.") are used.

EXAMPLE 1

Quorum Sensing in *Escherichia coli* and *Salmonella typhimurium*

There have been preliminary indications that *E. coli* senses cell density (Huisman et al., Science 265: 537–539, 1994; Sitnikov et al., Proc. Natl. Acad Sci USA 93 336–341, 1996; Garcia-Lara et al., J. Bacteriol. 178: 2742–2748, 1996). We took advantage of the reduced selectivity of the Signaling System 2 sensor in *V. harveyi* to develop a sensitive assay for detection of extracellular signal compounds produced by *E. coli* and *S. typhimurium*. Using this assay we could determine the conditions under which many strains of *E. coli* and *S. typhimurium* synthesize, secrete, and degrade a signaling substance that will interact with the *V. harveyi* System 2 detector.

Materials and Methods

Preparation of cell-free culture fluids. *E. coli* strains AB1157 and DH5 and *S. typhimurium* strain LT2 were grown at 30° C. overnight with aeration in LB broth containing glucose at the concentrations specified in the text. The following morning fresh LB medium containing the same concentration of glucose used for the overnight growth was inoculated at a 1:100 dilution with the over-night grown cultures. The fresh cultures were grown for various times at 30° C. with aeration. Cell-free culture fluids were prepared by removing the cells from the growth medium by centrifugation at 15,000 rpm for 5 min in a microcentrifuge. The cleared culture fluids were passed through 0.2 m HT Tuffryn filters (Gelman) and stored at −20° C. Cell-free culture fluids containing *V. harveyi* Autoin-ducer-2 were prepared from *V. harveyi* strain BB152 (Autoinducer 1−, Autoinducer 2+). *V. harveyi* BB120 (Autoinducer 1+, Autoin-ducer 2+) was used to prepare culture fluids containing Autoinducer-1. In both cases, the *V. harveyi* strains were grown overnight at 30° C. with aeration in AB (Autoinducer Bioassay) (Bassler et al., 1993, supra) medium. Cell-free culture fluids from *V. harveyi* were prepared from the overnight culture exactly as described above for *E. coli* and *S. typhimurium*.

Assay for production of signaling compounds. Cell-free culture fluids from *E. coli*, *S. typhimurium* and *V. harveyi* strains were tested for the presence of signaling substances that could induce luminescence in the *V. harveyi* reporter strain BB170 or BB886. In the assays, 10 µl of cell-free culture fluids from *E. coli* ABl157, *E. coli* DH5, and *S. typhimurium* LT2 strains grown and harvested as described above were added to 96-well microtiter dishes. The *V. harveyi* reporter strain BB170 or BB886 was grown for 16 h at 30° C. with aeration in AB medium, diluted 1:5000 into fresh AB medium, and 90 l of the diluted cells were added to the wells containing the *E. coli* and *S. typhimurium* cell-free culture fluids. Positive control wells contained 10 µl of cell-free culture fluid from strain *V. harveyi* BB152 (Autoinducer-1−, Autoinducer-2+) or *V. harveyi* BB120 (Autoinducer-1+, Autoinducer-2+). Negative control wells contained 10 µl of sterile growth medium. The microtiter dishes were shaken in a rotary shaker at 175 rpm at 30° C. Every hour, light production was measured using a Wallac Model 1450 Microbeta Plus liquid scintillation counter in the chemiluminescence mode. The *V. harveyi* cell density was measured by diluting the same aliquots of cells used for measuring luminescence, spreading the dilutions onto solid LM medium (Bassler et al., 1993, supra), incubating the plates overnight at 30° C., and counting the resulting colonies the following day.

Preparation of *E. coli* and *S. typhimurium* viable and UV-killed cells for the activity assay. *E. coli* ABl157, *E. coli* DH5 and *S. typhimurium* LT2 cultures were grown for 8 h in LB containing 0.5% glucose at 30° C. with aeration. The cultures were subjected to centrifugation for 5 min at 15,000 rpm in a microcentrifuge and the growth medium was removed from the cell pellets by aspiration. The cell pellets were resuspended in AB medium and washed by vigorous mixing. The cells were again subjected to centrifugation for 5 min at 15,000 rpm. The AB wash medium was removed and discarded and the cells were resuspended in fresh AB medium. Each cell suspension was diluted to give $1 \times 10^6$ cells/10 µl, and multiple 10 µl aliquots were added to wells of microtiter dishes. Half of the cell aliquots were treated with short wavelength ultraviolet light for 15 min at a distance of 10 cm. This treatment was sufficient to kill all of the cells as judged by plating and incubating the UV-treated cells, and ensuring that no growth occurred by the next day. 90 µl of the diluted *V. harveyi* reporter strain BB170 was next added to the wells containing either the viable or dead *E. coli* and *S. typhimurium* cells, and the activity assay was carried out exactly as described in the previous section.

Analysis of glucose in *S. typhimurium* LT2 culture fluids. Glucose concentrations were determined in cell-free culture fluids prepared from *S. typhimurium* using a Trinder assay (Diagnostic Chemicals Ltd.) according to the recommendations of the manufacturer, except that the glucose standards were prepared in LB medium. The assay was sensitive to less than 0.002% glucose. No interfering substances were present in LB medium or spent LB culture fluids.

Results and Discussion

*E. coli* ABI157 and *S. typhimurium* LT2 produce a signaling substance that specifically induces one of the two quorum sensing systems of *V. harveyi*. The *V. harveyi* reporter strain BB170 has the quorum sensing phenotype Sensor 1−, Sensor 2+. It induces lux expression in response to extracellular signals that act exclusively through the Signaling System 2 detector. Addition of 10% cell-free spent culture fluid prepared from *V. harveyi* strain BB152 (which contains the System 2 autoinducer) stimulates the reporter strain roughly 1000-fold over the endogenous level of luminescence expression. In FIG. 1, the light production by *V. harveyi* BB170 induced by the addition of 10% cell-free spent culture fluids is normalized to 100% activity.

Figure 1A:
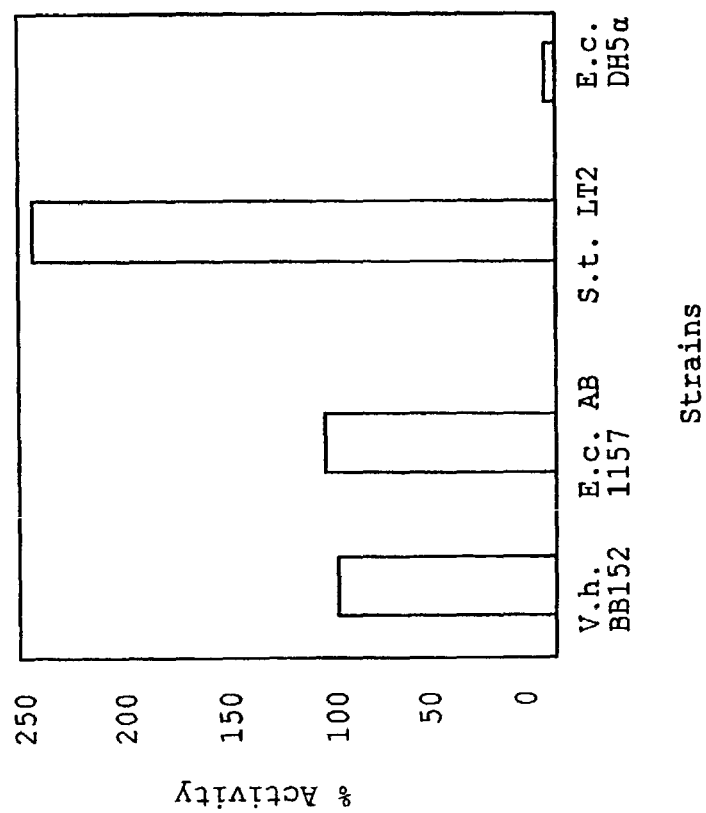

*E. coli* strain AB1157 and *S. typhimurium* strain LT2 were grown for 8 h in LB broth or LB broth containing 0.5% glucose. The *E. coli* and *S. typhimurium* cells were removed from the growth medium and the cell-free culture fluids were prepared and assayed for an activity that could induce luminescence expression in *V. harveyi*. Addition of 10% cell-free culture fluid from *S. typhimurium* LT2 or *E. coli* AB1157 grown in LB containing glucose maximally induced luminescence in the reporter strain BB170, similar to culture fluids from *V. harveyi* BB 152 (FIG. 1A). Specifically, *E. coli* AB1157 produced 106% and *S. typhimurium* produced 237% of the *V. harveyi* BB152 activity. When the *E. coli* and *S. typhimurium* were grown in LB without added glucose they did not produce the signaling factor. Substitution of 10% (v/v) of LB medium containing 0.5% glucose did not stimulate luminescence in the reporter strain, indicating that there is no substance in the LB-glucose growth medium that induces luminescence expression in *V. harveyi*. We tested obvious candidates for the signal including glucose, amino acids, cAMP, acetate, homoserine lactone, -ketoglutarate and other keto acids that are known to be excreted. None of these compounds has activity. These results suggest that *V. harveyi* BB170 can respond to some substance secreted by *E. coli* AB 1157 and *S. typhimurium* LT2 when they are grown on LB containing glucose.

Analogous experiments were performed with the *V. harveyi* reporter strain BB886 (Sensor 1+, Sensor 2−). *V. harveyi* BB886 is defective in its response to signaling compounds that act through the Signaling System 2 detector, but it is an otherwise wild type strain (Bassler et al., Mol. Microbiol. 13: 273–286, 1994). FIG. 1B shows the normalized 100% activation of *V. harveyi* BB886 by cell-free spent culture fluids prepared from *V. harveyi* BB120. *V. harveyi* BB120 produces the System 1 autoinducer N-(3-hydroxybutanoyl)-L-homoserine lactone (Bassler et al., 1993, supra). Addition of *S. typhimurium* LT2 and *E. coli* AB1157 cell-free culture fluids to *V. harveyi* strain BB886 caused a 5% and a 1% increase above the control level (FIG. 1B). Together the results of FIG. 1 shows that the signaling compound produced by *E. coli* and *S. typhimurium* must act specifically through *V. harveyi* Signaling System 2 and not some other, unidentified pathway.

Viable *E. coli* AB1157 and *S. typhimurium* LT2 are required for secretion of the signaling compound. We considered the possibility that growth of *E. coli* AB1157 and *S. typhimurium* LT2 in LB medium containing glucose simply allowed them to utilize and therefore remove some preexisting inhibitor of induction of luminescence. To show that the cells themselves produce the soluble signaling factor, we added washed *E. coli* and *S. typhimurium* cells directly to the luminescence assay. These results are presented in FIG. 2. In this experiment, *E. coli* AB1157 and *S. typhimurium* LT2 were grown for 8 h in LB containing 0.5% glucose; the conditions for maximal production of the signaling factor. The cells were removed from the LB-glucose growth medium by centrifugation, and sterile *V. harveyi* luminescence assay medium was used to wash and resuspend the cell pellets. $1 \times 10^6$ *E. coli* AB1157 or *S. typhimurium* LT2 cells were added to the diluted *V. harveyi* BB170 culture at the start of the experiment. In FIG. 2, the left-hand bar in each series shows that the presence of washed *E. coli* AB1157 or *S. typhimurium* LT2 cells is sufficient to fully induce luminescence in *V. harveyi* BB170. *E. coli* ABl157 and *S. typhimurium* LT2 stimulated lux expression in *V. harveyi* BB170 821-fold and 766-fold respectively. Identical aliquots of the washed *E. coli* or *S. typhimurium* cells were killed with short wave ultraviolet light prior to addition to the assay. When dead cells were included in the assay, no stimulation of luminescence occurred. In FIG. 2, these results are shown in the right-hand bar for each strain. Taken together, the results show that the stimulatory factor is produced by the *E. coli* AB1157 and *S. typhimurium* LT2 cells themselves during the time course of the experiment; the factor could not have come from the medium in which the cells had been grown. This factor is actively released into the medium by *E. coli* and *S. typhimurium* because dead cells have no activity.

*E. coli* DH5 does not produce the signaling activity. Clinical isolates of *E. coli* and Salmonella also produce the signaling compound. Ten clinical isolates of Salmonella and five pathogenic isolates of *E. coli* O157 were assayed and all produced the activity. It was conceivable that the signal was some normal byproduct of glucose metabolism that simply diffuses out of the cells. This is not the case however, because we show that *E. coli* DH5, which is equally capable of utilizing glucose as *E. coli* ABl157 and *S. typhimurium* LT2, does not produce the signaling activity. FIG. 1A demonstrates that unlike *E. coli* AB1157 and *S. typhimurium* LT2, the addition of 10% cell-free culture fluid prepared from *E. coli* DH5 grown 8 h in LB containing 0.5% glucose does not stimulate light production in *V. harveyi* BB170. Similarly, inclusion of washed viable or killed *E. coli* DH5 cells in the luminescence assay does not stimulate *V. harveyi* BB170 to produce light (FIG. 2). The inability of *E. coli* DH5 to produce the activity indicates that this highly domesticated strain lacks the gene or genes necessary for either the production or the export of the signaling activity. We assayed other laboratory strains of *E. coli* for the signaling activity (Table 1). Only *E. coli* DH5 was completely defective in producing the extracellular signal.

Table 1. The induction of luminescence in *V. harveyi* reporter strain BB 170 by cell-free culture fluids from *V. harveyi*, *S. typhimurium* and *E. coli* is shown. Cell-free culture fluids were prepared from various strains of *V. harveyi*, *S. typhimurium* and *E. coli* as described and tested for production of a signaling substance that could stimulate light production in the reporter strain *V. harveyi* BB170. The level of *V. harveyi* stimulation was normalized to 100%. The data for the 5 h time point are shown.

| Species and Strain | Induction of luminescence (%) |
| --- | --- |
| *V. harveyi* | |
| *V. harveyi* BB152 | 100 |
| Salmonella | |
| *S. typhimurium* LT2 | 237 |
| *E. coli* | |
| *E. coli* AB1157 | 106 |
| *E. coli* DH5 | 5 |
| *E. coli* JM109 | 76 |
| *E. coli* MG1655 | 100 |
| *E. coli* MC4100 | 93 |

Glucose regulates the production and degradation of the signaling factor by *S. typhimurium* LT2. Cell-free culture fluids from *S. typhimurium* LT2 and *E. coli* ABl157 cells grown in LB without added glucose did not stimulate the expression of luminescence in the reporter strain, indicating that metabolism of glucose is necessary for the production of the signal. We tested other carbohydrates, and in general, growth in the presence of PTS sugars (see Postma et al., in *Escherichia coli* and *Salmonella* Cellular and Molecular Biology, (F. C. Niehardt, ed), Am. Soc. Microbiol., Washington D.C., pp. 1149–1174, 1996) enabled *E. coli* AB1157 and *S. typhimurium* LT2 to produce the signal. Of the sugars tested, growth on glucose induced the synthesis of the highest level of activity. Growth on other carbon sources, for example TCA cycle intermediates and glycerol, did not induce significant production of the signaling activity.

Figures 3A, 3B:
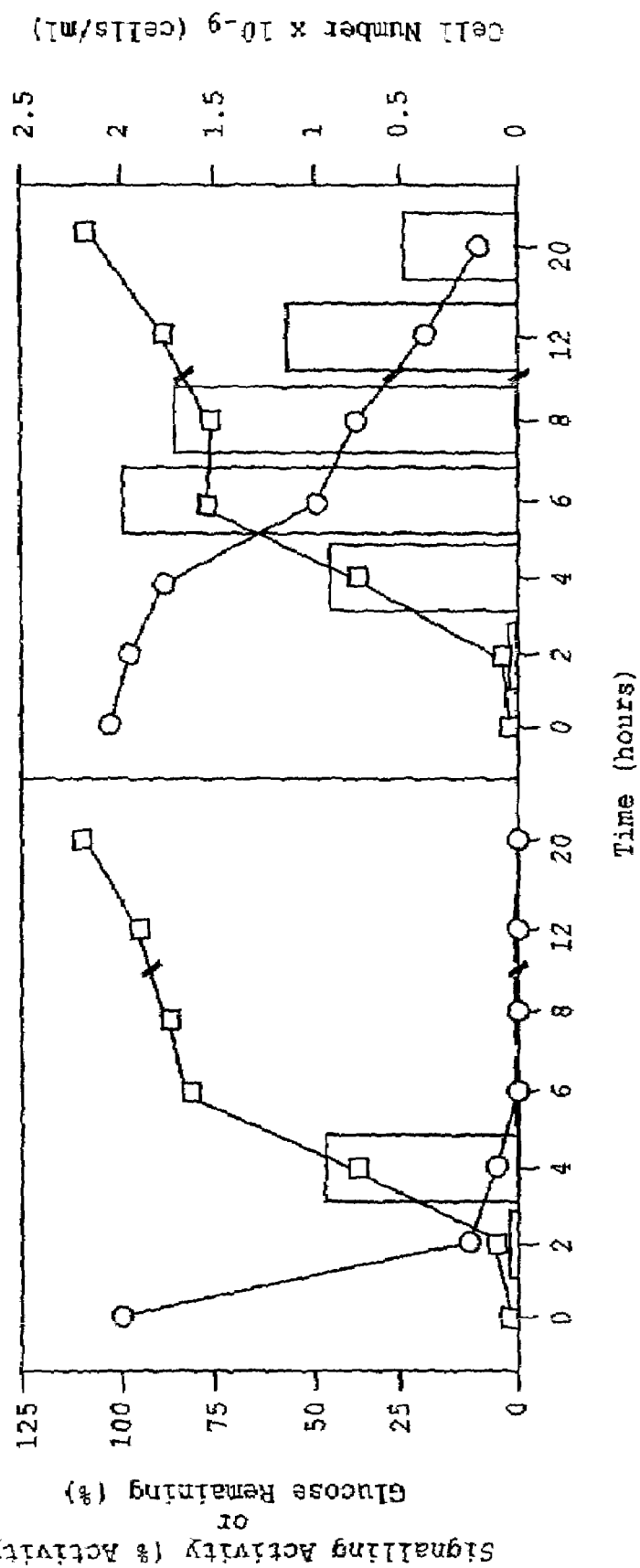
FIG. 3. Effect of glucose depletion on the production and degradation of the signaling activity by *S. typhimurium* LT2. *S. typhimurium* LT2 was grown in LB medium containing either 0.1% glucose (FIG. 3A) or 0.5% glucose (FIG. 3B). At the specified times cell-free culture fluids were prepared and assayed for signaling activity in the luminescence stimulation assay (Bars), and the concentration of glucose remaining (circles). The cell number was determined at each time by diluting and plating the *S. typhimurium* LT2 on LB medium and counting colonies the next day (squares). The signaling activity is presented as the percent of the activity obtained when *V. harveyi* cell-free spent culture fluids are added. These data correspond to the 5 h time point in the luminescence stimulation assay. The glucose concentration is shown as % glucose remaining. Cell number is cells/ml$\times 10^{-9}$. The symbol \\ indicates that the time axis is not drawn to scale after 8 h.

We tested whether the presence of glucose was required for the cells to continue to produce the signal. FIG. 3 shows results with *S. typhimurium* LT2 grown in LB containing limiting (0.1%) and nonlimiting (0.5%) glucose concentrations. FIG. 3A shows that when glucose is limiting, *S. typhimurium* LT2 produces the signal in mid-exponential phase (after 4 h growth), but stops producing the signaling activity once glucose is depleted from the medium. FIG. 3B shows that when glucose does not become limiting, *S. typhimurium* LT2 produces greater total activity and continues to produce the signaling activity throughout exponential phase, with maximal activity at 6 h growth. Furthermore, the Figure also shows that the signaling activity synthesized by midexponential phase cells is degraded by the time the cells reach stationary phase. In conditions of limiting glucose, no activity remained at stationary phase, and when glucose was plentiful, only 24% of the activity remained. Increasing the concentration of glucose in the growth medium did not change these results, i.e., the activity was secreted during midexponential growth and severely reduced activity remained in the spent culture fluids by stationary phase.

In sum, the results presented in this example show that *E. coli* and *S. typhimurium* produce a signaling substance that stimulates one specific quorum sensing system in *V. harveyi*. Many other bacteria have previously been assayed for such an activity, and only rarely were species identified that are positive for production of this factor (Bassler et al., 1997, supra). Furthermore, as shown here, the E. coli and S. typhimurium signal is potent, these bacteria make activity equal to that of V. harveyi. The degradation of the E. coli and S. typhimurium signal prior to stationary phase indicates that quorum sensing in these bacteria is tuned to low cell densities, suggesting that quorum sensing in E. coli and S. typhimurium is modulated so that the response to the signal does not persist into stationary phase. Additionally, quorum sensing in E. coli and S. typhimurium is influenced by several environmental factors. The production and the degradation of the signal are sensitive not only to growth phase but also to the metabolic activity of the cells. These results indicate that the quorum sensing signal in E. coli and S. typhimurium has two functions; it allows the cells to communicate to one another their growth phase and also the metabolic potential of the environment.

Understanding the regulation of quorum sensing in E. coli and S. typhimurium is important for understanding community structure and cell-cell interactions in pathogenesis. In the wild, pathogenic E. coli and S. typhimurium may never reach stationary phase because dispersion is critical. It is therefore appropriate that quorum sensing in E. coli and S. typhimurium should be functioning at low cell density. This situation is in contrast to that of V. fischeri, the luminescent marine symbiont, where the quorum sensing system is only operational at high cell densities; cell densities indicative of existence inside the specialized light organ of the host. The specific quorum sensing systems of V. fischeri and E. coli and S. typhimurium appear appropriately regulated for the niche in which each organism exists. In both cases, quorum sensing could be useful for communicating that the bacteria reside in the host, not free-living in the environment. Additional complexity exists in the E. coli and S. typhimurium systems because these bacteria channel both cell density information and metabolic cues into the quorum sensing circuit. Again, signals relaying information regarding the abundance of glucose or other metabolites could communicate to the bacteria that they should undergo the transition from a free-living mode to the mode of existence inside the host.

Under all the conditions we have tested, the signaling activity described in this example does not extract quantitatively into organic solvents and it does not bind to either a cation or anion exchange column. Preliminary characterization indicates that the signal is a small (less than 1000 MW) polar but apparently uncharged organic compound. The activity is acid stabile and base labile, it is heat resistant to 80 but not 100° C. Purification of the E. coli, S. typhimurium and V. harveyi signal is described in greater detail in the following examples.

EXAMPLE 2

Regulation of Autoinducer Production in Salmonella typhimurium

In this example, the conditions under which S. typhimurium LT2 produces AI-2, the extracellular factor that stimulates lux expression in the V. harveyi Sensor 1-, Sensor 2+ reporter strain, are elucidated. Production of the signaling compound by S. typhimurium occurs during growth on preferred carbohydrates that, upon utilization by the bacteria, result in a decrease in the pH of the medium. Lowering the pH of the growth medium in the absence of a preferred carbon source induces limited production of the factor, indicating that the cells are influenced by both the changing pH and the utilization of the carbon source. The signaling activity is degraded by the time the cells reach stationary phase, and protein synthesis is required for degradation of the activity. Osmotic shock following growth on an appropriate carbon source greatly increases the amount of activity present in the S. typhimurium culture fluids. This increased activity is apparently due to induction of synthesis of the autoinducer and repression of degradation of the activity. E. coli and S. typhimurium possess a protein called SdiA that is homologous to LuxR from V. fischeri (Wang et al., EMBO J. 10: 3363–3372, 1991; Ahmer et al., J. Bacteriol. 180: 1185–1193, 1998). SdiA is proposed to respond to an extracellular factor (Sitnikov et al., Proc. Natl. Acad. Sci. USA 93: 336–341, 1996; Garcia-Lara et al., J. Bacteriol. 178: 2742–2748, 1996), and it has been shown to control virulence factor production in S. typhimurium (Ahmer et al., 1998, supra). The analysis set forth below shows that the AI-2 autoinducer signaling activity does not function through the SdiA pathway.

Materials and Methods

Strains and Media. The bacterial strains used in this study and their genotypes and phenotypes are listed in Table 2.

TABLE 2

Bacterial strains; their genotypes and relevant phenotypes.

| Strain | Genotype | Relevant Phenotype |
| --- | --- | --- |
| S. typhimurium LT2 | | Wild type |
| E. coli O157 | | Wild type |
| E. coli MG1655 | F−, ilvG, rfb-50 | Wild type |
| E. coli MC4100 | (lac)U169, araD139, rpsL, thi | LacZ− |
| E. coli DH5 | supE44, hsdR17, recA1, endA1, gyrA96, thi-1, relA1 | AI-2− |
| V. harveyi BB170 | luxN::Tn5 | Sensor 1−, Sensor 2+ |
| V. harveyi BB152 | luxL::Tn5 | AI-1−, AI-2+ |
| V. harveyi JAF305 | luxN::Cm$^r$ | Sensor 1−, Sensor 2+ |

Luria broth (LB) contained 10 g Bacto Tryptone (Difco), 5 g Yeast Extract (Difco) and 10 g NaCl per liter (Sambrook et al., 1989). The recipe for Autoinducer Bioassay (AB) medium has been reported previously (Greenberg et al., Arch. Microbiol. 120: 87–91, 1979). LM medium (L-Marine) contains 20 g NaCl, 10 g Bacto Tryptone, 5 g Bacto Yeast Extract and 15 g Agar per liter (Bassler et al., 1994, supra). Regulation of AI-2 production similar to that reported here was also observed with the ATCC strain Salmonella enterica Serovar Typhimurium 14028, an independent clinical isolate of Salmonella enterica Serovar Typhimurium, and nine other Salmonella enterica serovars (other than Typhimurium).

Growth conditions for S. typhimurium LT2 and preparation of cell-free culture fluids. S. typhimurium LT2 was grown overnight in LB broth with shaking at 30° C. The next day, 30 μl of the overnight culture was used to inoculate 3 ml of fresh LB broth. In cultures containing additional carbon sources, at the time of inoculation, 20% sterile stock solutions were added to give the specified final concentrations. Following subculturing of the cells, the tubes were shaken at 200 rpm at 30° C. for the time periods indicated in the text. Cell-free culture fluids were prepared by removal of the cells from the culture medium by centrifugation for 5 min at 15,000 rpm in a microcentrifuge. The cleared supernatants were passed through 0.2 m cellulose acetate Spin X filters (CoStar, Cambridge, Mass.) by centrifugation for 1 min at 8000×g. Samples were stored at −20C. Similar results to those reported here were obtained when we grew the S.

*typhimurium* at 37° C. The preparation of cell-free culture fluids from *V. harveyi* strains has already been reported (Bassler et al., 1993, supra; Bassler et al., 1997, supra).

Density-dependent bioluminescence assay. The *V. harveyi* reporter strain BB170 (Sensor 1⁻, Sensor 2⁺) (Bassler et al., 1993, supra) was grown for 12 h at 30° C. in AB medium, and diluted 1:5000 into fresh AB medium. Luminescence was measured as a function of cell density by quantitating light production at different times during growth with a Wallac Model 1409 liquid scintillation counter (Wallac Inc., Gaithersburg, Md.). The cell density was measured by diluting the same aliquots of cells used for measuring luminescence, spreading the dilutions onto solid LM medium, incubating the plates overnight at 30° C., and counting the resulting colonies the following day. Relative Light Units are (counts $min^{-1}$ ml-1×10³)/(colony forming units $ml^{-1}$). Cell-free culture supernatants from *V. harveyi* or *S. typhimurium* strains were added to a final concentration of 10% (v/v) at the time of the first measurement. In control experiments, 10% (v/v) of AB medium, LB medium or LB medium containing 0.5% glucose was added instead of cell-free culture fluids.

*S. typhimurium* autoinducer activity assay. The quorum sensing signaling activity released by *S. typhimurium* LT2 was assayed following growth under various conditions. 10 μl of cell-free culture fluids from *S. typhimurium* LT2 grown and harvested as described above were added to 96-well microtiter dishes. The *V. harveyi* reporter strain BB170 was grown overnight and diluted as described above. 90 μl of the diluted *V. harveyi* cells were added to the wells containing the *S. typhimurium* cell-free culture fluids. Positive control wells contained 10 μl of cell-free culture fluid from *V. harveyi* BB152 (A1–1⁻, AI-2⁺) (Bassler et al., 1993, supra). The microtiter dishes were shaken in a rotary shaker at 200 rpm at 30° C. Light production was measured hourly using a Wallac Model 1450 Microbeta Plus liquid scintillation counter designed for microtiter dishes (Wallac Inc., Gaithersburg, Md.). In these experiments, the cell density was not measured at each time point. Rather, to ensure that increased light production was due to a signaling activity and not a growth medium component, the luminescence production by *V. harveyi* in wells containing cell-free culture fluids was compared to that produced by *V. harveyi* in wells containing 10 μl of the identical growth medium alone. Data are reported as fold-stimulation over that obtained for growth medium alone.

Factors controlling signal production in *S. typhimurium*. *S. typhimurium* LT2 was grown for 6 h in LB containing 0.5% glucose as described above. The mid-exponential phase culture was divided into several identical aliquots. One aliquot of cells was grown to stationary phase (24 h at 30° C. with shaking). In the remaining aliquots, the cells were removed from the LB-glucose growth medium by centrifugation for 5 min at 15,000 rpm in a microcentrifuge. The resulting cell pellets were resuspended at an $OD_{600}$ of 2.0 in either LB, LB+0.5% glucose, LB at pH 5.0, or in 0.1 M NaCl, or 0.4 M NaCl (in water). The resuspended cells were shaken at 30° C. or 43° C. for 2 h. Cell-free fluids were prepared from the stationary phase culture, and from the cells that had been resuspended and incubated in the various media or the osmotic shock solutions. The cell-free fluids were tested for signaling activity in the *S. typhimurium* activity assay as described above.

Effects of growth phase, pH, glucose concentration and osmolarity on autoinducer production by *S. typhimurium*. *S. typhimurium* LT2 was grown at 30° C. for various times in LB containing limiting (0.1%) and non-limiting (1.0%) glucose concentrations. At the times specified in the text, the cell number was determined by plating dilutions of the *S. typhimurium* cultures onto LB medium and counting colonies the following day. The pH of the two cultures was measured, and the percent glucose remaining in each culture was determined using the Trinder assay as described in Example 1. Cell-free culture fluids were prepared from the LB-glucose cultures as described above. The same cells from which the cell-free culture fluids were prepared were resuspended in 0.4 M NaCl osmotic shock solution and shaken at 200 rpm, 30° C. for 2 h. We determined that this timing was optimal for production of autoinducer. The cells were removed from the osmotic shock solution by centrifugation at 15,000 rpm for 5 min in a microcentrifuge. Cell-free osmotic shock fluids were prepared from the resuspended cells exactly as described for cell-free culture fluids. Signaling activity in both the cell-free culture fluids and the cell-free osmotic shock fluids was assayed as described above. In experiments in which the pH was maintained at 7.2, the cells were grown in LB+0.5% glucose containing 50 mM MOPS at pH 7.2. The pH was adjusted every 15–30 min using 1 M MOPS pH 7.2. In experiments performed at pH 5.0, LB broth was maintained between pH 5.0 and 5.2 with 1M NaOH.

Requirement for protein synthesis in signal production, release and degradation by *S. typhimurium* LT2. *S. typhimurium* LT2 was pregrown in LB containing 0.5% glucose at 30° C. to an $OD_{600}$ of 2.5 (approximately 6–8 h). The culture was divided into four identical aliquots. Two aliquots were treated with 100 g/ml Cm for 5 min at room temperature after which the cells were harvested by centrifugation at 15,000 rpm for 5 min. One Cm-treated cell pellet was resuspended in 0.1 M NaCl containing 30 g/ml Cm, and the second pellet was resuspended in 0.4 M NaCl containing 30 g/ml Cm. Each of these pellets was resuspended to a final $OD_{600}$ of 2.0. The remaining two culture aliquots were not treated with Cm. Instead, the cells in these two aliquots were harvested by centrifugation and resuspended in 0.1 M and 0.4 M NaCl exactly as described for the Cm-treated cells. The cell suspensions were incubated at 30° C. with shaking. At the times indicated in the text, 1.5 ml aliquots were removed from the cell suspensions and cell-free osmotic shock fluids were prepared by the procedure described above.

Analysis of the effect of autoinducer on SdiA regulated gene expression. A sequence that includes the ftsQ1p and ftsQ2p promoters (Wang et al., 1991, supra) was amplified from *E. coli* MG1655 chromosomal DNA using the following primers:

ftsQ1p, 5'-CGGAGATCTGCGTTTCAATGGATAAAC-TACG-3' (SEQ ID NO: 19);

ftsQ2p, 5'-CGCGGATCCTCTTCTTCGCT-GTTTCGCGTG-3' (SEQ ID NO: 20).

The amplified product contained both the ftsQ promoters and the first 14 codons of the ftsQ gene flanked by BamHI and BglII sites. The ftsQ1p2p PCR product was cloned into the BamHI site of vector pMLB1034 (Silhavy et al., Experiments with Gene Fusions, Cold Spring Harbor Press, 1984) to generate a lacZ fusion that contained the promoters, ribosome binding site, and initiation codon of ftsQ. A correctly oriented clone, pMS207, and a clone containing the ftsQ1p2p insert in the opposite orientation, pMS209, were chosen for further analysis. Both inserts were sequenced to ensure that no errors were introduced during the PCR reaction.

For ftsQ regulation in *E. coli*, the plasmids pMS207 and pMS209 were transformed into *E. coli* strain MC4100

(Silhavy et al., 1984, supra), and the transformants were grown overnight in LB containing 100 mg/L ampicillin at 30° C. with aeration. For rck regulation, *S. typhimurium* strains BA1105 (rck::MudJ) and BA1305 (rck::MudJ sdiA) were grown overnight in LB containing 100 mg/L kanamycin at 30° C. with aeration. The overnight cultures were diluted 20-fold into fresh medium and grown for an additional 4.5 h. At this time, each culture was divided into five identical aliquots and 10% (v/v) of one of the following was added to each aliquot: LB, 0.4 M NaCl, 0.4 M osmotic shock fluids from *S. typhimurium* LT2, *E. coli* O157 or *E. coli* strain DH5 (negative control). The osmotic shock fluids were prepared as described above, following pregrowth of the *S. typhimurium* LT2 and *E. coli* in LB containing 0.5% glucose for 6h. The cell suspensions were incubated at 30° C. for 2 h, after which standard -galactosidase reactions were performed on the samples (Miller, A Short Course in Bacterial Genetics, Cold Spring Harbor Laboratory Press, 1992).

Results

Figure 4:
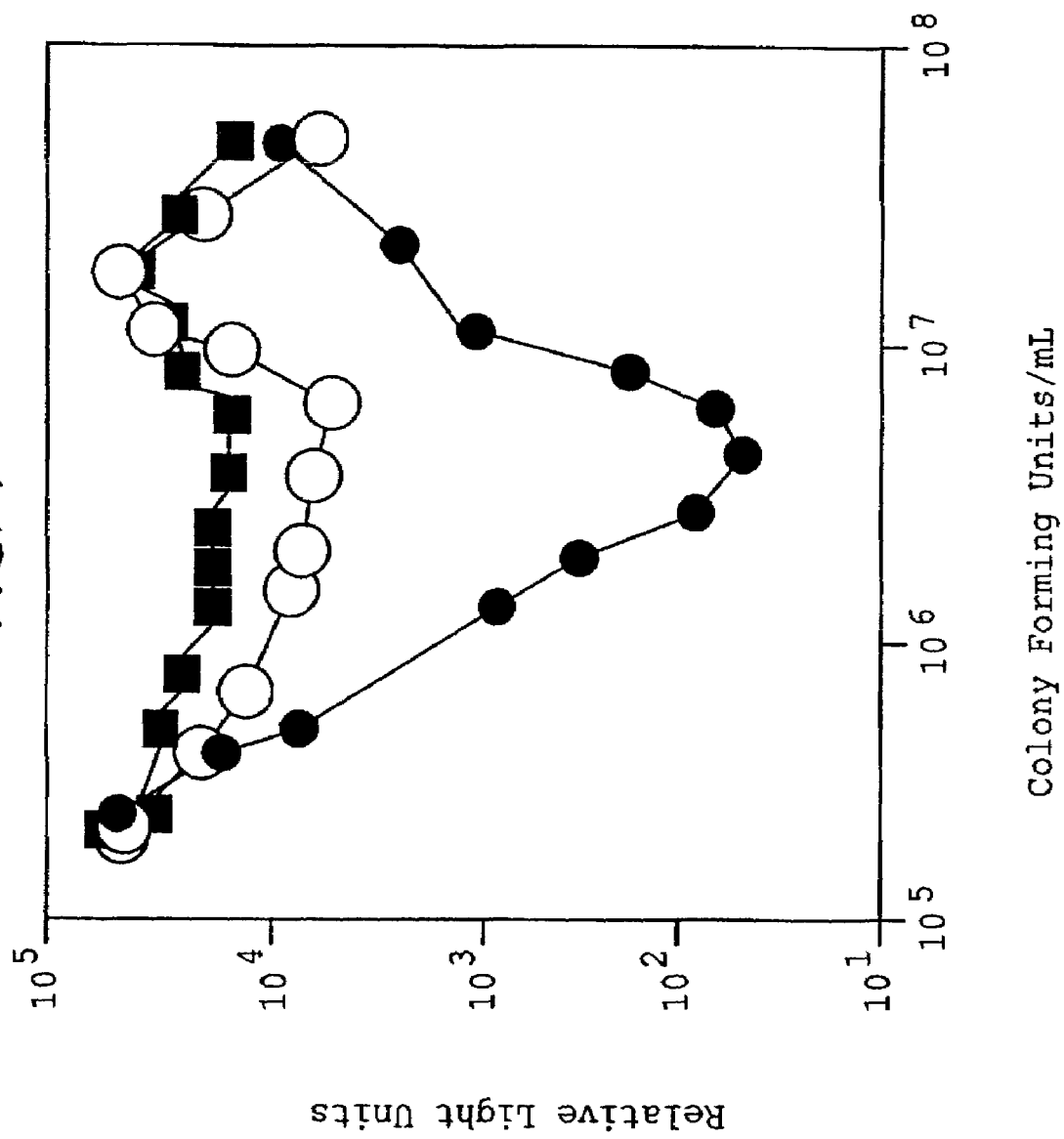
FIG. 4. Response curve of *V. harveyi* to AI-2 produced by *V. harveyi* and *S. typhimurium*. The *V. harveyi* reporter strain BB170 (Sensor 1−, Sensor 2+) was tested for its response to the addition of exogenous AI-2 made by *V. harveyi* strain BB152 (AI-1−, AI-2+) and to that made by *S. typhimurium* LT2. A bright culture of the reporter strain was diluted 1:5000 and either 10% (v/v) growth medium (closed circles), cell-free culture fluid from *V. harveyi* BB152 grown overnight in AB (open circles), or cell-free culture fluid from *S. typhimurium* LT2 grown for 6 h on LB+0.5% glucose (closed squares) was added at the start of the experiment. RLU denotes relative light units and is defined as (counts min$^{-1 \times 10^3}$)/(colony-forming units ml$^{-1}$).

*S. typhimurium* LT2 produces an autoinducer-like activity. In Example 1 it was demonstrated that *S. typhimurium* and *E. coli* strains produce a signaling activity that stimulates lux expression in *V. harveyi*, and the signaling compound acts exclusively through the *V. harveyi* quorum sensing System 2. FIG. 4 shows the induction of luminescence in the *V. harveyi* System 2 reporter strain BB170 (Sensor 1$^-$, Sensor 2$^+$). The characteristic quorum sensing behavior of *V. harveyi* is shown in the control experiment (closed circles). Immediately after dilution into fresh medium, the light emitted per cell by *V. harveyi* drops rapidly, over 1000-fold. At a critical cell density, which corresponds to the accumulation of a critical concentration of endogenously produced autoinducer (AI-2) in the medium, the luminescence per cell increases exponentially, approximately 3 orders of magnitude, to again reach the predilution level.

Addition of 10% cell-free culture fluid prepared from *V. harveyi* BB152 (AI-1$^-$, AI-2+) caused the reporter strain to maintain a high level of light output following dilution (open circles). The increased light output is due to the *V. harveyi* BB170 cells responding to the presence of AI-2 in the cell-free culture fluids prepared from *V. harveyi* strain BB152 (Bassler et al., 1993, supra). Similarly, addition of cell-free culture fluid from *S. typhimurium* LT2 grown in LB+0.5% glucose induced luminescence in the reporter strain approximately 800-fold over the control level (solid squares). No activity similar to *V. harveyi* AI-1 was produced by *S. typhimurium* LT2 under these conditions and there is no AI-1 or AI-2 activity in LB+0.5% glucose (see Example 1).

Environmental factors influence autoinducer production and degradation in *S. typhimurium*. Control of autoinducer production in *S. typhimurium* is different than in other described quorum sensing systems. FIG. 5A demonstrates three important aspects of the regulation of autoinducer production in *S. typhimurium*. First, no autoinducer activity is observed when *S. typhimurium* is grown for 6 h in LB in the absence of glucose. Second, growth in the presence of glucose for 6 h results in substantial production of autoinducer (760-fold activation of the reporter strain). Third, activity, while detectable, is severely reduced when the *S. typhimurium* culture is allowed to grow to stationary phase (33-fold activation of the reporter strain).

We subjected *S. typhimurium* LT2 to several different treatments including some environmental stresses in order to begin to understand what conditions favor autoinducer production versus those that favor autoinducer degradation. In the experiment presented in FIG. 5B, the *S. typhimurium* cells were induced for signal production by pregrowth in LB containing 0.5% glucose for 6 h. We have shown that under these conditions, the glucose is not depleted (Surette and Bassler, 1998). After the induction phase of growth, the culture fluid was removed and aliquots of the cells were resuspended and incubated for 2 h under a variety of conditions that are described in the description of FIG. 2. Following each of these treatments cell-free fluids were prepared and tested for activity on BB 170.

It is important to note that in the results presented in FIG. 5B, the *S. typhimurium* were pre-induced for autoinducer production at the start of the experiment, i.e., their cell-free culture fluid activated the reporter strain 760-fold. FIG. 5B shows that removal of the pre-growth culture fluid from these cells and resuspension of the cells in LB without glucose, in 0.1 M NaCl (hypotonic conditions), or heat shock at 43° C. for 2 h resulted in no or very low autoinducer production. These results indicate that the above treatments result in termination of autoinducer production, or degradation of newly released autoinducer, or both.

In contrast to the above results, resuspension of pre-induced cells in fresh LB+glucose resulted in continued high-level production of autoinducer (735-fold activation of the reporter). Similarly, acidic pH promoted continued production of autoinducer (600-fold activation), and hypertonic osmotic shock (0.4 M NaCl) resulted in 1300-fold induction of the reporter. Increased AI-2 activity was only observed in the pH 5.0 fluids or 0.4 M NaCl osmotic shock fluids of cells that were already actively producing AI-2, i.e., if glucose was not included during the pre-growth, no measurable activity was produced following the identical 2 h treatments.

Shifting *S. typhimurium* cells from LB+glucose to 0.4 M NaCl resulted in an accumulation of AI-2 activity to a level much greater than that observed under any other condition tested. Below it is shown that *S. typhimurium* cells resuspended in 0.4 M NaCl increase the biosynthesis and/or release of autoinducer, and furthermore they apparently do not degrade significant quantities of the released activity. A similar increase in AI-2 production occurs when the *S. typhimurium* cells are resuspended in 0.4 M NaCl, 0.4 M KCl or 0.8M sucrose, indicating that the NaCl effect on AI-2 production is an osmotic one, not an ionic one. This apparent osmotic shock effect on the *S. typhimurium* cells was extremely useful because it enabled us to measure maximal release of autoinducer activity in the absence of loss due to degradation.

The effect of glucose on signal production in *S. typhimurium*. In Example 1 we showed that the continued presence of glucose was required for *S. typhimurium* to produce the quorum sensing signaling factor. Because sugar utilization both increases the growth rate while decreasing the pH of the culture, we further analyzed the effect of metabolism of glucose, decreasing pH and increasing cell number on signal production by *S. typhimurium*. In the experiment presented in FIG. 6, we measured signal production, growth rate, and pH in growing *S. typhimurium* LT2 cultures containing limiting (0.1%) and nonlimiting (1.0%) concentrations of glucose. In the data presented in FIG. 6, at various times, the level of autoinducer produced in both the cell-free culture fluids and in the corresponding 0.4 M NaCl osmotic shock fluids was measured and normalized for $1\times10^9$ cells. It should be noted that unlike in FIG. 5, the cells in this experiment were not pre-induced for signal production.

FIG. 6 shows that the pattern of production and disappearance of autoinducer observed in 0.4 M NaCl osmotic shock fluids mimics that observed in cell-free culture fluids. However, at every time point that autoinducer is produced, much greater activity is detected in the osmotic shock fluids than in the corresponding cell-free culture fluids. Under conditions of limiting (0.1%) glucose (FIGS. 6A, 6C and 6E), S. typhimurium produces the signaling activity between 2–4 h (Bars). However, the glucose becomes completely depleted at 4 h, and at that time production of the factor ceases (FIG. 6A). In contrast, when the cells are grown in 1.0% glucose (FIGS. 6B, 6D, and 6F), glucose is present in the medium throughout the entire experiment (FIG. 6B). Under these conditions, the cells continue to synthesize activity for 12 hours. Similar to the results shown in FIG. 5 and those reported in Example 1, almost no activity was observed in cell-free culture fluids or osmotic shock fluids from stationary phase cells at 24 h regardless of the glucose concentration.

S. typhimurium grows at roughly the same rate in both high and low glucose media during exponential phase. In fact, the S. typhimurium culture grown in high glucose medium does not reach the cell density achieved by the S. typhimurium grown in the low glucose medium (FIGS. 6C and 6D). Cell growth is probably inhibited in this culture by the dramatically reduced pH that occurs from increased glucose utilization. These results show that the higher level of activity produced by S. typhimurium in the LB containing 1% glucose is not due to higher cell number, but due to induction of signal production caused by glucose metabolism.

FIGS. 6E and 6F show the pH of the low and high glucose cultures at each time point. Under conditions of low glucose (FIG. 6E), the pH of the culture initially decreases as the cells utilize the glucose. However, simultaneous to the complete depletion of the glucose, the pH begins to rise. In contrast, under conditions of high glucose, the pH of the medium decreases to below pH 5 (FIG. 6F). In the experiments presented in FIG. 6, both glucose catabolism and decreasing pH occur simultaneously suggesting that either or both of these factors could be responsible for signal production by S. typhimurium.

Both glucose metabolism and low pH independently control signal production in S. typhimurium. To distinguish between the contribution from glucose metabolism and that from low pH in signal production by S. typhimurium, we compared the activity produced by S. typhimurium grown in LB containing 0.5% glucose in a culture in which the pH was maintained at 7.2 (FIG. 7A), to that produced by S. typhimurium grown in LB without glucose where the pH was maintained at 5.0 (FIG. 7B). Again, we measured the signal present in cell-free culture fluids and in 0.4 M NaCl osmotic shock fluids. Similar to the data presented in FIG. 3, the level of signal observed in cell-free culture fluids was lower than that observed in the 0.4 M osmotic shock fluids.

When S. typhimurium was grown in LB+0.5% glucose at pH 7.2 increasing amounts of the quorum sensing signal were detected for 6 h. At 6 h, in 0.4 M NaCl osmotic shock fluids, there was an approximately 550-fold stimulation of light production of the V. harveyi reporter strain BB170. No activity was produced after the 6 h time point. FIG. 7A shows that the pH was maintained between 7.15 and 7.25 for 8 h, after this time, the pH of the culture no longer decreased, but began increasing presumably because the cells had depleted the glucose. We allowed the pH to continue to increase for the duration of the experiment. Also shown in the Figure is the cell number at each time point. At pH 7.2, the cells grew rapidly and reached a high cell density.

Analysis of time courses similar to those presented here, has shown that S. typhimurium does not produce any signal when it is grown in LB without glucose at neutral pH (see Example 1). However, S. typhimurium did transiently produce the quorum sensing factor in the absence of glucose when grown at pH 5.0 (FIG. 7B). Signal was produced for 4 h, and about 450-fold stimulation of the reporter was the maximum activity achieved in 0.4 M NaCl osmotic shock fluids. Very little signal was produced by 5 h, and signal was completely absent after 6 h of incubation. FIG. 7B shows that the pH was maintained between 5.0 and 5.2 in this experiment. Note that the cells grew much more slowly at pH 5.0 than at pH 7.2.

Preliminary characterization of the S. typhimurium autoinducer degradative apparatus. The quorum sensing activity produced by S. typhimurium LT2 is degraded by the onset of stationary phase. We have determined that the activity contained in cell-free culture supernatants and 0.4 M NaCl osmotic shock fluids from cells grown for 6 h in LB+glucose is stable for at least 24 h at 30° C., indicating that no degradative activity is present in these cell-free fluids. Furthermore, mixing cell-free culture fluids prepared from actively producing S. typhimurium (i.e., from cultures grown for 6 h in LB+glucose) with cell-free culture fluids prepared from S. typhimurium that have degraded the factor (i.e., from cultures grown for 12 or 24 h in LB+glucose) does not result in degradation of the activity. This result indicates that the degradative activity is not released, but instead, is associated with the cells.

We show in FIG. 5 that no further autoinducer is produced if S. typhimurium cells that are actively releasing autoinducer are shifted to 0.1 M NaCl. However, when these same cells are shifted to 0.4 M NaCl, we observe even greater autoinducer production. This result implies that low osmolarity could be a signal that induces the autoinducer degradative machinery. To begin to analyze the mechanism by which osmolarity affects autoinducer production and degradation in S. typhimurium, we investigated the requirement for protein synthesis in signal production and degradation by S. typhimurium in high and low osmolarity. As described in the legend to FIG. 5, S. typhimurium LT2 was grown in LB containing 0.5% glucose to achieve maximal induction of signal production then treated with 0.1 M or 0.4 M NaCl in the presence and absence of protein synthesis. Cell-free fluids were prepared and tested for signaling activity. Because half of the cell-free osmotic shock fluids contained chloramphenicol (Cm), V. harveyi JAF305 was used as the reporter strain in the activity assay. This V. harveyi strain contains a $Cm^r$ cassette in the luxN gene, and its phenotype is Sensor $1^-$, Sensor $2^+$, a phenotype identical to that of V. harveyi BB170.

Figure 8A:
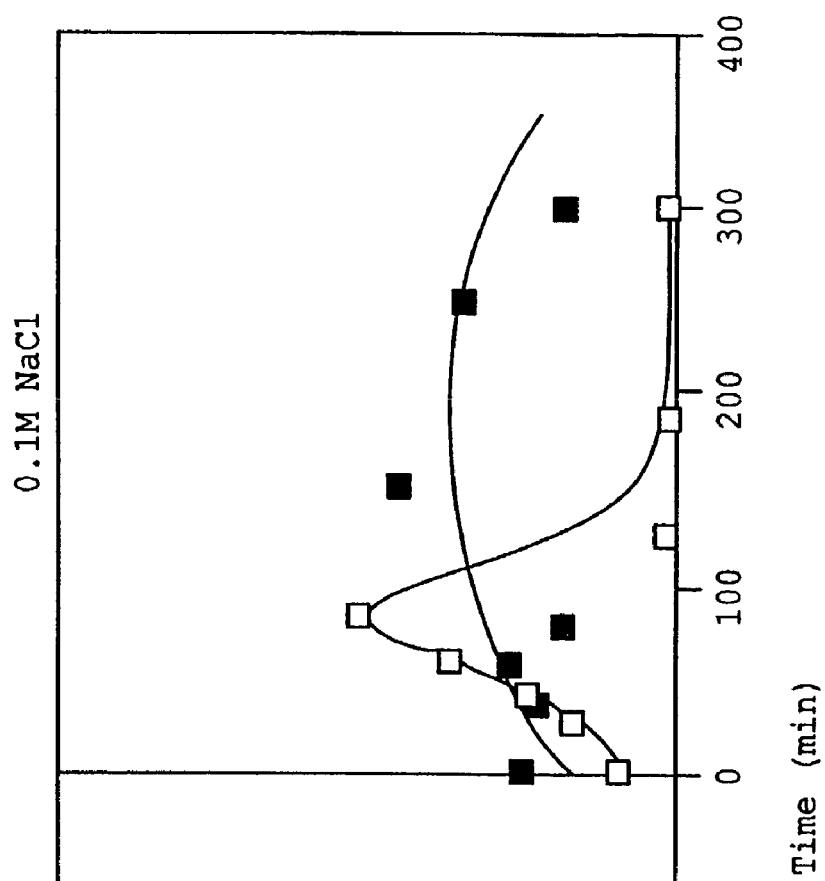
FIG. 8. High osmolarity induces signal release and low osmolarity induces signal degradation in *S. typhimurium* LT2. The quorum sensing signal released by *S. typhimurium* LT2 resuspended in 0.4 M NaCl and in 0.1 M NaCl was measured in the presence and absence of protein synthesis. *S. typhimurium* LT2 was pre-grown in LB containing 0.5% glucose for 6 h. The cells were harvested and resuspended in 0.4 M NaCl (FIG. 8A) or 0.1 M NaCl (FIG. 8B) in the presence or absence of 30 g/ml Cm for the time periods indicated. In each panel, the open symbols represent the activity measured in the absence of Cm and the closed symbols represent the activity measured in the presence of Cm.
Figure 8B:
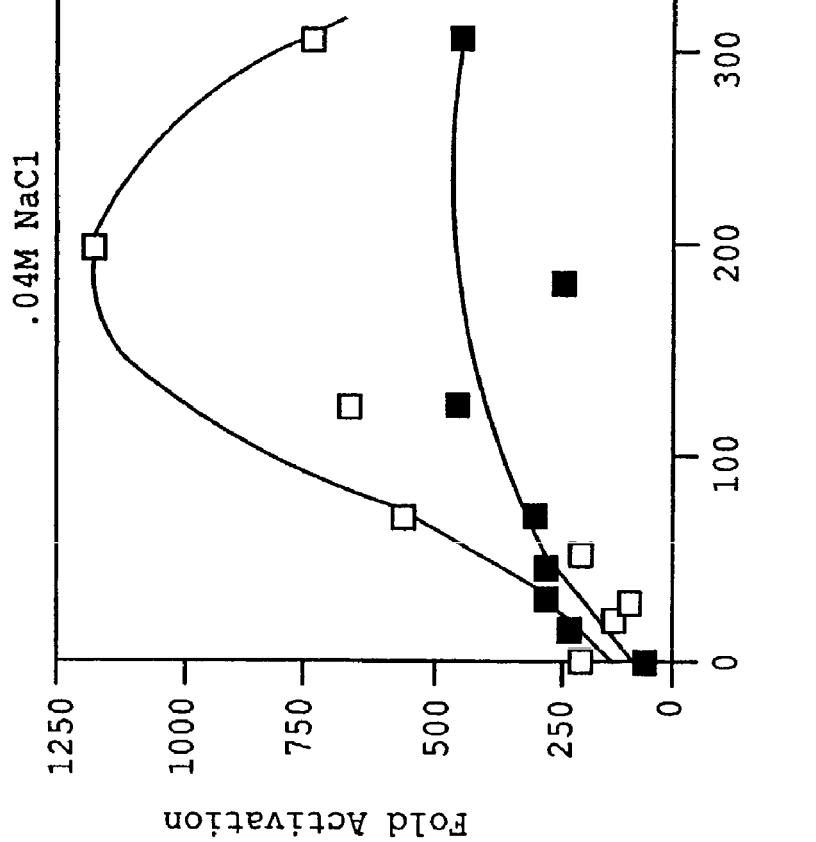
Figures 10A, 10B:
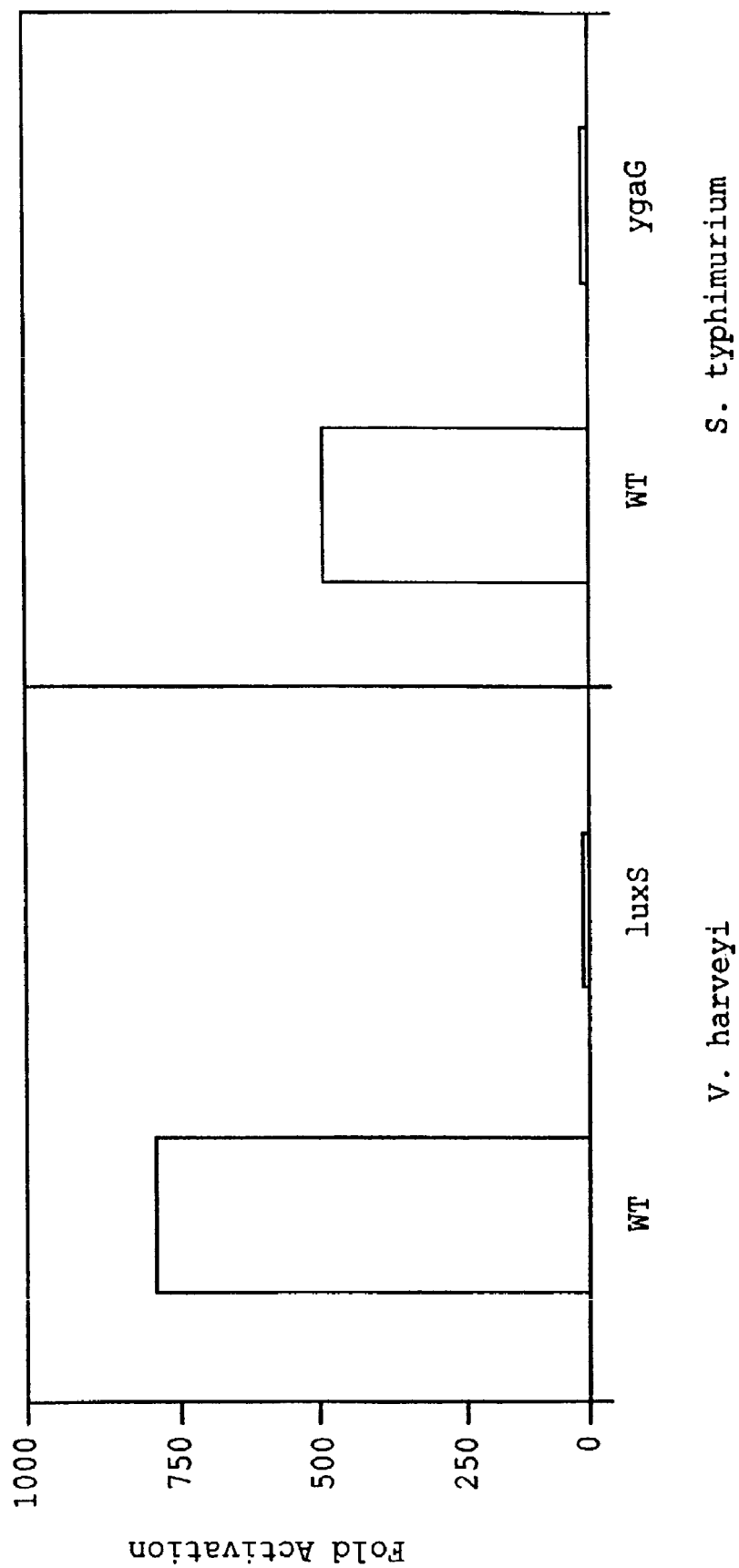
FIG. 10A: AI-2 production phenotypes of the wild type *V. harveyi* strain MM28 that contains a Tn5 insertion outside of luxS$_{V.h.}$ (denoted WT) and the luxS$_{V.h.}$::Tn5 mutant strain MM30 (denoted luxS$^-$).
FIG. 10B: AI-2 production phenotypes of wild type *S. typhimurium* LT2 (denoted WT) and the ygaG::MudJ insertion mutant strain CS 132 (denoted ygaG$^-$). Activity is reported as fold-induction of luminescence expression of the *V. harveyi* BB 170 reporter strain over that when sterile medium was added.

When the cells were resuspended in 0.4 M NaCl, the S. typhimurium produced and released increasing amounts of the signal for 200 min (FIG. 8A, open squares). After this time, the level of signaling activity present in the cell-free osmotic shock fluid decreased somewhat, suggesting that some of the released signal was degraded. Quite different results were obtained when the S. typhimurium cells were resuspended in 0.1 M NaCl (FIG. 8B, open squares). In this case, at early time points, the S. typhimurium produced a quantity of activity equivalent to that produced by cells resuspended in 0.4 M NaCl. However, by 120 min, no activity remained in the cell-free low osmolarity fluid. This result indicates that under conditions of low osmolarity, the released activity is rapidly degraded. We do not observe degradation of the activity in cell-free culture fluids, indicating that the disappearance of the activity from low osmolarity cell-free fluids is not due to chemical instability of the signaling compound.

Under conditions of high osmolarity, when the cells were treated with Cm to inhibit protein synthesis, only about one quarter of the activity was produced compared to untreated cells. The closed squares in FIG. 8A show that 300-fold induction of the reporter strain occurred in the presence of Cm as compared to 1200-fold induction with the untreated cells (FIG. 8A, open squares). When the S. typhimurium was resuspended in low osmolarity (FIG. 8B), roughly three-quarters of the activity produced in the absence of Cm (open squares) was produced in the presence of Cm (closed squares). In the presence of Cm, the released activity was not degraded by 300 min in high osmolarity and only partially degraded in low osmolarity.

To show that high osmolarity does not inhibit AI-2 signal degradation, we added the activity contained in the 0.4 M NaCl cell-free osmotic shock fluids to S. typhimurium cells that had been resuspended in 0.1 M NaCl for two hours. As shown in FIG. 8, these are cells that can degrade the factor. Table 3 shows that these S. typhimurium cells degraded greater than 98% of the signaling activity while incubated at high osmolarity. The table also shows that S. typhimurium cells that had been incubated in 0.4 M NaCl (these are cells that are actively producing the signal) released no further activity when resuspended in the 0.1 M NaCl incubation fluid obtained from the actively degrading cells. Furthermore, mixing active and inactive 0.4 M and 0.1 M cell-free osmotic fluids did not result in degradation of the activity in the 0.4 M fluids.

TABLE 3

High osmolarity induces release and low osmolarity induces degradation of the S. Typhimurium signaling factor.

| Treatment | Fold-induction of luminescence |
| --- | --- |
| 0.1 M NaCl activity[a] | 4 |
| 0.4 M NaCl activity[a] | 944 |
| 0.1 M cells + 0.4 M activity[b] | 17 |
| 0.4 M cells + 0.1 M activity[c] | 6 |

[a]S. typhimurium was grown for 6 h in LB containing 0.5% glucose. The cells were pelleted and resuspended in either 0.1 M or 0.4 M NaCl for 2 h. Cell-free fluids were prepared and tested for activity.
[b]S. typhimurium cells that had been incubated in 0.1 M NaCl for two hours were pelleted and resuspended in the activity contained in the cleared osmotic shock fluids obtained from cells suspended in 0.4 M NaCl for 2 h. Cell-free fluids were prepared after a 2 h incubation and assayed for signaling activity.
[c]S. typhimurium cells that had been suspended in 0.4 M NaCl were pelleted and incubated for 2 h in the cleared osmotic shock fluids obtained from cells suspended for 2 h in 0.1 M NaCl. Cell-free fluids were prepared after the 2 h incubation and assayed for signaling activity.

The LuxR homolog SdiA is not involved in response to the AI-2 autoinducer. A gene homologous to luxR of V. fischeri has been identified in E. coli and S. typhimurium and is called sdiA. Two reports suggest that in E. coli, SdiA modestly regulates the expression of the cell division locus ftsQAZ in response to a factor present in cell-free culture fluids (Garcia-Lara et al., 1996, supra), and in response to a few homoserine lactone autoinducers (Sitnikov, et al., 1996, supra). Completion of the sequence of the E. coli genome shows that no LuxI homologue exists in E. coli so the locus responsible for the biosynthesis of the hypothesized soluble factor(s) has not been determined. Overexpression of SdiA in S. typhimurium has recently been shown to influence the expression of several ORFs located on the S. typhimurium virulence plasmid (Ahmer, et al., 1998, supra). As in the E. coli studies, SdiA activity in S. typhimurium is proposed to be modulated by an extracellular factor.

It was possible that the AI-2 autoinducer that we have been characterizing in S. typhimurium and E. coli acted through SdiA. We tested whether AI-2 had an effect on genes regulated by SdiA in E. coli and S. typhimurium. In E. coli, we assayed an ftsQlp2p-lacZ reporter, and in S. typhimurium we assayed an rck::MudJ fusion in both an sdiA$^+$ and sdiA$^-$ background. We tested the effects of addition of LB, 0.4 M NaCl, 0.4 M NaCl osmotic shock fluids containing AI-2 activity from S. typhimurium LT2, E. coli O157, and 0.4 M NaCl osmotic shock fluid from E. coli DH5. We have shown previously in Example 1 that DH5 does not produce AI-2 activity under our growth conditions.

For the E. coli experiments we determined that MC4100 and MC4100/pMS209 (containing ftsQ1p2p in the incorrect orientation) had no measurable –galactosidase activity. The level of –galactosidase produced by MC4100/pMS207 (containing the ftsQ1p2p-lacZ fusion) was roughly 20–30 Miller units, and this level of activity did not change under any of the conditions tested here. This level of activity of the fusion was comparable to that reported previously (Sitnikov et al., 1996, supra; Garcia-Lara et al., 1996, supra). In the S. typhimurium SdiA studies, similar to Ahmer et al. (1998, supra), we obtained ~30 Miller units of rck::MudJ activity in the sdiA$^+$ background and this level was reduced to 10 units in the sdiA$^-$ background. No change in –galactosidase production occurred following the addition of AI-2 from E. coli or S. typhimurium. These results indicate that, if an extracellular factor exists that modulates the activity of SdiA, under the conditions we have tested, it is not AI-2.

Discussion

Quorum Sensing in E. coli and S. typhimurium. We have developed a heterologous bioassay that enables us to detect an extra-cellular signaling factor produced by S. typhimurium. The factor mimics the action of AI-2 of the quorum sensing bacterium V. harveyi, and it acts specifically through the V. harveyi Signaling System 2 detector LuxQ. Results using lacZ fusions to the ftsQ and rck promoters indicate that, under our assay conditions, the AI-2 quorum sensing factor does not signal to SdiA, at least with respect to regulation of these genes. The AI-2 quorum sensing system is therefore involved in a different S. typhimurium and E. coli signal transduction pathway than the one(s) investigated previously.

S. typhimurium LT2 produces an amount of activity roughly equivalent to that produced by V. harveyi. We observe approximately 800-fold stimulation of the V. harveyi reporter strain BB170 upon addition of 10% S. typhimurium cell-free culture fluids. The timing of lux induction and the shape of the response curve of V. harveyi to the S. typhimurium signal are indistinguishable from those of V. harveyi responding to its own AI-2. Furthermore, we have been successful at partially purifying both the V. harveyi AI-2 and the S. typhimurium signal compound using identical purification procedures. These two results lead us to believe that the S. typhimurium signaling compound is identical to or very closely related to AI-2 of V. harveyi.

Growth Conditions Regulate Signal Production and Degradation in S. typhimurium. In this example, we further characterize the regulation of the signaling activity in S. typhimurium LT2. Accumulation of signaling activity in S. typhimurium culture supernatants is maximal during mid-exponential phase when the cells are actively utilizing glucose in rich medium. Under these growth conditions, utilization of glucose is accompanied by a rapid drop in pH of the culture. The results demonstrate that either glucose metabolism or low pH is sufficient to induce S. typhimurium LT2 to produce the quorum sensing factor, indicating that both glucose and acidity generate independent signals for autoinducer production. In the presence of glucose, when the pH is not maintained, probably both the decreasing pH and the presence of an appropriate carbon source contribute to the regulation of quorum sensing in S. typhimurium. The results also show that production of the autoinducer ceases prior to stationary phase in the presence of glucose at neutral pH and in the absence of glucose at low pH. Therefore, a combination of acidic conditions and the absence of glucose is not required to cue S. typhimurium to terminate production of autoinducer.

In addition to glucose, growth on several other carbohydrates also induces production of the signaling activity. These include both PTS (fructose, mannose, glucitol, and glucosamine) and non-PTS (galactose and arabinose) sugars. These findings eliminate an exclusive role for the PTS in the regulation of autoinducer biosynthesis. When the S. typhimurium LT2 are grown on several other carbon sources (acetate, glycerol, citrate and serine) no significant accumulation of signaling activity is observed. We have demonstrated in Example 1 that the signal is not any of a number of substances known to be secreted by S. typhimurium including the major products of mixed acid fermentation. Clearly, production of the signaling compound is precisely regulated by the cells and is favored under conditions of growth on preferred carbohydrates for reasons that we do not yet understand. Identification of the signaling compound and cloning of the biosynthetic gene(s) will aid in a fuller understanding of the regulation process.

Results presented in this example show that, in contrast to other quorum sensing systems, the S. typhimurium signal does not accumulate in stationary phase. At least two competing processes contribute to this regulation; autoinducer production and autoinducer degradation. In this example we are defining autoinducer production as an increase in the signaling activity present in cell-free fluids. We recognize that an increase in activity could result from release of newly biosynthesized autoinducer, release of stored autoinducer, repression of degradation of autoinducer, or some combination of these activities. We define autoinducer degradation as the disappearance of signaling activity from the cell-free fluids. This disappearance could be due to destruction of the autoinducer, reuptake of the autoinducer, or a combination of these activities. It is possible that under some of the conditions used in our studies, autoinducer production and autoinducer degradation are occurring simultaneously. If this is the case, the activity detected in cell-free culture fluids is a measure of which of these processes, production or degradation, predominates. These findings indicate that quorum sensing in S. typhimurium is regulated such that the signal and presumably the response to the signal do not persist into stationary phase. Because the utilization of a preferred carbohydrate is also required for signal production, quorum sensing in S. typhimurium may be used both for measuring the cell density and for measuring the potential of the environment for growth.

Osmolarity Influences Signal Production and Degradation in S. typhimurium. S. typhimurium cells that are actively producing signal can be further stimulated to produce signal by specific environmental treatments, indicating that several independent regulatory pathways channel information into autoinducer synthesis. One of these treatments is 0.4 M NaCl osmotic shock. When autoinducer producing S. typhimurium cells are resuspended in 0.4 M NaCl, the cells release significantly greater activity when they have the capability to synthesize protein than when protein synthesis is blocked. Furthermore, degradation of the signal also requires protein synthesis. These results have several implications. First, in the presence of Cm, S. typhimurium resuspended at both high and low osmolarity produce a similar amount of activity. This result indicates that, following growth in the presence of glucose, the S. typhimurium cells have a predefined capacity to produce signaling activity (and/or to release already synthesized activity from the cell). Second, when the cells are resuspended at high osmolarity, signal production increases well beyond this level. This increase in signal production requires protein synthesis, and we interpret this to mean that high osmolarity is one environmental cue that induces S. typhimurium to synthesize more of the biosynthetic apparatus necessary for signal production and/or release. Third, under conditions of low osmolarity, we observe an initial release of activity, followed by a rapid degradation of the activity. And, signal degradation requires protein synthesis because it is not observed in the presence of Cm. These results imply that the environment has changed from conditions favoring autoinducer production (LB+a preferred carbohydrate, or high osmolarity) to conditions where autoinducer production is not favored (low osmolarity, or absence of a preferred carbon source). This environmental change induces S. typhimurium to synthesize the protein(s) required for degradation of the signaling activity When the S. typhimurium cells were incubated in 0.4 M NaCl no significant degradation of the activity occurred by 200 min. This result indicates that either the necessary degradative protein(s) are not synthesized under these conditions, or alternatively, the degradative apparatus is assembled, but its activity is inhibited by high osmolarity. The results show that high osmolarity does not inhibit signal degradation, because cells induced to degrade the activity can do so at high osmolarity. Therefore, the persistence of the activity in the high NaCl samples occurs because the degradation machinery is not synthesized, not because its activity is inhibited.

It is difficult to precisely determine when S. typhimurium cells are autoinducer producers and when they are autoinducer degraders because both processes could occur simultaneously. It appears, however, that no or very low degradation occurs in high osmolarity, and conversion of cells from overall signal producers to overall signal degraders occurs in low osmolarity and requires protein synthesis. Our preliminary characterization of the degradative process indicates that it is cell-associated because the autoinducer activity is stable in cell-free culture supernatants for long periods of time, and combining active with inactive cell-free culture fluids or active and inactive high and low osmolarity cell-free fluids does not promote degradation of the autoinducer. We have recently isolated a S. typhimurium mutant that does not produce the AI-2 activity. If this mutant retains the capability to degrade autoinducer, analysis of it will be informative for understanding the timing of degradation, and for identifying the cues that induce the degradative machinery. We are currently attempting to isolate S. typhimurium mutants capable of autoinducer production but incapable of autoinducer degradation.

The Role for Quorum Sensing in Salmonella Pathogenesis. The observations presented here on the regulation of signal production and degradation by S. typhimurium LT2 implicate a role for quorum sensing in pathogenesis of

*Salmonella.* The conditions favoring signal production (nutrient rich, high osmolarity and low pH) are those likely to be encountered upon the first interaction of an enteric pathogen with its host. Conditions favoring degradation of the signal (nutrient poor, low osmolarity) are those most probably encountered as the pathogen exits the host. The initial colonization of the host may be a concerted effort between a population of cells coordinated through this cell-cell signaling system. Other cues, that we have not yet tested, could also regulate quorum sensing in *S. typhimurium*. These may represent independent or overlapping signaling pathways involved in pathogenesis. We are isolating *S. typhimurium* mutants to test these hypotheses. Finally, *Salmonella* pathogenesis is a dynamic process of interaction between the host and metabolically active bacteria. Consistent with a role for quorum sensing in pathogenesis, our evidence suggests that this quorum sensing system is not functioning during stationary phase. We have shown that the signaling compound is not produced during stationary phase, and furthermore, existing signal is degraded. Perhaps quorum sensing is critical for *S. typhimurium* to undergo the transition between a host-associated and a free-living existence.

EXAMPLE 3

Quorum Sensing in *Escherichia coli, Salmonella typhimurium* and *Vibrio harveyi*: A New Family of Genes Responsible for Autoinducer Production In this example we report the analysis of a gene responsible for AI-2 production in *V. harveyi, E. coli* and *S. typhimurium*. The gene identified in all three species of bacteria is highly homologous, and we propose that these genes define a new family of proteins involved in autoinducer production. The genes, which we named $luxS_{V.h.}$, $luxS_{E.c.}$, and $luxS_{S.t.}$ have been identified in many species of bacteria by genome sequencing projects, but until now no function has been ascribed to this gene in any organism. The luxS genes do not bear homology to any other gene known to be involved in autoinducer production.

Materials and Methods

Bacterial strains, media and recombinant DNA techniques. *V. harveyi* BB120 is the wild type strain (Bassler et al., 1997, supra). *S. typhimurium* strain LT2 was obtained from Dr. K. Hughes (University of Washington), *S. typhimurium* 14028 is ATCC strain 14028 Organism: *Salmonella choleraesuis. E. coli* O157:H7 is a clinical isolate supplied by Dr. Paddy Gibb (University of Calgary). Luria broth (LB) contained 10 g Bacto Tryptone (Difco), 5 g Yeast Extract (Difco) and 10 g NaCl per liter. The recipe for Autoinducer Bioassay (AB) medium has been reported previously (Greenberg, E. P., Hastings, J. W., and Ulitzur, S. (1979) Arch. Microbiol. 120, 87–91). Where specified, glucose was added from a sterile 20% stock to a final concentration of 0.5%. Antibiotics were used at the following concentrations (mg/L): Ampicillin (Amp) 100, Chloramphenicol (Cm) 10, Gentamycin (Gn) 100, Kanamycin (Kn) 100, and Tetracycline (Tet) 10. DNA isolation, restriction analysis and transformation of *E. coli* was performed as described by Sambrook et al. Probes for Southern Blot analysis were labeled using the Multiprime DNA labeling system of Amersham. Sequencing was carried out using an Applied Biosystems sequencing apparatus. The *V. harveyi* BB120 genomic library was constructed in the cosmid pLAFR2 as described (Bassler et al., 1993, supra). The method for Tn5 mutagenesis of cloned *V. harveyi* genes, and the allelic replacement technique for inserting Tn5 mutated genes into the *V. harveyi* chromosome have been reported (Bassler et al., 1993, supra).

Bioluminescence Assay. The AI-2 bioassay using the *V. harveyi* reporter strain BB170 (Sensor 1⁻, Sensor 2⁺) has been discussed in the previous examples. Cell-free culture fluids from *V. harveyi, E. coli,* or *S. typhimurium* strains to be tested for AI-2 activity were prepared as described above, and assayed at 10% (v/v). AI-2 activity is reported as the fold-induction of the reporter strain over background, or as the percent of the activity obtained from *V. harveyi* BB120 (wild type) cell-free culture fluid.

Mutagenesis and analysis of the AI-2 production gene in *S. typhimurium* LT2. MudJ insertion mutants of *S. typhimurium* LT2 were generated using a phage P22 delivery system as described (Maloy, S. R., Stewart, V. J., and Taylor, R. K. (1996) Genetic analysis of pathogenic bacteria: a laboratory manual. Cold Spring Harbor Laboratory Press, Cold Spring Harbor, N.Y.). Following growth to mid-exponential phase in LB containing 0.5% glucose, the *S. typhimurium* insertion mutants were tested for AI-2 production using the *V. harveyi* BB170 bioassay. The site of the MudJ insertion that inactivated the AI-2 production function in *S. tyhimurium* was identified by PCR amplification and sequencing of the chromosomal DNA at the insertion junction. A two-step amplification procedure was used (Caetano-Annoles, G. (1993) Meth. Appl. 3, 85–92). In the first PCR reaction, the arbitrary primer 5'-GGCCACGCGTCGAC-TAG-TACNNNNNNNNACGCCC-3' (SEQ ID NO: 21), and the MudJ specific primer 5'-GCACTACAGGCTTG-CAAGCCC-3' (SEQ ID NO: 22) were used. Next, 1 μl of this PCR reaction was used as the template in a second PCR amplification employing a second arbitrary primer (5'-GGC-CACGCGTCGACTAGTCA-3')(SEQ ID NO: 23) and another MudJ specific primer (5'-TCTAATCCATCAGATC-CCG-3') (SEQ ID NO: 24). The PCT product from the second reaction was purified and sequenced.

Cloning and sequencing of the *E. coli* MG1655, *E. coli* O157:H7, and *E. coli* DH5 AI-2 production genes. The DNA sequence obtained from the *S. typhimurium* LT2 MudJ screen was used to search the *E. coli* MG1655 genome sequence to identify the corresponding *E. coli* region (Blattner et al., Science 277, 1453–1462, 1997). The gene identified from the sequencing project had the designation ygaG. Primers that flanked the ygaG gene and incorporated restriction sites were designed and used to amplify the *E. coli* MG1655, *E. coli* O157:H7 and *E. coli* DH5 ygaG genes. The primers used are: 5'-GTGAAGCTTGTTTACTGACTA-GATC-3' (SEQ ID NO: 24) and 5'-GTGTCTAGAAAAA-CACGCCTGACAG-3' (SEQ ID NO: 25). The PCR products were purified, digested and cloned into pUC19. In each case, the PCR products from three independent reactions were cloned and sequenced.

Results

Identification and cloning of the gene responsible for AI-2 production in *V. harveyi*. We have discussed in previous examples that, unlike many other *E. coli* strains, *E. coli* strain DH5 does not produce an AI-2 signal compound that can be detected by *V. harveyi*. We reasoned therefore, that we could use *E. coli* DH5 as a mutant to clone the *V. harveyi* AI-2 production gene. A library of wild type *V. harveyi* BB120 genomic DNA was transformed into *E. coli* strain DH5, and the transformants were screened for AI-2 production in the *V. harveyi* BB170 AI-2 detection bioassay. The library consisted of 2,500 clones each containing roughly 25 kb of *V. harveyi* genomic DNA. Five DH5 clones were identified that resulted in upwards of 300-fold stimulation of the reporter strain in the bioassay.

The recombinant cosmid DNA from the five AI-2 producing *E. coli* DH5 clones was analyzed by restriction analysis and Southern blotting. All five of the cosmids contained an overlapping subset of identical *V. harveyi* genomic restriction fragments, indicating that we had cloned the same locus several times. One cosmid, called pBB2929 was selected for further analysis. Random mutagenesis using transposon Tn5 was carried out on cosmid pBB2929, and pools of cosmids harboring Tn5 insertions were subsequently transformed into *E. coli* DH5 We tested 962 individual *E. coli* DH5/pBB2929::Tn5 strains for the loss of the ability to produce AI-2. Four *E. coli* DH5 strains harboring Tn5 insertions in pBB2929 were identified that failed to produce AI-2. We mapped the locations of these Tn5 insertions in pBB2929 and found that all four transposon insertions resided in the same 2.6 kb HindIII *V. harveyi* genomic DNA fragment (FIG. 9A).

Cosmid pBB2929 was digested with HindIII and the 8 resulting fragments were subcloned in both orientations into pALTER (Promega). The pALTER subclones were transformed into *E. coli* DH5, and subsequently tested for AI-2 production. The only strains capable of producing AI-2 contained the 2.6 kb HindIII fragment identified in the Tn5 mutagenesis. This fragment was sequenced, and only one open reading frame (ORF) could be identified, and its location corresponded to the map positions of the four Tn5 insertions that eliminated AI-2 production. We named the ORF $luxS_{V.h.}$ (FIG. 9A).

Mutagenesis of $luxS_{V.h.}$ in *V. harveyi*. We analyzed the effects of $luxS_{V.h.}$ null mutations on AI-2 production in *V. harveyi*. The four Tn5 insertions that mapped to the $luxS_{V.h.}$ gene and the control Tn5 insertion adjacent to the $luxS_{V.h.}$ locus were transferred to the corresponding locations in the *V. harveyi* BB120 chromosome to make strains MM37, MM30, MM36, MM38 and MM28 respectively (FIG. 9A). Southern blotting was used to confirm the correct placement of all five Tn5 insertions in the *V. harveyi* chromosome. The four *V. harveyi* $luxS_{V.h.}$::Tn5 insertion strains were tested for the ability to produce AI-2, and all four strains gave identical results.

In FIG. 10A, we show the AI-2 production phenotypes of the wild type control Tn5 insertion strain MM28 and one representative $luxS_{V.h.}$::Tn5 insertion strain, MM30. *V. harveyi* MM28 and MM30 were grown to high cell density, after which cell-free culture fluids were prepared. The culture fluids were assayed for AI-2 activity by the ability to induce luminescence in the AI-2 detector strain BB170. FIG. 10A shows that addition of culture fluids from the control Tn5 insertion strain MM28 induced luminescence in the reporter 780-fold, while culture fluid from the $luxS_{V.h.}$::Tn5 insertion strain MM30 did not induce the expression of luminescence in the reporter. Therefore, a null mutation in $luxS_{V.h.}$ in *V. harveyi* eliminates AI-2 production.

Identification and analysis of *S. typhimurium* autoinducer production mutants. In order to identify the gene responsible for AI-2 production in *S. typhimurium*, we randomly mutagenized *S. typhimunium* LT2 using the MudJ transposon (Maloy et al., 1996, supra). Ten-thousand *S. typhimurium* LT2 insertion mutants were assayed for AI-2 production in the *V. harveyi* BB170 bioassay. One *S. typhimurium* MudJ insertion mutant (strain CS132) was identified that lacked detectable AI-2 in culture fluids at mid-exponential phase.

FIG. 10B shows the AI-2 production phenotypes of *S. typhimurium* strain LT2 and the corresponding MudJ insertion strain CS132. The strains were grown to mid-exponential phase in LB containing glucose, and cell-free culture fluids were prepared and assayed for AI-2. *S. typhimurium* LT2 culture fluids induced the reporter strain 500-fold, while culture fluids from strain CS132 contained no AI-2 activity. Furthermore, strain CS132 did not produce AI-2 under any of the growth conditions that we have previously reported induce AI-2 production in *S. typhimurium* (not shown).

The site of the MudJ insertion in *S. typhimurium* CS132 was determined by PCR amplification followed by sequencing of the 110 bp of chromosomal DNA adjacent to the transposon. This sequence was used to search the database for DNA homologies. The sequence matched a site (89/105 bp identity) in the *E. coli* MG1655 genome that corresponded to an ORF of unknown function denoted ygaG (Blattner et al., 1997, supra). In the chromosome, the *E. coli* ygaG gene is flanked by the gshA and emrB genes (FIG. 9B). The ygaG gene is transcribed from its own promoter that is located immediately upstream of the gene, indicating that it is not in an operon with gshA. The emrB gene is transcribed in the opposite direction. We PCR amplified the ygaG region from the chromosomes of *E. coli* O157:H7 and *E. coli* MG1655, and the two *E. coli* ygaG genes were cloned into pUC19.

Complementation of *S. typhimurium* and *E. coli* AI-2$^-$ mutants. We tested whether the *E. coli* O157:H7 ygaG gene and the *V. harveyi* $luxS_{V.h.}$ gene could restore AI-2 production in the AI-2$^-$ strains *S. typhimurium* CS132 and *E. coli* DH5. In FIG. 11A, we show the AI-2 activity produced by wild type *V. harveyi* BB120, *E. coli* O157:H7 and *S. typhimurium* LT2. In this figure, the level of AI-2 activity present in *V. harveyi* BB120 cell-free culture fluids was normalized to 100%, and the activities in cell-free culture fluids from *E. coli* and *S. typhimurium* compared to that. In this experiment, *E. coli* O157:H7 produced 1.5 times and *S. typhimurium* LT2 produced 1.4 times more AI-2 activity than *V. harveyi* BB120 (i.e., 150% and 141% respectively).

FIGS. 12A and 12B show the AI-2 complementation results for *S. typhimurium* CS132 and *E. coli* DH5. FIG. 12A demonstrates that introduction of the *E. coli* O157:H7 ygaG gene into *S. typhimurium* CS132 restored AI-2 production beyond the level of production of wild type *S. typhimurium* (i.e., 209% activity). Comparison of the data in FIGS. 12A and 12B shows that the *E. coli* ygaG gene in *S. typhimurium* resulted in AI-2 production exceeding that produced in vivo by *E. coli* O157:H7. Introduction of the *V. harveyi* $luxS_{V.h.}$ gene into *S. typhimurium* resulted in AI-2 production at slightly less than the level produced by wild type *V. harveyi* BB120 (i.e., 73% of the level of *V. harveyi* BB120). FIG. 12B shows that *E. coli* DH5 was also complemented to AI-2 production by both the cloned *E. coli* O157:H7 and the *V. harveyi* BB120 AI-2 production genes. However, introduction of *E. coli* O157:H7 ygaG and *V. harveyi* BB120 $luxS_{V.h.}$ into *E. coli* DH5 resulted in only 31% and 43% of the *V. harveyi* BB 120 AI-2 activity respectively. FIGS. 12A and 12B show that the control vectors produced no activity in the complementation experiments.

Analysis of the AI-2 production genes from *V. harveyi, E. coli* and *S. typhimurium*. We sequenced the AI-2 production gene $luxS_{V.h.}$ from *V. harveyi* BB120 and the ygaG loci from *E. coli* O157:H7, *E. coli* MG1655 and *E. coli* DH5. The translated protein sequences encoded by the ygaG ORF's are shown in FIG. 13, and they are aligned with the translated LuxS protein sequence from *V. harveyi*. The nonbold, underlined amino acids indicate the residues in the *E. coli* proteins that differ from the *V. harveyi* LuxS protein. The ygaG loci from *E. coli* encode proteins that are highly homologous to one another and also to LuxS from *V. harveyi*. The *E. coli* MG1655 and the *E. coli* O157:H7 YgaG proteins are 77% and 76 % identical to LuxS from *V. harveyi* BB120. The DNA sequence we determined for ygaG from *E. coli* O157: H7 differs at five sites from the reported (and our) sequence for the *E. coli* MG1655 ygaG gene. Four of the changes are silent, the fifth results in a conservative Ala to Val alteration at amino acid residue 103 in the *E. coli* O157:H7 protein.

Figure 11:
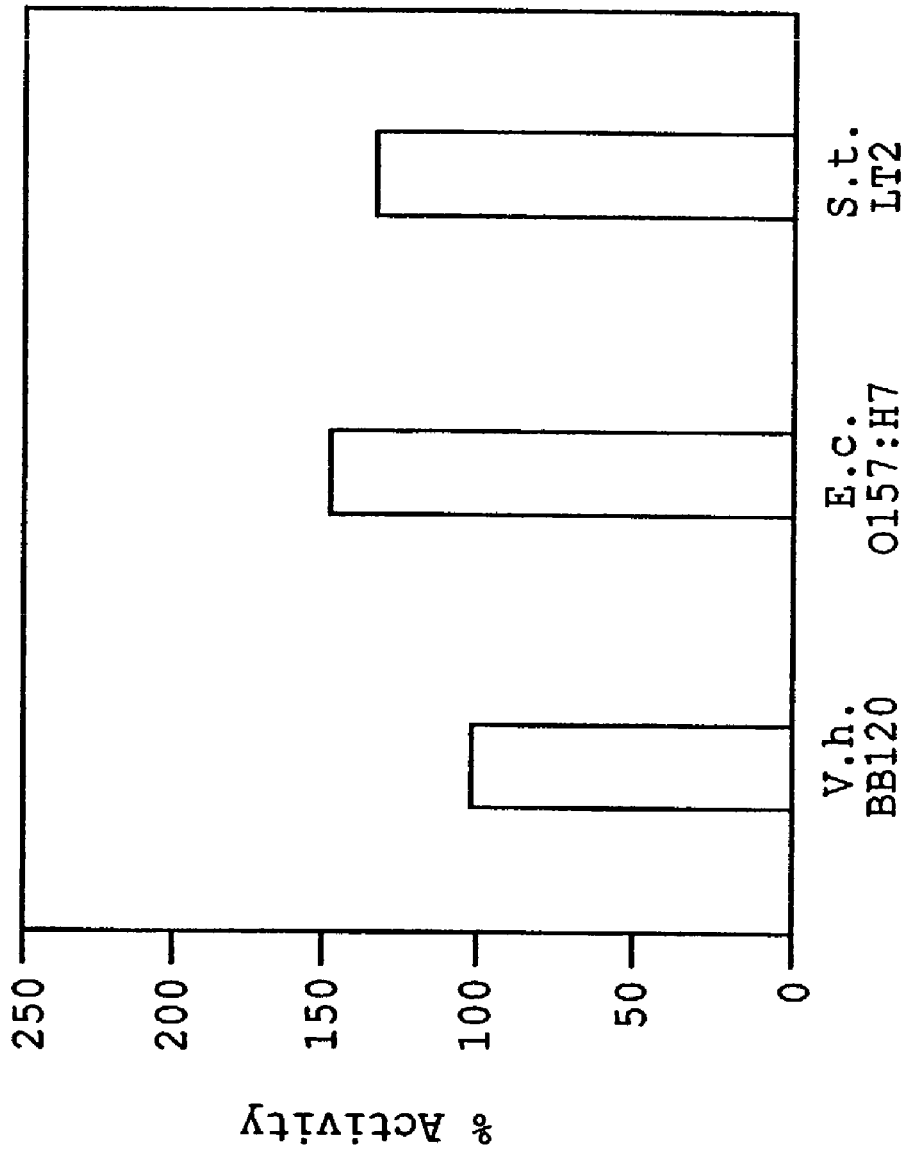
FIG. 11. Complementation of AI-2 production in *S. typhimurium* CS 132 and *E. coli* DH5. Cell-free culture fluids from *E. coli* and *S. typhimurium* strains were tested for AI-2 activity in the bioassay. The activity present in these fluids was compared to that produced by wild type *V. harveyi* BB120. In the figure, the level of BB120 activity was normalized to 100%. : AI-2 activity in cell-free fluids from wild type *V. harveyi* BB120, *E. coli* O157:H7, and *S. typhimurium* LT2.
Figure 12:
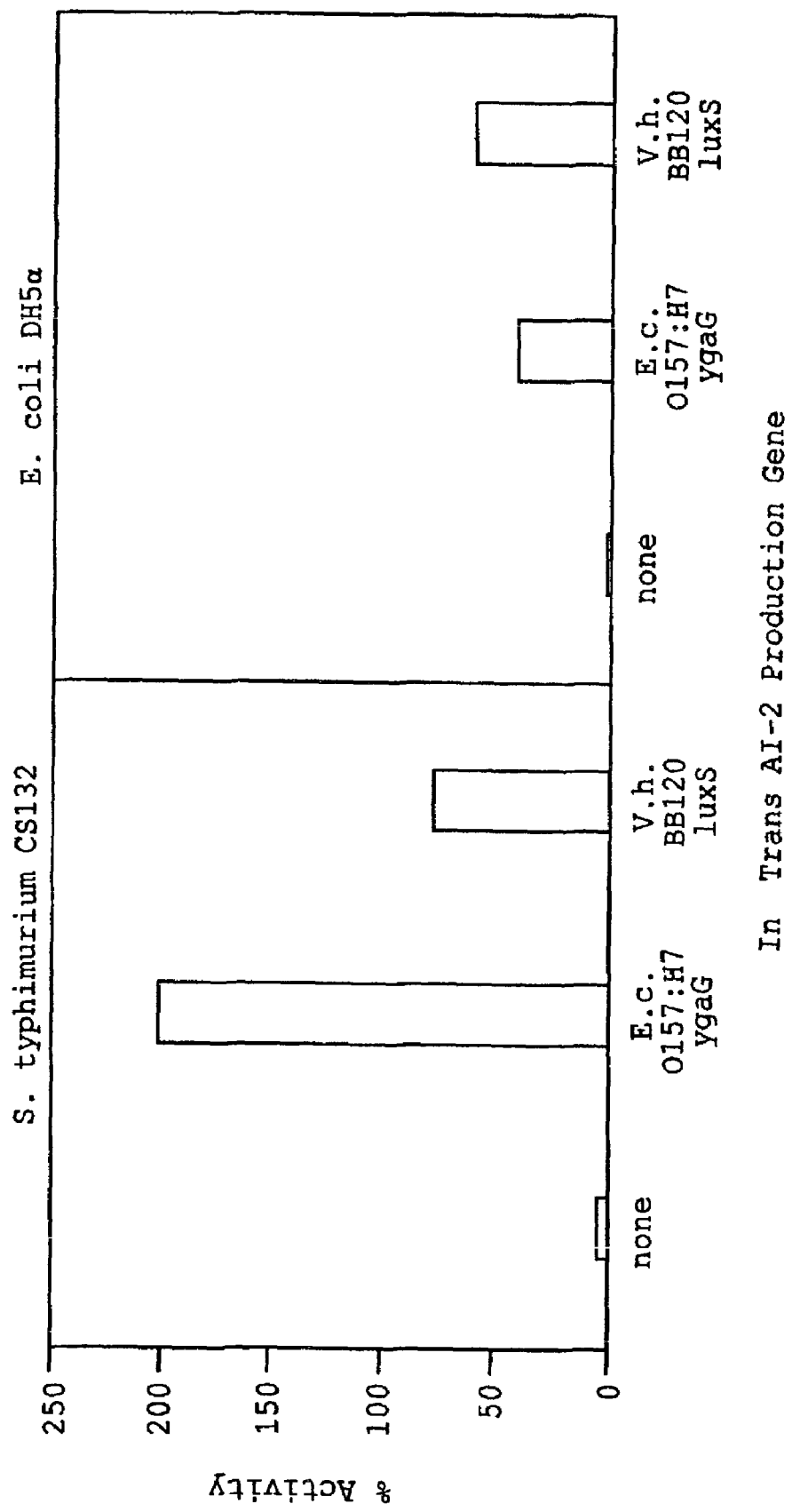
FIG. 12 Complementation of *S. typhimurium* CS132 (ygaG::MudJ) (panel A) and of *E. coli* DH5 (panel B). The in trans AI-2 production genes are the following: vector control (denoted: none), *E. coli* O157:H7 ygaG; and *V. harveyi* BB120 luxS$_{V.h.}$ *E. coli* and *V. harveyi* are abbreviated E.c. and V.h. respectively.

Identification of the ygaG locus in *E. coli* MG1655 and *E. coli* O157:H7 allowed us to investigate the AI-2 production defect in *E. coli* DH5. *E. coli* DH5 possesses the ygaG gene because we could PCR amplify this region from the chromosome using the same primers we employed to amplify it from *E. coli* MG1655 and *E. coli* O157:H7. Examination of the *E. coli* DH5 ygaG promoter showed that it is identical to that of *E. coli* MG1655, indicating that the AI-2 defect in *E. coli* DH5 is not simply due to decreased transcription of ygaG. However, sequence analysis of the *E. coli* DH5 ygaG coding region showed that a one G-C base pair deletion and a T to A transversion exist at bp 222 and 224 respectively. The frameshift mutation resulting from the G/C deletion causes premature truncation of the *E. coli* DH5 protein. FIG. 13 shows that the truncated *E. coli* DH5 protein is 111 amino acids, while the *E. coli* MG1655 and *E. coli* O157:H7 proteins are 171 residues. Twenty altered amino acids are translated after the frame shift and prior to termination of the protein. Our complementation results (FIGS. 11 and 12) demonstrate that the AI-2 production defect in *E. coli* DH5 is recessive to in trans expression of ygaG, which is consistent with the defect being due to a null mutation caused by the frame shift in the *E. coli* DH5 ygaG gene.

We searched the *S. typhimurium* database using the sequence we obtained adjacent to the MudJ that inactivated the AI-2 production function in *S. typhimurium* CS 132. A perfect match (110/110 bp) was identified to fragment B_TR7095.85-T7 in the *S. typhimurium* LT2 genome sequencing database (Genome Sequencing Center, Washington University, St. Louis). However, the *S. typhimurium* LT2 database ygaG sequence is incomplete (FIG. 13). The translated sequence matches the *E. coli* and *V. harveyi* sequences beginning at amino acid residue 8. The translated sequence shows that the *S. typhimurium* protein is 75% identical to LuxS of *V. harveyi*. In order to align the *S. typhimurium* sequence with the *V. harveyi* LuxS protein, we corrected three apparent frame shift errors in the database sequence. Considering that only crude, unannotated sequence data is currently available for *S. typhimurium*, we predict that the *S. typhimurium* protein contains 7 more amino acids, and that the frame shift mutations are sequencing errors. We were unsuccessful at PCR amplifying either the *S. typhimurium* 14028 or the *S. typhimurium* LT2 ygaG gene using the primers designed for *E. coli*, so we do not yet have the complete sequence of the *S. typhimurium* gene.

The results set forth above indicate that the genes we have identified and analyzed encode a novel family of proteins responsible for autoinducer production. Members of this new family of genes, referred to herein as LuxS, are highly homologous to one another but not to any other identified genes. The encoded product of the LuxS genes catalyze an essential step in the synthesis of the signaling compounds of the present invention.

EXAMPLE 4

Construction of a Sensor $1^-$, AI-$2^-$ *V. harveyi* Reporter Strain

*V. harveyi* null mutants in each of the lux genes luxL, luxM, luxN, luxS and luxQ have been constructed. These mutants fail to either make or respond to one specific autoinducer, but they still produce light because, in each case, one quorum sensing system remains operational. A double luxN, luxS *V. harveyi* mutant will not emit light without the addition of exogenous AI-2 because this mutant will not respond to AI-1 and it will not produce AI-2.

The *V. harveyi* luxS gene has been cloned into *E. coli* DH5α on a broad host range mobilizable cosmid called pLAFR2. This construction restores AI-2 production to *E. coli* DH5α. A marked null mutation was engineered into the luxS gene by introducing a chloramphenicol resistance ($Cm^r$) cassette into an internal restriction site. Placement of the $Cm^r$ cassette at this site in luxS subsequently eliminated AI-2 production in *E. coli* DH5α.

The luxS::$Cm^r$ null allele was transferred onto the chromosome of *V. harveyi* strain BB170. Strain BB170 contains a Tn5$Kan^r$ in luxN and does not respond to AI-1. To construct the double mutant, triparental conjugations were carried out by mixing stationary phase cultures of *E. coli* DH5α carrying the *V. harveyi* luxS::$Cm^r$ construction in pLAFR2 (pLAFR2 carries tetracycline resistance), *E. coli* DH5α carrying the tra donor plasmid pRK2013 and the *V. harveyi* recipient strain BB170. Exchange of the luxS::$Cm^r$ mutant allele for the wild type luxS allele on the chromosome occurs by homologous recombination. The exogenote cosmid in *V. harveyi* was eliminated by the introduction of a second incompatible plasmid pPH1JI. This was accomplished by mating *E. coli* DH5α containing pPH1JI with the *V. harveyi* BB170 recipient containing the luxS::$Cm^r$ cosmid, and selecting for exconjugants on plates containing ampicillin (for counter selection of the *E. coli* donor) chloramphenicol (for inheritance of the mutant luxS::$Cm^r$ allele) and gentamicin (for maintenance of the plasmid pPH1JI). Southern blot analysis was used to verify that the exogenote pLAFR2 cosmid has been eliminated and that the luxS::$Cm^r$ construction had been transferred to the corresponding position in the genome of *V. harveyi*. The pPH1JI cosmid was subsequently eliminated by growth in the absence of gentamicin selection.

Verification that the luxN, luxS Double Mutant Responds to AI-2. The *V harveyi* strain that is mutant in luxN and luxS was stimulated to produce light in response to the exogenous addition of AI-2 but not AI-1. This was verified in a luminescence assay for response to *V. harveyi* AI-1 and AI-2. *V. harveyi* strain MM30 (luxS::Tn5) that is phenotypically AI-$1^+$, AI-$2^-$, and *V. harveyi* strain BB152 (luxM::Tn5) that is phenotypically AI-$1^-$, AI-$2^+$ were used as the sources of AI-1 and AI-2 respectively. The AI-1 and AI-2 present in culture fluids of these strains was tested for stimulation of light production of the *V. harveyi* luxN, luxS double mutant reporter strain. In this assay, autoinducer preparations from MM30, BB152 or sterile medium controls were added to the wells of microtiter plates, followed by the addition of the *V. harveyi* reporter strain. The resulting light production was monitored using a liquid scintillation counter in the chemiluminescence mode. Maximal stimulation of light production in the *V. harveyi* luxN, luxS reporter strain was compared to that produced by the Sensor $1^+$, Sensor $2^-$ *V. harveyi* strain BB886 and the Sensor $1^-$, Sensor $2^+$ *V. harveyi* strain BB170. These two *V. harveyi* strains are routinely used in this assay as reporters of AI-1 and AI-2 activity respectively.

Determine optimum concentrations of AI-2 in microtiter assays. The aforementioned screen will be optimized for use in 96-well microtiter assays. The screen will be used in inhibitor assays for identifying inhibitors of AI-2. Purified or synthetic AI-2 will be added to the microtiter wells containing the newly constructed reporter strain and inhibition will be measured by a decrease in light emission from the wells containing an inhibitor. The assay will be optimized by determining the concentration of cells and AI-2 in the microtiter wells that will allow for maximal sensitivity. The optimal AI-2 concentration will be that that stimulates half-maximal light output for a given concentration of cells per unit time. Initial experiments will be conducted in this concentration range to determine the range of AI-2 concentration that produces the greatest change in light output. Similar experiments using AI-$^1$ and a non self-stimulating sensor-1$^+$, sensor-2$^-$ mutant (BB886) showed that the assay was sensitive to concentrations as low as 100 nM AI-1 and that light emission was linear over 6 orders of magnitude (light emission from a self-stimulating strain was linear over 3 orders). Similar results for AI-2 using the new reporter strain that will not self-stimulate and therefore have zero background light emission are predicted. Light emission from the microtiter wells will be measured with a Wallac TriLux liquid scintillation counter model 1450–021 in the chemiluminescence mode. This machine will accommodate 16 plates and will therefore allow for 1536 separate concentration experiments per run.

EXAMPLE 5

In-Vitro Method for Synthesizing AI-2

Purification and Identification of AI-2. The AI-2 class of compound is refractory to purification by conventional techniques used for the isolation of acyl-homoserine lactone (HSL) autoinducers such as AI-1 from *V. harveyi*. Unlike other HSL autoinducers, under the conditions tested, the AI-2 activity does not extract quantitatively into organic solvents. Furthermore, it fails to bind to either a cation or anion exchange column. The present characterization of AI-2 indicates that it has a molecular weight of less than 1000 kDa, and is a polar but apparently uncharged organic compound. The AI-2 activity is acid stable and base labile and heat resistant to about 80 but not 100° C. These results indicate that the AI-2's are not acyl-homoserine lactones. The luxS genes identified in the present study bear no homology to other genes known to be involved in production of HSL autoinducers further indicating that the present AI-2 class of autoinducers is novel.

Thus, in addition to providing a cloned, overexpressed and purified *S. typhimurium* LuxS protein, the present invention also provides a method for producing AI-2 in vitro. The present invention provides a mechanism for generating large quantities of pure AI-2 useful for mass spectral and NMR analysis, and for screening compounds that modulate the activity of AI-2. Moreover, the present invention provides a method for determining the in vivo biosynthetic pathway for AI-2 synthesis.

Figure 14:
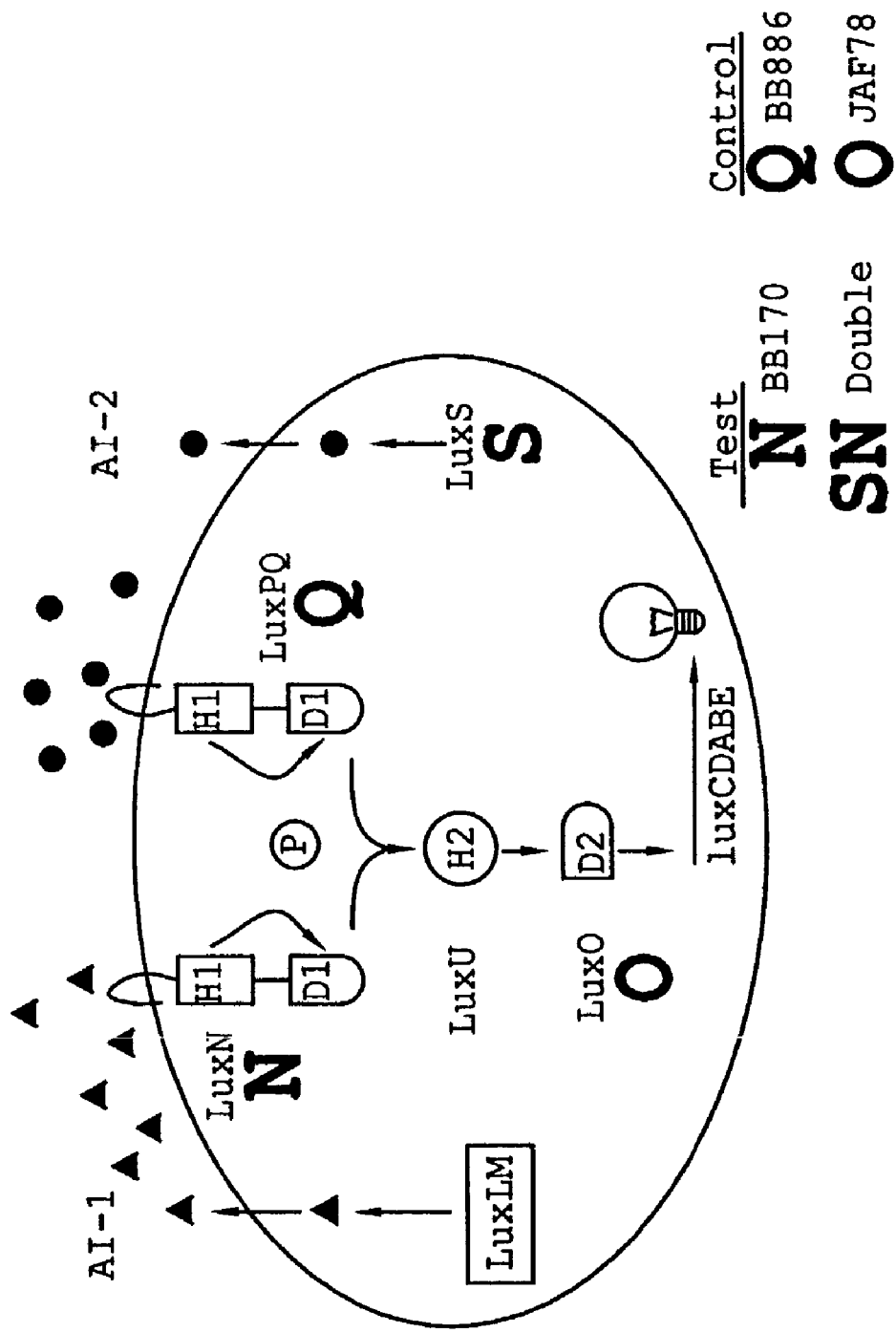
FIG. 14. A diagram of the hybrid quorum sensing circuit of *Vibrio harveyi* is provided. The AI-1 and AI-2 circuits are independently stimulated but integrate their signals for light expression. Each pathway, however, is also independently competent to generate light. This allows for reciprocal mutations in the LuxN or LuxQ sensors to be used to construct a reporter specific for AI-2 or AI-1, respectively.

The analysis of the genomic locations of the various luxS genes identified in the present invention indicates that the luxS genes do not consistently reside in any one location in the chromosome, nor are they typically found in close proximity to any specific gene(s). However, in one case, the luxS gene is the third gene in a three-gene operon with two genes (metK and pfs). In *E. coli*, Salmonella and many other bacteria, MetK and Pfs are involved in the conversion of S-adenosyl methionine (SAM) to homocysteine and 4,5-dihydroxy-2,3 pentanedione (FIG. 14). The function of MetK is to convert methionine to SAM that is an important cofactor in one-carbon metabolism. SAM is used to methylate DNA, RNA and a variety of cell proteins, and several SAM dependent methyl transferases act at this step. S-adenosyl homocysteine (SAH) is produced when the methyl group is transferred from SAM to its substrates. SAH functions as a potent inhibitor of SAM dependent methyltransferases. Therefore, bacteria rapidly degrade SAH via the enzyme Pfs. The designation "pfs" refers to an open reading frame in the *E. coli* genome that has recently been determined to encode the enzyme 5'-methylthioadenosine/S-adenosylhomocysteine nucleosidase, also known as MTA/SAH nucleosidase. In the present system, the enzyme cleaves the glycosidic bond in S-adenosylhomocycteine (SAH). Thus, the function of Pfs is to convert SAH to adenine and S-ribosyl homocysteine. In a final step, S-ribosyl homocysteine is converted to homocysteine and 4,5-dihydroxy-2,3-pentanedione. Homocysteine can reenter this pathway; it is methylated to generate methionine that can be converted to SAM by MetK.

The catabolism of SAH is considered a salvage pathway for recycling metabolic intermediates (adenine and homocysteine). However, some species of bacteria eliminate SAH by a different pathway. In this alternative pathway, adenosine is directly removed from SAH that generates homocysteine. Therefore, cells that use this second mechanism do not produce 4,5-dihydroxy-2,3-pentanedione. In the pathway shown in FIG. 16, the enzyme responsible for conversion of S-ribosyl homocysteine to 4,5-dihydroxy-2,3-pentanedione has never been identified, cloned or purified. Furthermore, no role for 4,5-dihydroxy-2,3-pentanedione is known.

LuxS is involved in the pathway shown in FIG. 16, and SAM and SAH are involved in AI-2 production. The structure of AI-2 could be 4,5-dihydroxy-2,3-pentanedione, in which case LuxS is the uncharacterized enzyme that acts on S-ribosyl homocysteine. Second, LuxS could act on one of the intermediates to make AI-2. LuxS would represent a branch point off the known pathway.

To confirm that LuxS is involved in the conversion of SAM to AT-2, the gene encoding the *S. typhimurium* LuxS protein was cloned, overexpressed and the *S. typhimurium* LuxS protein was purified. This protein was used in combination with dialyzed cell-free extracts prepared from a *S. typhimurium* luxS null mutant to show that addition of SAM and LuxS protein could restore AI-2 production to dialyzed LuxS– cell extracts. Reaction mixtures were prepared containing 10 mM Sodium Phosphate buffer pH 7.0, dialyzed *S. typhimurium* LuxS— cell extract and SAM. Purified LuxS protein was added to some of these mixtures. The reactions were incubated at room temperature for 60 min, followed by centrifugation in a 5000 MWCO centricon. The material with MW<5000 was added to the standard *V. harveyi* bioassay as previously described. Dialyzed LuxS– cell extracts to which SAM was added or extracts containing LuxS protein without the addition of SAM produced no AI-2 activity. However, identical extracts to which LuxS protein and SAM had been added produced AI-2 that resulted in over 500-fold stimulation in light production in the bioassay.

Further investigation showed that SAM is not the direct substrate for LuxS, and that LuxS must act at a step subsequent to the conversion of SAM to SAH (FIG. 16). It was determined that AI-2 was not produced if SAM was added directly to LuxS protein, however activity was produced by pre-incubation of SAM with the LuxS– extracts, filtration, and subsequent addition of LuxS protein to the filtrate. Importantly, these studies indicate that SAM can react with an element in the cell extract before it can be used by LuxS to make AI-2. Presumably, the SAM dependent methyl transferases present in the cell extract use SAM as a methyl donor and convert it to SAH in the process. To verify this, SAH was substituted for SAM in an in vitro assay. Addition of SAH to the in vitro assay resulted in much greater AI-2 production than when SAM was added. This result indicates that LuxS functions in the pathway subsequent to the conversion of SAM to SAH. Again, addition of SAH directly to LuxS protein is not sufficient for production of AI-2 activity, while pre-incubation of SAH with dialyzed LuxS– extracts followed by filtration and subsequent addition of LuxS protein to the filtrates does result in AI-2 production. Presumably SAH is converted to S-ribosyl homocysteine and then LuxS acts to produce AI-2.

The proposed pathway shown in FIG. 16 is not a salvage pathway for recycling secondary metabolites, but rather is the pathway for production of AI-2. The present invention has narrowed the possibilities for point of LuxS activity in the biosynthesis of AI-2. The remaining possibilities are shown in FIG. 16 (designated LuxS?).

According to the invention, AI-2 is a derivative of ribose. It is noteworthy that, in *V. harveyi*, LuxP, the primary sensor for AI-2, is a homologue of the *E. coli* and *S. typhimurium* ribose binding protein.

Characterization and Biosynthesis of AI-2. The invention further provides a method for an in vitro procedure for large scale production of pure AI-2. As indicated in FIG. 16, SAH is a precursor in the LuxS dependent biosynthesis of AI-2. Furthermore, LuxS does not act directly on SAH. Prior to the action of LuxS, SAH must first be acted on by some enzyme in dialyzed cell extracts. Presumably this step is the conversion of SAH to S-ribosyl homocysteine by Pfs. Therefore the substrate for LuxS is S-ribosyl homocysteine.

To confirm that LuxS acts on S-ribosyl homocysteine, the Pfs enzyme can be purified and used to convert SAH to S-ribosyl homocysteine. Toward this end, the pfs gene has been cloned from *S. typhimurium* 14028 placed into the overexpression vector pLM-1. The Pfs enzyme will be overexpressed and SAH will be added to purified Pfs to produce S-ribosyl homocysteine. The conversion of SAH to S-ribosyl homocysteine will be confirmed by reverse phase HPLC analysis (SAH is UV active while S-ribosyl homocysteine is not). Subsequently, the S-ribosyl homocysteine produced by Pfs will be added to purified LuxS. Following incubation, the mixture will be filtered over a 5000 MWCO centricon. The filtrate will be tested for AI-2 activity in the previously described *V. harveyi* bioassay. The identification of activity will confirm that 4,5-dihydroxy-2,3-pentanedione is AI-2.

In addition, AI-2 structure obtained from *E. coli* and *V. harveyi* AI-2 will be determined. The *E. coli* and *V. harveyi* luxS genes have been cloned in to overexpression vectors. The identity/biosynthesis of the *S. typhimurium* AI-2 provided by the present invention should greatly facilitate these analyses. In the event that the *S. typhimurium*, *E. coli* and *V. harveyi* AI-2's are identical these data will indicate that AI-2's are the same.

EXAMPLE 6

Identification of Compounds that Modulate the Response to AI-2

A library of chemical compounds generated by combinatorial chemistry techniques is obtained. A plurality of test mixtures is generated wherein each test mixture contains one or more of the compounds from the library and AI-2. Each of the test mixtures is placed in contact with a culture of *Vibrio harveyi* MM32 cells and bioluminesce is measured as described above. The amount of bioluminescence from each the cultures contacted with the test mixtures is compared to the amount of bioluminescence from a control culture of *Vibrio harveyi* MM32 cells that was contacted with AI-2 but not with a compound from the library.

A test mixture that resulted in a reduced level of bioluminescence relative to the control culture is identified. This test mixture contains a compound that decreases the response to AI-2. The compound is purified and its structure is determined. The compound may be directly useful as an antimicrobial compound to reduce the extent of an infection or, alternatively, the compound may be further optimized to produce a compound that may be used to to reduce the extent of an infection.

EXAMPLE 7

Bacterial Strains and Media Used to Discover the lsr Operon

The bacterial strains and plasmids used to discover the lsr operon are listed in Table 4 below.

TABLE 4

*S. typhimurium* Strains and Plasmids

| Strain | Genotype | Source |
| --- | --- | --- |
| *S. typhimurium* Strains | | |
| 14028 | Wild type | ATCC |
| SS007 | luxS::T-POP | (Schauder et al., 2001) |
| MET89 | pqiA::T-POP | This study |
| JS14 | lsrA::MudJ | This study |
| JS15 | lsrA::MudJ luxS::T-POP | This study |
| MET442 | JS15 with pUC18 | This study |
| MET444 | JS15 with pAB15 | This study |
| MET235 | lsrC::MudJ | This study |
| MET236 | lsrC::MudJ luxS::T-POP | This study |
| MET281 | MET236 with pUC18 | This study |
| MET276 | MET236 with pAB15 | This study |
| MET259 | lsrB::MudJ | This study |
| MET260 | lsrB::MudJ luxS::T-POP | This study |
| MET285 | MET260 with pUC18 | This study |
| MET280 | MET260 with pAB15 | This study |
| MET233 | lsrF::MudJ | This study |
| MET234 | lsrF::MudJ luxS::T-POP | This study |
| MET231 | lsrF::MudJ | This study |
| MET239 | lsrF::MudJ | This study |
| MET240 | lsrF::MudJ luxS::T-POP | This study |
| MET283 | MET239 with pUC18 | This study |
| MET278 | MET239 with pAB15 | This study |
| MET237 | lsrE::MudJ | This study |
| MET238 | lsrE::MudJ luxS::T-POP | This study |
| MET282 | MET238 with pUC18 | This study |
| MET277 | MET238 with pAB15 | This study |
| MET328 | rpsL null | This study |
| MET341 | MET328 ΔlsrR | This study |
| MET342 | MET328 ΔlsrR luxS::T-POP | This study |

TABLE 4-continued

S. typhimurium Strains and Plasmids

| Strain | Genotype | Source |
|---|---|---|
| MET371 | lsrC::MudJ ΔlsrR luxS::T-POP | This study |
| MET370 | lsrC::MudJ ΔlsrR | This study |
| MET450 | MET236 with pMET1035 | This study |
| MET449 | MET235 with pMET1035 | This study |
| MET492 | MET371 with pMET1035 | This study |
| MET453 | MET370 with pMET1035 | This study |
| MET269 | luxS::pKAS32 | This study |
| MET270 | lsrC::MudJ luxS::pKAS32 | This study |
| MET301 | lsrC::MudJ luxS::pKAS32 lsrRA21T undefined T-POP insertion | This study |
| MET294 | lsrC::MudJ luxS::pKAS32 lsrRA120T undefined T-POP insertion | This study |
| MET293 | lsrC::MudJ luxS::pKAS32 lsrRG208R undefined T-POP insertion | This study |
| MET299 | lsrC::MudJ luxS::pKAS32 Δ($P_{lsr}$ – 5'lsrR) undefined T-POP insertion | This study |
| MET305 | lsrC::MudJ luxS::pKAS32 lsrRL145Q undefined T-POP insertion | This study |
| MET303 | lsrC::MudJ luxS::pKAS32 lsrRL134P | This study |
| MET309 | lsrC::MudJ luxS::pKAS32 lsrRL39P | This study |
| MET312 | lsrC::MudJ luxS::pKAS32 lsrRY25H | This study |
| MET378 | lsrC::MudJ luxS::pKAS32 lsrR::T-POP | This study |
| JS128 | metE551 metA22 ilv452 trpB2 hisC527(am) galE496 xyl-404 rpsL120 flaA66 hsdL6 hsdA29 zjg8103::pir | Slauch, J. |
| Plasmids | | |
| pUC18 | $Amp^R$ | (Sambrook et al., 1989) |
| pAB15 | pUC18 ($Amp^R$) containing luxS | This study |
| pJAF329 | pALTER-1 $Tet^S$, $Amp^R$ | This study |
| pMET1035 | pJAF329 ($Amp^R$) with lsrR | This study |
| pKAS32 | $Amp^R$, $rpsL^+$ Suicide vector | (Skorupski and Taylor, 1996) |
| pNK2880 | $Amp^R$, $P_{tac}$ – tnpA | (Bender and Kleckner, 1992) |

S. typhimurium 14028 is ATCC strain 14028, Organism: Salmonella choleraesuis. All strains were grown in Luria Broth (LB), which contained 10 g Bacto Tryptone (Difco), 5 g Yeast Extract (Difco), and 10 g NaCl per liter (Sambrook et al., 1989). When necessary, media were supplemented by antibiotics at the following concentrations (mg/liter): ampicillin (Amp), 100; kanamycin (Kan), 100; tetracycline (Tet), 10 or 15; and streptomycin (Sm), 1000. 5-Bromo-4-Chloro-3-indoylyl-β-D-galactoside (X-gal) was added to LB agar plates to a final concentration of 40 mg/liter. MacConkey-lactose and M63-lactose minimal plates were prepared as described (Miller, 1992). AB medium was prepared as described (Greenberg et al., 1979). All E. coli and S. typhimurium. strains were grown at 37 C with aeration.

EXAMPLE 8

Genetic and Molecular Techniques used in the Discovery of the lsr Operon

DNA ligation reactions were transformed into either E. coli strain JM109 (supE Δ(lac-proAB) hsdR17 recA1 F⁻ traD36 proAB⁺ lacI$^q$ lacZΔM15) or MC4100 λpir (F⁻ araD139 Δ(argF-lac)U169 rpsL150 relA1 thi fib5301 deoC1 ptsF25 rbsR λpir) by electroporation. Electroporation of plasmids into bacterial cells was carried out as previously described (Sambrook et al., 1989). Plasmids were maintained in E. coli strains, and passaged through the restriction deficient strain S. typhimurium JS128 before introduction into other S. typhimurium strains. P22 transductions were performed using P22HT int, as described (Davis et al., 1980). Sequencing reactions were performed by the Princeton University SynSeq facility. Polymerase chain reaction (PCR) reactions were performed using Taq DNA Polymerase (Boeringer Mannheim Biochemicals) or Ex-Taq DNA Polymerase (Takara Biochemicals). Restriction endonucleases and T4 DNA ligase were purchased from New England Biolabs. All enzymes were used as recommended by the suppliers. Primers used in PCR and sequencing reactions are listed in Table 5 below

TABLE 5

PCR and Sequencing Primers

| Primer Name | Oligonucleotide |
|---|---|
| St-11 | ATAAGAATGCGGCCGCAGAGGCGTTAAATGACTGCAACGC |
| St-12 | GCGGAGCTCTATCGCTCATTGTCATAACCTGGC |
| St-13 | GCGGAGCTCACTATATCAATGCACTGGTTACCG |
| St-14 | GCGGAATTCAACAGACTACGTTTCCAGTTGCGG |
| St-15 | GCGGAATTCTGAAAAAGAAATTGTTCAAAACGG |
| Pop1 | CCAAATGATGTTATTCCGCG |
| luxS01 | CGGGGATCCTTACCGTAATCTGTTACGCG |
| luxS04 | GGGGATCCGAAAAGCAAGCACCGATCATC |
| St-18 | GCGAAGCTTAGCCAGGTTATGACAATGAGCG |
| St-16 | GCGGGATCCTAATTTGAATTATTTTCCCTGCGG |
| St-9 | AATAAGTATGCGGCCGCCATTCCGAACAAAGAAGTGATG |
| St-10 | GGGGAATTCCGCTGCTCGTCCGGCGTGCCAATC |

EXAMPLE 9

Identification of AI-2 regulated genes in S. typhimurium

The following strategy allowed us to generate 11,000 isogenic wild type luxS and luxS null strains harboring random MudJ (lacZ) reporter insertions in the S. typhimurium chromosome. Wild type S. typhimurium 14028 was mutagenized with the transposon MudJ by a P22 delivery system, as described (Hughes and Roth, 1988). 11,000 insertion mutants were ordered onto grids on LB plates that contained Kan to select for MudJ and 5 mM EGTA to inhibit phage adsorption. In order to create the isogenic wild type luxS and luxS null pairs of mutants for each MudJ insertion, the mutants were replica plated onto two different petri plates. One plate contained a P22 lysate that had been propagated on the luxS null strain SS007 (14028 luxS::T-POP) (Schauder et al., 2001). The second plate contained a P22 lysate that was harvested from wild type luxS strain MET89 (14028 pqiA::T-POP). The pqiA gene is expected to have no effect on AI-2 signalling, and thus serves as control for the P22 transduction procedure (Koh and Roe, 1995). Both lysates were used at a concentration of 2%. In addition, all petri plates contained Tet, Kan, X-gal, and 5 mM CaCl2. Tet was included in the plates to select for T-POP transductants. Kan was added to ensure that all colonies retained a MudJ insertion. Addition of CaCl2 allowed the cells to be infected with P22 on the petri plates. X-gal was used as a visual monitor for LacZ activity from the MudJ reporter. The insertion mutants were compared to identify those with differential β-galactosidase activity in the wild type luxS and luxS null backgrounds. Colonies containing potential luxS regulated fusions were purified and tested in quantitative β-galactosidase assays. Fusions that showed differential β-galactosidase activity were backcrossed by P22 transduction into wild type strain 14028 and luxS null strain SS007, and subsequently re-examined for differential LacZ activity using β-galactosidase assays. In strains that maintained differential β-galactosidase activity, the chromosome-MudJ transposon fusion junction was amplified by a two-step PCR method. The fusion junction was sequenced in order to identify the regulated gene, as described (Surette et al., 1999).

EXAMPLE 10

Isolation of Suppressors of lsr Operon Expression

Strain MET270 (luxS::pKAS32, lsrC::MudJ) is Lac–, and is therefore unable to grow on M63-lactose minimal plates. To identify mutations in regulators of the lsr operon, a genetic selection was performed for spontaneous mutations in MET270 that resulted in a Lac+ phenotype, indicating that the lsrC::MudJ reporter was transcribed in the absence of a functional luxS gene. Mutants were selected by plating aliquots (0.1 ml) of overnight cultures of MET270 onto M63-lactose plates containing Amp and Kan, and incubating at 37 C. Amp and Kan were included on the plates to ensure that colonies retained their luxS::pKAS32 and lsrC::MudJ markers, respectively.

In an analogous strategy, transposon T-POP mutagenesis was used to identify mutants in which the lsr operon was expressed in a luxS null background. A library of 12,000 random T-POP insertions was generated in an *S. typhimurium* strain containing the lsrC::MudJ fusion and the Tn10 transposase expressing plasmid pNK2880, as described (Rappleye and Roth, 1997). A P22 lysate was generated on this library of T-POP insertion mutants to transduce the T-POP insertions into MET270. Transductants were plated on M63-lactose minimal plates containing Amp, Kan, and Tet. Amp and Kan were included to ensure retention of the luxS::pKAS32 and lsrC::MudJ markers, respectively. Tet was included to select for T-POP transductants. To verify that the suppressor mutations were associated with the T-POP insertions, linkage of the suppressor mutations to the T-POP insertions was determined by transduction. The T-POP marker was transduced into MET270 and plated on MacConkey-lactose plates containing Amp, Kan, and Tet, to select for the luxS::pKAS32, lsrC::MudJ, and T-POP markers, respectively. A Lac+ phenotype was taken as evidence that the suppressor mutation was associated with the T-POP insertion.

To determine whether the suppressor mutations were linked to the lsr operon, the lsrC::MudJ marker from each mutant was transduced into strain MET269 (luxS::Pkas32) and plated on MacConkey-lactose plates containing Kan and Amp. Amp was included in these plates to maintain the luxS::Pkas32 construct, and Kan was included to select for MudJ. Co-transduction of the suppressor mutation with the lsrC::MudJ fusion was assessed by scoring the presence of Lac+ colonies, which indicated that the suppressor mutation was linked to the lsr operon. To determine whether the T-POP transposon had inserted in lsrR, the lsrR gene was PCR amplified from the suppressor strains using primers St-11 and St-14. Suppressors generating no PCR product from this reaction were inferred to have a T-POP insertion in the lsrR gene. The T-POP-lsrR fusion junction was PCR amplified from these strains using T-POP primer Pop1 and lsrR primers St-14 and St-15. The products were sequenced to define the positions of the T-POP insertions in lsrR. The lsrR gene of the spontaneous Lac+suppressors was PCR amplified and sequenced to identify the mutations.

EXAMPLE 11

Plasmid Constructions

To construct plasmid pAB15, the *S. typhimurium* luxS gene and flanking sequences were amplified from the chromosome of *S. typhimurium* 14028 by polymerase chain reaction (PCR), using primers luxS01 and luxS04. These primers introduce BamHI restriction sites. The resulting PCR product was digested with BamHI and ligated into BamHI-digested pUC18. To construct plasmid pMET1035, the lsrR gene was amplified by PCR from the chromosome of *S. typhimurium* 14028 using primers St-18 and St-16, which introduce HindIII and BamHI restriction sites, respectively. The parent vector for this cloning procedure, pJAF329, was created by site-directed mutagenesis of plasmid pALTER-1 (Promega) to create an AmPR, Tets version of the vector. The lsrR PCR product was digested with HindIII and BamHI and ligated into similarly digested pJAF329. Transcription of the lsrR gene in this construct is driven from a constitutive promoter in pJAF329.

EXAMPLE 12

Construction of the luxS::pKAS32 Null Strain

A 200 bp DNA fragment internal to luxS was amplified by PCR from the chromosome of *S. typhimurium* 14028 using primers St-9 and St-10 (Table 2). The PCR product was digested with NotI and EcoRI and ligated into the suicide plasmid pKAS32 (Skorupski and Taylor, 1996). The resulting luxS suicide plasmid was transformed into *S. typhimurium* 14028. Selection on LB plates containing Amp induced the plasmid to integrate into the chromosome at the luxS locus. Inactivation of luxS was verified by demonstrating that this strain produced no AI-2 in our AI-2 bioassay (Bassler et al., 1997). This strain is called MET269.

EXAMPLE 13

Construction of an Inframe lsrR Deletion

The DNA flanking the 5' region of lsrR was PCR amplified from *S. typhimurium* 14028 using primers St-11 and St-12. Similarly, the 3' flanking region was amplified with primers St-13 and St-14. The 5' sequence was digested with NotI and SacI, and the 3' sequence with SacI and EcoRI. The suicide plasmid Pkas32 was digested with NotI and EcoRI. A three-part ligation was performed in order to clone the lsrR flanking regions into Pkas32. This lsrR deletion construct was transformed into *E. coli* strain MC4100 pir by electroporation. The lsrR deletion was subsequently transferred to the chromosome of *S. typhimurium* strain MET328 by the two step suicide delivery system of Skorupski and Taylor (Skorupski and Taylor, 1996).

EXAMPLE 14

AI-2 Activity Assay

Relative levels of AI-2 in cell-free culture fluids of *S. typhimurium* strains of interest were measured using a *V. harveyi* bioluminescence assay, as described previously (Bassler et al., 1993; Bassler et al., 1997). Cell-free culture fluids were prepared as described (Surette and Bassler, 1998; Surette et al., 1999). These preparations were assayed for AI-2 activity at 10% (vol/vol), using *V. harveyi* reporter strain BB170 (luxN::Tn5), as described (Bassler et al., 1993). AI-2 activity is reported as fold induction over background of bioluminescence. To examine the role of Lsr in the uptake of AI-2, cultures of *S. typhimurium* were grown overnight, diluted 1:100 into fresh LB, and grown for a total of 4 hours. During the final hour of growth, the cells were incubated with 70 μM in vitro prepared AI-2 for specified times (Schauder et al., 2001). Subsequently, the cultures were chilled on ice and cell-free culture fluids were prepared. The AI-2 remaining in these preparations was measured in the *V. harveyi* bioluminescence assay. Assays were performed in duplicate.

EXAMPLE 15

β-Galactosidase Assays

Cultures of *S. typhimurium* that had been grown overnight were diluted 1:100 into fresh LB and grown for 4 hours. For strains containing plasmids, cultures were diluted in LB supplemented with Amp. When necessary, AI-2 was synthesized in vitro and added to the growth media at the time of inoculation (Schauder et al., 2001). Cells from 1 ml of these cultures were harvested and resuspended in 1 ml Z buffer. β-galactosidase assays were performed using a microtitre plate assay, as described (Slauch and Silhavy, 1991). β-galactosidase units were calculated as $(0.1*mOD420/min)/[OD_{600}$ of cells*Volume (ml)]. All assays were performed in triplicate.

The present invention is not limited to the embodiments described and exemplified above, but is capable of variation and modification within the scope of the appended claims.

The following references are incorporate by reference herein in their entireties:

REFERENCES

Altschul, S. F., Gish, W., Miller, W., Myers, E. W., and Lipman, D. J. (1990) Basic local alignment search tool. J Mol Biol 215: 403–410.

Bassler, B. L. (1999) How bacteria talk to each other: regulation of gene expression by quorum sensing. Curr Opin Microbiol 2: 582–587.

Bassler, B. L., Greenberg, E. P., and Stevens, A. M. (1997) Cross-species induction of luminescence in the quorum-sensing bacterium *Vibrio harveyi*. J Bacteriol 179: 4043–4045.

Bassler, B. L., Wright, M., Showalter, R. E., and Silverman, M. R. (1993) Intercellular signalling in *Vibrio harveyi*: sequence and function of genes regulating expression of luminescence. Mol Microbiol 9: 773–786.

Bassler, B. L., Wright, M., and Silverman, M. R. (1994a) Multiple signalling systems controlling expression of luminescence in *Vibrio harveyi*: sequence and function of genes encoding a second sensory pathway. Mol Microbiol 13: 273–286.

Bassler, B. L., Wright, M., and Silverman, M. R. (1994b) Sequence and function of LuxO, a negative regulator of luminescence in *Vibrio harveyi*. Mol Microbiol 12: 403–412.

Bell, A. W., Buckel, S. D., Groarke, J. M., Hope, J. N., Kingsley, D. H., and Hermodson, M. A. (1986) The nucleotide sequences of the rbsD, rbsA, and rbsC genes of *Escherichia coli* K12. J Biol Chem 261: 7652–7658.

Bender, J., and Kleckner, N. (1992) IS10 transposase mutations that specifically alter target site recognition. Embo J 11: 741–750.

Blattner, F. R., Plunkett, G., 3rd, Bloch, C. A., Perna, N. T., Burland, V., Riley, M., Collado-Vides, J., Glasner, J. D., Rode, C. K., Mayhew, G. F., Gregor, J., Davis, N. W., Kirkpatrick, H. A., Goeden, M. A., Rose, D. J., Mau, B., and Shao, Y. (1997) The complete genome sequence of *Escherichia coli* K-12. Science 277: 1453–1474.

Boos, W., and Lucht, J. M. (1996) Periplasmic binding protein-dependent ABC transporters. In *Escherichia coli* and *Salmonella typhimurium* Cellular and Molecular Biology. Vol. 1. Neidhardt, F. (ed=) Washington D.C.: ASM Press, pp. 1175–1209.

Buckel, S. D., Bell, A. W., Rao, J. K., and Hermodson, M. A. (1986) An analysis of the structure of the product of the rbsA gene of *Escherichia coli* K12. J Biol Chem 261: 7659–7662.

Caetano-Anolles, G. (1993) Amplifying DNA with arbitrary oligonucleotide primers. PCR Methods Appl 3: 85–94.

Cao, J. G., and Meighen, E. A. (1989) Purification and structural identification of an autoinducer for the luminescence system of *Vibrio harveyi*. J Biol Chem 264: 21670–21676.

Davis, R. W., Botstein, D., and Roth, J. R. (1980) Advanced Bacterial Genetics. Cold Spring Harbor: Cold Spring Harbor Laboratory Press.

Day, W. A., Jr., and Maurelli, A. T. (2001) *Shigella flexneri* LuxS quorum-sensing system modulates virB expression but is not essential for virulence. Infect Immun 69: 15–23.

de Kievit, T. R., and Iglewski, B. H. (2000) Bacterial quorum sensing in pathogenic relationships. Infect Immun 68: 4839–4849.

Engebrecht, J., Nealson, K., and Silverman, M. (1983) Bacterial bioluminescence: isolation and genetic analysis of functions from *Vibrio fischeri*. Cell 32: 773–781.

Engebrecht, J., and Silverman, M. (1984) Identification of genes and gene products necessary for bacterial bioluminescence. Proc Natl Acad Sci U S A 81: 4154–4158.

Engebrecht, J., and Silverman, M. (1987) Nucleotide sequence of the regulatory locus controlling expression of bacterial genes for bioluminescence. Nucleic Acids Res 15: 10455–10467.

Freeman, J. A., and Bassler, B. L. (1999a) A genetic analysis of the function of LuxO, a two-component response regulator involved in quorum sensing in *Vibrio harveyi*. Mol Microbiol 31: 665–677.

Freeman, J. A., and Bassler, B. L. (1999b) Sequence and function of LuxU: a two-component phosphorelay protein that regulates quorum sensing in *Vibrio harveyi*. J Bacteriol 181: 899–906.

Freeman, J. A., Lilley, B. N., and Bassler, B. L. (2000) A genetic analysis of the functions of LuxN: a two-component hybrid sensor kinase that regulates quorum sensing in *Vibrio harveyi*. Mol Microbiol 35: 139–149.

Fuqua, C., Winans, S. C., and Greenberg, E. P. (1996) Census and consensus in bacterial ecosystems: the LuxR- LuxI family of quorum-sensing transcriptional regulators. Annu Rev Microbiol 50: 727–751.

Greenberg, E. P., Hastings, J. W., and Ulitzer, S. (1979) Induction of luciferase synthesis in *Beneckea harveyi* by other marine bacteria. Arch Microbiol 120: 87–91.

Holland, I. B., and Blight, M. A. (1999) ABC-ATPases, adaptable energy generators fuelling transmembrane movement of a variety of molecules in organisms from bacteria to humans. J Mol Biol 293: 381–399.

Hope, J. N., Bell, A. W., Hermodson, M. A., and Groarke, J. M. (1986) Ribokinase from *Escherichia coli* K12. Nucleotide sequence and overexpression of the rbsK gene and purification of ribokinase. J Biol Chem 261: 7663–7668.

Hughes, K. T., and Roth, J. R. (1988) Transitory cis complementation: a method for providing transposition functions to defective transposons. Genetics 119: 9–12.

Iida, A., Harayama, S., Iino, T., and Hazelbauer, G. L. (1984) Molecular cloning and characterization of genes required for ribose transport and utilization in *Escherichia coli* K-12. J Bacteriol 158: 674–682.

Kim, S. Y., Lee, S. E., Kim, Y. R., Kim, J. H., Ryu, P. Y., Chung, S. S., and Rhee, J. H. (2000) Virulence regulatory role of luxS quorum sensing system in *Vibrio vulmificus*. In ASM General Meeting. Vol. Abstract B-248, pp. 97–98.

Kleerebezem, M., Quadri, L. E., Kuipers, O. P., and de Vos, W. M. (1997) Quorum sensing by peptide pheromones and two-component signal-transduction systems in Gram-positive bacteria. Mol Microbiol 24: 895–904.

Koh, Y. S., and Roe, J. H. (1995) Isolation of a novel paraquat-inducible (pqi) gene regulated by the soxRS locus in *Escherichia coli*. J Bacteriol 177: 2673–2678.

Lazazzera, B. A., and Grossman, A. D. (1998) The ins and outs of peptide signaling. Trends Microbiol 6: 288–294.

Lilley, B. N., and Bassler, B. L. (2000) Regulation of quorum sensing in *Vibrio harveyi* by LuxO and sigma-54. Mol Microbiol 36: 940–954.

Lyon, W. R., Madden, J. C., Stein, J., and Caparon, M. G. (2001) Mutation of luxS affects growth and virulence factor expression in *Streptococcus pyogenes*. Mol Microbiol In press.

Mauzy, C. A., and Hermodson, M. A. (1992) Structural and functional analyses of the repressor, RbsR, of the ribose operon of *Escherichia coli*. Protein Sci 1: 831–842.

Miller, J. H. (1992) A Short Course in Bacterial Genetics. Cold Spring Harbor: Cold Spring Harbor Laboratory Press.

Miller, M. B., and Bassler, B. L. (2001) Quorum Sensing in Bacteria. Ann. Rev. Microbiol. 55: 165–199.

Nikaido, H., and Hall, J. A. (1998) Overview of bacterial ABC transporters. Methods Enzymol 292: 3–20.

Park, Y., Cho, Y. J., Ahn, T., and Park, C. (1999) Molecular interactions in ribose transport: the binding protein module symmetrically associates with the homodimeric membrane transporter. Embo J 18: 4149–4156.

Rappleye, C. A., and Roth, J. R. (1997) A Tn10 derivative (T-POP) for isolation of insertions with conditional (tetracycline-dependent) phenotypes. J Bacteriol 179: 5827–5834.

Sambrook, J., Fritsch, E. F., and Maniatis, T. (1989) Molecular Cloning: A Laboratory Manual. Cold Spring Harbor, N.Y.: Cold Spring Harbor Laboratory Press.

Schauder, S., and Bassler, B. L. (2001) The languages of Bacteria. Genes and Dev. in press.

Schauder, S., Shokat, K., Surette, M. G., and Bassler, B. L. (2001) The LuxS family of bacterial autoinducers: biosynthesis of a novel quorum sensing signal molecule. Mol Microbiol in press.

Skorupski, K., and Taylor, R. K. (1996) Positive selection vectors for allelic exchange. Gene 169: 47–52.

Slauch, J. M., and Silhavy, T. J. (1991) cis-acting ompF mutations that result in OmpR-dependent constitutive expression. J Bacteriol 173: 4039–4048.

Sperandio, V., Mellies, J. L., Nguyen, W., Shin, S., and Kaper, J. B. (1999) Quorum sensing controls expression of the type III secretion gene transcription and protein secretion in enterohemorrhagic and enteropathogenic *Escherichia coli*. Proc Natl Acad Sci U S A 96: 15196–15201.

Sprenger, G. A. (1995) Genetics of pentose-phosphate pathway enzymes of *Escherichia coli* K-12. Arch Microbiol 164: 324–330.

Surette, M. G., and Bassler, B. L. (1998) Quorum sensing in *Escherichia coli* and *Salmonella typhimurium*. Proc Natl Acad Sci U S A 95: 7046–7050.

Surette, M. G., and Bassler, B. L. (1999) Regulation of autoinducer production in *Salmonella typhimurium*. Mol Microbiol 31: 585–595.

Surette, M. G., Miller, M. B., and Bassler, B. L. (1999) Quorum sensing in *Escherichia coli*, *Salmonella typhimurium*, and *Vibrio harveyi*: a new family of genes responsible for autoinducer production. Proc Natl Acad Sci U S A 96: 1639–1644.

Urbanowski, M. L., and Stauffer, G. V. (1989) Genetic and biochemical analysis of the MetR activator-binding site in the metE metR control region of *Salmonella typhimurium*. J Bacteriol 171: 5620–5629.

Wehmeier, U. F., and Lengeler, J. W. (1994) Sequence of the sor-operon for L-sorbose utilization from *Klebsiella pneumoniae* KAY2026. Biochim Biophys Acta 1208: 348–351.

Weissbach, H., and Brot, N. (1991) Regulation of methionine synthesis in *Escherichia coli*. Mol Microbiol 5: 1593–1597.

What is claimed is:

1. An isolated bacterial strain having an increased expression level of a transporter relative to a wildtype strain wherein the transporter transports a pentanedione autoinducer into the strain and wherein the transporter comprises at least one polypeptide having at least 80% amino acid identity using a BLAST search or FASTA version 3.0t78 algorithm with the default parameters, or equivalent search to a peptide selected from the group consisting of SEQ ID NO. 37, SEQ ID NO. 38, SEQ ID NO. 39, and SEQ ID NO. 40, and wherein the autoinducer can interact with the *Vibrio harveyi* LuxP-LuxQ protein complex, thereby inducing *Vibric harveyi* bioluminescence.

2. The strain of claim 1, wherein the strain comprises at least one synthetic vector from which one or more of the transporter polypeptides are expressed.

3. The strain of claim 1, wherein the transporter comprises polypeptides having at least 80% amino acid identity using a BLASTP, BLASTX, or TBLASTN with the default parameters to SEQ ID NO. 37, SEQ ID NO. 38, SEQ ID NO. 39, and SEQ ID NO. 40.

4. The strain of claim 1, wherein the strain comprises a mutation in a LsrR repressor gene that increases the expression level of the transporter.

5. The strain of claim 1, wherein the autoinducer is 4,5-dihydroxy-2,3-pentanedione.

6. The strain of claim 1, wherein the strain is within a species selected from the group consisting of *S. typhimurium* and *E. coli*.

\* \* \* \* \*

SEQUENCE LISTING

<160> NUMBER OF SEQ ID NOS: 58

<210> SEQ ID NO 1
<211> LENGTH: 519
<212> TYPE: DNA
<213> ORGANISM: Vibrio harveyi

<400> SEQUENCE: 1
atgcctttat tagacagctt taccgtagac cacacgcgta tgaatgcacc agcggttcgt    60

```
gtggctaaaa cgatgcaaac tccaaaagga gacaccatca cggtattcga cctacgtttc      120
actgctccaa acaaagacat cctttctgag aaaggaattc atacattaga gcatttgtac      180
gcaggcttta tgcgtaatca cctaaatggt gatagcgttg agatcattga tatctcacca      240
atggggtgcc gtactggttt ctacatgagc ttgattggta cgccttcaga gcagcaagtg      300
gctgacgctt ggattgccgc gatggaagac gtactaaaag tagaaaacca aaacaagatc      360
cctgagttga cgaatacca atgtggtaca gcagcgatgc actctctgga tgaagcgaag      420
caaatcgcga gaacattct agaagtgggt gtggcggtga ataagaatga tgaattggca      480
ctgccagagt caatgctgag agagctacgc atcgactaa                            519

<210> SEQ ID NO 2
<211> LENGTH: 516
<212> TYPE: DNA
<213> ORGANISM: Escherichia coli

<400> SEQUENCE: 2
atgccgttgt tagatagctt cacagtcgat catacccgga tggaagcgcc tgcagttcgg       60
gtggcgaaaa caatgaacac cccgcatggc gacgcaatca ccgtgttcga tctgcgcttc      120
tgcgtgccga acaaagaagt gatgccagaa gagggatcc ataccctgga gcacctgttt       180
gctggtttta tgcgtaacca tcttaacggt aatggtgtag agattatcga tatctcgcca      240
atgggctgcc gcaccggttt ttatatgagt ctgattggta cgccagatga gcagcgtgtt      300
gctgatgcct ggaaagcggc aatggaagac gtgctgaaag tgcaggatca gaatcagatc      360
ccggaactga acgtctacca gtgtggcact taccagatgc actcgttgca ggaagcgcag      420
gatattgcgc gtagcattct ggaacgtgac gtacgcatca acagcaacga gaactggca      480 ctgccgaaag agaagttgca ggaactgcac atctag                               516

<210> SEQ ID NO 3
<211> LENGTH: 110
<212> TYPE: DNA
<213> ORGANISM: Salmonella typhimurium
<220> FEATURE:
<221> NAME/KEY: misc_feature
<222> LOCATION: (1)...(110)
<223> OTHER INFORMATION: sequence from MudJ

<400> SEQUENCE: 3
gatgtgctga agtgcagga tcaaaaccag atcccggagc tgaacgttta ccagtgcggt       60
acgtatcaga tgcactcgct cagtgaagcg caggacattg cccgtcatat                 110

<210> SEQ ID NO 4
<211> LENGTH: 492
<212> TYPE: DNA
<213> ORGANISM: Salmonella typhimurium

<400> SEQUENCE: 4
aattcggatc ataccggatg caagcgccgg cggtccgggt tgcaaaaacg atgaacaccc       60
cgcatggcga cgcaatcacg tgtttgatct gcgttttgc attccgaaca agaagtgat       120 gccggaaaaa gggattcata cgcttgagca tctgtttgct ggctttatgc gcgaccacct      180
caacggtaac ggcgttgaga ttatcgatat ctcgccgatg gctgccgca ccggcttta       240 catgagcctg attggcacgc cggacgagca gcgtgttgcc gacgcctgga aagcggcgat      300
ggcggatgtg ctgaaagtgc aggatcaaaa ccagatcccg gagctgaacg tttaccagtg      360
cggtacgtat cagatgcact cgctcagtga agcgcaggac attgcccgtc atattctgga      420
```

-continued

```
gcgtgatgtg cgcgtgaaca gcaataaaga gctggcgctg ccgaaagaaa aactgcagga      480
actgatattt ag                                                         492

<210> SEQ ID NO 5
<211> LENGTH: 504
<212> TYPE: DNA
<213> ORGANISM: Haemophilus influenzae

<400> SEQUENCE: 5
atgccattac ttgatagttt taaagtggat cacacaaaaa tgaacgcacc tgcagtacgc       60
attgcaaaaa cgatgctcac gccaaaaggc gataatatta ctgttttga tttacgtttt      120 tgtattccaa acaagaaat tctttcccca aaaggcattc atacacttga acatttattt      180
gctggattta tgcgcgatca tttaaatggc gatagcatag aaattattga tatttctccg      240
atgggatgtc gcacgggatt ttatatgtct ttgattggca caccaaatga acagaaagtg      300
tctgaggctt ggttagcttc aatgcaagat gttttaggtg tacaagatca agcttctatt      360
cctgaattaa atatctatca atgcggaagc tatacggaac attccttaga agatgcacac      420
gaaattgcca aaatgttat cgcacgcggt ataggtgtaa ataaaaatga agatttgtca      480
ctcgataatt ccttattaaa atag                                            504

<210> SEQ ID NO 6
<211> LENGTH: 468
<212> TYPE: DNA
<213> ORGANISM: Helicobacter pylori

<400> SEQUENCE: 6
atgaaaacac caaaaatgaa tgtagagagt tttaatttgg atcacaccaa agtcaaagcc       60
ccttatgtgc gtgtcgctga tcgcaaaaag ggcgttaatg gggatttgat tgtcaaatac      120
gatgtgcgct tcaagcagcc caaccaagat cacatggaca tgcctagcct acattcttta      180
gagcatttag tcgctgaaat tatccgcaac catgccagtt atgtcgtgga ttggtcgcct      240
atgggttgcc aaacgggatt ttatctcaca gtgttaaacc atgacaatta cacagagatt      300
ttagaggttt tagaaaagac catgcaagat gtgttaaagg ctacagaagt gcctgccagc      360
aatgaaaagc aatgcggttg gcggctaac cacactttag agggtgctaa ggatttagcg      420
cgcgcttttt tagacaaacg cgctgagtgg tctgaagtgg gggtttga                   468

<210> SEQ ID NO 7
<211> LENGTH: 482
<212> TYPE: DNA
<213> ORGANISM: Bacillus subtilis

<400> SEQUENCE: 7
atgccttcag tagaaagttt tgagcttgat cataatgcgg ttgttgctcc atatgtaaga       60
cattgcggcg tgcataaagt gggaacagac ggcgttgtaa ataaatttga cattcgtttt      120
tgccagccaa ataaacaggc gatgaagcct gacaccattc acacactcga gcatttgctc      180
gcgtttacga ttcgttctca cgctgagaaa tacgatcatt ttgatatcat tgatatttct      240
ccaatgggct gccagacagg ctattatcta gttgtgagcg agagccgac atcagcggaa      300 atcgttgatc tgcttgaaga cacaatgaag gaagcggtag agattacaga aatacctgct      360
gcgaatgaaa agcagtgcgg ccaagcgaag cttcatgatc tggaaggcgc taaacgttta      420
atgcgtttct ggctttcaca ggataaagaa gaattgctaa aagtatttgg ctaaaataga      480
```

-continued aa                                                                        482

<210> SEQ ID NO 8
<211> LENGTH: 537
<212> TYPE: DNA
<213> ORGANISM: Borrelia burdorferi

<400> SEQUENCE: 8
atgaatttga atgggaaaaa ttagattttg taaaaaaaat acaaacagcg ctaaaaaaat      60
gaaaaaaata acaagcttta caatagatca tacaaaactc aaccctggca tatatgtctc     120
aagaaaagat acctttgaaa atgtaatatt tactacaata gacattagaa tcaaagctcc     180
caacatcgaa ccaataattg aaaacgcagc aatacataca atagagcaca taggagctac     240
tttacttaga ataatgaag tttggaccga aaaaatagta tattttggcc ctatgggatg      300
cagaactggt ttttacttaa taattttggg agactatgaa agtaaagatc ttgttgactt     360
agtctcatgg ctttttttccg aaatcgtaaa tttttcagaa cctatcccag gcgcaagtga    420
taaggaatgc ggaaattaca agaacataa ccttgatatg gctaaatatg aatcttctaa      480
atacttacaa atattaaaca atattaaaga agaaaattta aatatccctt agctcat        537

<210> SEQ ID NO 9
<211> LENGTH: 519
<212> TYPE: DNA
<213> ORGANISM: Vibrio cholerae

<400> SEQUENCE: 9
atgccattat tagacagttt taccgtcgat catactcgta tgaatgcacc ggcggtgcgt      60
gttgccaaaa ccatgcaaac cccaaaaggg gatacgatta ccgtatttga tttgcgtttt     120
actatgccaa acaaagatat cttgtctgag cgcggtatcc atactctaga gcatctctac     180
gcgggcttta tgcgcaatca ccttaacggg agccaagtgg agatcatcga tatttcacca     240
atgggttgcc gtacaggttt ctacatgagc ttgattggtg cgccgacaga acagcaagtg     300
gcacaagcat ggctagccgc aatgcaagat gtgttgaaag ttgaaagcca agagcaaatt     360
cctgagctga atgagtacca gtgcggcact gcggcgatgc actcgtcgga agaagccaaa    420
gcgattgcga aaacgtgat tgcggcaggc atcggtta accgtaacga tgagttggcg       480
ctgcccgaat ctatgctcaa tgagctgaag gttcactaa                            519

<210> SEQ ID NO 10
<211> LENGTH: 172
<212> TYPE: PRT
<213> ORGANISM: Vibrio harveyi

<400> SEQUENCE: 10

Met Pro Leu Leu Asp Ser Phe Thr Val Asp His Thr Arg Met Asn Ala
  1               5                  10                  15

Pro Ala Val Arg Val Ala Lys Thr Met Gln Thr Pro Lys Gly Asp Thr
                 20                  25                  30

Ile Thr Val Phe Asp Leu Arg Phe Thr Ala Pro Asn Lys Asp Ile Leu
             35                  40                  45

Ser Glu Lys Gly Ile His Thr Leu Glu His Leu Tyr Ala Gly Phe Met
         50                  55                  60

Arg Asn His Leu Asn Gly Asp Ser Val Glu Ile Ile Asp Ile Ser Pro
 65                  70                  75                  80

Met Gly Cys Arg Thr Gly Phe Tyr Met Ser Leu Ile Gly Thr Pro Ser
                 85                  90                  95

```
Glu Gln Gln Val Ala Asp Ala Trp Ile Ala Ala Met Glu Asp Val Leu
                100                 105                 110

Lys Val Glu Asn Gln Asn Lys Ile Pro Glu Leu Asn Glu Tyr Gln Cys
            115                 120                 125

Gly Thr Ala Ala Met His Ser Leu Asp Glu Ala Lys Gln Ile Ala Lys
        130                 135                 140

Asn Ile Leu Glu Val Gly Val Ala Val Asn Lys Asn Asp Glu Leu Ala
145                 150                 155                 160

Leu Pro Glu Ser Met Leu Arg Glu Leu Arg Ile Asp
                165                 170

<210> SEQ ID NO 11
<211> LENGTH: 171
<212> TYPE: PRT
<213> ORGANISM: Escherichia coli

<400> SEQUENCE: 11

Met Pro Leu Leu Asp Ser Phe Thr Val Asp His Thr Arg Met Glu Ala
1               5                   10                  15

Pro Ala Val Arg Val Ala Lys Thr Met Asn Thr Pro His Gly Asp Ala
                20                  25                  30

Ile Thr Val Phe Asp Leu Arg Phe Cys Val Pro Asn Lys Glu Val Met
            35                  40                  45

Pro Glu Arg Gly Ile His Thr Leu Glu His Leu Phe Ala Gly Phe Met
        50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Ile Gly Thr Pro Asp
                85                  90                  95

Glu Gln Arg Val Ala Asp Ala Trp Lys Ala Ala Met Glu Asp Val Leu
                100                 105                 110

Lys Val Gln Asp Gln Asn Gln Ile Pro Glu Leu Asn Val Tyr Gln Cys
            115                 120                 125

Gly Thr Tyr Gln Met His Ser Leu Gln Glu Ala Gln Asp Ile Ala Arg
        130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His Ile
                165                 170

<210> SEQ ID NO 12
<211> LENGTH: 164
<212> TYPE: PRT
<213> ORGANISM: Salmonella typhimurium

<400> SEQUENCE: 12

Asn Ser Asp His Thr Arg Met Gln Ala Pro Ala Val Arg Val Ala Lys
1               5                   10                  15

Thr Met Asn Thr Pro His Gly Asp Ala Ile Thr Val Phe Asp Leu Arg
                20                  25                  30

Phe Cys Ile Pro Asn Lys Glu Val Met Pro Glu Lys Gly Ile His Thr
            35                  40                  45

Leu Glu His Leu Phe Ala Gly Phe Met Arg Asp His Leu Asn Gly Asn
        50                  55                  60

Gly Val Glu Ile Ile Asp Ile Ser Pro Met Gly Cys Arg Thr Gly Phe
65                  70                  75                  80
```

```
Tyr Met Ser Leu Ile Gly Thr Pro Asp Glu Gln Arg Val Ala Asp Ala
                85                  90                  95

Trp Lys Ala Ala Met Ala Asp Val Leu Lys Val Gln Asp Gln Asn Gln
            100                 105                 110

Ile Pro Glu Leu Asn Val Tyr Gln Cys Gly Thr Tyr Gln Met His Ser
        115                 120                 125

Leu Ser Glu Ala Gln Asp Ile Ala Arg His Ile Leu Gly Arg Asp Val
    130                 135                 140

Arg Val Asn Ser Asn Lys Glu Leu Ala Leu Pro Lys Glu Lys Leu Gln
145                 150                 155                 160

Glu Thr Asp Ile
```

<210> SEQ ID NO 13
<211> LENGTH: 167
<212> TYPE: PRT
<213> ORGANISM: Haemophilus influenzae

<400> SEQUENCE: 13

```
Met Pro Leu Leu Asp Ser Phe Lys Val Asp His Thr Lys Met Asn Ala
1               5                   10                  15

Pro Ala Val Arg Ile Ala Lys Thr Met Leu Thr Pro Lys Gly Asp Asn
            20                  25                  30

Ile Thr Val Phe Asp Leu Arg Phe Cys Ile Pro Asn Lys Glu Ile Leu
        35                  40                  45

Ser Pro Lys Gly Ile His Thr Leu Glu His Leu Phe Ala Gly Phe Met
    50                  55                  60

Arg Asp His Leu Asn Gly Asp Ser Ile Glu Ile Ile Asp Ile Ser Pro
65                  70                  75                  80

Met Gly Cys Arg Thr Gly Phe Tyr Met Ser Leu Ile Gly Thr Pro Asn
                85                  90                  95

Glu Gln Lys Val Ser Glu Ala Trp Leu Ala Ser Met Gln Asp Val Leu
            100                 105                 110

Gly Val Gln Asp Gln Ala Ser Ile Pro Glu Leu Asn Ile Tyr Gln Cys
        115                 120                 125

Gly Ser Tyr Thr Glu His Ser Leu Glu Asp Ala His Glu Ile Ala Lys
    130                 135                 140

Asn Val Ile Ala Arg Gly Ile Gly Val Asn Lys Asn Glu Asp Leu Ser
145                 150                 155                 160

Leu Asp Asn Ser Leu Leu Lys
                165
```

<210> SEQ ID NO 14
<211> LENGTH: 155
<212> TYPE: PRT
<213> ORGANISM: Helicobacter pylori

<400> SEQUENCE: 14

```
Met Lys Thr Pro Lys Met Asn Val Glu Ser Phe Asn Leu Asp His Thr
1               5                   10                  15

Lys Val Lys Ala Pro Tyr Val Arg Val Ala Asp Arg Lys Lys Gly Val
            20                  25                  30

Asn Gly Asp Leu Ile Val Lys Tyr Asp Val Arg Phe Lys Gln Pro Asn
        35                  40                  45

Gln Asp His Met Asp Met Pro Ser Leu His Ser Leu Glu His Leu Val
    50                  55                  60
```

-continued

```
Ala Glu Ile Ile Arg Asn His Ala Ser Tyr Val Val Asp Trp Ser Pro
65                  70                  75                  80

Met Gly Cys Gln Thr Gly Phe Tyr Leu Thr Val Leu Asn His Asp Asn
                85                  90                  95

Tyr Thr Glu Ile Leu Glu Val Leu Glu Lys Thr Met Gln Asp Val Leu
            100                 105                 110

Lys Ala Thr Glu Val Pro Ala Ser Asn Glu Lys Gln Cys Gly Trp Ala
        115                 120                 125

Ala Asn His Thr Leu Glu Gly Ala Lys Asp Leu Ala Arg Ala Phe Leu
    130                 135                 140

Asp Lys Arg Ala Glu Trp Ser Glu Val Gly Val
145                 150                 155

<210> SEQ ID NO 15
<211> LENGTH: 157
<212> TYPE: PRT
<213> ORGANISM: Bacillus subtilis

<400> SEQUENCE: 15

Met Pro Ser Val Glu Ser Phe Glu Leu Asp His Asn Ala Val Val Ala
 1               5                  10                  15

Pro Tyr Val Arg His Cys Gly Val His Lys Val Gly Thr Asp Gly Val
            20                  25                  30

Val Asn Lys Phe Asp Ile Arg Phe Cys Gln Pro Asn Lys Gln Ala Met
        35                  40                  45

Lys Pro Asp Thr Ile His Thr Leu Glu His Leu Leu Ala Phe Thr Ile
    50                  55                  60

Arg Ser His Ala Glu Lys Tyr Asp His Phe Asp Ile Ile Asp Ile Ser
65                  70                  75                  80

Pro Met Gly Cys Gln Thr Gly Tyr Tyr Leu Val Val Ser Gly Glu Pro
                85                  90                  95

Thr Ser Ala Glu Ile Val Asp Leu Leu Glu Asp Thr Met Lys Glu Ala
            100                 105                 110

Val Glu Ile Thr Glu Ile Pro Ala Ala Asn Glu Lys Gln Cys Gly Gln
        115                 120                 125

Ala Lys Leu His Asp Leu Glu Gly Ala Lys Arg Leu Met Arg Phe Trp
    130                 135                 140

Leu Ser Gln Asp Lys Glu Glu Leu Leu Lys Val Phe Gly
145                 150                 155

<210> SEQ ID NO 16
<211> LENGTH: 173
<212> TYPE: PRT
<213> ORGANISM: Borrelia burgdorferi

<400> SEQUENCE: 16

Met Gly Lys Ile Arg Phe Cys Lys Lys Asn Thr Asn Ser Ala Lys Lys
 1               5                  10                  15

Met Lys Lys Ile Thr Ser Phe Thr Ile Asp His Thr Lys Leu Asn Pro
            20                  25                  30

Gly Ile Tyr Val Ser Arg Lys Asp Thr Phe Glu Asn Val Ile Phe Thr
        35                  40                  45

Thr Ile Asp Ile Arg Ile Lys Ala Pro Asn Ile Glu Pro Ile Ile Glu
    50                  55                  60

Asn Ala Ala Ile His Thr Ile Glu His Ile Gly Ala Thr Leu Leu Arg
65                  70                  75                  80
```

```
                Asn Asn Glu Val Trp Thr Glu Lys Ile Val Tyr Phe Gly Pro Met Gly
                                85                  90                  95

Cys Arg Thr Gly Phe Tyr Leu Ile Ile Phe Gly Asp Tyr Glu Ser Lys
                            100                 105                 110

Asp Leu Val Asp Leu Val Ser Trp Leu Phe Ser Glu Ile Val Asn Phe
                        115                 120                 125

Ser Glu Pro Ile Pro Gly Ala Ser Asp Lys Glu Cys Gly Asn Tyr Lys
                    130                 135                 140

Glu His Asn Leu Asp Met Ala Lys Tyr Glu Ser Ser Lys Tyr Leu Gln
                145                 150                 155                 160

Ile Leu Asn Asn Ile Lys Glu Glu Asn Leu Lys Tyr Pro
                                165                 170

<210> SEQ ID NO 17
<211> LENGTH: 172
<212> TYPE: PRT
<213> ORGANISM: Vibrio cholerae

<400> SEQUENCE: 17

Met Pro Leu Leu Asp Ser Phe Thr Val Asp His Thr Arg Met Asn Ala
                1               5                   10                  15

Pro Ala Val Arg Val Ala Lys Thr Met Gln Thr Pro Lys Gly Asp Thr
                            20                  25                  30

Ile Thr Val Phe Asp Leu Arg Phe Thr Met Pro Asn Lys Asp Ile Leu
                        35                  40                  45

Ser Glu Arg Gly Ile His Thr Leu Glu His Leu Tyr Ala Gly Phe Met
                    50                  55                  60

Arg Asn His Leu Asn Gly Ser Gln Val Glu Ile Ile Asp Ile Ser Pro
                65                  70                  75                  80

Met Gly Cys Arg Thr Gly Phe Tyr Met Ser Leu Ile Gly Ala Pro Thr
                                85                  90                  95

Glu Gln Gln Val Ala Gln Ala Trp Leu Ala Ala Met Gln Asp Val Leu
                            100                 105                 110

Lys Val Glu Ser Gln Glu Gln Ile Pro Glu Leu Asn Glu Tyr Gln Cys
                        115                 120                 125

Gly Thr Ala Ala Met His Ser Leu Glu Glu Ala Lys Ala Ile Ala Lys
                    130                 135                 140

Asn Val Ile Ala Ala Gly Ile Ser Val Asn Arg Asn Asp Glu Leu Ala
                145                 150                 155                 160

Leu Pro Glu Ser Met Leu Asn Glu Leu Lys Val His
                                165                 170

<210> SEQ ID NO 18
<211> LENGTH: 32
<212> TYPE: DNA
<213> ORGANISM: Artificial Sequence
<220> FEATURE:
<223> OTHER INFORMATION: oligonucleotide primer for fts Q1P promoter

<400> SEQUENCE: 18
cggagatctg cgctttcaat ggataaacta cg                                    32

<210> SEQ ID NO 19
<211> LENGTH: 30
<212> TYPE: DNA
<213> ORGANISM: Artificial Sequence
<220> FEATURE:
<223> OTHER INFORMATION: oligonucleotide primer for fts Q2P promoter
```

```
<400> SEQUENCE: 19
cgcggatcct cttcttcgct gtttcgcgtg                                    30

<210> SEQ ID NO 20
<211> LENGTH: 36
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)...(36)
<223> OTHER INFORMATION: n = A,T,C or G

<400> SEQUENCE: 20
ggccacgcgt cgactagtac nnnnnnnnnn acgccc                             36

<210> SEQ ID NO 21
<211> LENGTH: 21
<212> TYPE: DNA
<213> ORGANISM: Artificial Sequence
<220> FEATURE:
<223> OTHER INFORMATION: MudJ specific oligonucleotide primer

<400> SEQUENCE: 21
gcactacagg cttgcaagcc c                                             21

<210> SEQ ID NO 22
<211> LENGTH: 20
<212> TYPE: DNA
<213> ORGANISM: Artificial Sequence
<220> FEATURE:
<223> OTHER INFORMATION: arbitrary oligonucleotide primer

<400> SEQUENCE: 22
ggccacgcgt cgactagtca                                               20

<210> SEQ ID NO 23
<211> LENGTH: 20
<212> TYPE: DNA
<213> ORGANISM: Artificial Sequence
<220> FEATURE:
<223> OTHER INFORMATION: MudJ specific oligonucleotide primer

<400> SEQUENCE: 23
tctaatccca tcagatcccg                                               20

<210> SEQ ID NO 24
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 24
gtgaagcttg tttactgact agatc                                         25

<210> SEQ ID NO 25
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 25
gtgtctagaa aaacacgcct gacag                                         25
```

<210> SEQ ID NO 26
<211> LENGTH: 171
<212> TYPE: PRT
<213> ORGANISM: Escherichia coli

<400> SEQUENCE: 26

```
Met Pro Leu Leu Asp Ser Phe Thr Val Asp His Thr Arg Met Glu Ala
 1               5                  10                  15

Pro Ala Val Arg Val Ala Lys Thr Met Asn Thr Pro His Gly Asp Ala
            20                  25                  30

Ile Thr Val Phe Asp Leu Arg Phe Cys Val Pro Asn Lys Glu Val Met
        35                  40                  45

Pro Glu Arg Gly Ile His Thr Leu Glu His Leu Phe Ala Gly Phe Met
    50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Ile Gly Thr Pro Asp
                85                  90                  95

Glu Gln Arg Val Ala Asp Ala Trp Lys Ala Ala Met Glu Asp Val Leu
            100                 105                 110

Lys Val Gln Asp Gln Asn Gln Ile Pro Glu Leu Asn Val Tyr Gln Cys
        115                 120                 125

Gly Thr Tyr Gln Met His Ser Leu Gln Glu Ala Gln Asp Ile Ala Arg
    130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His Ile
                165                 170
```

<210> SEQ ID NO 27
<211> LENGTH: 111
<212> TYPE: PRT
<213> ORGANISM: Escherichia coli

<400> SEQUENCE: 27

```
Met Pro Leu Leu Asp Ser Phe Thr Val Asp His Thr Arg Met Glu Ala
 1               5                  10                  15

Pro Ala Val Arg Val Ala Lys Thr Met Asn Thr Pro His Gly Asp Ala
            20                  25                  30

Ile Thr Val Phe Asp Leu Arg Phe Cys Val Pro Asn Lys Glu Val Met
        35                  40                  45

Pro Glu Arg Gly Ile His Thr Leu Glu His Leu Phe Ala Gly Phe Met
    50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Leu Val Arg Gln Met
                85                  90                  95

Ser Ser Val Leu Leu Met Pro Gly Lys Arg Gln Trp Lys Thr Cys
            100                 105                 110
```

<210> SEQ ID NO 28
<211> LENGTH: 960
<212> TYPE: DNA
<213> ORGANISM: Salmonella typhimurium
<220> FEATURE:
<221> NAME/KEY: CDS
<222> LOCATION: (1)...(960)

<223> OTHER INFORMATION: LsrR

<400> SEQUENCE: 28

| | | | | | | | | | | | | | | | | |
|---|---|---|---|---|---|---|---|---|---|---|---|---|---|---|---|---|
| atg | agc | gat | aat | acg | ttg | gta | tct | gat | tat | gga | atg | tgc | gaa | gaa | gag | 48 |
| Met | Ser | Asp | Asn | Thr | Leu | Val | Ser | Asp | Tyr | Gly | Met | Cys | Glu | Glu | Glu | |
| 1 | | | | 5 | | | | | 10 | | | | | 15 | | |
| cag | gtg | gcg | cgt | att | gcc | tgg | ttc | tac | tat | cac | gat | gga | ttg | acg | cag | 96 |
| Gln | Val | Ala | Arg | Ile | Ala | Trp | Phe | Tyr | Tyr | His | Asp | Gly | Leu | Thr | Gln | |
| | | | 20 | | | | | 25 | | | | | 30 | | | |
| agt | gaa | atc | agc | gag | cgt | ctg | ggg | cta | acc | cgg | cta | aag | gtt | tct | cgt | 144 |
| Ser | Glu | Ile | Ser | Glu | Arg | Leu | Gly | Leu | Thr | Arg | Leu | Lys | Val | Ser | Arg | |
| | | 35 | | | | | 40 | | | | | 45 | | | | |
| ctg | ctg | gag | aaa | ggg | cat | cag | tcc | ggt | att | att | cgc | gta | caa | atc | aac | 192 |
| Leu | Leu | Glu | Lys | Gly | His | Gln | Ser | Gly | Ile | Ile | Arg | Val | Gln | Ile | Asn | |
| | 50 | | | | | 55 | | | | | 60 | | | | | |
| tcc | cgc | ttc | gaa | ggg | tgt | ctt | gag | tat | gaa | aat | gcc | ttg | cgc | aac | cac | 240 |
| Ser | Arg | Phe | Glu | Gly | Cys | Leu | Glu | Tyr | Glu | Asn | Ala | Leu | Arg | Asn | His | |
| 65 | | | | | 70 | | | | | 75 | | | | | 80 | |
| ttc | gca | ttg | cag | aat | atc | cgc | gtg | ctg | ccg | gca | tta | ccc | gat | gcc | gat | 288 |
| Phe | Ala | Leu | Gln | Asn | Ile | Arg | Val | Leu | Pro | Ala | Leu | Pro | Asp | Ala | Asp | |
| | | | | 85 | | | | | 90 | | | | | 95 | | |
| att | ggt | ctg | cgc | tta | gga | atc | ggc | gcc | gcc | cat | atg | ttg | atg | gag | tca | 336 |
| Ile | Gly | Leu | Arg | Leu | Gly | Ile | Gly | Ala | Ala | His | Met | Leu | Met | Glu | Ser | |
| | | | 100 | | | | | 105 | | | | | 110 | | | |
| ctg | cgg | cca | cag | caa | ctg | ctg | gcc | gtc | ggc | ttt | ggc | gaa | gcc | acg | atg | 384 |
| Leu | Arg | Pro | Gln | Gln | Leu | Leu | Ala | Val | Gly | Phe | Gly | Glu | Ala | Thr | Met | |
| | | 115 | | | | | 120 | | | | | 125 | | | | |
| acc | aca | tta | aaa | cgc | ctc | agc | gga | ttt | atc | tcg | gcg | caa | caa | atc | cga | 432 |
| Thr | Thr | Leu | Lys | Arg | Leu | Ser | Gly | Phe | Ile | Ser | Ala | Gln | Gln | Ile | Arg | |
| | 130 | | | | | 135 | | | | | 140 | | | | | |
| ctg | gtc | acg | tta | tcc | ggc | ggc | gtg | ggg | ccg | tat | atg | acc | gga | ata | ggc | 480 |
| Leu | Val | Thr | Leu | Ser | Gly | Gly | Val | Gly | Pro | Tyr | Met | Thr | Gly | Ile | Gly | |
| 145 | | | | | 150 | | | | | 155 | | | | | 160 | |
| cag | ctt | gat | gcc | gct | tgt | agc | gta | agt | att | atg | ccc | gcg | ccg | ctg | cgc | 528 |
| Gln | Leu | Asp | Ala | Ala | Cys | Ser | Val | Ser | Ile | Met | Pro | Ala | Pro | Leu | Arg | |
| | | | | 165 | | | | | 170 | | | | | 175 | | |
| gca | tca | tcg | cag | gaa | att | gcc | tgc | acg | ctg | cgc | aat | gaa | aat | agc | gtg | 576 |
| Ala | Ser | Ser | Gln | Glu | Ile | Ala | Cys | Thr | Leu | Arg | Asn | Glu | Asn | Ser | Val | |
| | | | 180 | | | | | 185 | | | | | 190 | | | |
| cgg | gat | gtg | atg | ctc | aca | gcg | caa | gct | gcc | gat | gcc | gcc | atc | gtg | ggg | 624 |
| Arg | Asp | Val | Met | Leu | Thr | Ala | Gln | Ala | Ala | Asp | Ala | Ala | Ile | Val | Gly | |
| | | 195 | | | | | 200 | | | | | 205 | | | | |
| att | ggg | gca | att | aac | cag | aaa | gat | caa | gcc | agt | atc | tta | aaa | tcc | ggt | 672 |
| Ile | Gly | Ala | Ile | Asn | Gln | Lys | Asp | Gln | Ala | Ser | Ile | Leu | Lys | Ser | Gly | |
| | 210 | | | | | 215 | | | | | 220 | | | | | |
| tat | atc | act | cag | ggt | gaa | caa | ctc | atg | att | ggc | cgc | aaa | ggc | gca | gta | 720 |
| Tyr | Ile | Thr | Gln | Gly | Glu | Gln | Leu | Met | Ile | Gly | Arg | Lys | Gly | Ala | Val | |
| 225 | | | | | 230 | | | | | 235 | | | | | 240 | |
| ggc | gat | att | ctg | ggc | tat | ttt | ttt | gat | gct | cat | ggc | gaa | att | att | cca | 768 |
| Gly | Asp | Ile | Leu | Gly | Tyr | Phe | Phe | Asp | Ala | His | Gly | Glu | Ile | Ile | Pro | |
| | | | | 245 | | | | | 250 | | | | | 255 | | |
| gac | atc | aaa | atc | cat | aac | gaa | tta | att | ggc | ctg | aag | tta | aat | tca | ctt | 816 |
| Asp | Ile | Lys | Ile | His | Asn | Glu | Leu | Ile | Gly | Leu | Lys | Leu | Asn | Ser | Leu | |
| | | | 260 | | | | | 265 | | | | | 270 | | | |
| tcc | acg | atc | cca | acc | gtg | att | ggc | gtc | gcc | ggc | ggc | gaa | caa | aaa | gca | 864 |
| Ser | Thr | Ile | Pro | Thr | Val | Ile | Gly | Val | Ala | Gly | Gly | Glu | Gln | Lys | Ala | |
| | | 275 | | | | | 280 | | | | | 285 | | | | |
| gaa | gct | att | att | gcc | gct | atg | cgc | ggt | aac | tat | atc | aat | gca | ctg | gtt | 912 |
| Glu | Ala | Ile | Ile | Ala | Ala | Met | Arg | Gly | Asn | Tyr | Ile | Asn | Ala | Leu | Val | |
| | 290 | | | | | 295 | | | | | 300 | | | | | |

```
acc gat cag aaa acc gca ggg aaa ata att caa att att gaa aaa taa        960
Thr Asp Gln Lys Thr Ala Gly Lys Ile Ile Gln Ile Ile Glu Lys *
305                 310                 315
```

<210> SEQ ID NO 29
<211> LENGTH: 1536
<212> TYPE: DNA
<213> ORGANISM: Salmonella typhimurium
<220> FEATURE:
<221> NAME/KEY: CDS
<222> LOCATION: (1)...(1535)
<223> OTHER INFORMATION: LsrA

<400> SEQUENCE: 29

```
atg caa atc agt cac aat act gca tcc cct ctg att tgt gtg cag aac         48
Met Gln Ile Ser His Asn Thr Ala Ser Pro Leu Ile Cys Val Gln Asn
 1               5                  10                  15 att tat aaa agt tat tcc ggc gtc gaa gta cta aag gga att gac ttt         96
Ile Tyr Lys Ser Tyr Ser Gly Val Glu Val Leu Lys Gly Ile Asp Phe
             20                  25                  30 act ctg cat gcg gga gag gtg cac gca ttg ctt ggc ggc aat ggt gcg        144
Thr Leu His Ala Gly Glu Val His Ala Leu Leu Gly Gly Asn Gly Ala
         35                  40                  45 ggt aaa tca aca tta atg aag att att gcc ggt ata gtc ccg cca gat        192
Gly Lys Ser Thr Leu Met Lys Ile Ile Ala Gly Ile Val Pro Pro Asp
     50                  55                  60 gga ggg act atc gat att gct ggt gtg cgt tgc agt cat tta acg cct        240
Gly Gly Thr Ile Asp Ile Ala Gly Val Arg Cys Ser His Leu Thr Pro
 65                  70                  75                  80 ctg aag gcg cac cag tat ggc att tac ctg gtt ccc cag gag cct ctg        288
Leu Lys Ala His Gln Tyr Gly Ile Tyr Leu Val Pro Gln Glu Pro Leu
                 85                  90                  95 tta ttt ccg agt tta tct gtg cgg gaa aat atc ttg ttt ggc ttg cag        336
Leu Phe Pro Ser Leu Ser Val Arg Glu Asn Ile Leu Phe Gly Leu Gln
            100                 105                 110 gga cgt cag gcc tcc acg gaa aaa atg cag cag cta tta aag gcg atg        384
Gly Arg Gln Ala Ser Thr Glu Lys Met Gln Gln Leu Leu Lys Ala Met
        115                 120                 125 gga tgc caa ctc gat ccg gcg agc gct gcg ggt acg ctt gat gtt gca        432
Gly Cys Gln Leu Asp Pro Ala Ser Ala Ala Gly Thr Leu Asp Val Ala
    130                 135                 140 gac cgc cag atc gtt gaa att atg cgc ggc ttg atg cgc gac tcg cga        480
Asp Arg Gln Ile Val Glu Ile Met Arg Gly Leu Met Arg Asp Ser Arg
145                 150                 155                 160 atc tta att ctt gat gag ccc acg gcg tcg tta acg cca gcc gaa act        528
Ile Leu Ile Leu Asp Glu Pro Thr Ala Ser Leu Thr Pro Ala Glu Thr
                165                 170                 175 gat cgg tta ttt acg cgt ctg caa gag ttg ctg aaa aag ggt gtc gga        576
Asp Arg Leu Phe Thr Arg Leu Gln Glu Leu Leu Lys Lys Gly Val Gly
            180                 185                 190 att gta ttt att tct cat aag cta cca gaa att aga cag tta gct cac        624
Ile Val Phe Ile Ser His Lys Leu Pro Glu Ile Arg Gln Leu Ala His
        195                 200                 205 tgc gtt agc gtg atg cgt gac ggt aaa atc gca tta ttc gga aaa acg        672
Cys Val Ser Val Met Arg Asp Gly Lys Ile Ala Leu Phe Gly Lys Thr
    210                 215                 220 cat gac ctt tct acc gac gag att att caa gct atc acc ccg gca acg        720
His Asp Leu Ser Thr Asp Glu Ile Ile Gln Ala Ile Thr Pro Ala Thr
225                 230                 235                 240 cag ggc gtc agt ctt tcc gcg aat caa aag ttg tgg ctg gaa ttg cct        768
Gln Gly Val Ser Leu Ser Ala Asn Gln Lys Leu Trp Leu Glu Leu Pro
```

```
ggc agc cgc ccg cag aac gaa cgc ggc gcg aca gta tta gcg ctg gag        816
Gly Ser Arg Pro Gln Asn Glu Arg Gly Ala Thr Val Leu Ala Leu Glu
            260                 265                 270 tca ctg acg ggc gaa ggt ttt atg aat atc aac ctt gag gtg cgg gca        864
Ser Leu Thr Gly Glu Gly Phe Met Asn Ile Asn Leu Glu Val Arg Ala
        275                 280                 285 ggc gaa atc ctt ggt ctg gcc ggg ttg gtc ggc gcg gga cgc aca gaa        912
Gly Glu Ile Leu Gly Leu Ala Gly Leu Val Gly Ala Gly Arg Thr Glu
    290                 295                 300 ctg gct gaa acg ctg tac ggt att aga ccg gtc aat gcg ggg cgg atg        960
Leu Ala Glu Thr Leu Tyr Gly Ile Arg Pro Val Asn Ala Gly Arg Met
305                 310                 315                 320 ctg ttc aat ggt caa gaa att aac gcc ctg aca acc caa cag cgg ttg       1008
Leu Phe Asn Gly Gln Glu Ile Asn Ala Leu Thr Thr Gln Gln Arg Leu
                325                 330                 335 cag ctc ggc ctg gtc tat ttg ccg gaa gat cgg cag tca tcc ggg ctg       1056
Gln Leu Gly Leu Val Tyr Leu Pro Glu Asp Arg Gln Ser Ser Gly Leu
            340                 345                 350 tat ctt gac gct tcc ctg gca tgg aat gtc tgt tcg ctg acc cac aac       1104
Tyr Leu Asp Ala Ser Leu Ala Trp Asn Val Cys Ser Leu Thr His Asn
        355                 360                 365 caa aaa gga ttt tgg ata aag ccc cag cgg gat aac gcc acc ctt gaa       1152
Gln Lys Gly Phe Trp Ile Lys Pro Gln Arg Asp Asn Ala Thr Leu Glu
    370                 375                 380 cgt tac cac cgc gcg tta aat atc aaa ctc aat aat gcc gaa cag gcg       1200
Arg Tyr His Arg Ala Leu Asn Ile Lys Leu Asn Asn Ala Glu Gln Ala
385                 390                 395                 400 gcg cgt act tta tcc ggc ggt aac cag caa aaa gta ttg att gcc aaa       1248
Ala Arg Thr Leu Ser Gly Gly Asn Gln Gln Lys Val Leu Ile Ala Lys
                405                 410                 415 tgc ctg gag gcc tct ccg caa tta ctg att gtc gat gaa ccg acc cgc       1296
Cys Leu Glu Ala Ser Pro Gln Leu Leu Ile Val Asp Glu Pro Thr Arg
            420                 425                 430 ggt gtc gat gtc tcc gcc cgc agc gat att tat cag ctg ttg cgc agt       1344
Gly Val Asp Val Ser Ala Arg Ser Asp Ile Tyr Gln Leu Leu Arg Ser
        435                 440                 445 atc gcg caa caa aat gtc gcg gtg cta ttt att tcc tcc gat ctg gaa       1392
Ile Ala Gln Gln Asn Val Ala Val Leu Phe Ile Ser Ser Asp Leu Glu
    450                 455                 460 gag ata gag cag atg gcc gat cgc gta tat gtc atg cac cag ggg gaa       1440
Glu Ile Glu Gln Met Ala Asp Arg Val Tyr Val Met His Gln Gly Glu
465                 470                 475                 480 ctg ggg ggg cct gcg tta tgc ggc gag gaa att aac gtt gat acc atc       1488
Leu Gly Gly Pro Ala Leu Cys Gly Glu Glu Ile Asn Val Asp Thr Ile
                485                 490                 495 atg cac gtt gcg ttt ggc gaa cat ggt gcg tcg gag gca aca tgt tga       1536
Met His Val Ala Phe Gly Glu His Gly Ala Ser Glu Ala Thr Cys
            500                 505                 510

<210> SEQ ID NO 30
<211> LENGTH: 1044
<212> TYPE: DNA
<213> ORGANISM: Salmonella typhimurium
<220> FEATURE:
<221> NAME/KEY: CDS
<222> LOCATION: (1)...(1044)
<223> OTHER INFORMATION: LsrC

<400> SEQUENCE: 30 atg ttg aaa ttc atc caa aat aac cgg gaa gcg acg gca ctg ctg gca        48
```

-continued

```
                Met Leu Lys Phe Ile Gln Asn Asn Arg Glu Ala Thr Ala Leu Leu Ala
                 1               5                  10                 15 ata gtc tgt tta ttc gtg ttt cct ggc gcg ctg gat agt cag tat ttg        96
Ile Val Cys Leu Phe Val Phe Pro Gly Ala Leu Asp Ser Gln Tyr Leu
             20                  25                  30 agc gtg caa acg ctg aca atg gtt ttc agt agc gcg caa att ttg atg       144
Ser Val Gln Thr Leu Thr Met Val Phe Ser Ser Ala Gln Ile Leu Met
         35                  40                  45 ctg ttg gcg att ggc gcg acg atg gta atg ctc acc cgc aat att gat       192
Leu Leu Ala Ile Gly Ala Thr Met Val Met Leu Thr Arg Asn Ile Asp
     50                  55                  60 gta tcg gtg ggc tcg acg aca gga atg tgc gcg gta ttg ctg gga gtg       240
Val Ser Val Gly Ser Thr Thr Gly Met Cys Ala Val Leu Leu Gly Val
 65                  70                  75                  80 atg tta aac gcc ggc tat agc ctg ccg gtc gcc tgc ctg gcc aca cta       288
Met Leu Asn Ala Gly Tyr Ser Leu Pro Val Ala Cys Leu Ala Thr Leu
                 85                  90                  95 ata tta gga att gtc gcc gga ttt ttt aat ggc gta ctg gtt gcc tgg       336
Ile Leu Gly Ile Val Ala Gly Phe Phe Asn Gly Val Leu Val Ala Trp
            100                 105                 110 ttg aag ata ccc gcc att gtc gcc act ctg gga acg ctg ggc ttg tat       384
Leu Lys Ile Pro Ala Ile Val Ala Thr Leu Gly Thr Leu Gly Leu Tyr
        115                 120                 125 cgt ggg atc atg ctg cta tgg aca ggg ggg aaa tgg att gaa gga tta       432
Arg Gly Ile Met Leu Leu Trp Thr Gly Gly Lys Trp Ile Glu Gly Leu
    130                 135                 140 ccc gca ggc tta aag caa ctc tct gct ccg gtg ttt ctg gga att tcc       480
Pro Ala Gly Leu Lys Gln Leu Ser Ala Pro Val Phe Leu Gly Ile Ser
145                 150                 155                 160 gca atc ggc tgg ttt acc ctg gtg tta gcg ctg ctt atg gcc tgg ctc       528
Ala Ile Gly Trp Phe Thr Leu Val Leu Ala Leu Leu Met Ala Trp Leu
                165                 170                 175 ctg gcg aaa acc gcc ttt ggc cgc aat ttt tac gcc acc ggc gat aac       576
Leu Ala Lys Thr Ala Phe Gly Arg Asn Phe Tyr Ala Thr Gly Asp Asn
            180                 185                 190 ctg cag ggc gcc cgg caa ttg ggt gtc cgt acc gag atg gta cgc atc       624
Leu Gln Gly Ala Arg Gln Leu Gly Val Arg Thr Glu Met Val Arg Ile
        195                 200                 205 atg gca ttt tca ctt aat ggc ggt atg gcg gca ttg gct gga atc gtg       672
Met Ala Phe Ser Leu Asn Gly Gly Met Ala Ala Leu Ala Gly Ile Val
    210                 215                 220 ttt gcc tcg cag att ggc ttc att ccc aat caa acc ggc acg ggg ctg       720
Phe Ala Ser Gln Ile Gly Phe Ile Pro Asn Gln Thr Gly Thr Gly Leu
225                 230                 235                 240 gaa atg aaa gcc atc gcg gcc tgc gta ttg ggg gga att agc ctg tta       768
Glu Met Lys Ala Ile Ala Ala Cys Val Leu Gly Gly Ile Ser Leu Leu
                245                 250                 255 ggc ggg tca ggc acg gtc atc ggc gct att ctc ggc gct tat ttt ctt       816
Gly Gly Ser Gly Thr Val Ile Gly Ala Ile Leu Gly Ala Tyr Phe Leu
            260                 265                 270 acg caa atc gat agt gtg tta gtg ctg ctg cgt atc ccc gcc tgg tgg       864
Thr Gln Ile Asp Ser Val Leu Val Leu Leu Arg Ile Pro Ala Trp Trp
        275                 280                 285 aac gat ttt att gct ggc ctg gta ttg ttg ggc gta ctg gta ttc gat       912
Asn Asp Phe Ile Ala Gly Leu Val Leu Leu Gly Val Leu Val Phe Asp
    290                 295                 300 ggg cgg ctg cgt tgc gca tta caa cgc aat ctg cgc cgc cag aaa tat       960
Gly Arg Leu Arg Cys Ala Leu Gln Arg Asn Leu Arg Arg Gln Lys Tyr
305                 310                 315                 320
```

-continued

```
gcc cgt ttt ata tca cca ccc act cca cta cag acg gaa gca aaa acg      1008
Ala Arg Phe Ile Ser Pro Pro Thr Pro Leu Gln Thr Glu Ala Lys Thr
            325                 330                 335 cac gca caa cag aat aaa aac aaa gag gtg gca tga                      1044
His Ala Gln Gln Asn Lys Asn Lys Glu Val Ala  *
        340                 345
```

<210> SEQ ID NO 31
<211> LENGTH: 999
<212> TYPE: DNA
<213> ORGANISM: Salmonella typhimurium
<220> FEATURE:
<221> NAME/KEY: CDS
<222> LOCATION: (1)...(999)
<223> OTHER INFORMATION: LsrD

<400> SEQUENCE: 31

```
atg aat cca tgg cga cgc tat agc tgg gaa att gcg ctg gca gcc tta       48
Met Asn Pro Trp Arg Arg Tyr Ser Trp Glu Ile Ala Leu Ala Ala Leu
 1               5                  10                  15 ttg atc ttt gaa att ctg gct ttc ggt ctg att aat cca cgt tta tta       96
Leu Ile Phe Glu Ile Leu Ala Phe Gly Leu Ile Asn Pro Arg Leu Leu
            20                  25                  30 gat att aat gtc tta ctt ttt agc act agc gat ttt att tgt atc ggt      144
Asp Ile Asn Val Leu Leu Phe Ser Thr Ser Asp Phe Ile Cys Ile Gly
        35                  40                  45 att gtc gct ttg ccg cta aca atg gtt att gtc agc ggt ggt atg gat      192
Ile Val Ala Leu Pro Leu Thr Met Val Ile Val Ser Gly Gly Met Asp
    50                  55                  60 att tca ttt ggt tct aca atc ggg cta tgc gcg att acc ctg ggt gtg      240
Ile Ser Phe Gly Ser Thr Ile Gly Leu Cys Ala Ile Thr Leu Gly Val
65                  70                  75                  80 ctg ttt cag ctc ggt atg ccg cta cct tta gcg att att att acc cta      288
Leu Phe Gln Leu Gly Met Pro Leu Pro Leu Ala Ile Ile Ile Thr Leu
                85                  90                  95 cta ctt ggc gca ata tgt ggg ctg ata aat gcc gga ctt att att tat      336
Leu Leu Gly Ala Ile Cys Gly Leu Ile Asn Ala Gly Leu Ile Ile Tyr
            100                 105                 110 acc ggc gta aac ccg ttg gtg att acc ctg gga acc atg tat tta ttt      384
Thr Gly Val Asn Pro Leu Val Ile Thr Leu Gly Thr Met Tyr Leu Phe
        115                 120                 125 ggt ggt agc gca tta ttg tta tct ggt atg gct ggc gcg acg ggt tat      432
Gly Gly Ser Ala Leu Leu Leu Ser Gly Met Ala Gly Ala Thr Gly Tyr
    130                 135                 140 gaa ggt att ggt gga ttt ccc aca gcg ttc act gac ttt gcc aat att      480
Glu Gly Ile Gly Gly Phe Pro Thr Ala Phe Thr Asp Phe Ala Asn Ile
145                 150                 155                 160 tca ttt ctt ggt att ccc atg ccg ctt att ttt ttt ctt gtg tgc tgt      528
Ser Phe Leu Gly Ile Pro Met Pro Leu Ile Phe Phe Leu Val Cys Cys
                165                 170                 175 ctg ttt ttc tgg ctg ctc atg cat cgt acg cat atg gga cgc aac gtt      576
Leu Phe Phe Trp Leu Leu Met His Arg Thr His Met Gly Arg Asn Val
            180                 185                 190 ttc ctg att ggc cag agc gcc cgt gtc gcg cag tac agc gcg atc ccg      624
Phe Leu Ile Gly Gln Ser Ala Arg Val Ala Gln Tyr Ser Ala Ile Pro
        195                 200                 205 gtg aat cgc acg ttg tat acc gtg tat gcc atg acc gga tgc gcc tcc      672
Val Asn Arg Thr Leu Tyr Thr Val Tyr Ala Met Thr Gly Cys Ala Ser
    210                 215                 220 gcg atc gcc gcc gta tta ctg gtt tct tac ttt ggc tcc gca cgt tcg      720
Ala Ile Ala Ala Val Leu Leu Val Ser Tyr Phe Gly Ser Ala Arg Ser
```

-continued

```
                225                 230                 235                 240
gat ctg ggc gcc tct ttc ctg atg ccg gcc att acg gcg gtt gtg ctg         768
Asp Leu Gly Ala Ser Phe Leu Met Pro Ala Ile Thr Ala Val Val Leu
                    245                 250                 255 gga ggc gcc aat att tat ggc ggc tcc ggg tcg att atg ggg tcc gcg         816
Gly Gly Ala Asn Ile Tyr Gly Gly Ser Gly Ser Ile Met Gly Ser Ala
                260                 265                 270 ttg gcg gcg ctg ctg gtg gga ttt tta cag cag ggg cta cag atg gcc         864
Leu Ala Ala Leu Leu Val Gly Phe Leu Gln Gln Gly Leu Gln Met Ala
            275                 280                 285 gga gtg ccg aat caa att tcc agc gca ttg tcc ggt gcg ctt ctc att         912
Gly Val Pro Asn Gln Ile Ser Ser Ala Leu Ser Gly Ala Leu Leu Ile
        290                 295                 300 gtt gtt gtc gtt ggt cgt tcc gtc agt ttg cat cgt cac caa atc ctt         960
Val Val Val Val Gly Arg Ser Val Ser Leu His Arg His Gln Ile Leu
305                 310                 315                 320 gaa tgg tac tca cgc cgt cgc aat gcg cat cag gca tga                     999
Glu Trp Tyr Ser Arg Arg Arg Asn Ala His Gln Ala *
                325                 330

<210> SEQ ID NO 32
<211> LENGTH: 1023
<212> TYPE: DNA
<213> ORGANISM: Salmonella typhimurium
<220> FEATURE:
<221> NAME/KEY: CDS
<222> LOCATION: (1)...(1023)
<223> OTHER INFORMATION: LsrB

<400> SEQUENCE: 32 atg gca aga cac agc att aaa atg atc gcc tta ctc act gcg ttt ggt         48
Met Ala Arg His Ser Ile Lys Met Ile Ala Leu Leu Thr Ala Phe Gly
1               5                   10                  15 ctg gca tct gcg gca atg acc gtg cag gcg gca gag cgg att gct ttt         96
Leu Ala Ser Ala Ala Met Thr Val Gln Ala Ala Glu Arg Ile Ala Phe
            20                  25                  30 att ccc aaa ctg gtt ggc gtg ggc ttt ttt acc agc ggc ggc aat ggc        144
Ile Pro Lys Leu Val Gly Val Gly Phe Phe Thr Ser Gly Gly Asn Gly
        35                  40                  45 gcg cag gaa gcg gga aaa gcg ctg ggc att gac gta act tac gat ggc        192
Ala Gln Glu Ala Gly Lys Ala Leu Gly Ile Asp Val Thr Tyr Asp Gly
    50                  55                  60 cct aca gag ccc agc gtc tca ggc cag gtt caa ctg gtg aat aac ttt        240
Pro Thr Glu Pro Ser Val Ser Gly Gln Val Gln Leu Val Asn Asn Phe
65                  70                  75                  80 gtc aat cag ggg tat gac gcc att atc gtt tct gcc gtt tcg cct gat        288
Val Asn Gln Gly Tyr Asp Ala Ile Ile Val Ser Ala Val Ser Pro Asp
                85                  90                  95 ggc ctg tgc ccg gcg ttg aag cgg gca atg caa aga ggc gtg aaa ata        336
Gly Leu Cys Pro Ala Leu Lys Arg Ala Met Gln Arg Gly Val Lys Ile
            100                 105                 110 tta acc tgg gat tcc gat acc aag ccg gag tgc cgt tct tac tat atc        384
Leu Thr Trp Asp Ser Asp Thr Lys Pro Glu Cys Arg Ser Tyr Tyr Ile
        115                 120                 125 aat caa ggg acg cca aaa cag ctc ggc agc atg ctg gta gag atg gcc        432
Asn Gln Gly Thr Pro Lys Gln Leu Gly Ser Met Leu Val Glu Met Ala
    130                 135                 140 gct cat cag gtg gac aaa gag aaa gcg aaa gtc gct ttc ttc tat tcc        480
Ala His Gln Val Asp Lys Glu Lys Ala Lys Val Ala Phe Phe Tyr Ser
145                 150                 155                 160 agc cca acg gtg acc gac cag aac cag tgg gtg aaa gaa gct aaa gcc        528
```

```
Ser Pro Thr Val Thr Asp Gln Asn Gln Trp Val Lys Glu Ala Lys Ala
            165                 170                 175 aaa att agc cag gaa cat ccg ggg tgg gag ata gtc act acc cag ttt      576
Lys Ile Ser Gln Glu His Pro Gly Trp Glu Ile Val Thr Thr Gln Phe
            180                 185                 190 ggc tat aac gat gcc acg aaa tcg ctc cag acg gcg gaa ggt atc atc      624
Gly Tyr Asn Asp Ala Thr Lys Ser Leu Gln Thr Ala Glu Gly Ile Ile
            195                 200                 205 aaa gcg tat ccc gat ctg gat gcc atc atc gcg cct gac gct aac gct      672
Lys Ala Tyr Pro Asp Leu Asp Ala Ile Ile Ala Pro Asp Ala Asn Ala
    210                 215                 220 tta cct gct gcg gca cag gcg gcg gag aac ctt aaa cgc aat aat ctc      720
Leu Pro Ala Ala Ala Gln Ala Ala Glu Asn Leu Lys Arg Asn Asn Leu
225                 230                 235                 240 gcg att gtt ggt ttt agt acg ccg aat gta atg cgc cct tat gtt cag      768
Ala Ile Val Gly Phe Ser Thr Pro Asn Val Met Arg Pro Tyr Val Gln
            245                 250                 255 cgc ggc act gtt aaa gag ttt ggc ctg tgg gat gtc gtc caa cag gga      816
Arg Gly Thr Val Lys Glu Phe Gly Leu Trp Asp Val Val Gln Gln Gly
            260                 265                 270 aaa att tcc gta tat gtc gcc aat gcg ttg ctg aaa aat atg cca atg      864
Lys Ile Ser Val Tyr Val Ala Asn Ala Leu Leu Lys Asn Met Pro Met
            275                 280                 285 aat gtc ggt gat tca ctg gat att ccc ggc atc ggc aaa gtc acc gtt      912
Asn Val Gly Asp Ser Leu Asp Ile Pro Gly Ile Gly Lys Val Thr Val
            290                 295                 300 tca cct aat agt gag cag gga tat cac tat gag gca aaa ggt aac ggc      960
Ser Pro Asn Ser Glu Gln Gly Tyr His Tyr Glu Ala Lys Gly Asn Gly
305                 310                 315                 320 att gtg tta ttg ccg gag cgt gtc att ttc aac aaa gac aat atc gac     1008
Ile Val Leu Leu Pro Glu Arg Val Ile Phe Asn Lys Asp Asn Ile Asp
            325                 330                 335 aaa tat gat ttc tga                                                 1023
Lys Tyr Asp Phe *    *    *    *
            340

<210> SEQ ID NO 33
<211> LENGTH: 876
<212> TYPE: DNA
<213> ORGANISM: Salmonella typhimurium
<220> FEATURE:
<221> NAME/KEY: CDS
<222> LOCATION: (1)...(876)
<223> OTHER INFORMATION: LsrF

<400> SEQUENCE: 33 atg gct gat tta gat gat att aaa gat ggc aaa gat ttt cac acc gat       48
Met Ala Asp Leu Asp Asp Ile Lys Asp Gly Lys Asp Phe His Thr Asp
1               5                   10                  15 aaa cca caa act aac act ttg ttc gca tta aaa ggc tgt ggc gcg ctg       96
Lys Pro Gln Thr Asn Thr Leu Phe Ala Leu Lys Gly Cys Gly Ala Leu
                20                  25                  30 gat tgg gga atg cag tcc aga ctg gcg agg att ttt aat ccc aag acc      144
Asp Trp Gly Met Gln Ser Arg Leu Ala Arg Ile Phe Asn Pro Lys Thr
            35                  40                  45 aga aaa acg gtc atg ctg gcc ttt gac cat gga tat ttc cag ggg ccg      192
Arg Lys Thr Val Met Leu Ala Phe Asp His Gly Tyr Phe Gln Gly Pro
        50                  55                  60 aca acc gga ctt gag cgt att gat atc aat att gcg ccg ctc ttt gaa      240
Thr Thr Gly Leu Glu Arg Ile Asp Ile Asn Ile Ala Pro Leu Phe Glu
65                  70                  75                  80
```

-continued

| | |
|---|---|
| tat gct gat gtc tta atg tgt act cgc ggc ata tta cgc agt gtg gta<br>Tyr Ala Asp Val Leu Met Cys Thr Arg Gly Ile Leu Arg Ser Val Val<br>                           85                         90                     95 | 288 |
| cct ccg gca atc aat aaa cca gtc gtt tta cgc gcg tcc ggg gcg aat<br>Pro Pro Ala Ile Asn Lys Pro Val Val Leu Arg Ala Ser Gly Ala Asn<br>               100                     105                     110 | 336 |
| tct att ctc act gaa tta agc aat gag gcg gtt gcg gtg gcg atg gat<br>Ser Ile Leu Thr Glu Leu Ser Asn Glu Ala Val Ala Val Ala Met Asp<br>               115                     120                     125 | 384 |
| gac gct gtg cgg ttg aat agc tgt gct gct gcc gca cag gtt tat att<br>Asp Ala Val Arg Leu Asn Ser Cys Ala Ala Ala Gln Val Tyr Ile<br>             130                     135                     140 | 432 |
| ggt agt gag cat gaa cat cag tcg att aaa aat att att caa ctg att<br>Gly Ser Glu His Glu His Gln Ser Ile Lys Asn Ile Ile Gln Leu Ile<br>145                     150                     155                     160 | 480 |
| gat gcc ggg tta cgc gtc ggg atg cca ata atg gca gtg acc ggg gtg<br>Asp Ala Gly Leu Arg Val Gly Met Pro Ile Met Ala Val Thr Gly Val<br>               165                     170                     175 | 528 |
| ggt aaa gat atg gct cgc gac cag cgt tat ttt tca ctg gca acg cgt<br>Gly Lys Asp Met Ala Arg Asp Gln Arg Tyr Phe Ser Leu Ala Thr Arg<br>             180                     185                     190 | 576 |
| atc gct gcg gaa atg ggg gcg caa att atc aaa acg tat tat gtc gat<br>Ile Ala Ala Glu Met Gly Ala Gln Ile Ile Lys Thr Tyr Tyr Val Asp<br>               195                     200                     205 | 624 |
| aaa ggt ttt gag cgt att gcg gca ggt tgt ccg gtg ccg att gtc atc<br>Lys Gly Phe Glu Arg Ile Ala Ala Gly Cys Pro Val Pro Ile Val Ile<br>             210                     215                     220 | 672 |
| gcc ggc ggt aaa aaa ctg cct gaa cgt gaa gca ttg gaa atg tgc tat<br>Ala Gly Gly Lys Lys Leu Pro Glu Arg Glu Ala Leu Glu Met Cys Tyr<br>225                     230                     235                     240 | 720 |
| cag gcg att gac cag ggg gct tct ggc gta gat atg ggg cgt aat ata<br>Gln Ala Ile Asp Gln Gly Ala Ser Gly Val Asp Met Gly Arg Asn Ile<br>             245                     250                     255 | 768 |
| ttc cag tca gaa gat ccg gta gcc atg att aaa gcg gta cat gct gtc<br>Phe Gln Ser Glu Asp Pro Val Ala Met Ile Lys Ala Val His Ala Val<br>             260                     265                     270 | 816 |
| gtt cat cat aac gaa aca gca gag cgt gct tat gag ctg ttt ttg agt<br>Val His His Asn Glu Thr Ala Glu Arg Ala Tyr Glu Leu Phe Leu Ser<br>             275                     280                     285 | 864 |
| gag aaa agt taa<br>Glu Lys Ser *<br>         290 | 876 |

```
<210> SEQ ID NO 34
<211> LENGTH: 291
<212> TYPE: DNA
<213> ORGANISM: Salmonella typhimurium
<220> FEATURE:
<221> NAME/KEY: CDS
<222> LOCATION: (1)...(291)
<223> OTHER INFORMATION: LsrG

<400> SEQUENCE: 34
```

| | |
|---|---|
| atg cac gtt acg ctg gtt gaa att aac gtt cat gat gac aag gtt gaa<br>Met His Val Thr Leu Val Glu Ile Asn Val His Asp Asp Lys Val Glu<br>1                   5                     10                     15 | 48 |
| caa ttt atc gat gtt ttt cgg cag aat cat ctg ggc tca att aaa gag<br>Gln Phe Ile Asp Val Phe Arg Gln Asn His Leu Gly Ser Ile Lys Glu<br>               20                     25                     30 | 96 |
| ccg ggt aac ttg cgt ttt gat gtt ctg cag gat ccg cag gtg ctt acg<br>Pro Gly Asn Leu Arg Phe Asp Val Leu Gln Asp Pro Gln Val Leu Thr<br>               35                     40                     45 | 144 |

```
cga ttt tat att tat gaa gcc tac gtt gat gaa cag gcc gtc gct ttt      192
Arg Phe Tyr Ile Tyr Glu Ala Tyr Val Asp Glu Gln Ala Val Ala Phe
     50                  55                  60 cac aag aca acg cca cac tac aaa act tgc gtg gag cag ctt gaa ccg      240
His Lys Thr Thr Pro His Tyr Lys Thr Cys Val Glu Gln Leu Glu Pro
 65                  70                  75                  80 ttg atg acc ggt ccg cgg aca aaa aaa gtt ttt atg ggt ttg atg cct      288
Leu Met Thr Gly Pro Arg Thr Lys Lys Val Phe Met Gly Leu Met Pro
                 85                  90                  95 taa                                                                  291
 *

<210> SEQ ID NO 35
<211> LENGTH: 765
<212> TYPE: DNA
<213> ORGANISM: Salmonella typhimurium
<220> FEATURE:
<221> NAME/KEY: CDS
<222> LOCATION: (1)...(765)
<223> OTHER INFORMATION: LsrE

<400> SEQUENCE: 35 atg aac agc cag ttt gcc gga tta acg cgc gaa gca tgt gtg gca ttg       48
Met Asn Ser Gln Phe Ala Gly Leu Thr Arg Glu Ala Cys Val Ala Leu
  1               5                  10                  15 tta gcg tca tat ccg ctt agt gtg ggt att ctg gca ggg cag tgg att       96
Leu Ala Ser Tyr Pro Leu Ser Val Gly Ile Leu Ala Gly Gln Trp Ile
                 20                  25                  30 gcg ttg cat cgc tat ctg caa cag ttg gaa gcg cta aac cag ccg ctg      144
Ala Leu His Arg Tyr Leu Gln Gln Leu Glu Ala Leu Asn Gln Pro Leu
             35                  40                  45 ttg cat ttg gat ttg atg gat ggt caa ttt tgc ccg cag ttt acc gtt      192
Leu His Leu Asp Leu Met Asp Gly Gln Phe Cys Pro Gln Phe Thr Val
         50                  55                  60 ggg cca tgg gca gtt ggg caa ctg ccg caa acc ttt atc aaa gat gtt      240
Gly Pro Trp Ala Val Gly Gln Leu Pro Gln Thr Phe Ile Lys Asp Val
 65                  70                  75                  80 cat ttg atg gta gcg gat caa tgg acg gcg gcg caa gcc tgc gtg aag      288
His Leu Met Val Ala Asp Gln Trp Thr Ala Ala Gln Ala Cys Val Lys
                 85                  90                  95 gcg ggc gca cac tgc atc acg ctt cag gct gaa ggc gat att cat ctg      336
Ala Gly Ala His Cys Ile Thr Leu Gln Ala Glu Gly Asp Ile His Leu
                100                 105                 110 cat cat acg cta agc tgg ctt ggt cag cag acc gtg ccc gtt att ggc      384
His His Thr Leu Ser Trp Leu Gly Gln Gln Thr Val Pro Val Ile Gly
            115                 120                 125 ggt gaa atg ccg gtg atc cgg ggg att agt tta tgc ccg gca acg cct      432
Gly Glu Met Pro Val Ile Arg Gly Ile Ser Leu Cys Pro Ala Thr Pro
        130                 135                 140 ctg gat gtc att atc ccc att ctg agc gac gtt gag gtt att caa cta      480
Leu Asp Val Ile Ile Pro Ile Leu Ser Asp Val Glu Val Ile Gln Leu
145                 150                 155                 160 ctg gca gta aac cct gga tac ggc agt aaa atg cgc tcc agt gat ttg      528
Leu Ala Val Asn Pro Gly Tyr Gly Ser Lys Met Arg Ser Ser Asp Leu
                165                 170                 175 cac gag cgc gtg gcg cag ctt ctc tgt cta ctt ggt gat aaa cgc gaa      576
His Glu Arg Val Ala Gln Leu Leu Cys Leu Leu Gly Asp Lys Arg Glu
            180                 185                 190 ggt aaa att atc gtt att gat ggg tcg tta acg cag gat cag ttg cct      624
Gly Lys Ile Ile Val Ile Asp Gly Ser Leu Thr Gln Asp Gln Leu Pro
        195                 200                 205
```

```
tcg ctg att gca cag ggc atc gat cgt gtt gtt tct ggt agt gcg tta    672
Ser Leu Ile Ala Gln Gly Ile Asp Arg Val Val Ser Gly Ser Ala Leu
    210                 215                 220 ttt cgt gat gat cgg ctg gtt gag aat acg cgg agc tgg agg gcg atg    720
Phe Arg Asp Asp Arg Leu Val Glu Asn Thr Arg Ser Trp Arg Ala Met
225                 230                 235                 240 ttt aag gtt gcc ggg gat act act ttc tta ccc tcc aca gca taa        765
Phe Lys Val Ala Gly Asp Thr Thr Phe Leu Pro Ser Thr Ala *
                245                 250
```

<210> SEQ ID NO 36
<211> LENGTH: 319
<212> TYPE: PRT
<213> ORGANISM: Salmonella typhimurium
<220> FEATURE:
<223> OTHER INFORMATION: LsrR

<400> SEQUENCE: 36

```
Met Ser Asp Asn Thr Leu Val Ser Asp Tyr Gly Met Cys Glu Glu Glu
 1               5                  10                  15

Gln Val Ala Arg Ile Ala Trp Phe Tyr Tyr His Asp Gly Leu Thr Gln
            20                  25                  30

Ser Glu Ile Ser Glu Arg Leu Gly Leu Thr Arg Leu Lys Val Ser Arg
        35                  40                  45

Leu Leu Glu Lys Gly His Gln Ser Gly Ile Ile Arg Val Gln Ile Asn
    50                  55                  60

Ser Arg Phe Glu Gly Cys Leu Glu Tyr Glu Asn Ala Leu Arg Asn His
65                  70                  75                  80

Phe Ala Leu Gln Asn Ile Arg Val Leu Pro Ala Leu Pro Asp Ala Asp
                85                  90                  95

Ile Gly Leu Arg Leu Gly Ile Gly Ala Ala His Met Leu Met Glu Ser
            100                 105                 110

Leu Arg Pro Gln Gln Leu Leu Ala Val Gly Phe Gly Glu Ala Thr Met
        115                 120                 125

Thr Thr Leu Lys Arg Leu Ser Gly Phe Ile Ser Ala Gln Gln Ile Arg
    130                 135                 140

Leu Val Thr Leu Ser Gly Gly Val Gly Pro Tyr Met Thr Gly Ile Gly
145                 150                 155                 160

Gln Leu Asp Ala Ala Cys Ser Val Ser Ile Met Pro Ala Pro Leu Arg
                165                 170                 175

Ala Ser Ser Gln Glu Ile Ala Cys Thr Leu Arg Asn Glu Asn Ser Val
            180                 185                 190

Arg Asp Val Met Leu Thr Ala Gln Ala Ala Asp Ala Ala Ile Val Gly
        195                 200                 205

Ile Gly Ala Ile Asn Gln Lys Asp Gln Ala Ser Ile Leu Lys Ser Gly
    210                 215                 220

Tyr Ile Thr Gln Gly Glu Gln Leu Met Ile Gly Arg Lys Gly Ala Val
225                 230                 235                 240

Gly Asp Ile Leu Gly Tyr Phe Phe Asp Ala His Gly Glu Ile Ile Pro
                245                 250                 255

Asp Ile Lys Ile His Asn Glu Leu Ile Gly Leu Lys Leu Asn Ser Leu
            260                 265                 270

Ser Thr Ile Pro Thr Val Ile Gly Val Ala Gly Gly Glu Gln Lys Ala
        275                 280                 285

Glu Ala Ile Ile Ala Ala Met Arg Gly Asn Tyr Ile Asn Ala Leu Val
    290                 295                 300
```

```
Thr Asp Gln Lys Thr Ala Gly Lys Ile Ile Gln Ile Ile Glu Lys
305                 310                 315

<210> SEQ ID NO 37
<211> LENGTH: 511
<212> TYPE: PRT
<213> ORGANISM: Salmonella typhimurium
<220> FEATURE:
<223> OTHER INFORMATION: LsrA

<400> SEQUENCE: 37

Met Gln Ile Ser His Asn Thr Ala Ser Pro Leu Ile Cys Val Gln Asn
1               5                   10                  15

Ile Tyr Lys Ser Tyr Ser Gly Val Glu Val Leu Lys Gly Ile Asp Phe
            20                  25                  30

Thr Leu His Ala Gly Glu Val His Ala Leu Leu Gly Gly Asn Gly Ala
        35                  40                  45

Gly Lys Ser Thr Leu Met Lys Ile Ile Ala Gly Ile Val Pro Pro Asp
    50                  55                  60

Gly Gly Thr Ile Asp Ile Ala Gly Val Arg Cys Ser His Leu Thr Pro
65                  70                  75                  80

Leu Lys Ala His Gln Tyr Gly Ile Tyr Leu Val Pro Gln Glu Pro Leu
                85                  90                  95

Leu Phe Pro Ser Leu Ser Val Arg Glu Asn Ile Leu Phe Gly Leu Gln
            100                 105                 110

Gly Arg Gln Ala Ser Thr Glu Lys Met Gln Gln Leu Leu Lys Ala Met
        115                 120                 125

Gly Cys Gln Leu Asp Pro Ala Ser Ala Ala Gly Thr Leu Asp Val Ala
130                 135                 140

Asp Arg Gln Ile Val Glu Ile Met Arg Gly Leu Met Arg Asp Ser Arg
145                 150                 155                 160

Ile Leu Ile Leu Asp Glu Pro Thr Ala Ser Leu Thr Pro Ala Glu Thr
                165                 170                 175

Asp Arg Leu Phe Thr Arg Leu Gln Glu Leu Leu Lys Lys Gly Val Gly
            180                 185                 190

Ile Val Phe Ile Ser His Lys Leu Pro Glu Ile Arg Gln Leu Ala His
        195                 200                 205

Cys Val Ser Val Met Arg Asp Gly Lys Ile Ala Leu Phe Gly Lys Thr
210                 215                 220

His Asp Leu Ser Thr Asp Glu Ile Ile Gln Ala Ile Thr Pro Ala Thr
225                 230                 235                 240

Gln Gly Val Ser Leu Ser Ala Asn Gln Lys Leu Trp Leu Glu Leu Pro
                245                 250                 255

Gly Ser Arg Pro Gln Asn Glu Arg Gly Ala Thr Val Leu Ala Leu Glu
            260                 265                 270

Ser Leu Thr Gly Glu Gly Phe Met Asn Ile Asn Leu Glu Val Arg Ala
        275                 280                 285

Gly Glu Ile Leu Gly Leu Ala Gly Leu Val Gly Ala Gly Arg Thr Glu
290                 295                 300

Leu Ala Glu Thr Leu Tyr Gly Ile Arg Pro Val Asn Ala Gly Arg Met
305                 310                 315                 320

Leu Phe Asn Gly Gln Glu Ile Asn Ala Leu Thr Thr Gln Gln Arg Leu
                325                 330                 335

Gln Leu Gly Leu Val Tyr Leu Pro Glu Asp Arg Gln Ser Ser Gly Leu
            340                 345                 350
```

```
Tyr Leu Asp Ala Ser Leu Ala Trp Asn Val Cys Ser Leu Thr His Asn
            355                 360                 365

Gln Lys Gly Phe Trp Ile Lys Pro Gln Arg Asp Asn Ala Thr Leu Glu
        370                 375                 380

Arg Tyr His Arg Ala Leu Asn Ile Lys Leu Asn Asn Ala Glu Gln Ala
385                 390                 395                 400

Ala Arg Thr Leu Ser Gly Gly Asn Gln Gln Lys Val Leu Ile Ala Lys
                405                 410                 415

Cys Leu Glu Ala Ser Pro Gln Leu Leu Ile Val Asp Glu Pro Thr Arg
                420                 425                 430

Gly Val Asp Val Ser Ala Arg Ser Asp Ile Tyr Gln Leu Leu Arg Ser
                435                 440                 445

Ile Ala Gln Gln Asn Val Ala Val Leu Phe Ile Ser Ser Asp Leu Glu
            450                 455                 460

Glu Ile Glu Gln Met Ala Asp Arg Val Tyr Val Met His Gln Gly Glu
465                 470                 475                 480

Leu Gly Gly Pro Ala Leu Cys Gly Glu Ile Asn Val Asp Thr Ile
                485                 490                 495

Met His Val Ala Phe Glu His Gly Ala Ser Glu Ala Thr Cys
            500                 505                 510

<210> SEQ ID NO 38
<211> LENGTH: 347
<212> TYPE: PRT
<213> ORGANISM: Salmonella typhimurium
<220> FEATURE:
<223> OTHER INFORMATION: LsrC

<400> SEQUENCE: 38

Met Leu Lys Phe Ile Gln Asn Asn Arg Glu Ala Thr Ala Leu Leu Ala
 1               5                  10                  15

Ile Val Cys Leu Phe Val Phe Pro Gly Ala Leu Asp Ser Gln Tyr Leu
                20                  25                  30

Ser Val Gln Thr Leu Thr Met Val Phe Ser Ser Ala Gln Ile Leu Met
            35                  40                  45

Leu Leu Ala Ile Gly Ala Thr Met Val Met Leu Thr Arg Asn Ile Asp
        50                  55                  60

Val Ser Val Gly Ser Thr Thr Gly Met Cys Ala Val Leu Leu Gly Val
65                  70                  75                  80

Met Leu Asn Ala Gly Tyr Ser Leu Pro Val Ala Cys Leu Ala Thr Leu
                85                  90                  95

Ile Leu Gly Ile Val Ala Gly Phe Phe Asn Gly Val Leu Val Ala Trp
                100                 105                 110

Leu Lys Ile Pro Ala Ile Val Ala Thr Leu Gly Thr Leu Gly Leu Tyr
            115                 120                 125

Arg Gly Ile Met Leu Leu Trp Thr Gly Gly Lys Trp Ile Glu Gly Leu
        130                 135                 140

Pro Ala Gly Leu Lys Gln Leu Ser Ala Pro Val Phe Leu Gly Ile Ser
145                 150                 155                 160

Ala Ile Gly Trp Phe Thr Leu Val Leu Ala Leu Leu Met Ala Trp Leu
                165                 170                 175

Leu Ala Lys Thr Ala Phe Gly Arg Asn Phe Tyr Ala Thr Gly Asp Asn
            180                 185                 190

Leu Gln Gly Ala Arg Gln Leu Gly Val Arg Thr Glu Met Val Arg Ile
        195                 200                 205
```

```
Met Ala Phe Ser Leu Asn Gly Gly Met Ala Ala Leu Ala Gly Ile Val
    210                 215                 220

Phe Ala Ser Gln Ile Gly Phe Ile Pro Asn Gln Thr Gly Thr Gly Leu
225                 230                 235                 240

Glu Met Lys Ala Ile Ala Ala Cys Val Leu Gly Gly Ile Ser Leu Leu
                245                 250                 255

Gly Gly Ser Gly Thr Val Ile Gly Ala Ile Leu Gly Ala Tyr Phe Leu
            260                 265                 270

Thr Gln Ile Asp Ser Val Leu Val Leu Arg Ile Pro Ala Trp Trp
        275                 280                 285

Asn Asp Phe Ile Ala Gly Leu Val Leu Leu Gly Val Leu Val Phe Asp
    290                 295                 300

Gly Arg Leu Arg Cys Ala Leu Gln Arg Asn Leu Arg Arg Gln Lys Tyr
305                 310                 315                 320

Ala Arg Phe Ile Ser Pro Pro Thr Pro Leu Gln Thr Glu Ala Lys Thr
                325                 330                 335

His Ala Gln Gln Asn Lys Asn Lys Glu Val Ala
            340                 345

<210> SEQ ID NO 39
<211> LENGTH: 332
<212> TYPE: PRT
<213> ORGANISM: Salmonella typhimurium
<220> FEATURE:
<223> OTHER INFORMATION: LsrD

<400> SEQUENCE: 39

Met Asn Pro Trp Arg Arg Tyr Ser Trp Glu Ile Ala Leu Ala Ala Leu
1               5                   10                  15

Leu Ile Phe Glu Ile Leu Ala Phe Gly Leu Ile Asn Pro Arg Leu Leu
                20                  25                  30

Asp Ile Asn Val Leu Leu Phe Ser Thr Ser Asp Phe Ile Cys Ile Gly
            35                  40                  45

Ile Val Ala Leu Pro Leu Thr Met Val Ile Val Ser Gly Gly Met Asp
        50                  55                  60

Ile Ser Phe Gly Ser Thr Ile Gly Leu Cys Ala Ile Thr Leu Gly Val
65                  70                  75                  80

Leu Phe Gln Leu Gly Met Pro Leu Pro Leu Ala Ile Ile Ile Thr Leu
                85                  90                  95

Leu Leu Gly Ala Ile Cys Gly Leu Ile Asn Ala Gly Leu Ile Ile Tyr
                100                 105                 110

Thr Gly Val Asn Pro Leu Val Ile Thr Leu Gly Thr Met Tyr Leu Phe
            115                 120                 125

Gly Gly Ser Ala Leu Leu Ser Gly Met Ala Gly Ala Thr Gly Tyr
        130                 135                 140

Glu Gly Ile Gly Gly Phe Pro Thr Ala Phe Thr Asp Phe Ala Asn Ile
145                 150                 155                 160

Ser Phe Leu Gly Ile Pro Met Pro Leu Ile Phe Phe Leu Val Cys Cys
                165                 170                 175

Leu Phe Phe Trp Leu Leu Met His Arg Thr His Met Gly Arg Asn Val
                180                 185                 190

Phe Leu Ile Gly Gln Ser Ala Arg Val Ala Gln Tyr Ser Ala Ile Pro
            195                 200                 205

Val Asn Arg Thr Leu Tyr Thr Val Tyr Ala Met Thr Gly Cys Ala Ser
        210                 215                 220
```

```
Ala Ile Ala Ala Val Leu Leu Val Ser Tyr Phe Gly Ser Ala Arg Ser
225                 230                 235                 240

Asp Leu Gly Ala Ser Phe Leu Met Pro Ala Ile Thr Ala Val Val Leu
            245                 250                 255

Gly Gly Ala Asn Ile Tyr Gly Gly Ser Gly Ser Ile Met Gly Ser Ala
            260                 265                 270

Leu Ala Ala Leu Leu Val Gly Phe Leu Gln Gln Gly Leu Gln Met Ala
            275                 280                 285

Gly Val Pro Asn Gln Ile Ser Ser Ala Leu Ser Gly Ala Leu Leu Ile
            290                 295                 300

Val Val Val Val Gly Arg Ser Val Ser Leu His Arg His Gln Ile Leu
305                 310                 315                 320

Glu Trp Tyr Ser Arg Arg Arg Asn Ala His Gln Ala
                325                 330

<210> SEQ ID NO 40
<211> LENGTH: 340
<212> TYPE: PRT
<213> ORGANISM: Salmonella typhimurium
<220> FEATURE:
<223> OTHER INFORMATION: LsrB

<400> SEQUENCE: 40

Met Ala Arg His Ser Ile Lys Met Ile Ala Leu Leu Thr Ala Phe Gly
1               5                   10                  15

Leu Ala Ser Ala Ala Met Thr Val Gln Ala Ala Glu Arg Ile Ala Phe
            20                  25                  30

Ile Pro Lys Leu Val Gly Val Gly Phe Phe Thr Ser Gly Gly Asn Gly
            35                  40                  45

Ala Gln Glu Ala Gly Lys Ala Leu Gly Ile Asp Val Thr Tyr Asp Gly
    50                  55                  60

Pro Thr Glu Pro Ser Val Ser Gly Gln Val Gln Leu Val Asn Asn Phe
65                  70                  75                  80

Val Asn Gln Gly Tyr Asp Ala Ile Ile Val Ser Ala Val Ser Pro Asp
                85                  90                  95

Gly Leu Cys Pro Ala Leu Lys Arg Ala Met Gln Arg Gly Val Lys Ile
            100                 105                 110

Leu Thr Trp Asp Ser Asp Thr Lys Pro Glu Cys Arg Ser Tyr Tyr Ile
            115                 120                 125

Asn Gln Gly Thr Pro Lys Gln Leu Gly Ser Met Leu Val Glu Met Ala
            130                 135                 140

Ala His Gln Val Asp Lys Glu Lys Ala Lys Val Ala Phe Phe Tyr Ser
145                 150                 155                 160

Ser Pro Thr Val Thr Asp Gln Asn Gln Trp Val Lys Glu Ala Lys Ala
                165                 170                 175

Lys Ile Ser Gln Glu His Pro Gly Trp Glu Ile Val Thr Thr Gln Phe
            180                 185                 190

Gly Tyr Asn Asp Ala Thr Lys Ser Leu Gln Thr Ala Glu Gly Ile Ile
            195                 200                 205

Lys Ala Tyr Pro Asp Leu Asp Ala Ile Ile Ala Pro Asp Ala Asn Ala
            210                 215                 220

Leu Pro Ala Ala Ala Gln Ala Ala Glu Asn Leu Lys Arg Asn Asn Leu
225                 230                 235                 240

Ala Ile Val Gly Phe Ser Thr Pro Asn Val Met Arg Pro Tyr Val Gln
                245                 250                 255
```

-continued

```
Arg Gly Thr Val Lys Glu Phe Gly Leu Trp Asp Val Val Gln Gln Gly
            260                 265                 270

Lys Ile Ser Val Tyr Val Ala Asn Ala Leu Leu Lys Asn Met Pro Met
        275                 280                 285

Asn Val Gly Asp Ser Leu Asp Ile Pro Gly Ile Gly Lys Val Thr Val
        290                 295                 300

Ser Pro Asn Ser Glu Gln Gly Tyr His Tyr Glu Ala Lys Gly Asn Gly
305                 310                 315                 320

Ile Val Leu Leu Pro Glu Arg Val Ile Phe Asn Lys Asp Asn Ile Asp
                325                 330                 335

Lys Tyr Asp Phe
            340

<210> SEQ ID NO 41
<211> LENGTH: 291
<212> TYPE: PRT
<213> ORGANISM: Salmonella typhimurium
<220> FEATURE:
<223> OTHER INFORMATION: LsrF

<400> SEQUENCE: 41

Met Ala Asp Leu Asp Asp Ile Lys Asp Gly Lys Asp Phe His Thr Asp
  1               5                  10                  15

Lys Pro Gln Thr Asn Thr Leu Phe Ala Leu Lys Gly Cys Gly Ala Leu
                 20                  25                  30

Asp Trp Gly Met Gln Ser Arg Leu Ala Arg Ile Phe Asn Pro Lys Thr
             35                  40                  45

Arg Lys Thr Val Met Leu Ala Phe Asp His Gly Tyr Phe Gln Gly Pro
 50                  55                  60

Thr Thr Gly Leu Glu Arg Ile Asp Ile Asn Ile Ala Pro Leu Phe Glu
 65                  70                  75                  80

Tyr Ala Asp Val Leu Met Cys Thr Arg Gly Ile Leu Arg Ser Val Val
                 85                  90                  95

Pro Pro Ala Ile Asn Lys Pro Val Val Leu Arg Ala Ser Gly Ala Asn
            100                 105                 110

Ser Ile Leu Thr Glu Leu Ser Asn Glu Ala Val Ala Val Ala Met Asp
        115                 120                 125

Asp Ala Val Arg Leu Asn Ser Cys Ala Ala Ala Gln Val Tyr Ile
130                 135                 140

Gly Ser Glu His Glu His Gln Ser Ile Lys Asn Ile Gln Leu Ile
145                 150                 155                 160

Asp Ala Gly Leu Arg Val Gly Met Pro Ile Met Ala Val Thr Gly Val
                165                 170                 175

Gly Lys Asp Met Ala Arg Asp Gln Arg Tyr Phe Ser Leu Ala Thr Arg
            180                 185                 190

Ile Ala Ala Glu Met Gly Ala Gln Ile Ile Lys Thr Tyr Tyr Val Asp
        195                 200                 205

Lys Gly Phe Glu Arg Ile Ala Ala Gly Cys Pro Val Pro Ile Val Ile
    210                 215                 220

Ala Gly Gly Lys Lys Leu Pro Glu Arg Glu Ala Leu Glu Met Cys Tyr
225                 230                 235                 240

Gln Ala Ile Asp Gln Gly Ala Ser Gly Val Asp Met Gly Arg Asn Ile
                245                 250                 255

Phe Gln Ser Glu Asp Pro Val Ala Met Ile Lys Ala Val His Ala Val
            260                 265                 270
```

```
Val His His Asn Glu Thr Ala Glu Arg Ala Tyr Glu Leu Phe Leu Ser
        275                 280                 285

Glu Lys Ser
    290

<210> SEQ ID NO 42
<211> LENGTH: 96
<212> TYPE: PRT
<213> ORGANISM: Salmonella typhimurium
<220> FEATURE:
<223> OTHER INFORMATION: LsrG

<400> SEQUENCE: 42

Met His Val Thr Leu Val Glu Ile Asn Val His Asp Asp Lys Val Glu
1               5                   10                  15

Gln Phe Ile Asp Val Phe Arg Gln Asn His Leu Gly Ser Ile Lys Glu
            20                  25                  30

Pro Gly Asn Leu Arg Phe Asp Leu Gln Asp Pro Gln Val Leu Thr
        35                  40                  45

Arg Phe Tyr Ile Tyr Glu Ala Tyr Val Asp Glu Gln Ala Val Ala Phe
    50                  55                  60

His Lys Thr Thr Pro His Tyr Lys Thr Cys Val Glu Gln Leu Glu Pro
65                  70                  75                  80

Leu Met Thr Gly Pro Arg Thr Lys Lys Val Phe Met Gly Leu Met Pro
                85                  90                  95

<210> SEQ ID NO 43
<211> LENGTH: 254
<212> TYPE: PRT
<213> ORGANISM: Salmonella typhimurium
<220> FEATURE:
<223> OTHER INFORMATION: LsrE

<400> SEQUENCE: 43

Met Asn Ser Gln Phe Ala Gly Leu Thr Arg Glu Ala Cys Val Ala Leu
1               5                   10                  15

Leu Ala Ser Tyr Pro Leu Ser Val Gly Ile Leu Ala Gly Gln Trp Ile
            20                  25                  30

Ala Leu His Arg Tyr Leu Gln Gln Leu Glu Ala Leu Asn Gln Pro Leu
        35                  40                  45

Leu His Leu Asp Leu Met Asp Gly Gln Phe Cys Pro Gln Phe Thr Val
    50                  55                  60

Gly Pro Trp Ala Val Gly Gln Leu Pro Gln Thr Phe Ile Lys Asp Val
65                  70                  75                  80

His Leu Met Val Ala Asp Gln Trp Thr Ala Gln Ala Cys Val Lys
                85                  90                  95

Ala Gly Ala His Cys Ile Thr Leu Gln Ala Glu Gly Asp Ile His Leu
            100                 105                 110

His His Thr Leu Ser Trp Leu Gly Gln Gln Thr Val Pro Val Ile Gly
        115                 120                 125

Gly Glu Met Pro Val Ile Arg Gly Ile Ser Leu Cys Pro Ala Thr Pro
    130                 135                 140

Leu Asp Val Ile Pro Ile Leu Ser Asp Val Glu Ile Gln Leu
145                 150                 155                 160

Leu Ala Val Asn Pro Gly Tyr Gly Ser Lys Met Arg Ser Ser Asp Leu
                165                 170                 175

His Glu Arg Val Ala Gln Leu Leu Cys Leu Leu Gly Asp Lys Arg Glu
```

180                 185                 190
Gly Lys Ile Ile Val Ile Asp Gly Ser Leu Thr Gln Asp Gln Leu Pro
        195                 200                 205

Ser Leu Ile Ala Gln Gly Ile Asp Arg Val Val Ser Gly Ser Ala Leu
    210                 215                 220

Phe Arg Asp Asp Arg Leu Val Glu Asn Thr Arg Ser Trp Arg Ala Met
225                 230                 235                 240

Phe Lys Val Ala Gly Asp Thr Thr Phe Leu Pro Ser Thr Ala
                245                 250

<210> SEQ ID NO 44
<211> LENGTH: 7888
<212> TYPE: DNA
<213> ORGANISM: Salmonella typhimurium

<400> SEQUENCE: 44

| | | | | | |
|---|---|---|---|---|---|
| ttatttttca | ataatttgaa | ttattttccc | tgcggttttc | tgatcggtaa | ccagtgcatt |   60 |
| gatatagtta | ccgcgcatag | cggcaataat | agcttctgct | ttttgttcgc | cgccggcgac |  120 |
| gccaatcacg | gttgggatcg | tggaaagtga | atttaacttc | aggccaatta | attcgttatg |  180 |
| gattttgatg | tctggaataa | tttcgccatg | agcatcaaaa | aaatagccca | gaatatcgcc |  240 |
| tactgcgcct | ttgcggccaa | tcatgagttg | ttcaccctga | gtgatataac | cggattttaa |  300 |
| gatactggct | tgatctttct | ggttaattgc | cccaatcccc | acgatggcgg | catcggcagc |  360 |
| ttgcgctgtg | agcatcacat | cccgcacgct | attttcattg | cgcagcgtgc | aggcaatttc |  420 |
| ctgcgatgat | gcgcgcagcg | gcgcgggcat | aatacttacg | ctacaagcgg | catcaagctg |  480 |
| gcctattccg | gtcatatacg | gccccacgcc | gccggataac | gtgaccagtc | ggatttgttg |  540 |
| cgccgagata | aatccgctga | ggcgttttaa | tgtggtcatc | gtggcttcgc | caaagccgac |  600 |
| ggccagcagt | tgctgtggcc | gcagtgactc | catcaacata | tgggcggcgc | cgattcctaa |  660 |
| gcgcagacca | atatcggcat | cgggtaatgc | cggcagcacg | cggatattct | gcaatgcgaa |  720 |
| gtggttgcgc | aaggcatttt | catactcaag | acacccttcg | aagcgggagt | tgatttgtac |  780 |
| gcgaataata | ccggactgat | gcccttttctc | cagcagacga | gaaacctttta | gccgggttag |  840 |
| ccccagacgc | tcgctgattt | cactctgcgt | caatccatcg | tgatagtaga | accaggcaat |  900 |
| acgcgccacc | tgctcttctt | cgcacattcc | ataatcagat | accaacgtat | tatcgctcat |  960 |
| tgtcataacc | tggctttact | ttgaacattt | ctaaatcatt | aacacaattg | ttcagttatc | 1020 |
| actccgaaat | aaccgtgatt | aacgccacaa | aaacgcgcca | aatctgaaca | tttatcatct | 1080 |
| aaaaattcat | ttattcagaa | aacgtgatct | ggatgagagt | ttttttgacca | aataactact | 1140 |
| accgttttga | acaatttctt | tttcaaaaaa | catttgttca | gtcccgtcag | tcaacattga | 1200 |
| gggagcggag | gcaacatgca | aatcagtcac | aatactgcat | ccctctgat | ttgtgtgcag | 1260 |
| aacatttata | aaagttattc | cggcgtcgaa | gtactaaagg | gaattgactt | tactctgcat | 1320 |
| gcgggagagg | tgcacgcatt | gcttggcggc | aatggtgcgg | gtaaatcaac | attaatgaag | 1380 |
| attattgccg | gtagtcccg | ccagatgga | gggactatcg | atattgctgg | tgtgcgttgc | 1440 |
| agtcatttaa | cgcctctgaa | ggcgcaccag | tatggcattt | acctggttcc | ccaggagcct | 1500 |
| ctgttatttc | cgagtttatc | tgtgcgggaa | aatatcttgt | ttggcttgca | gggacgtcag | 1560 |
| gcctccacgg | aaaaaatgca | gcagctatta | aaggcgatgg | gatgccaact | cgatccggcg | 1620 |
| agcgctgcgg | gtacgcttga | tgttgcagac | cgccagatcg | ttgaaattat | gcgcggcttg | 1680 |
| atgcgcgact | cgcgaatctt | aattcttgat | gagcccacgg | cgtcgttaac | gccagccgaa | 1740 |

-continued

```
actgatcggt tatttacgcg tctgcaagag ttgctgaaaa agggtgtcgg aattgtattt     1800
atttctcata agctaccaga aattagacag ttagctcact gcgttagcgt gatgcgtgac     1860
ggtaaaatcg cattattcgg aaaaacgcat gacctttcta ccgacgagat tattcaagct     1920
atcaccccgg caacgcaggg cgtcagtctt tccgcgaatc aaaagttgtg gctggaattg     1980
cctggcagcc gcccgcagaa cgaacgcggc gcgacagtat tagcgctgga gtcactgacg     2040
ggcgaaggtt ttatgaatat caaccttgag gtgcgggcag gcgaaatcct tggtctggcc     2100
gggttggtcg cgcgggacg cacagaactg gctgaaacgc tgtacggtat tagaccggtc      2160
aatgcgggc ggatgctgtt caatggtcaa gaaattaacg ccctgacaac ccaacagcgg      2220
ttgcagctcg gcctggtcta tttgccggaa gatcggcagt catccgggct gtatcttgac     2280
gcttccctgg catggaatgt ctgttcgctg acccacaacc aaaaaggatt ttggataaag     2340
ccccagcggg ataacgccac ccttgaacgt taccaccgcg cgttaaatat caaactcaat     2400
aatgccgaac aggcggcgcg tactttatcc ggcggtaacc agcaaaaagt attgattgcc    2460
aaatgcctgg aggcctctcc gcaattactg attgtcgatg aaccgacccg cggtgtcgat    2520
gtctccgccc gcagcgatat ttatcagctg ttgcgcagta tcgcgcaaca aaatgtcgcg    2580
gtgctatttta tttcctccga tctggaagag atagagcaga tggccgatcg cgtatatgtc   2640
atgcaccagg gggaactggg ggggcctgcg ttatgcggcg aggaaattaa cgttgatacc    2700
atcatgcacg ttgcgtttgg cgaacatggt gcgtcggagg caacatgttg aaattcatcc    2760
aaaataaccg ggaagcgacg gcactgctgg caatagtctg tttattcgtg tttcctggcg    2820
cgctggatag tcagtatttg agcgtgcaaa cgctgacaat ggttttcagt agcgcgcaaa    2880
ttttgatgct gttggcgatt ggcgcgacga tggtaatgct cacccgcaat attgatgtat    2940
cggtgggctc gacgacagga atgtgcgcgg tattgctggg agtgatgtta aacgccggct    3000
atagcctgcc ggtcgcctgc ctggccacac taatattagg aattgtcgcc ggatttttta    3060
atggcgtact ggttgcctgg ttgaagatac ccgccattgt cgccactctg gaacgctgg     3120
gcttgtatcg tgggatcatg ctgctatgga caggggggaa atggattgaa ggattacccg    3180
caggcttaaa gcaactctct gctccggtgt ttctgggaat ttccgcaatc ggctggttta    3240
ccctggtgtt agcgctgctt atggcctggc tcctggcgaa aaccgccttt ggccgcaatt    3300
tttacgccac cggcgataac ctgcagggcg cccggcaatt gggtgtccgt accgagatgg    3360
tacgcatcat ggcattttca cttaatggcg gtatggcggc attggctgga atcgtgtttg    3420
cctcgcagat tggcttcatt cccaatcaaa ccggcacggg gctggaaatg aaagccatcg    3480
cggcctgcgt attgggggga attagcctgt taggcgggtc aggcacggtc atcggcgcta    3540
ttctcggcgc ttatttttctt acgcaaatcg atagtgtgtt agtgctgctg cgtatccccg    3600
cctggtggaa cgatttttatt gctggcctgg tattgttggg cgtactggta ttcgatgggc    3660
ggctgcgttg cgcattacaa cgcaatctgc gccgccagaa atatgcccgt tttatatcac    3720
cacccactcc actacagacg gaagcaaaaa cgcacgcaca acagaataaa acaaagagg     3780
tggcatgatg aatccatggc gacgctatag ctgggaaatt gcgctggcag ccttattgat    3840
ctttgaaatt ctggcttttcg gtctgattaa tccacgtttta ttagatatta atgtcttact   3900
ttttagcact agcgattttta tttgtatcgg tattgtcgct ttgccgctaa caatggttat   3960
tgtcagcggt ggtatggata tttcatttgg ttctacaatc gggctatgcg cgattacccct   4020
gggtgtgctg tttcagctcg gtatgccgct acctttagcg attattatta ccctactact    4080
```

-continued

```
tggcgcaata tgtgggctga taaatgccgg acttattatt tataccggcg taaacccgtt   4140
ggtgattacc ctgggaacca tgtatttatt tggtggtagc gcattattgt tatctggtat   4200
ggctggcgcc acgggttatg aaggtattgg tggatttccc acagcgttca ctgactttgc   4260
caatatttca tttcttggta ttcccatgcc gcttattttt tttcttgtgt gctgtctgtt   4320
tttctggctg ctcatgcatc gtacgcatat gggacgcaac gttttcctga ttggccagag   4380
cgcccgtgtc gcgcagtaca gcgcgatccc ggtgaatcgc acgttgtata ccgtgtatgc   4440
catgaccgga tgcgcctccg cgatcgccgc cgtattactg gtttcttact ttggctccgc   4500
acgttcggat ctgggcgcct cttcctgat gccggccatt acgcggttg tgctgggagg     4560 cgccaatatt tatggcggct ccgggtcgat tatggggtcc gcgttggcgg cgctgctggt   4620
gggattttta cagcagggc tacagatggc cggagtgccg aatcaaattt ccagcgcatt    4680
gtccggtgcg cttctcattg ttgttgtcgt tggtcgttcc gtcagtttgc atcgtcacca   4740
aatccttgaa tggtactcac gccgtcgcaa tgcgcatcag gcatgatttc cttttgaaat   4800
ttatggagaa aaaaatggca agacacagca ttaaaatgat cgccttactc actgcgtttg   4860
gtctggcatc tgcggcaatg accgtgcagg cggcagagcg gattgctttt attcccaaac   4920
tggttggcgt gggcttttt accagcggcg gcaatggcgc gcaggaagcg ggaaaagcgc    4980
tgggcattga cgtaacttac gatggcccta cagagcccag cgtctcaggc caggttcaac   5040
tggtgaataa ctttgtcaat caggggtatg acgccattat cgtttctgcc gtttcgcctg   5100
atggcctgtg cccggcgttg aagcgggcaa tgcaaagagg cgtgaaaata ttaacctggg   5160
attccgatac caagccggag tgccgttctt actatatcaa tcaagggacg ccaaaacagc   5220
tcggcagcat gctggtagag atggccgctc atcaggtgga caaagagaaa gcgaaagtcg   5280 cttttcttcta ttccagccca acggtgaccg accagaacca gtgggtgaaa aagctaaag   5340 ccaaaattag ccaggaacat ccggggtggg agatagtcac tacccagttt ggctataacg   5400
atgccacgaa atcgctccag acggcggaag gtatcatcaa agcgtatccc gatctggatg   5460
ccatcatcgc gcctgacgct aacgctttac ctgctgcggc acaggcggcg gagaacctta   5520
aacgcaataa tctcgcgatt gttggttta gtacgccgaa tgtaatgcgc ccttatgttc    5580
agcgcggcac tgttaaagag tttggcctgt gggatgtcgt ccaacaggga aaaatttccg   5640
tatatgtcgc caatgcgttg ctgaaaaata tgccaatgaa tgtcggtgat tcactggata   5700
ttcccggcat cggcaaagtc accgtttcac ctaatagtga gcagggatat cactatgagg   5760
caaaaggtaa cggcattgtg ttattgccgg agcgtgtcat tttcaacaaa gacaatatcg   5820
acaaatatga tttctgataa ctgttatgta tcgacggagt aaagaatggc tgatttagat   5880
gatattaaag atgcaaaga ttttcacacc gataaaccac aaactaacac tttgttcgca   5940
ttaaaaggct gtggcgcgct ggattgggga atgcagtcca gactggcgag gatttttaat   6000
cccaagacca gaaaaacggt catgctggcc tttgaccatg gatatttcca ggggccgaca   6060
accggacttg agcgtattga tatcaatatt gcgccgctct ttgaatatgc tgatgtctta   6120
atgtgtactc gcggcatatt acgcagtgtg gtacctccgg caatcaataa accagtcgtt   6180
ttacgcgcgt ccggggcgaa ttctattctc actgaattaa gcaatgaggc ggttgcggtg   6240
gcgatggatg acgctgtgcg gttgaatagc tgtgctgctg ccgcacaggt ttatattggt   6300
agtgagcatg aacatcagtc gattaaaaat attattcaac tgattgatgc cgggttacgc   6360
gtcgggatgc caataatggc agtgaccggg gtgggtaaag atatggctcg cgaccagcgt   6420
tatttttcac tggcaacgcg tatcgctgcg gaaatggggg cgcaaattat caaaacgtat   6480
```

-continued

```
tatgtcgata aaggtttga gcgtattgcg gcaggttgtc cggtgccgat tgtcatcgcc    6540
ggcggtaaaa aactgcctga acgtgaagca ttggaaatgt gctatcaggc gattgaccag    6600
ggggcttctg gcgtagatat ggggcgtaat atattccagt cagaagatcc ggtagccatg    6660
attaaagcgg tacatgctgt cgttcatcat aacgaaacag cagagcgtgc ttatgagctg    6720 ttttgagtg agaaaagtta aatgagatcg cttccccatc ttttaccgat gcgaggagat    6780
ggggatgact gttattttat ttggaataat caggggtta atgatgcacg ttacgctggt    6840
tgaaattaac gttcatgatg acaaggttga acaatttatc gatgttttc ggcagaatca    6900 tctgggctca attaaagagc cgggtaactt gcgttttgat gttctgcagg atccgcaggt    6960
gcttacgcga ttatattt atgaagccta cgttgatgaa caggccgtcg cttttcacaa    7020
gacaacgcca cactacaaaa cttgcgtgga gcagcttgaa ccgttgatga ccggtccgcg    7080
gacaaaaaaa gttttatgg gtttgatgcc ttaaggagcg ctcatgaaca gccagtttgc    7140
cggattaacg cgcgaagcat gtgtggcatt gttagcgtca tatccgctta gtgtgggtat    7200
tctggcaggg cagtggattg cgttgcatcg ctatctgcaa cagttggaag cgctaaacca    7260
gccgctgttg catttggatt tgatggatgg tcaattttgc ccgcagttta ccgttgggcc    7320
atgggcagtt gggcaactgc cgcaaaacctt tatcaaagat gttcatttga tggtagcgga    7380
tcaatggacg gcggcgcaag cctgcgtgaa ggcgggcgca cactgcatca cgcttcaggc    7440
tgaaggcgat attcatctgc atcatacgct aagctggctt ggtcagcaga ccgtgccccgt    7500 tattggcggt gaaatgccgg tgatccgggg gattagttta tgcccggcaa cgcctctgga    7560
tgtcattatc cccattctga gcgacgttga ggttattcaa ctactggcag taaaccctgg    7620
atacggcagt aaaatgcgct ccagtgattt gcacgagcgc gtggcgcagc ttctctgtct    7680
acttggtgat aaacgcgaag gtaaaattat cgttattgat gggtcgttaa cgcaggatca    7740
gttgccttcg ctgattgcac agggcatcga tcgtgttgtt tctggtagtg cgttatttcg    7800
tgatgatcgg ctggttgaga atacgcggag ctggagggcg atgtttaagg ttgccgggga    7860
tactactttc ttaccctcca cagcataa    7888
```

<210> SEQ ID NO 45
<211> LENGTH: 40
<212> TYPE: DNA
<213> ORGANISM: Artificial Sequence
<220> FEATURE:
<223> OTHER INFORMATION: Oligonucleotide

<400> SEQUENCE: 45
ataagaatgc ggccgcagag gcgttaaatg actgcaacgc        40

<210> SEQ ID NO 46
<211> LENGTH: 33
<212> TYPE: DNA
<213> ORGANISM: Artificial Sequence
<220> FEATURE:
<223> OTHER INFORMATION: Oligonucleotide

<400> SEQUENCE: 46
gcggagctct atcgctcatt gtcataacct ggc        33

<210> SEQ ID NO 47
<211> LENGTH: 33
<212> TYPE: DNA
<213> ORGANISM: Artificial Sequence
<220> FEATURE:

```
<223> OTHER INFORMATION: Oligonucleotide

<400> SEQUENCE: 47
gcggagctca ctatatcaat gcactggtta ccg                               33

<210> SEQ ID NO 48
<211> LENGTH: 33
<212> TYPE: DNA
<213> ORGANISM: Artificial Sequence
<220> FEATURE:
<223> OTHER INFORMATION: Oligonucleotide

<400> SEQUENCE: 48
gcggaattca acagactacg tttccagttg cgg                               33

<210> SEQ ID NO 49
<211> LENGTH: 33
<212> TYPE: DNA
<213> ORGANISM: Artificial Sequence
<220> FEATURE:
<223> OTHER INFORMATION: Oligonucleotide

<400> SEQUENCE: 49
gcggaattct gaaaagaaa ttgttcaaaa cgg                                33

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide

<400> SEQUENCE: 50
ccaaatgatg ttattccgcg                                              20

<210> SEQ ID NO 51
<211> LENGTH: 29
<212> TYPE: DNA
<213> ORGANISM: Artificial Sequence
<220> FEATURE:
<223> OTHER INFORMATION: Oligonucleotide

<400> SEQUENCE: 51
cggggatcct taccgtaatc tgttacgcg                                    29

<210> SEQ ID NO 52
<211> LENGTH: 29
<212> TYPE: DNA
<213> ORGANISM: Artificial Sequence
<220> FEATURE:
<223> OTHER INFORMATION: Oligonucleotide

<400> SEQUENCE: 52
ggggatccga aaagcaagca ccgatcatc                                    29

<210> SEQ ID NO 53
<211> LENGTH: 31
<212> TYPE: DNA
<213> ORGANISM: Artificial Sequence
<220> FEATURE:
<223> OTHER INFORMATION: Oligonucleotide

<400> SEQUENCE: 53
gcgaagctta gccaggttat gacaatgagc g                                 31
```

<210> SEQ ID NO 54
<211> LENGTH: 33
<212> TYPE: DNA
<213> ORGANISM: Artificial Sequence
<220> FEATURE:
<223> OTHER INFORMATION: Oligonucleotide

<400> SEQUENCE: 54
gcgggatcct aatttgaatt attttccctg cgg                                    33

<210> SEQ ID NO 55
<211> LENGTH: 39
<212> TYPE: DNA
<213> ORGANISM: Artificial Sequence
<220> FEATURE:
<223> OTHER INFORMATION: Oligonucleotide

<400> SEQUENCE: 55
aataagtatg cggccgccat tccgaacaaa gaagtgatg                              39

<210> SEQ ID NO 56
<211> LENGTH: 33
<212> TYPE: DNA
<213> ORGANISM: Artificial Sequence
<220> FEATURE:
<223> OTHER INFORMATION: Oligonucleotide

<400> SEQUENCE: 56
ggggaattcc gctgctcgtc cggcgtgcca atc                                    33

<210> SEQ ID NO 57
<211> LENGTH: 2550
<212> TYPE: DNA
<213> ORGANISM: Vibrio harveyi
<220> FEATURE:
<221> NAME/KEY: CDS
<222> LOCATION: (1)...(2550)
<223> OTHER INFORMATION: LuxN

<400> SEQUENCE: 57
atgtttgatt ttagcctaga ggctatcgtc tacgccaaag ccattagcct cctcgcgacc        60
gtggcagtcg tcatgatgtg gctcttctat tactgctatc gacttaagca aaaaaatgaa       120
gtgatctttg gtactcacca cgcagcttat attgcgtact cggtgtgtat cattgcgtgg       180
atcagcagca atgcttattt ccataccgat ttactgcccg agctcggagc ttcggctggc       240
atgttcatgg ccaagtttgc caacctcgct tccttcttcg catttgcttt tgcctattat       300
ttctcatgcc agttggcggc ggagcaacgc aaaggcaaag tacaccgatg gcagcaaggt       360
atctttgttt cattaactgt gtactcactg tttatcaatt tgcgtcccgg tttgaccgta       420
gagcacgtcg atattgtcgg cccaagtcaa ttcatcatcg agtttggccc tcatacctct       480 tatttctttta tcggcctcgt tagctttgtt gttctgactc tcgtcaatct tgtcgccatg       540
cgaacaaaca gcagtaagct gactctagcc aagaccaact acatgatcgc cggtatctta       600
gtgtttatgc tttcgacggc agtcattcat cttggtatga cttactttat gggagatttc       660
tcattgactt ggttaccacc agccttgtcg ataagtgaaa tgctctttgt cggctatgca       720
ctgctgacct cccgcttcta cagcgtaaag tacattgctt acctcgctct cagcgtgctg       780
ctggtctgtg ctattttcgt tctgcctttta ggcgcaatat tcatcccact tacggaaagt       840
aatcagtggc ttatcgccat acctatctgc gcccttattg gtattacttg gcagcttttg       900
tataaaaaga ccagccgata tgcatcgttc ttgatatatg gcgacaagaa aacaccagta       960

```
cagcaaatct tgtcacttga agaggatttt aagctttcta ttgatgatgc gatgcgccgt    1020
ctgggtaagc tgctgcaaat tccaaatgac aaactacgcc tcgtaaccag taactacaac    1080 gaaaccttt acgaagagta cctttcatca aaccgctcgg tgttggtgtt tgatgaactc     1140
tctgaagagc tcgaatacaa ggtatcggca aagcgttcaa tgaaggcgct gtatgacaaa    1200
atgagctcaa acaacaccgc tttggttatg ccgctgtttg ggcaaggtaa atcggttacg    1260
cacttattga tttctcccca aagagcaac aaccaaatgt tctcgaacga ggaaatctca     1320
gcagttcaaa ccttgcttac tcgagtacaa agtaccattg aagcggatcg ccgtattcga    1380
caaagccgcg cactagctaa ctctattgct cacgaaatgc gtaaccctct tgctcaagtt    1440
cagttgcaat tgaagcatt gaagcagcat attgagaatc atgcgcccgt gaacagatc     1500 acactagata ttgaaaatgg ccaagccgca attcagcgcg tcgccaact catcgatatc     1560 attttgcgag aagtgagtga cagctcgcca gagcacgaac ctatcgctat gacctcaatt    1620
cacaaagccg tcgaccaagc tgtcagccat acggttttg aaaatgagaa gatcatcgaa     1680
aggattcgtc tgccacagca cactgatttt gtggcaaaac tcaacgagac cttatttaac    1740
tttgtcattt tcaatctgat tcgtaacgca atttactatt ttgactcgta tccggacagt    1800
caaattgaga tcagcacgaa acgggcccca tatgaaaata cgttgatttt ccgcgacact    1860
ggcccaggta tcgatgaaac catctctcac aagatctttg acgactttt ctcttaccaa     1920 aagagcggtg gcagcggctt aggtttgggc tactgccagc gcgtaatgcg ttcttttggc    1980
ggcagaattg agtgtaagtc taaacttggc acattcacgg aatttcattt gtacttccct    2040
gtcgtcccga atgcaccaaa agcagacaca ttacgcacgc cttacttcaa cgattggaag    2100
caaaataaac gaagtaatga acataaagtc gcgcccaacg tacaaataaa taaccaatca    2160
ccaacagtgc ttatcgtcga cgataaagag gtccaacggg cgctcgttca gatgtatttg    2220
aaccaacttg gcgtgaatag cttacaagca acaacggtg aaaatgccgt cgaagtgttt     2280
aaggcaaacc acgtagattt gattctgatg gatgtacaaa tgcctgttat gaatgggttt    2340
gatgcaagcc aaaggatcaa agagctgtct cctcaaaccc caattgtcgc tttatcaggg    2400
gagtctggag aacgcgaatt agacatgatc aataagctaa tggatggtag gctagaaaag    2460
ccaacaacgt taaacgcctt acgtcatgtt ttaggaaact ggttgaacaa aaataccgca    2520
tcgagcgctt gtgaagctga gagagaatag                                     2550
```

<210> SEQ ID NO 58
<211> LENGTH: 848
<212> TYPE: PRT
<213> ORGANISM: Vibrio harveyi
<220> FEATURE:
<223> OTHER INFORMATION: LuxN
<400> SEQUENCE: 58

```
Met Phe Asp Phe Ser Leu Glu Ala Ile Val Tyr Ala Lys Ala Ile Ser
  1               5                  10                  15

Leu Leu Ala Thr Val Ala Val Val Met Met Trp Leu Phe Tyr Tyr Cys
             20                  25                  30

Tyr Arg Leu Lys Gln Lys Asn Glu Val Ile Phe Gly Thr His His Ala
         35                  40                  45

Ala Tyr Ile Ala Tyr Ser Val Cys Ile Ile Ala Trp Ile Ser Ser Asn
     50                  55                  60

Ala Tyr Phe His Thr Asp Leu Leu Pro Glu Leu Gly Ala Ser Ala Gly
 65                  70                  75                  80
```

```
Met Phe Met Ala Lys Phe Ala Asn Leu Ala Ser Phe Ala Phe Ala
                85                  90                  95

Phe Ala Tyr Tyr Phe Ser Cys Gln Leu Ala Ala Glu Gln Arg Lys Gly
                100                 105                 110

Lys Val His Arg Trp Gln Gln Gly Ile Phe Val Ser Leu Thr Val Tyr
                115                 120                 125

Ser Leu Phe Ile Asn Leu Arg Pro Gly Leu Thr Val Glu His Val Asp
    130                 135                 140

Ile Val Gly Pro Ser Gln Phe Ile Ile Glu Phe Gly Pro His Thr Ser
145                 150                 155                 160

Tyr Phe Phe Ile Gly Leu Val Ser Phe Val Leu Thr Leu Val Asn
                165                 170                 175

Leu Val Ala Met Arg Thr Asn Ser Ser Lys Leu Thr Leu Ala Lys Thr
                180                 185                 190

Asn Tyr Met Ile Ala Gly Ile Leu Val Phe Met Leu Ser Thr Ala Val
                195                 200                 205

Ile His Leu Gly Met Thr Tyr Phe Met Gly Asp Phe Ser Leu Thr Trp
    210                 215                 220

Leu Pro Pro Ala Leu Ser Ile Ser Glu Met Leu Phe Val Gly Tyr Ala
225                 230                 235                 240

Leu Leu Thr Ser Arg Phe Tyr Ser Val Lys Tyr Ile Ala Tyr Leu Ala
                245                 250                 255

Leu Ser Val Leu Val Cys Ala Ile Phe Val Leu Pro Leu Gly Ala
                260                 265                 270

Ile Phe Ile Pro Leu Thr Glu Ser Asn Gln Trp Leu Ala Ile Pro
    275                 280                 285

Ile Cys Ala Leu Ile Gly Ile Thr Trp Gln Leu Leu Tyr Lys Lys Thr
    290                 295                 300

Ser Arg Tyr Ala Ser Phe Leu Ile Tyr Gly Asp Lys Lys Thr Pro Val
305                 310                 315                 320

Gln Gln Ile Leu Ser Leu Glu Glu Asp Phe Lys Leu Ser Ile Asp Asp
                325                 330                 335

Ala Met Arg Arg Leu Gly Lys Leu Leu Gln Ile Pro Asn Asp Lys Leu
        340                 345                 350

Arg Leu Val Thr Ser Asn Tyr Asn Glu Thr Phe Tyr Glu Glu Tyr Leu
        355                 360                 365

Ser Ser Asn Arg Ser Val Leu Val Phe Asp Glu Leu Ser Glu Glu Leu
    370                 375                 380

Glu Tyr Lys Val Ser Ala Lys Arg Ser Met Lys Ala Leu Tyr Asp Lys
385                 390                 395                 400

Met Ser Ser Asn Asn Thr Ala Leu Val Met Pro Leu Phe Gly Gln Gly
                405                 410                 415

Lys Ser Val Thr His Leu Leu Ile Ser Pro His Lys Ser Asn Asn Gln
            420                 425                 430

Met Phe Ser Asn Glu Glu Ile Ser Ala Val Gln Thr Leu Leu Thr Arg
        435                 440                 445

Val Gln Ser Thr Ile Glu Ala Asp Arg Arg Ile Arg Gln Ser Arg Ala
    450                 455                 460

Leu Ala Asn Ser Ile Ala His Glu Met Arg Asn Pro Leu Ala Gln Val
465                 470                 475                 480

Gln Leu Gln Phe Glu Ala Leu Lys Gln His Ile Glu Asn His Ala Pro
                485                 490                 495

Val Glu Gln Ile Thr Leu Asp Ile Glu Asn Gly Gln Ala Ala Ile Gln
```

-continued

```
                500             505             510
Arg Gly Arg Gln Leu Ile Asp Ile Ile Leu Arg Glu Val Ser Asp Ser
            515                 520                 525
Ser Pro Glu His Glu Pro Ile Ala Met Thr Ser Ile His Lys Ala Val
        530                 535                 540
Asp Gln Ala Val Ser His Tyr Gly Phe Glu Asn Glu Lys Ile Ile Glu
545                 550                 555                 560
Arg Ile Arg Leu Pro Gln His Thr Asp Phe Val Ala Lys Leu Asn Glu
                565                 570                 575
Thr Leu Phe Asn Phe Val Ile Phe Asn Leu Ile Arg Asn Ala Ile Tyr
            580                 585                 590
Tyr Phe Asp Ser Tyr Pro Asp Ser Gln Ile Glu Ile Ser Thr Lys Thr
            595                 600                 605
Gly Pro Tyr Glu Asn Thr Leu Ile Phe Arg Asp Thr Gly Pro Gly Ile
            610                 615                 620
Asp Glu Thr Ile Ser His Lys Ile Phe Asp Asp Phe Phe Ser Tyr Gln
625                 630                 635                 640
Lys Ser Gly Gly Ser Gly Leu Gly Leu Gly Tyr Cys Gln Arg Val Met
                645                 650                 655
Arg Ser Phe Gly Gly Arg Ile Glu Cys Lys Ser Lys Leu Gly Thr Phe
                660                 665                 670
Thr Glu Phe His Leu Tyr Phe Pro Val Val Pro Asn Ala Pro Lys Ala
            675                 680                 685
Asp Thr Leu Arg Thr Pro Tyr Phe Asn Asp Trp Lys Gln Asn Lys Arg
            690                 695                 700
Ser Asn Glu His Lys Val Ala Pro Asn Val Gln Ile Asn Asn Gln Ser
705                 710                 715                 720
Pro Thr Val Leu Ile Val Asp Asp Lys Glu Val Gln Arg Ala Leu Val
                725                 730                 735
Gln Met Tyr Leu Gln Leu Gly Val Asn Ser Leu Gln Ala Asn Asn Gly
            740                 745                 750
Glu Asn Ala Val Glu Val Phe Lys Ala Asn His Val Asp Leu Ile Leu
            755                 760                 765
Met Asp Val Gln Met Pro Val Met Asn Gly Phe Asp Ala Ser Gln Arg
            770                 775                 780
Ile Lys Glu Leu Ser Pro Gln Thr Pro Ile Val Ala Leu Ser Gly Glu
785                 790                 795                 800
Ser Gly Glu Arg Glu Leu Asp Met Ile Asn Lys Leu Met Asp Gly Arg
                805                 810                 815
Leu Glu Lys Pro Thr Thr Leu Asn Ala Leu Arg His Val Leu Gly Asn
                820                 825                 830
Trp Leu Asn Lys Asn Thr Ala Ser Ser Ala Cys Glu Ala Glu Arg Glu
            835                 840                 845
```